(12) United States Patent
Lemire et al.

(10) Patent No.: US 7,690,059 B2
(45) Date of Patent: Apr. 6, 2010

(54) HOSPITAL BED

(75) Inventors: Guy Lemire, Beaumont (CA); Luc Petitpas, Québec (CA); Sébastien Lessard, Saint-Nicolas (CA)

(73) Assignee: Stryker Corporation, Kalamazoo, MI (US)

( * ) Notice: Subject to any disclaimer, the term of this patent is extended or adjusted under 35 U.S.C. 154(b) by 425 days.

(21) Appl. No.: 11/612,428

(22) Filed: Dec. 18, 2006

(65) Prior Publication Data

US 2007/0157385 A1 Jul. 12, 2007

Related U.S. Application Data

(60) Provisional application No. 60/751,770, filed on Dec. 19, 2005, provisional application No. 60/874,287, filed on Dec. 11, 2006.

(51) Int. Cl.
*A61G 7/012* (2006.01)
(52) U.S. Cl. ............................................... 5/600; 5/616
(58) Field of Classification Search .................... 5/600, 5/611, 616; 180/19.3, 15, 65.1
See application file for complete search history.

(56) References Cited

U.S. PATENT DOCUMENTS

| | | | |
|---|---|---|---|
| 4,723,808 A | 2/1988 | Hines | |
| 5,377,372 A | 1/1995 | Rudolf et al. | |
| 5,450,639 A | 9/1995 | Weismiller et al. | |
| 5,715,548 A | 2/1998 | Weismiller et al. | |
| 5,745,937 A | 5/1998 | Weismiller et al. | |
| 5,987,671 A | 11/1999 | Heimbrock et al. | |
| 6,226,816 B1 | 5/2001 | Webster et al. | |
| 6,240,579 B1 | 6/2001 | Hanson et al. | |
| 6,296,261 B1 | 10/2001 | deGoma | |
| 6,314,597 B2 | 11/2001 | Heimbrock et al. | |
| 6,320,510 B2 | 11/2001 | Menkedick et al. | |
| 6,460,205 B1 | 10/2002 | Lewandowski et al. | |
| 6,473,921 B2 | 11/2002 | Brooke et al. | |
| 6,505,359 B2 | 1/2003 | Heimbrock et al. | |
| 6,575,052 B2 | 6/2003 | Toennesland et al. | |
| 6,658,680 B2 | 12/2003 | Osborne et al. | |
| 6,691,346 B2 | 2/2004 | Osborne et al. | |
| 6,728,984 B2 | 5/2004 | Dietrich | |
| 6,735,794 B1 | 5/2004 | Way et al. | |
| 6,749,034 B2 | 6/2004 | Vogel et al. | |
| 6,772,460 B2 | 8/2004 | Heimbrock et al. | |
| 6,820,294 B2 | 11/2004 | Shiery et al. | |
| 6,865,775 B2 | 3/2005 | Ganance | |
| 6,874,800 B2 | 4/2005 | George | |
| 6,877,572 B2 | 4/2005 | Vogel et al. | |
| 6,951,034 B2 | 10/2005 | Shiery et al. | |
| 6,978,500 B2 | 12/2005 | Osborne et al. | |
| 7,014,000 B2 * | 3/2006 | Kummer et al. ............ 180/19.3 |
| 7,062,805 B2 | 6/2006 | Hopper et al. | |
| 7,302,717 B2 | 12/2007 | Reinke et al. | |
| 7,346,942 B2 | 3/2008 | Reinke et al. | |

(Continued)

*Primary Examiner*—Fredrick Conley
(74) *Attorney, Agent, or Firm*—Van Dyke, Gardner, Linn & Burkhart, LLP

(57) ABSTRACT

A patient bed includes a patient support, a base, and an electrical control system. The patient support is mounted relative to said base, which has a plurality of bearing members for moving the base and the patient support across a surface. Each of the bearing members includes a brake operatively associated therewith, with the electrical control system having a user actuatable device and being configured to actuate one or more of the brakes upon actuation of the user actuatable device.

16 Claims, 105 Drawing Sheets

U.S. PATENT DOCUMENTS

2006/0026762 A1 2/2006 Hornbach et al.
2007/0163043 A1 7/2007 Lemire et al.
2007/0169268 A1 7/2007 Lemire et al.
2007/0174964 A1 8/2007 Lemire et al.

* cited by examiner

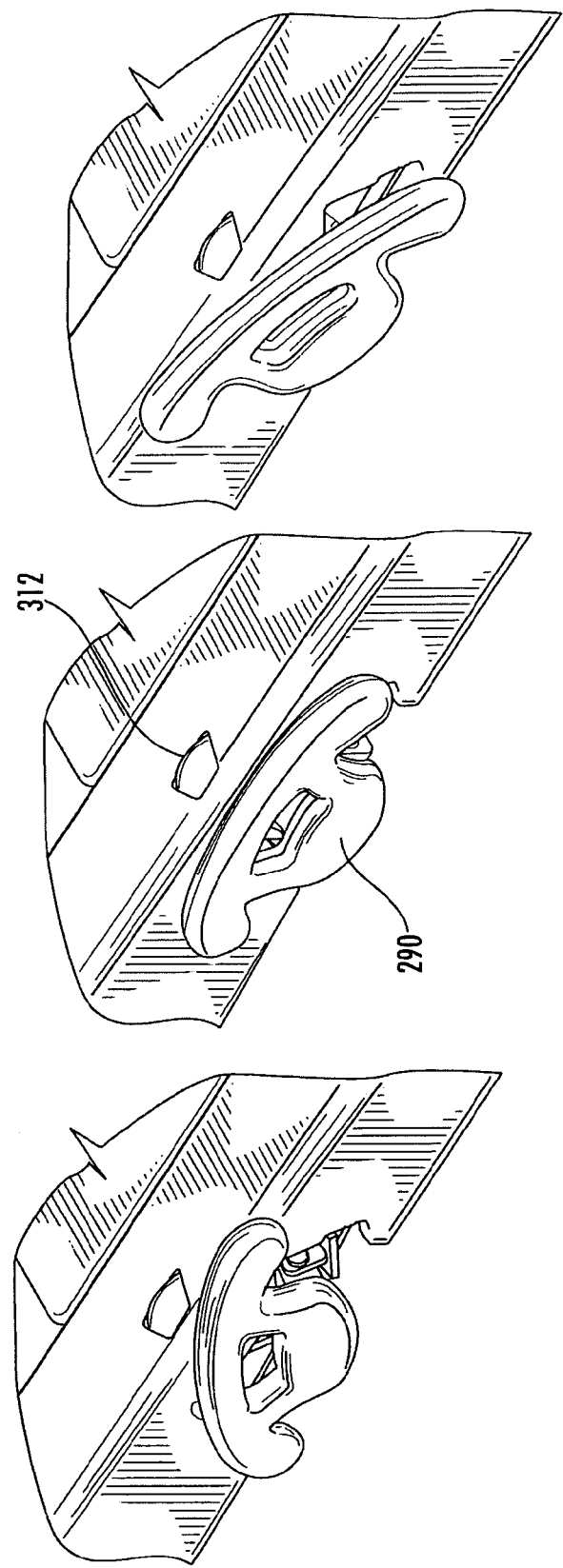

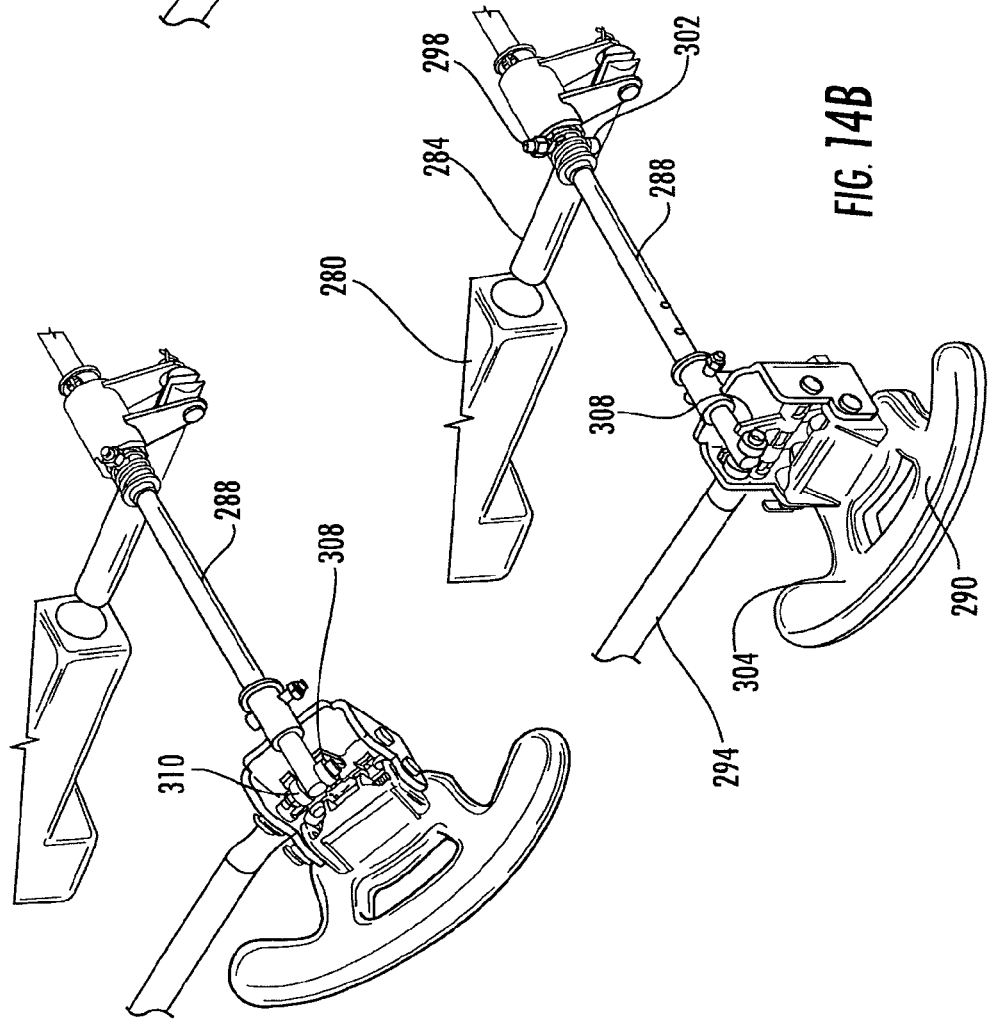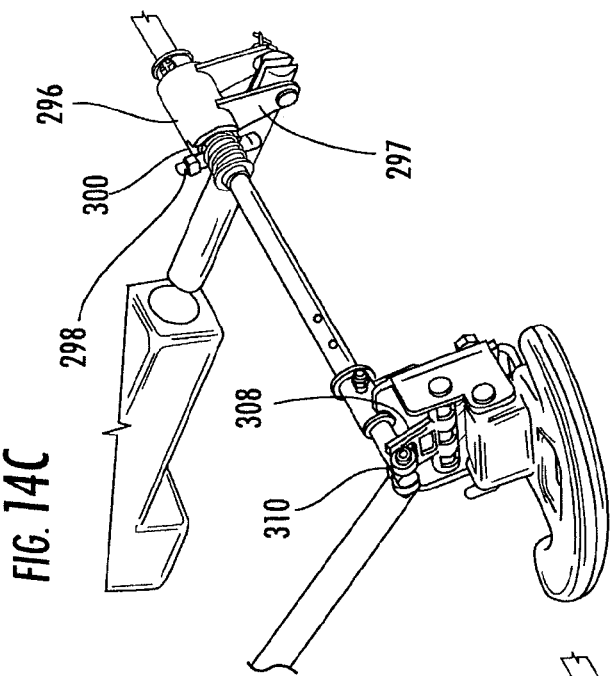

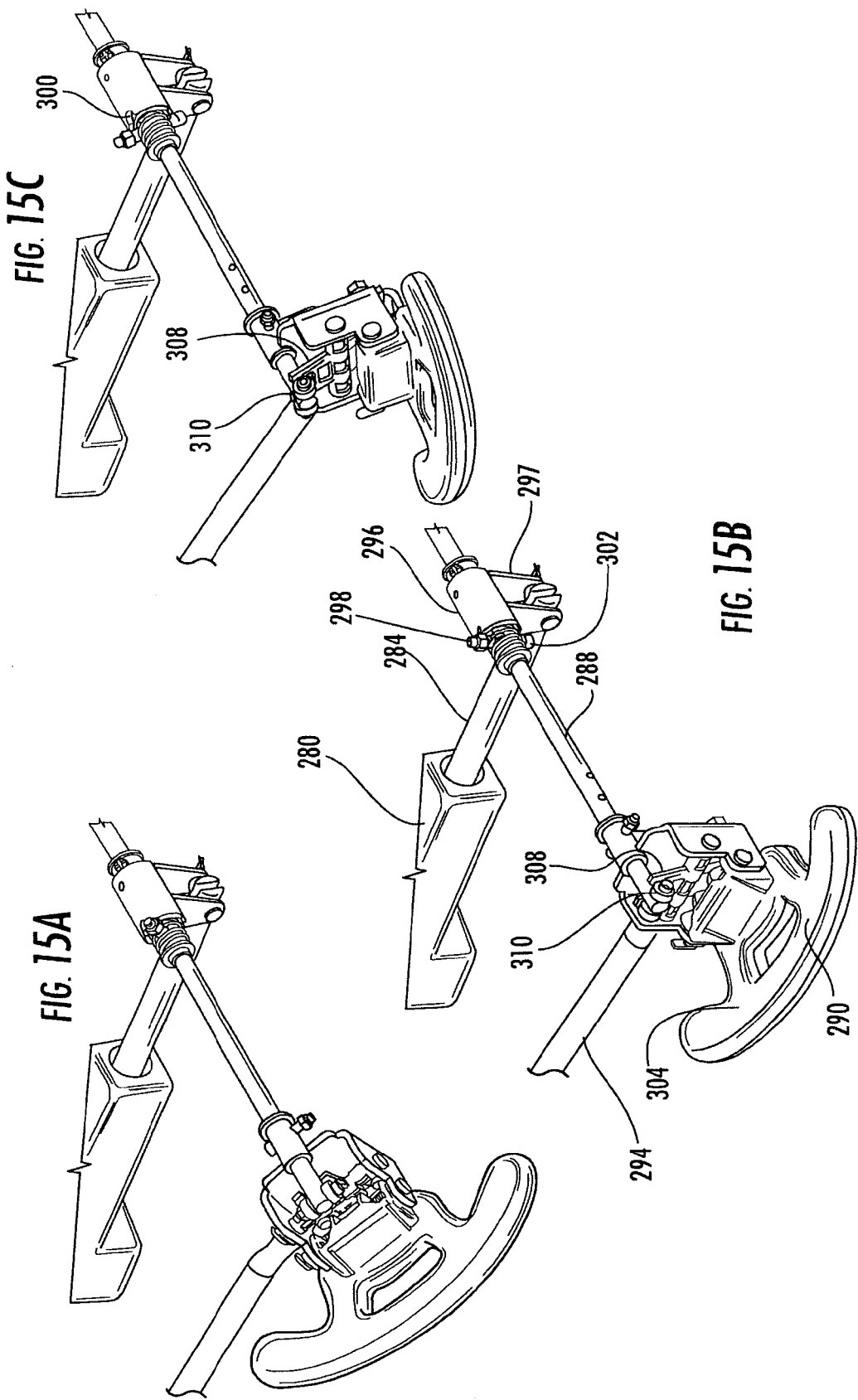

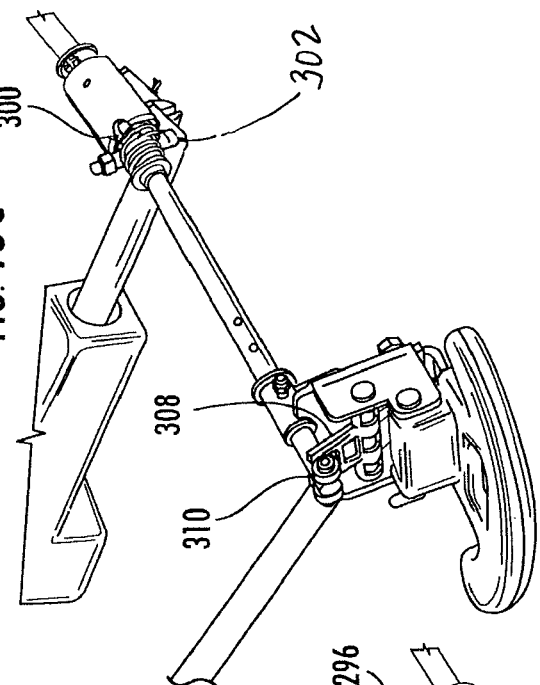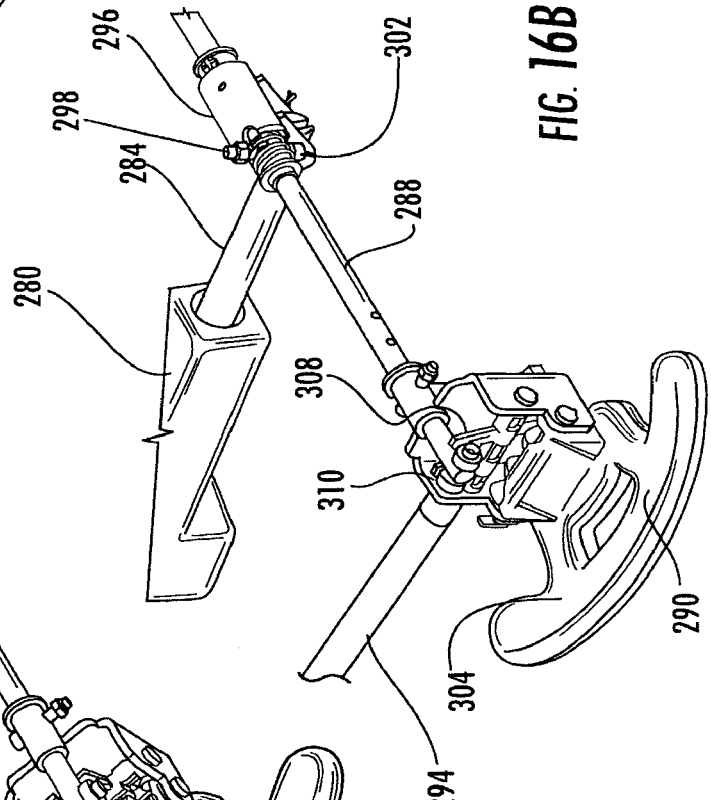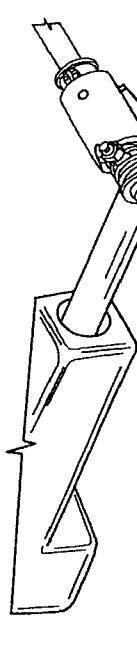

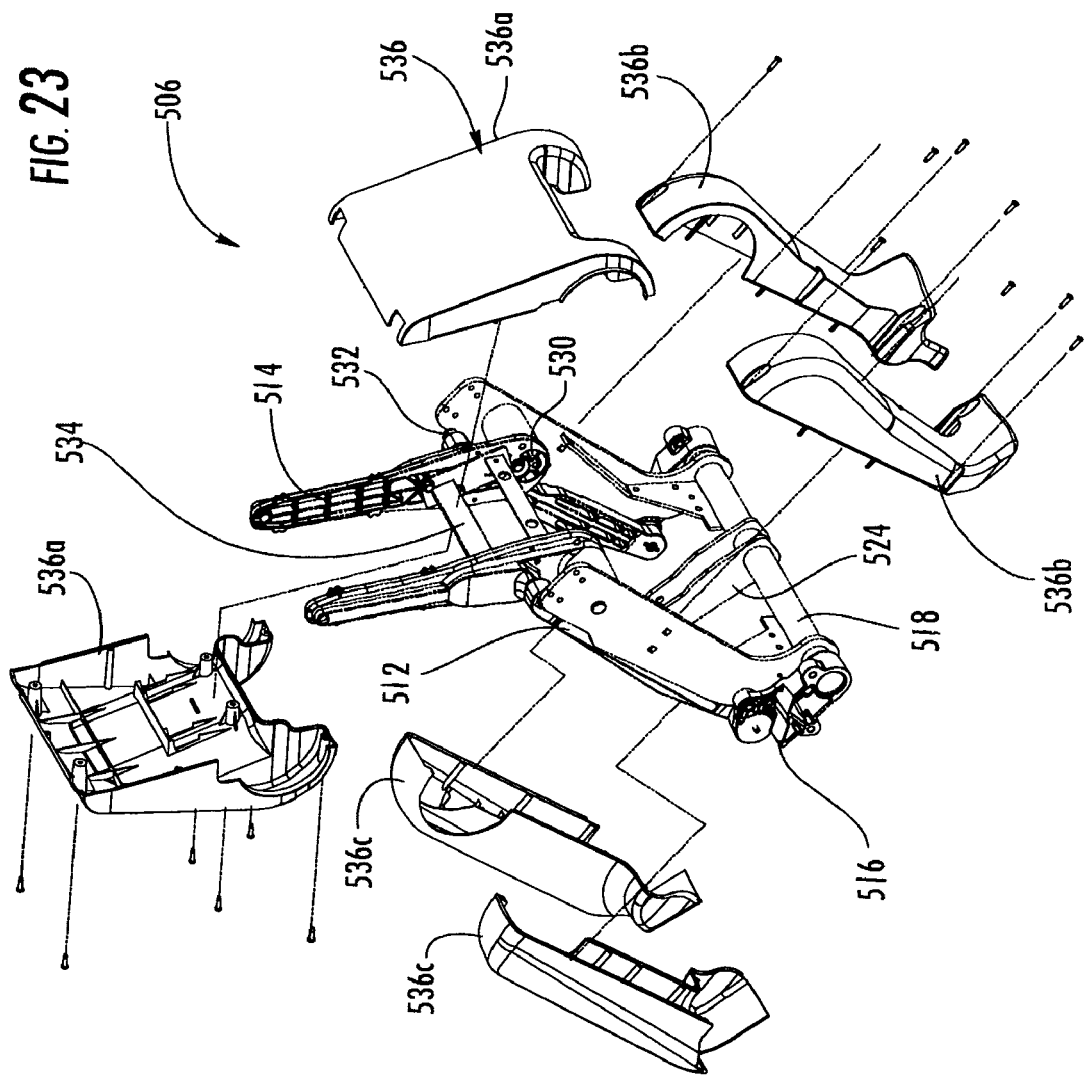

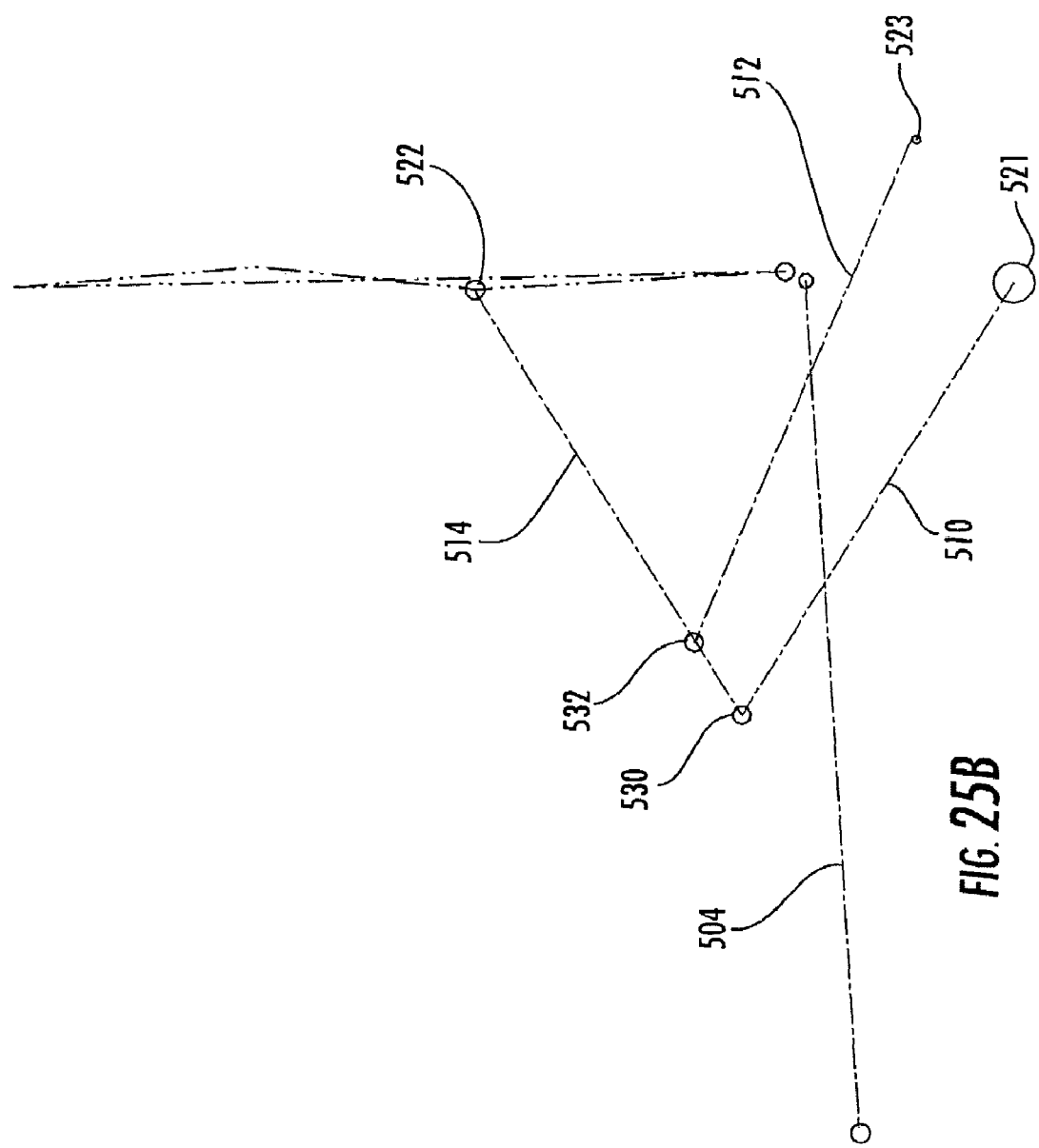

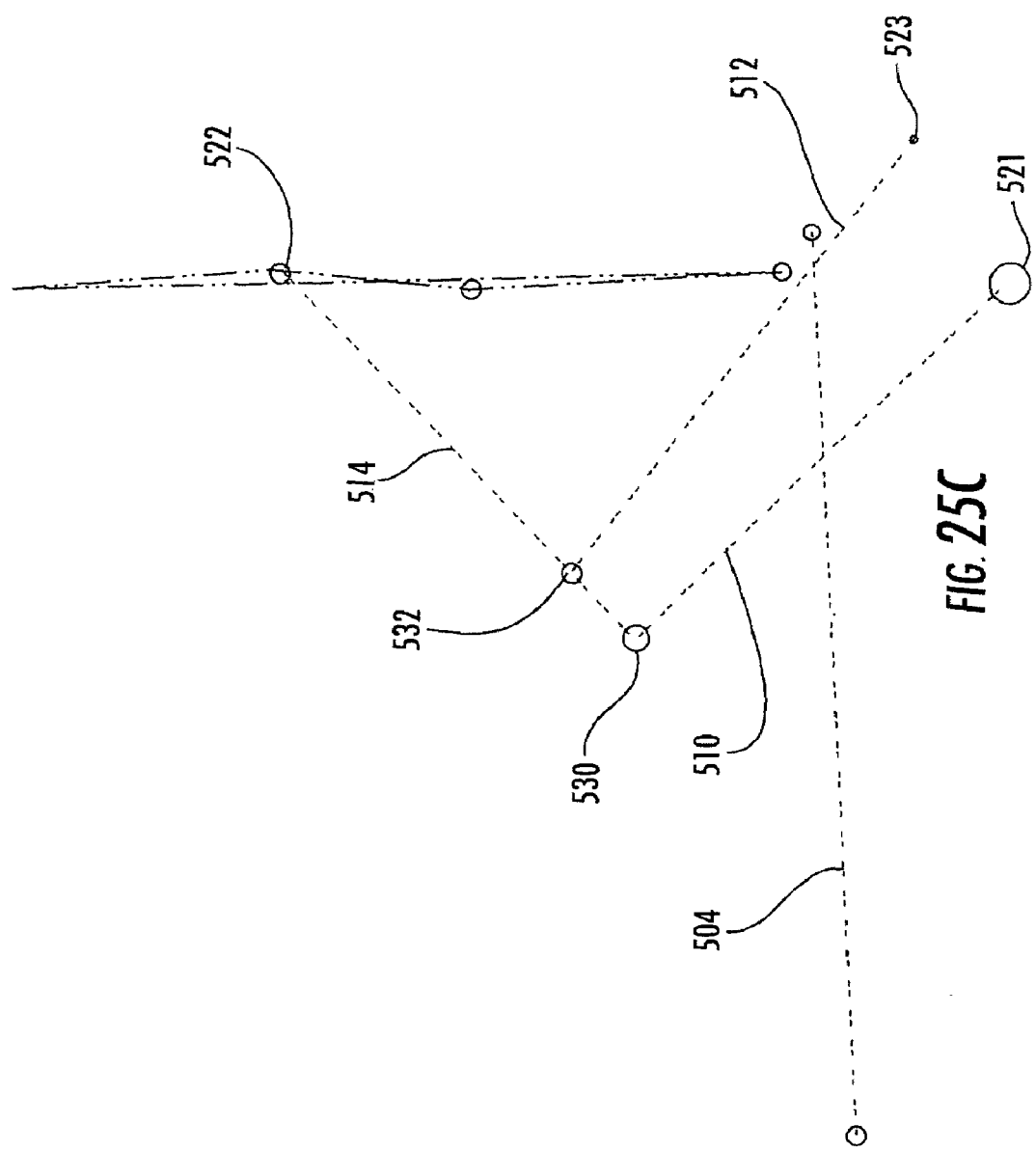

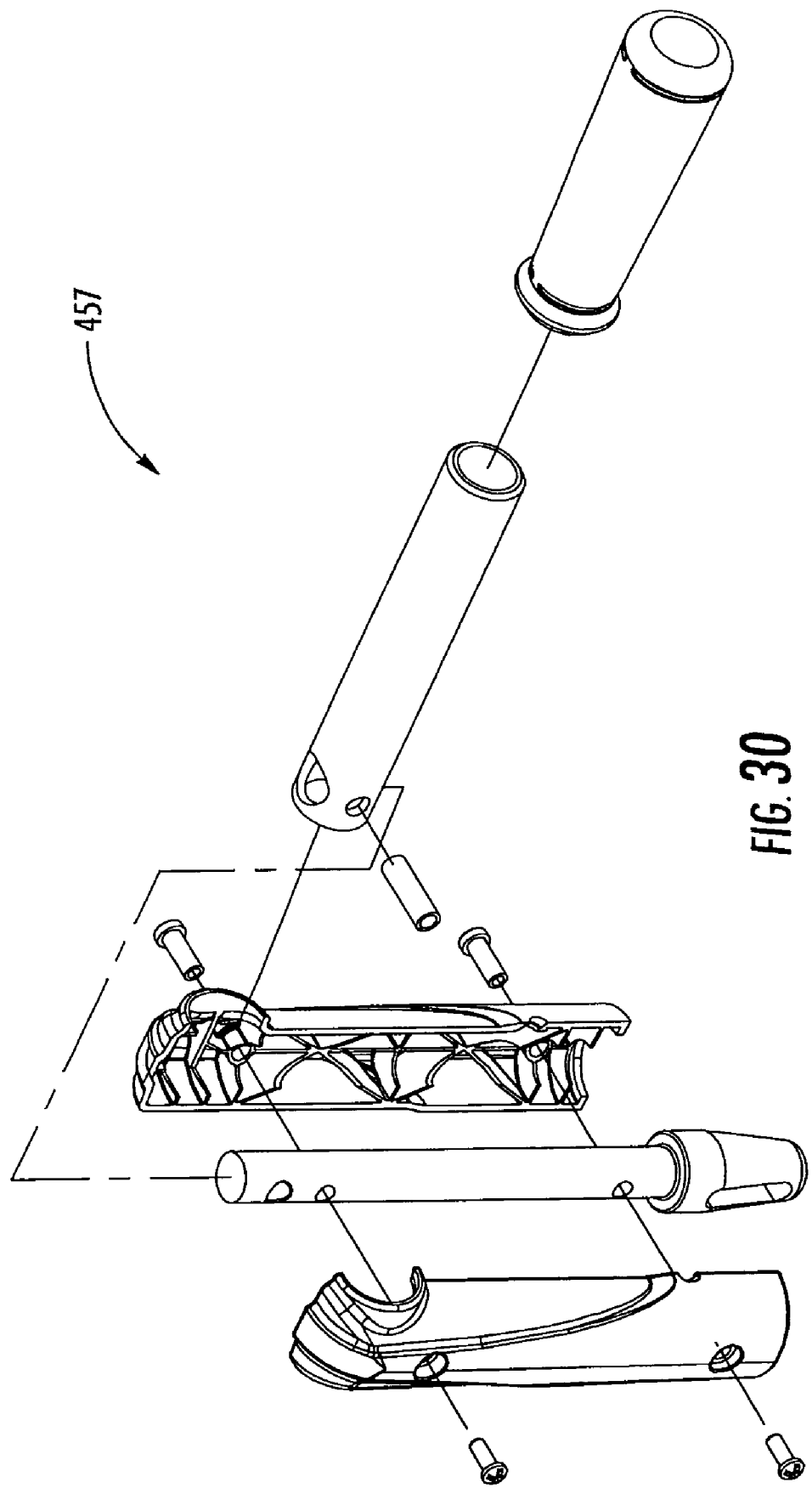

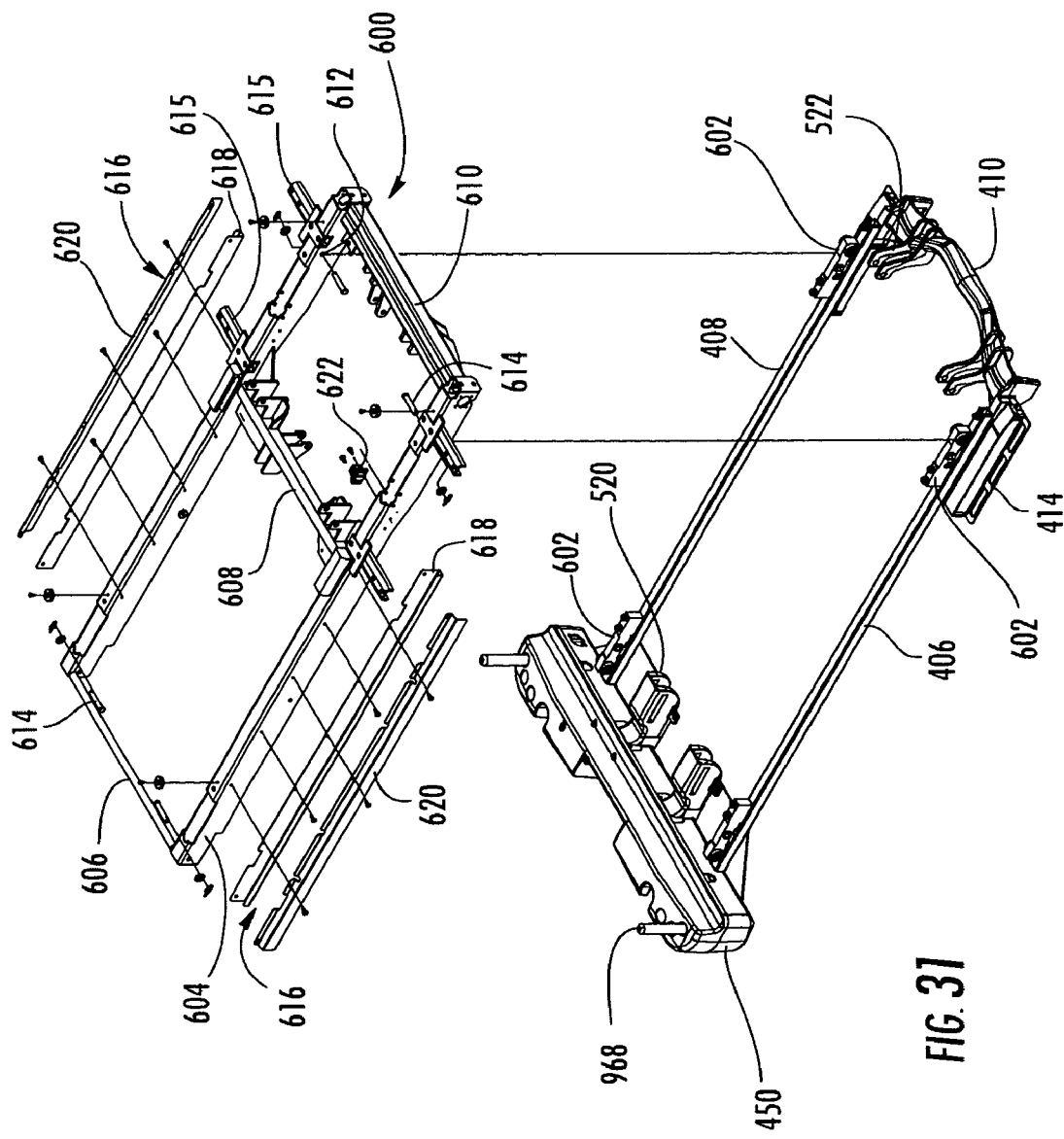

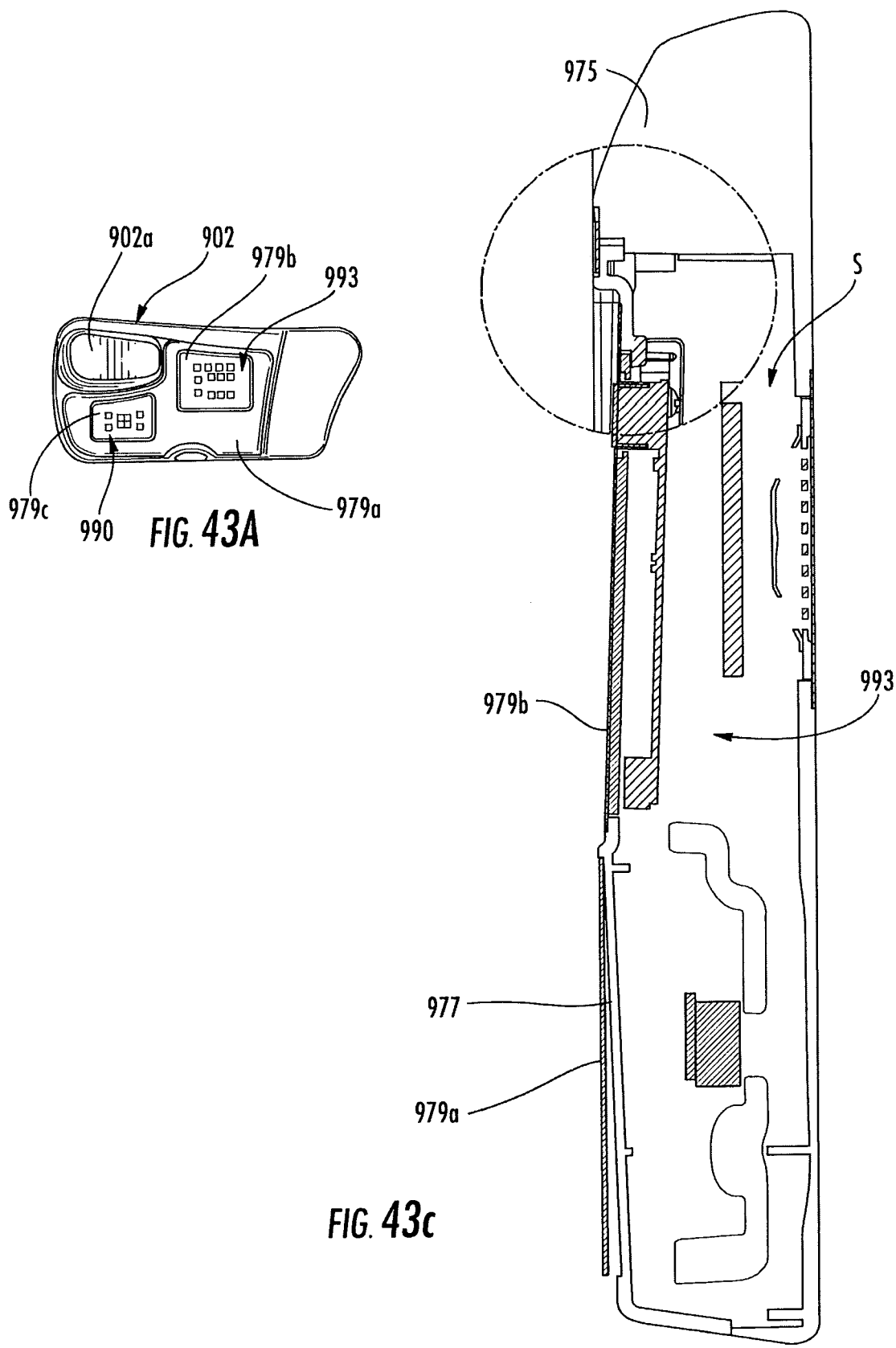

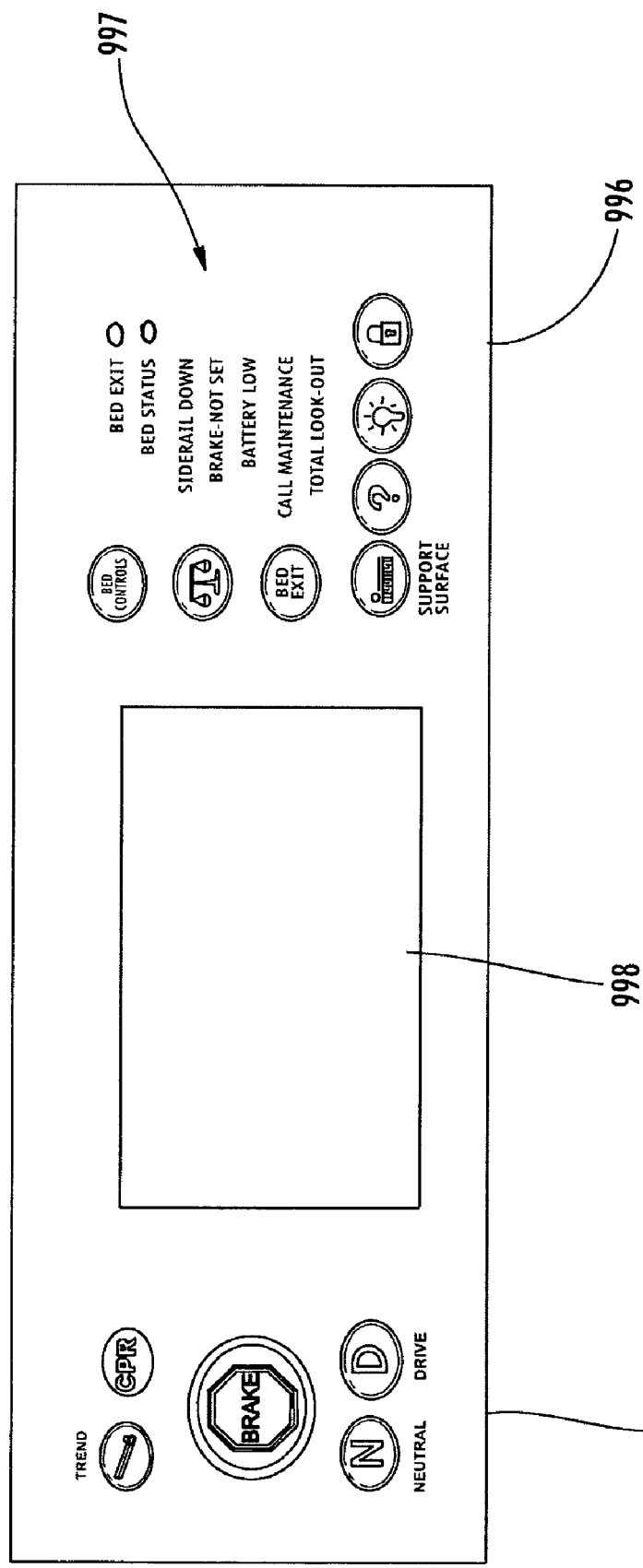

HOSPITAL BED

CROSS-REFERENCE TO RELATED APPLICATIONS

This application claims priority from U.S. provisional application Ser. No. 60/874,287, filed Dec. 11, 2006, entitled HOSPITAL BED, by Applicant Guy Lemire, and U.S. provisional application Ser. No. 60/751,770, filed Dec. 19, 2005, entitled HOSPITAL BED, by Applicant Guy Lemire, which are incorporated by reference herein in their entireties.

FIELD OF THE INVENTION

The present invention relates in general to the field of patient support apparatuses such as hospital beds. In particular, the invention relates to critical care patient support apparatuses with improved safety features, expanded configurability and accessible control and electronics for users.

BACKGROUND OF THE INVENTION

Hospital beds comprise complex mechanical and electronic components for movement, functionality and convenience.

Foot brakes of prior art hospital beds are typically located on the side under the bed. There are certain disadvantages associated with such foot brakes. For example, during activation, a user such as a nurse has to hold on to the bed, balance on one foot and stretch the other foot under the bed to engage or disengage the brake. As such, if the side rail is in the lower position, visibility is reduced. In addition, if the patient is exiting the bed, the bed may move which is unsafe. Furthermore, the weight of present day beds and patients are relatively large, requiring sufficient braking force to hold a bed in a desired location in a hospital.

There is a need for a braking system which is convenient and safe to use. Such a system can be powered in any manner. There is a further need for a braking mechanism that can be manually overridden such as if there is a power failure.

Generally, a bed is moved by a series of internal motors and controlled by means of an interface that can be used by users such as hospital personnel or the patient to adjust the bed to suit the comfort and needs of the patient. For safety reasons, the movement of the bed is quite slow and there is a need for an override control, to quickly and efficiently bring the bed into a relatively flat position in case of emergency or for routine tasks such as cleaning, patient transfer or surgery. In past designs, this override function has been initiated through hand controls, foot controls, or a combination of hand and foot controls.

In an emergency situation, it is desirable to reposition a bed quickly and easily into a CPR or Trendelenburg position, to facilitate administration of CPR or other resuscitation efforts. The manual- or motor-driven mechanism utilized to raise and lower the Fowler section typically moves too slowly to be acceptable in an emergency situation. Accordingly, emergency releases have been developed to quickly disengage the Fowler section from the drive mechanism to allow for rapid movement, however, these arrangements can be complex, bulky, expensive and difficult to engage and disengage.

Movement of the foot-end of a hospital bed to various positions that are not aligned with the remainder of the bed, such as a chair position, is difficult when it forms part of the main bed frame For a patient support apparatus in which movement of the Fowler section is effected by a motor-driven mechanism, it would be advantageous to be able to increase the speed at which the Fowler section could be lowered for CPR and Trendelenburg, beyond that speed which is currently obtainable with the motor-driven mechanism powered by a conventional electrical power source.

Early designs of adjustable beds often employed the concept of a hand crank and gearing to adjust the height of a bed. Such manual systems suffer from the need for considerable physical effort to adjust the bed height. Other designs include elevation systems incorporating mechanical jacks using hydraulic piston cylinders or screw drives to adjust the height of the hospital bed. Such hydraulic systems are known to be relatively expensive and prone to leakage. Additionally, prior mechanical systems suffer from excessive complexity, excessive size, a lack of load capacity, and manufacturing difficulties.

Hospital bed side rails of the prior art comprise support arms which form undesirable pinch points for users. The movement of such side rails from the deployed to the stowed positions is often hampered by side rail oscillations. The side rail falls due to gravity and the movement can jar the bed and disturb patients.

In addition, the patient support apparatus of the prior art relies on batteries to provide all power to the bed's electronic systems. When the battery power runs out, the battery itself must be recharged before power can be supplied to the electronics. This is problematic in circumstances where the life of the battery itself has run out or in settings where a suitable power supply to recharge the battery is not available.

In existing apparatuses, the control interface is located on the side or foot-end of a bed. Often, the operator directs movement of the bed from the head-end by pushing on the head-end or push handles located at the head-end. In the event the position of the patient needs to be adjusted while a prior art hospital bed is in motion, the operator has to stop the bed and move around the bed in order to access the bed control interface. If the bed is in a confined space, such as a narrow corridor or elevator, this action may be difficult to execute and result in an undesirable delay in effecting the change in position of the patient.

Currently, the angular position of the patient can be determined by measuring the patient's current position with respect to a plane of reference (e.g., the floor or the bed frame). This technique, however, suffers from the drawback that any misalignment in the frame of reference severely affects the integrity of the sensed angular position. Another method for inclinometry is by way of gravitational accelerometers. When the accelerometer is in a stationary position, the only force acting on it is the vertical gravitational force having a constant acceleration. Accordingly, the angular position of the patient can be calculated by measuring the deviation in the inclination angle between the inclination axis and the vertical gravitational force. Although the accelerometers can provide an effective way to measure the inclination in the patient's position, the resolution of the gravitational accelerometers is restricted to a limited range of inclination angles.

Currently, nurses and other hospital staff hang pumps (or other hospital equipment) on the top edge of the footboards of hospital beds. Since footboards were not designed to support the hanging of pumps (or other hospital equipment), this current practice reduces access to the controls on footboards, damages foot controls and footboards, generates bed motions and causes damage to pumps (and other equipment) that fall from its hangers.

Ordinarily, there is a tendency for detached headboards or footboards placed in an upright position against an object or structure to slip, thereby causing the headboard or footboard to fall and potentially suffer damage. This is a particularly acute concern in the situation of a medical emergency during which headboards and footboards may need to be removed and set aside in haste. In a busy hospital, a discarded headboard or footboard that has fallen to the floor creates a tripping hazard to both staff, who may be carrying equipment or medication and thus have an obstructed view of the floor, and patients, who may have compromised mobility owing to illness. Preventing slippage, therefore, reduces the likelihood of personal injury stemming from hastily removed headboards and footboards.

Existing motorized hospital beds utilize a single speed or multiple defined and preprogrammed speeds for bed movement resulting in the user having to manually switch speeds. Variable speeds in these beds are not automatic Therefore, there is a need to provide a patient support apparatus such as a hospital bed which overcomes the problems of the prior art.

SUMMARY OF THE INVENTION

An object of the present invention is to provide a hospital bed. In one form of the invention, a patient bed includes a patient support, a base, and an electrical control system. The patient support is mounted relative to the base, which has a plurality of bearing members for moving the base and the patient support across a surface. Each of the bearing members includes a brake operatively associated therewith. The electrical control system includes a user actuatable device and is configured to actuate one or more of the brakes upon actuation of the user actuatable device.

In one aspect, the user actuatable device comprises a button or a touch screen.

In another aspect, the patient support comprises a support frame system with the user actuatable device located on the support frame system.

In further aspect, the electrical control system includes an actuator for actuating at least one of the brakes. Additionally, a manual override mechanism may be provided for decoupling the actuator from the brake. For example, the manual override mechanism may include a manual override pedal or handle.

In other aspects, the control system includes a plurality of actuators, which are operatively associated with the brakes for selectively actuating the brakes. For example, the bearing members include forward bearing members and rearward bearing members, with one of the actuators being operatively associated with the forward bearing members and another of the actuators being operatively associated with the rearward bearing members.

In another form of the invention, a patient bed includes a patient support and a base, with the patient support movably mounted relative to the base. The bed further comprises a headboard, a footboard, and a plurality of side rails. One or more surfaces of the side rails or the headboard or the footboard includes a gap and a sealing cover for sealing the gap to facilitate cleaning and disinfection of the patient bed.

In one aspect, the sealing cover comprises a removable cover, such as a removable membrane. In another aspect, the removable membrane includes an adhesive surface for applying and releasably securing the removable membrane to the surface.

In yet another aspect, the surface includes a recessed portion, with the recessed portion including the gap, and with the cover located in the recessed portion. For example, the cover may be flush with the surface surrounding the recess when the cover is mounted in the recess over the gap.

In other aspects, the surface includes an opening, with the patient bed further comprising an electronic user interface located in the opening and the cover sealing a gap between the user interface and the surface.

According to yet another aspect, the side rail includes the surface. For example, the surface of the side rail may include a plurality of openings and a control interface associated with each of the openings. The cover or covers seal the gaps between the control interfaces and the surface. Further, each of the control interfaces may include one or more user actuatable devices operatively associated therewith.

According to another form of the invention, a patient bed includes a base, a support frame system supported by the base, and a control system. The support frame system includes a deck frame, with a pivotal head-end section. The control system includes an actuator to pivot the head-end section and is adapted to control the speed of the actuator and, further, to selectively increase the speed of the actuator to pivot the head-end section at a greater speed.

In one aspect, the deck support further includes a pivotal seat section and a pivotal foot section, with the control system further including an actuator to selectively pivot the seat section and an actuator to selectively pivot the foot section. The control system is adapted to control the speed of the actuators and, further, to selectively increase the speed of at least one of the actuators to pivot the head section, the seat section, or the foot section at a greater speed.

In one aspect, the control system includes a user actuatable device, with the control system selectively increasing the speed of the actuator when the user actuatable device is actuated. For example, the user actuatable device may comprise a button, a touch pad, a touch screen, a handle or pedal. When the user actuatable device comprises a touch screen, the touch screen may include an icon associated with the actuator, wherein when the icon on the touch screen is touched the speed of the actuator is varied.

In another aspect, control system increases the voltage to the actuator to thereby increase the speed of the actuator. Further, the control system may be adapted to couple to a remote power supply, which has a voltage, with the control system converting the voltage supplied by the remote power supply to deliver a first voltage to the actuator. Further, the control system converts the voltage of the remote power supply to a second voltage to deliver a second voltage to the actuator wherein the second voltage is greater than the first voltage to increase the speed of the actuator and thereby increase the speed of the movement of the head-end section.

In another aspect, the bed includes a battery. The control system is adapted to couple to a remote power supply and is adapted to convert the voltage of the remote power supply into a first voltage and to deliver the first voltage to the actuator. Further, the control system uses the voltage of the battery to increase the first voltage to the actuator. For example, the control system delivers about 12 volts to the actuator and selectively increases the voltage to the actuator from about 12 volts to about 24 volts to thereby increase the speed of the head-end section.

In a further aspect, the control system increases the voltage until the head-end section is moved to a substantially horizontal position. For example, the control system further comprises a sensor, which detects when the head-end section is moved to a substantially horizontal position.

In another form of the invention, a patient bed includes a base, a support frame system for supporting a lying surface on the base, and an elevation mechanism for raising or lowering the support frame system relative to the base. The bed further comprises a control system, which includes one or more actuators for activating the elevation mechanism to raise or lower the support frame system relative to the base. The control system is powered by (1) a remote power supply or (2) at least one battery. When powered by the remote power supply the control system operates the actuator independent of the battery. When powered by the battery, the control system operates the actuator in dependent of the remote power supply.

In a further aspect, when there is a loss of power in the remote power supply, the control system is powered by the battery.

In a further aspect, the control system recharges the battery with the remote power supply.

In another form of the invention, a patient bed includes a base, a support frame system for supporting a lying surface relative to the base, and an elevation mechanism. The elevation mechanism includes a first pair of arms and a second pair of arms, which are mounted relative to the support frame system and the base. Each of the arms has an upper arm portion and a lower arm portion. The upper arm portions are pivotally mounted to the respective lower arm portions and to the frame system. The lower arm portions are pivotally mounted to the base. The upper arm portions are biased upwardly relative to the lower arm portions by a spring force. The elevation mechanism further includes a linear actuator cooperating with each pair of the arms, which is selectively actuated to pivot the lower arm portions relative to the base. In addition, the lower arm portions are linked to the upper arm portions by linkages, which are configured to pivot the upper arm portions relative to the lower arm portions when the lower arm portions pivot about the base wherein the lower arm portions pivot the upper arm portions when the lower arm portions are pivoted by the actuator to thereby raise or lower the support frame system relative to the base.

In one aspect, the support frame system is located between two vertical generally parallel planes when the support frame system is lowered to the base, and wherein the elevation mechanism moves the support frame system relative to the base and is configured to generally maintain the support frame system between the two vertical planes when moving the support frame system.

In another aspect, the base includes a longitudinal axis and the elevation mechanism is configured to raise or lower the support frame system relative to the base with a longitudinal deviation relative to the longitudinal axis of less than about 1 inch. In a further aspect, the deviation is less than about ¾ of an inch, and, more optimally, less than about ½ inch.

In yet another aspect, the upper arm portions of at least one pair of the arms are pivotally mounted relative to the support frame system at a pair of pivot joints, which move in a sinusoidal path when the support frame system is moved relative to the base by the elevation mechanism. For example, the sinusoidal path has a maximum amplitude of about 1 inch, or more optimally a maximum of ½ inch.

In a further aspect, each of the lower arm portions is connected to a respective upper arm portion by first and second linkage. Further, each of the first and second linkages includes a longitudinal extent, with the longitudinal extent of each first linkage being non-parallel with the longitudinal extent of its respective second linkage.

In yet other aspects, the lower arm portions are pivotally mounted to the base about a first pivot axis. The first and second linkages of each of the lower arm portions are pivotally mounted to the base about a second pivot axis spaced from the first pivot axis. The opposed ends of each of the first and second linkages are being pivotally mounted to the upper arm portion offset from the pivot axes of the upper arm portions relative to the lower arm portions.

According to yet another aspect, each of the arms includes a spring, such as a torsion spring, for applying the biasing force to the upper arm portions of the respective arm.

In another form of the invention, a patient bed includes a base, a patient support mounted for movement relative to the base, an elevation mechanism for raising or lowering the patient support relative to the base, and wherein the elevation mechanism is configured to move the patient support relative to the base in a manner to generally maintain the patient support between two vertical parallel planes when moving the patient support relative to the base.

In one aspect, the elevation mechanism is configured to raise or lower the patient support relative to the base with a maximum longitudinal deviation of less than about 1 inch and, more optimally, of less about ½ inch.

In another form of the invention, a patient bed includes a base, a support frame system for supporting a lying surface relative to the base, and an angle sensor mounted to a component of the base or the support frame system. The angle sensor measures an angle of the component based on gravity wherein the angle sensor may detect the angular orientation of the component independent of any frame of reference.

In one aspect, the angle sensor comprises a gravitational accelerometer.

In another aspect, the support frame system includes a deck frame, which includes a head-end section and a foot-end section, with the sensor located at the head-end section or the foot-end section.

In addition the patient bed may include a microcontroller that is in communication with the sensor.

In another form of the invention, a patient bed includes a base, a support frame system, and a visual indicator. The support frame system includes an intermediate frame and a deck frame supported by the intermediate frame. The deck frame includes a head-end section and a foot-end section, with the head-end section being pivotally mounted relative to the intermediate frame. The support frame system further includes a side rail with a body. The visual indicator is located on the body of the side rail adjacent the perimeter of the body so that the visual indicator provides a visual indication of the angular orientation of the head-end section of the deck frame when the head-end section is pivoted to an inclined position relative to the intermediate frame.

In one aspect, the visual indicator includes a plurality of spaced apart markings adjacent the perimeter of the body, with each of the markings being associated with an angle.

The visual indicator may be formed by a membrane applied to the body or may be molded in the body, for example.

In another form of the invention, an ICU patient bed includes a base and a support frame system supported relative to the base. The support frame system includes a deck frame, which includes a head-end section, a seat section, and a foot-end section, and further side rails, a footboard, and a headboard. A display comprising a touch screen is mounted to the headboard or the footboard or one of the side rails.

In one aspect, the touch screen includes a menu with a plurality of icons.

In another aspect, the bed further includes a control system with a graphical user interface for displaying icons on the touch screen. For example, the touch screen may display a function selected from a group consisting of apparatus motion, mattress air pressure, patient motion, patient biometrics, scale, bed security, alerts, exit and event log/history, help screens, diagnostics, run lights, or door/windows, and motion sensors.

In a further aspect, the touch screen displays a summary of the patient's status.

In yet another aspect, the touch screen is located in the footboard. For example, the touch screen may be mounted in a console, which is then mounted at the footboard. For example, the console may be pivotally mounted in the footboard.

In another form of the invention, a patient bed includes a base, a patient support mounted relative to the base, a bed communication network, and a control system. The control system includes a control module located at the bed, which is in communication with the bed communication network and is in communication with one or more devices at the bed through the bed network for monitoring or controlling the one or more devices.

For example, the sensor may comprise a sensor, with the control module monitoring the status of the bed through the sensor.

In one aspect, the device comprises a patient monitoring device, and the control module monitors the status of the patient through the patient monitoring device.

For example, the bed network may comprise a serial communication network, a CAN-based network, Echelon™-based network, or a peer-to-peer network. The bed network may comprise a wireless, based network, such as an RF communications network, a Bluetooth® communications network, an infra-red communications network or an ultrasound communications network.

In one aspect, the control module comprises a digital recognition system that positively identifies only pre-authorized individuals to operate the control module. For example, the digital recognition system may positively identify only pre-authorized individuals to operate the control module based on image or signal or field. For example, the signal may be generated by an RFID tag. The image may be based on a fingerprint, iris, or vein pattern.

The field may be generated by a magnetic device.

In a further aspect, wherein the control module is configured to communicate with a remote communication system.

In yet a further aspect, the control module may include a camera, which provides visual communication between a patient and a third party, such as a health care provider.

In another form of the invention, a patient bed includes a base, which includes a frame and a plurality of bearing members for moving the base across a surface, and a support frame system supported by the base. The support frame system includes an intermediate frame and a deck frame, with the deck frame including a pivotal head-end section, a seat section, and a pivotal foot-end section. The intermediate frame has a longitudinal extent shorter than the deck frame wherein the intermediate frame longitudinal extent terminates adjacent the foot-end section wherein the foot-end section is pivotal relative to the seat section independent of the movement of the seat section.

In one aspect, the bed further includes a control system, which includes a plurality of actuators for selectively pivoting the head-end section, the seat section or the foot-end section independent of the other sections.

In another form of the invention, a frame elevating mechanism includes a first frame configured to be supported on a floor surface, a second frame oriented above the first frame and configured to be moveably supported by the first frame, and first and second drive mechanisms capable of operating at variable speeds for selectively adjusting an elevation of the second frame. The first drive mechanism controls the elevation of a first end of the second frame. The second drive mechanism controls the elevation of a second end of the second frame. In addition, the first drive mechanism is configured to initially operate at a first maximum operating speed, and the second drive mechanism is configured to initially operate at a second maximum operating speed that is substantially equal to the first maximum operating speed. At least one angle sensor is located on the second frame for determining an angle of inclination of the second frame. A control unit for selectively controlling the elevation of the second frame is also provided wherein during a change in elevation of the second frame, the control unit repeatedly compares a starting angle of inclination of the second frame to a present angle of inclination of the second frame. If not substantially equal, the control unit adjusts the operating speed of one of the drive mechanisms to compensate.

In another form of the invention, a method of changing an elevation of a platform subject to an uneven distribution of load while maintaining an angle of inclination of the platform includes determining a starting angle of inclination of the platform by means of at least one angle sensor located on the platform, activating first and second drive mechanisms configured to change an elevation of first and second ends of the platform, respectively, with the first and second drive mechanisms configured to initially operate at substantially equivalent maximum speeds, and determining a present angle of inclination of the platform by means of the at least one angle sensor. The starting angle of inclination is compared to the present angle of inclination. If not equal, the speed of one of the drive mechanisms is adjusted to compensate. It is then determined whether the platform has obtained a desired elevation, which is repeated until the desired elevation is obtained. The drive mechanisms are then stopped upon obtaining the desired elevation.

In another form of the invention, a patient bed includes a base, a patient support, and an elevation mechanism for selectively raising or lower the patient support relative to the base. The patient support includes a support system frame and a side rail, which is movable between a raised position and a lowered position. The base has a plurality of bearing members for moving the base and the patient support across a surface, with each of the bearing members including a brake operatively associated therewith. The bed also includes a power supply and a control system for controlling the elevation mechanism. In addition, the bed includes a detection system, which is in communication with the control system and is adapted to sense the status of the elevation system, the power supply, the position of the side rail, the brakes of the bearing members, or the control system. The detection system is in communication with a display, which displays the status detected by the detection system.

In one aspect, the detection system includes at least one sensor sensing the status of the elevation system, the power supply, the position of the side rail, or the brakes of the bearing members.

In a further aspect, the detection system includes a data logger for logging the status, with the display displaying a scrolling text of the status data logged by the data logger.

In yet another aspect, the bed also includes a driver for selectively moving the base across a support surface and a handle mounted to the bed. The control system adjusts the speed of the driver as a function of an actuating input at the handle. For example, the actuating input may include a force applied on the handle, a signal from a switch at the handle, or a signal from a heat sensor at the handle.

BRIEF DESCRIPTION OF DRAWINGS

The detailed description particularly refers to the accompanying figures in which:

FIGS. 12A to 12C are right perspective views of an indicator system for the braking system of FIG. 1, shown in steer, neutral and brake indication respectively;

FIGS. 14A to 14C are right perspective views of the braking system of FIG. 13A in override mode, wherein the central levering mechanism is in a steer position and wherein an override pedal is in a brake, neutral and steer position respectively;

FIGS. 15A to 15C are right perspective views of the braking system of FIG. 13B in override mode, wherein the central levering mechanism is in a neutral position and wherein an override pedal is in a brake, neutral and steer position respectively;

FIGS. 16A to 16C are right perspective views of the braking system of FIG. 13C in override mode, wherein the central levering mechanism is in a brake position and wherein an override pedal is in a brake, neutral and steer position respectively;

FIG. 23 is an exploded perspective view of the head-end elevation arms of FIG. 22A, showing assembly of mounting covers thereto;

FIGS. 25A to 25D are side views of the elevation mechanism geometry of FIGS. 24A and 24B shown at respective positions;

FIG. 30 is an exploded view of an operating handle of the head-end operating console as shown in FIGS. 27 and 28;

FIG. 31 is an exploded right perspective view of a load bearing frame as it is mounted to the load cells of the intermediate frame of FIG. 26;

FIG. 43A is an elevation view of a side rail of the present invention incorporating covers for sealing the joints or gaps between the interface panels and the side rail body;

FIG. 43C is an enlarged cross-section taken along line XXXXIIIC-XXXXIIIC of FIG. 43A;

FIG. 58 is a diagrammatic view of a control interface provided by the footboard control console of FIG. 54;

FIG. 27 illustrates a part of a user interface embedded into a patient support according to an embodiment of the present invention;

DETAILED DESCRIPTION OF THE INVENTION

Figure 1:
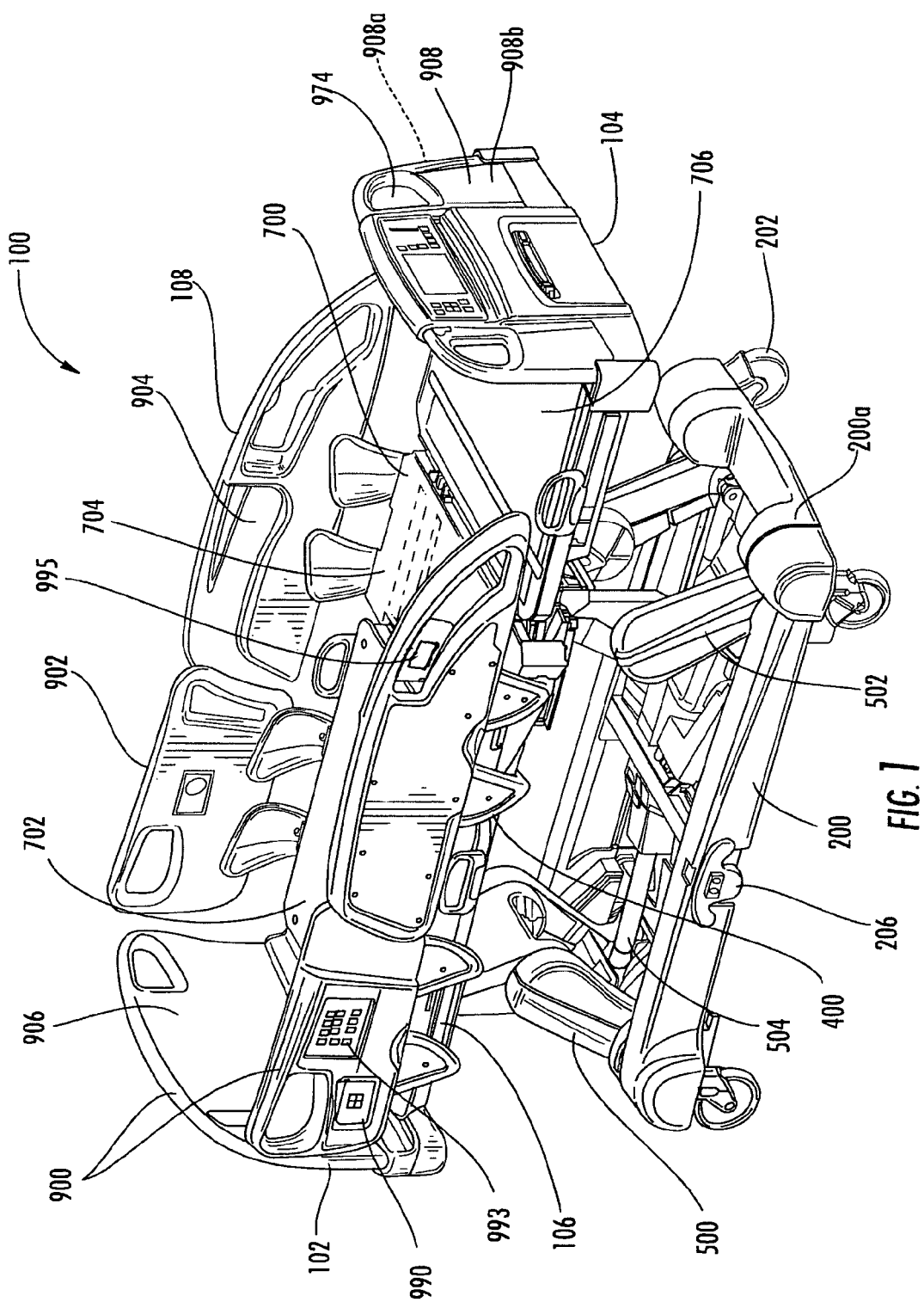
FIG. 1 is a right perspective view of a patient support apparatus in accordance with an embodiment of the present invention.

The bed of the present invention comprises structural elements (Section I), power and control systems (Section II); structural informatics systems (Section III); user-bed communication interfaces (Section IV); and bed-network communications systems (Section V).

Unless defined otherwise, all technical and scientific terms used herein have the same meaning as commonly understood by one of ordinary skill in the art to which this invention pertains.

I. Structural Elements

A hospital bed, generally referred to using the numeral 100 and in accordance with an embodiment of the present invention, is generally shown in FIGS. 1 to 8. For the purpose of this description, the bed 100 may be defined to include a head-end 102 and an opposing foot-end 104, respectively defining the ends of the bed 100 at which a user's head and feet may be positioned, and right and left sides 106 and 108 joining these ends.

The bed 100 generally includes a frame system that forms a patient support and a base. In the illustrated embodiment, the base comprises a base frame 200 (e.g. see FIGS. 9 to 16); though it should be understood that other bases may be used, including any structure that supports the patient support, including a plurality of legs that extend downwardly from the patient support. The patient support comprises a support frame system that includes an intermediate frame 400 (e.g. see FIG. 26) operatively coupled to the base via an elevation system 500 configured to raise and lower the support frame system relative to the base (e.g. see FIGS. 17 to 25) and thereby orient the intermediate frame 400 in various positions. As noted below, base frame 200 forms a movable base for the support frame system.

In general, the base frame 200 comprises a transport system including a set of bearing members, such as wheels, casters 202 or the like, allowing for motion and maneuverability of the bed 100. An optional drive wheel system 204 (e.g. see FIG. 10) may also be provided to facilitate movement of the bed 100 by an operator. A braking system 206, optionally comprising an emergency override system 208 (e.g. see FIGS. 11 to 16), may also be provided. A head-end control module 450 (e.g. see FIGS. 27 to 29), as well as various other control modules, panels and/or consoles described further below, is generally provided on the intermediate frame 400 and provides various controls, such as push handles 451 (detailed in FIG. 30) for the above and other such systems, described below.

The support frame system also comprises a load bearing frame 600, disposed atop the intermediate frame 400 via intermediary load cells 602 or the like (e.g. see FIG. 31), which are configured to sense and/or monitor a load positioned on the bed 100. In particular, a deck support 700 fitted to the load-bearing frame 600 (e.g. see FIGS. 32 to 39) may be provided upon which may be mounted a lying surface 800, such as a mattress or the like, for receiving a user of the bed 100 thereon. As such, as will be discussed further below, as the weight of a user is applied to the lying surface 800, or again shifted thereon, the load cells 602 may detect this weight.

As illustrated in FIGS. 1 to 6 and 32, for example, the deck support 700 generally comprises a head or Fowler section 702, toward the head-end 102 of the bed 100, which is pivotally coupled to a seat/thigh or Knee Gatch section 704, itself pivotally coupled to a foot section 706, toward the foot-end 104 of the bed 100. Each of the head, seat/thigh and foot sections 702, 704, and 706 are configured to articulate the deck support 700 between a plurality of positions, such as for example, a substantially horizontal position (FIGS. 1 to 3 and 32), a legs-down position (FIG. 4), a substantially seated position (FIGS. 5 and 6), etc. The lying surface 800, fitted on the deck support 700, is adapted to move therewith thereby also comprising a head or Fowler section 802, a seat/thigh or Knee Gatch section 804, and a foot section 806 that may be oriented with the deck support's various sections, as seen for example in FIGS. 7 and 8. The lying surface may comprise any one of a variety of mattresses, including for example, Gaymar, or foam or air mattress. The deck support 700 and lying surface 800 will be described in greater detail below.

Figure 40A:
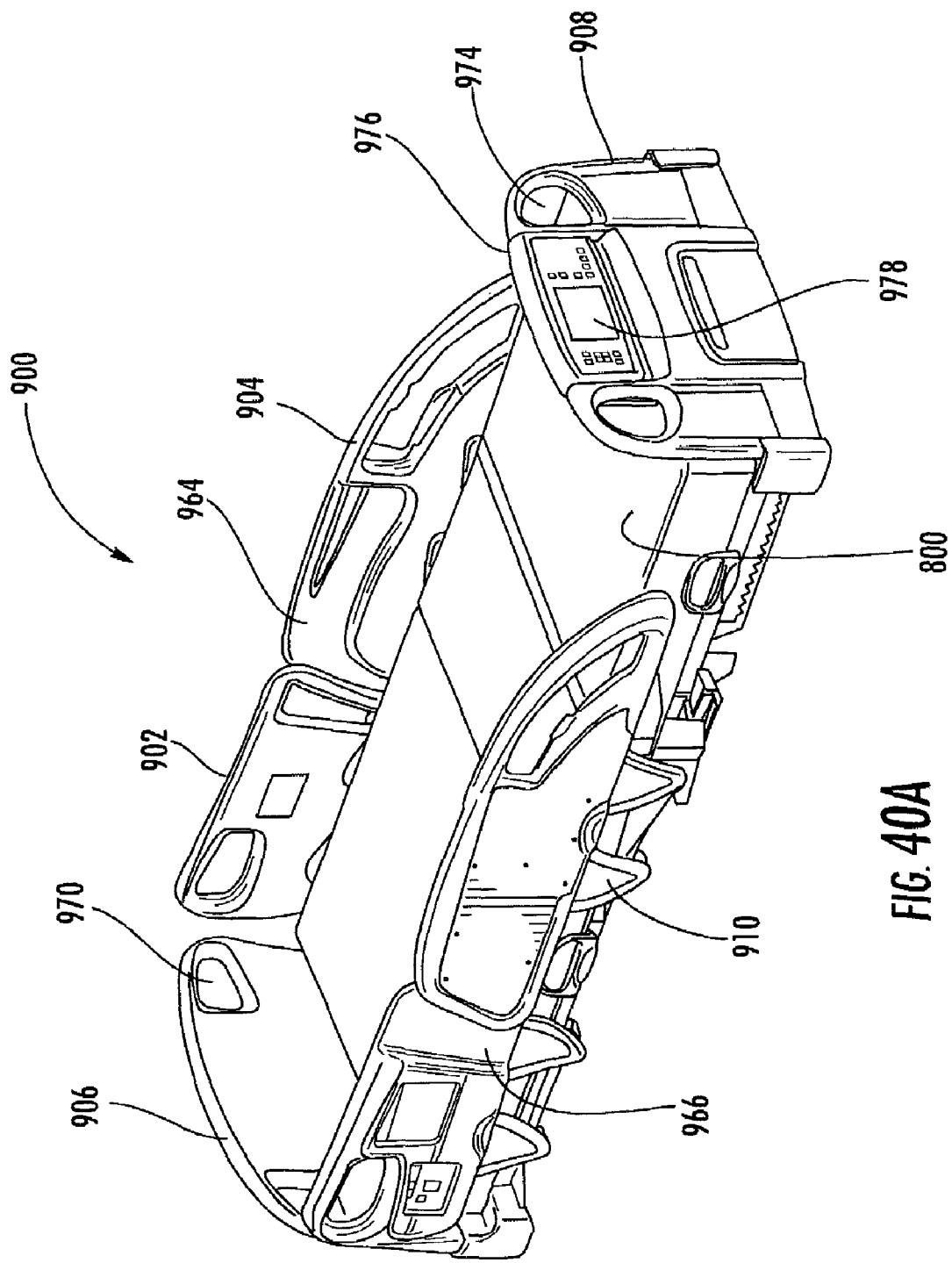
FIGS. 40A and 40B are right perspective views of a barrier system of the patient support apparatus of FIG. 1 in fully extended and fully retracted positions respectively, the barrier system comprising a headboard, a footboard, and retractable head-end and foot-end side rails.
Figure 40B:
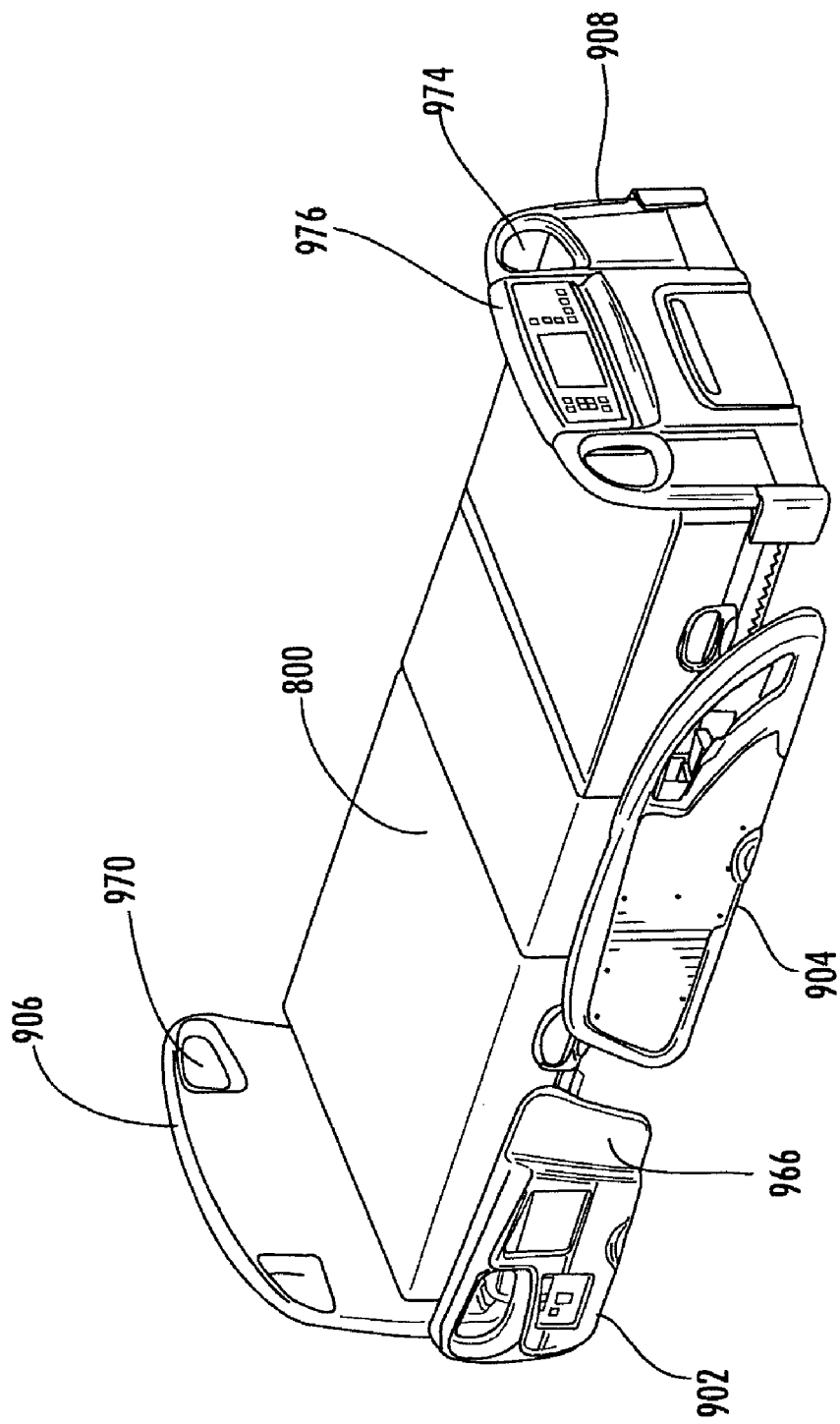

The bed 100 may further comprise a barrier system 900, which may include any combination of head-end side rails 902, foot-end side rails 904, a headboard 906 and a footboard 908. The various side rails 902, 904 may be adjustably coupled to the frame system and moveable relative thereto between fully extended and fully retracted positions. For example, in FIGS. 1 to 5 and 40A, both the head-end side rails 902 and foot-end side rails 904 are shown in their fully extended positions, whereas in FIGS. 6 and 7, the left head-end side rail 902 and the right foot-end side rail 904 are shown in their retracted positions. In FIGS. 8 and 40B, all side rails 902, 904 are shown in their fully retracted positions. The barrier system 900 will be described in greater detail below.

The bed 100 may also comprise a control system 1000 (FIG. 8A), comprising one or more control interfaces (e.g. head-end panel 453, footboard console 976, side rail panels 990, 993, 995, remote panels, etc.) and/or devices (e.g. push handles 452 for controlling power to the drive wheel mechanism 204, etc.) disposed on or near the bed 100, providing a user and/or patient control access to the bed's 100 various features and/or commands, which may include various functions of patient support. The control system 1000, and other patient support functions requiring power, are powered by an AC plug connection to a remote power supply, such as a building outlet, or a battery supported by the frame system, as will be discussed in greater detail below. In one embodiment, the control system 1000 may be configured to operate and monitor a plurality of linear actuators provided to move, for example, the intermediate frame 400 relative to the base frame 200 (e.g. to control the elevation system 500), to move the head, seat and foot sections 702, 704 and 706 of the deck support 700 to provide various lying surface positions. Operation of the bed's braking system 206 and/or optional drive wheel system 204, and/or other such systems, may also be considered herein, as will be readily understood by the person skilled, without departing from the general scope and nature of the present disclosure.

Furthermore, a structural informatics system, which may comprise a diagnostic and control system component, may also be provided, wherein the bed 100 comprises a plurality of electronic elements including for example, load sensors, tilt or angular sensors (e.g. inclinometers, etc.), linear sensors, temperature sensors, electronic controls and keyboards, wiring actuators for adjusting bed angles and the like, in addition to other electronic elements. For example, with reference to the illustrative embodiments depicted in the appended Figures, load sensors may include, but are not limited to, load frame load cells 602 (e.g. see FIG. 26) for detecting and/or monitoring a load distribution and variation on the deck support 700, a drive handle load cell 462 (e.g. see FIG. 27) for communicating a pressure applied to the drive handles 451 in view of controllably operating the optional drive mechanism 204 (e.g. see FIG. 10). Furthermore, tilt or angular sensors may include, but are note limited to, a base frame sensor 203

Figure 42:
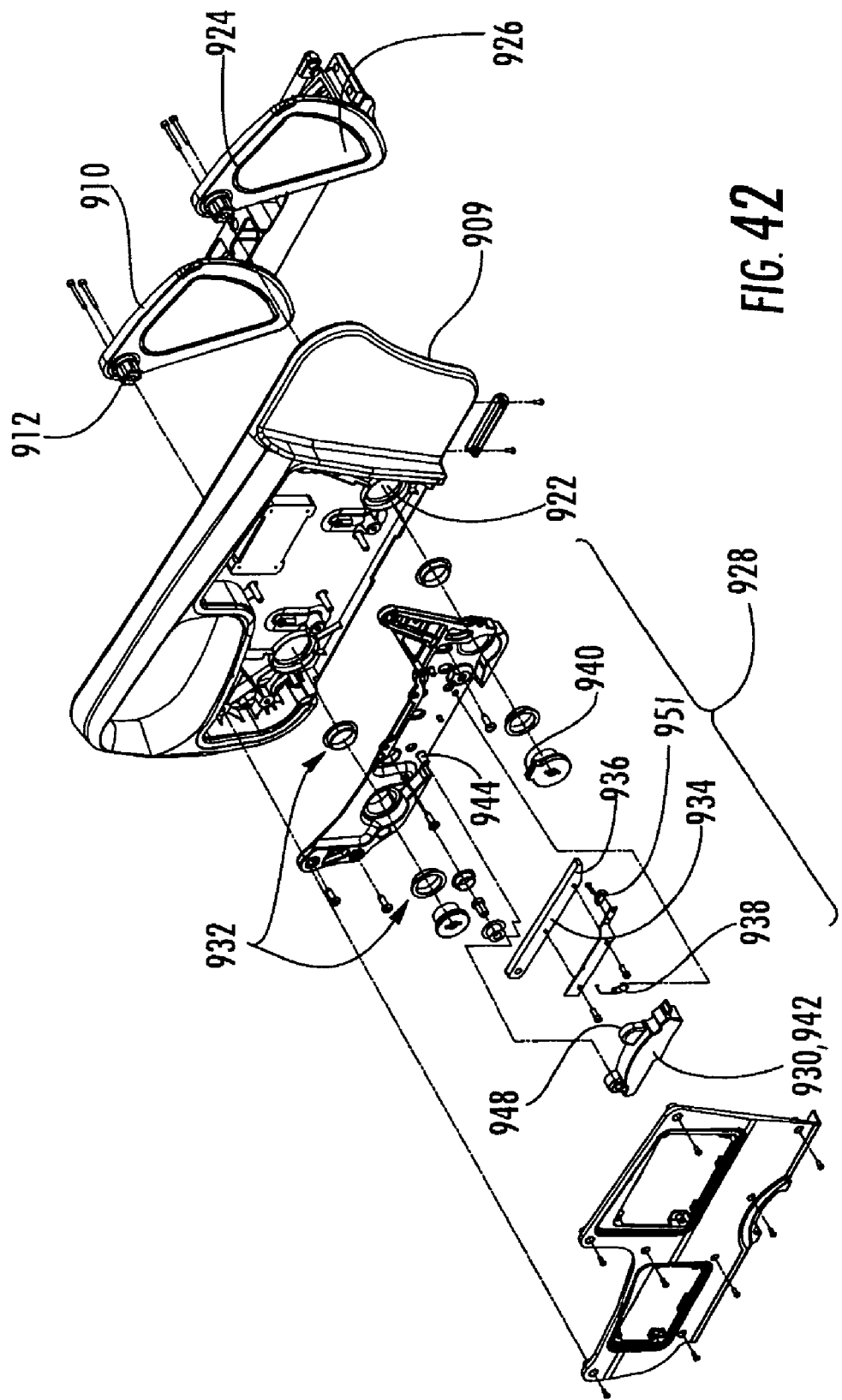
FIGS. 42 and 43 are respective exploded views of an internal assembly of the head-end side rail of FIG. 41 and an internal assembly of head-end side rail control panels thereof.
Figure 43:
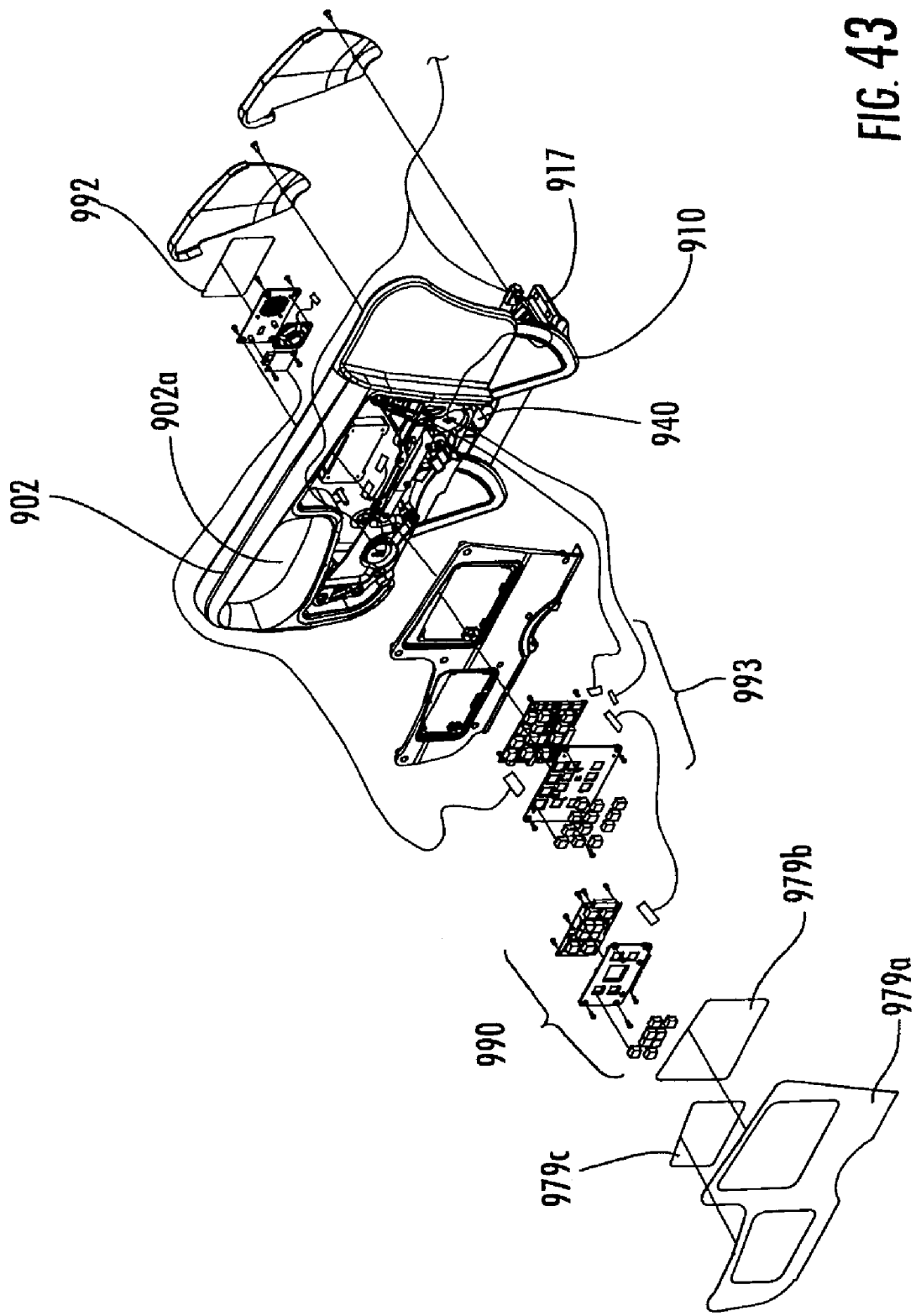
Figure 43B:
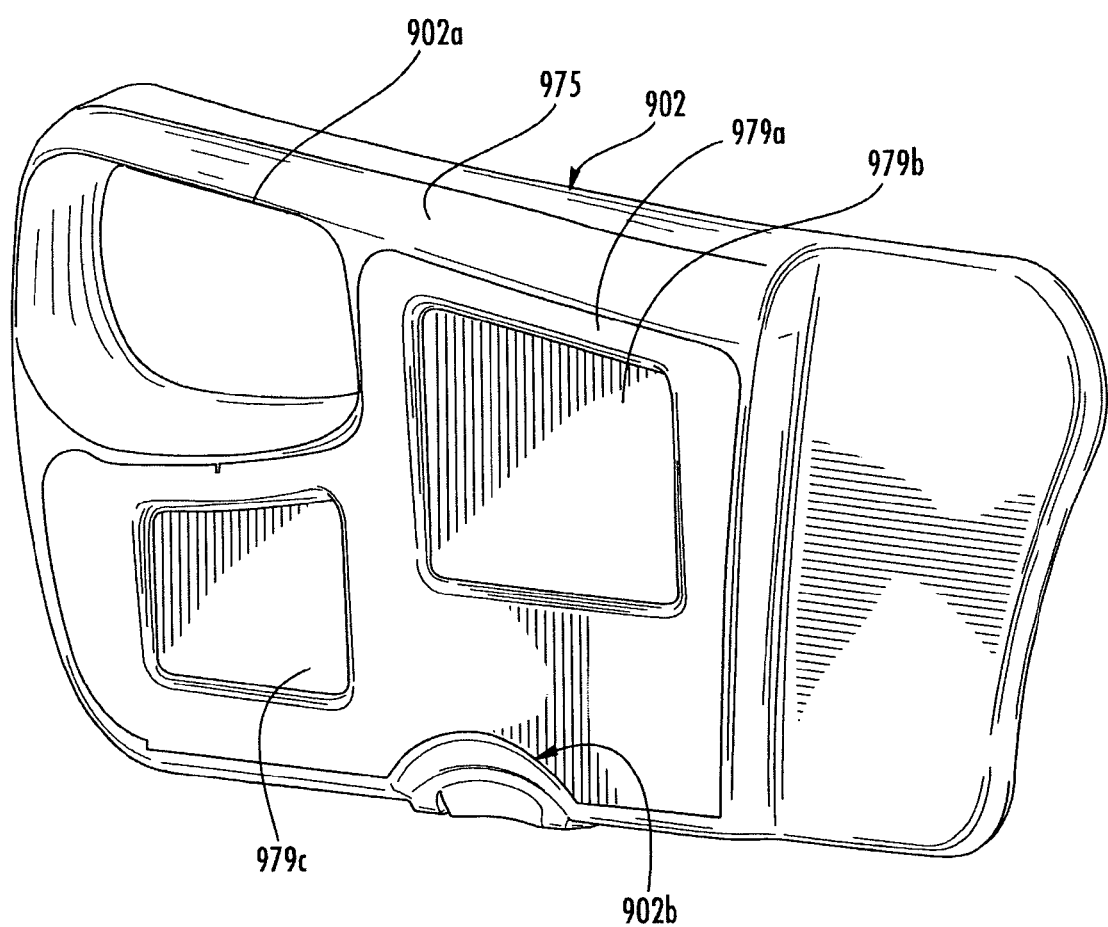
FIG. 43B is an enlarged perspective view of the side rail of FIG. 43A.
Figure 43D:
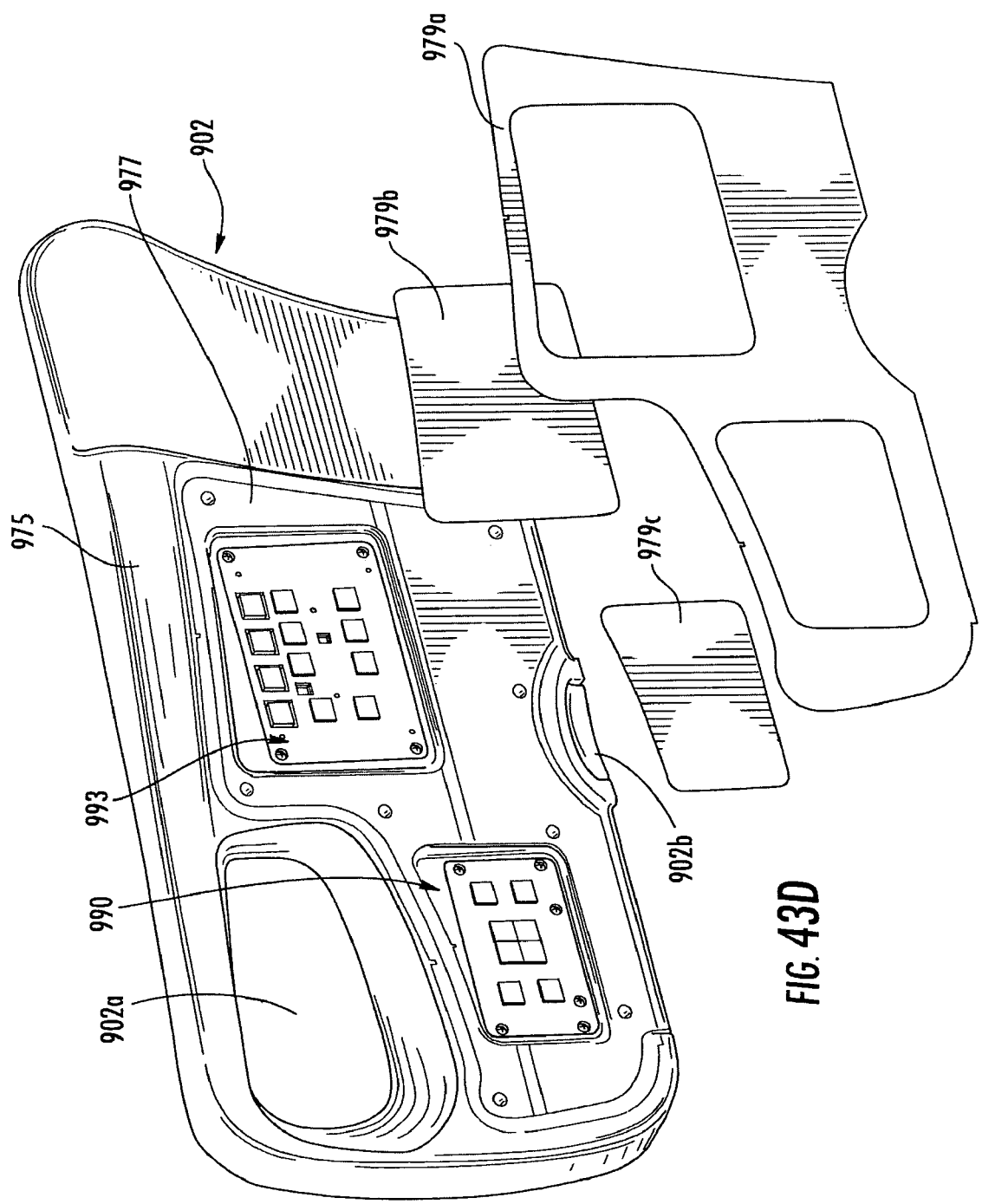
FIG. 43D is an exploded perspective view of the side rail of FIG. 43B.

(e.g. see FIG. 11), a load frame sensor 622 (e.g. see FIG. 31), a head section sensor 758 and a seat section sensor 772 (e.g. see FIG. 33), a foot section sensor, a side rail lock mechanism sensor 951 for detecting whether a given side rail 902, 904 is secured in a desired position (e.g. see FIGS. 42 and 45), and other such sensors for used independently or in combination with any number of the above exemplary sensors. Additional sensors may include sensors that detect when devices are mounted to the bed, which sensors communicate to control system when a device is coupled to the bed. Further, the control system may detect and identify the device and, further, generate a signal to one or more of the displays to display an icon or display associated with the device, which can provide an input/control for that device at the display. In this manner, the control system can update the displays to reflect any devices that are mounted to the bed.

Also, a number of monitoring switches, such as brake status and/or override status switches 314 and 291 respectively, (e.g. see FIG. 11), a side rail position status switch, and other such switches may be provided and used independently, or again in combination with any number of the above or other such switches and/or sensors.

The diagnostic and control system can enable the specific control of each of these electronic elements for desired operation thereof and further can enable the monitoring of the operating conditions of these electronic elements and additional bed conditions. The diagnostic and control system further enables the evaluation and determination of the existence of one or more faults relating to the operation of the bed 100.

The Frame System

As discussed hereinabove, the bed 100 generally comprises a frame system comprised of a base frame 200 and a support frame system comprising an intermediate frame 400 operatively coupled to base frame 200 via an elevation system 500 configured to raise and lower the intermediate frame 400 relative to the base frame 200 and thereby orient the intermediate frame 400 in various positions. The support frame system further includes load-bearing frame 600 mounted on the intermediate frame 400 via a set of load-cells 602 or the like, atop which is mounted the deck support 700 and lying surface 800. A barrier system 900 is further coupled to various components of the frame system and/or deck support 700, as described further below.

As stated above, the base frame 200 comprises a transport system including a set of wheels, such as casters 202 or the like, allowing for motion and maneuverability of the bed 100. An optional drive wheel system 204, operated for example using push handles 1004, may also be provided to facilitate movement of the bed 100 by an operator. A brake system 206, optionally comprising an emergency override system 208, may also be provided.

Figure 20A:
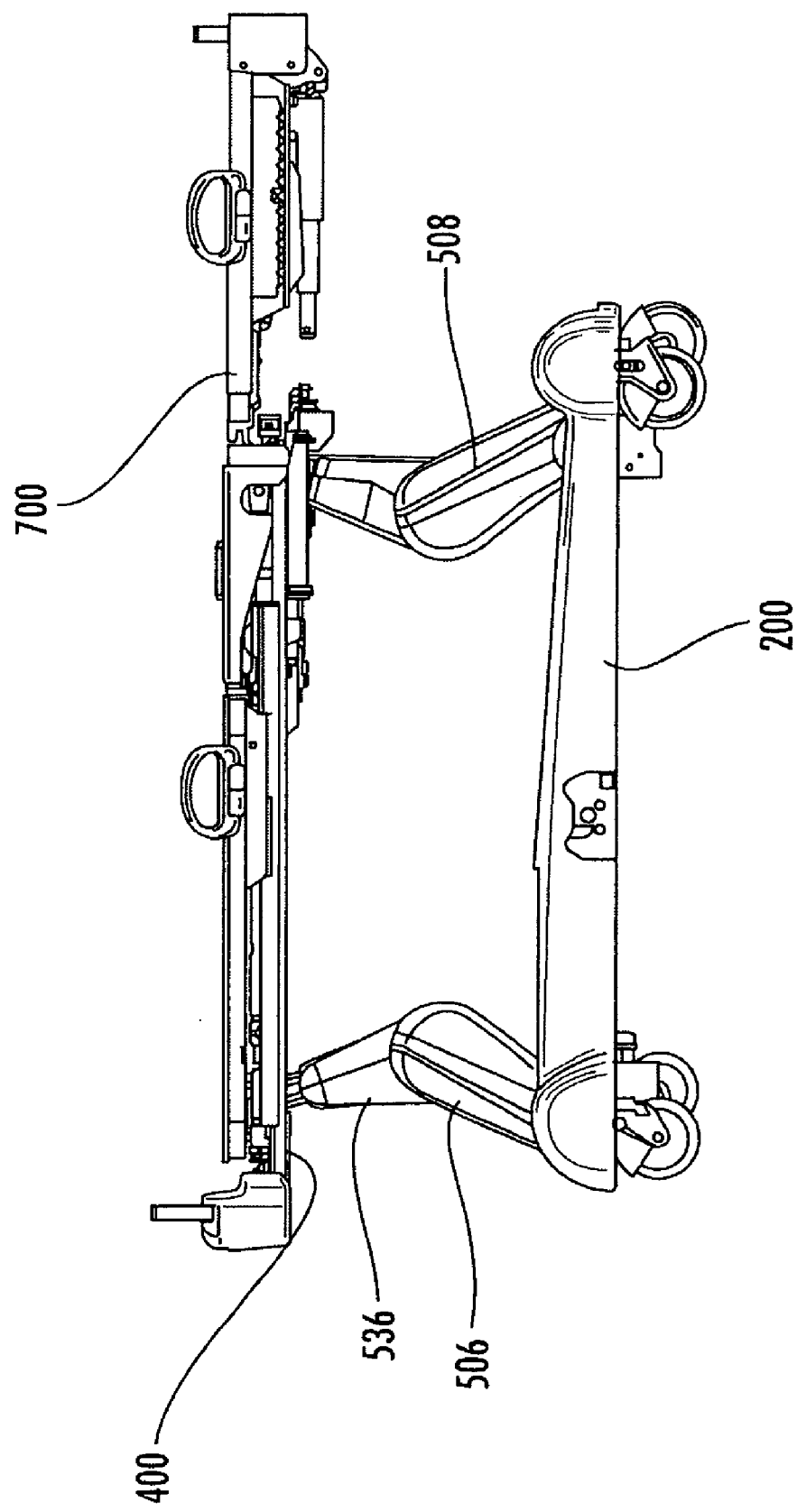
FIGS. 20A to 20C are right side views of an intermediate frame, load bearing frame and deck support mounted via an elevation mechanism to the base frame of FIG. 9, wherein the intermediate frame, load bearing frame and deck support are in a flat and elevated position, a reverse Trendelenburg position, and a lowered reverse Trendelenburg position, respectively.
Figure 20B:
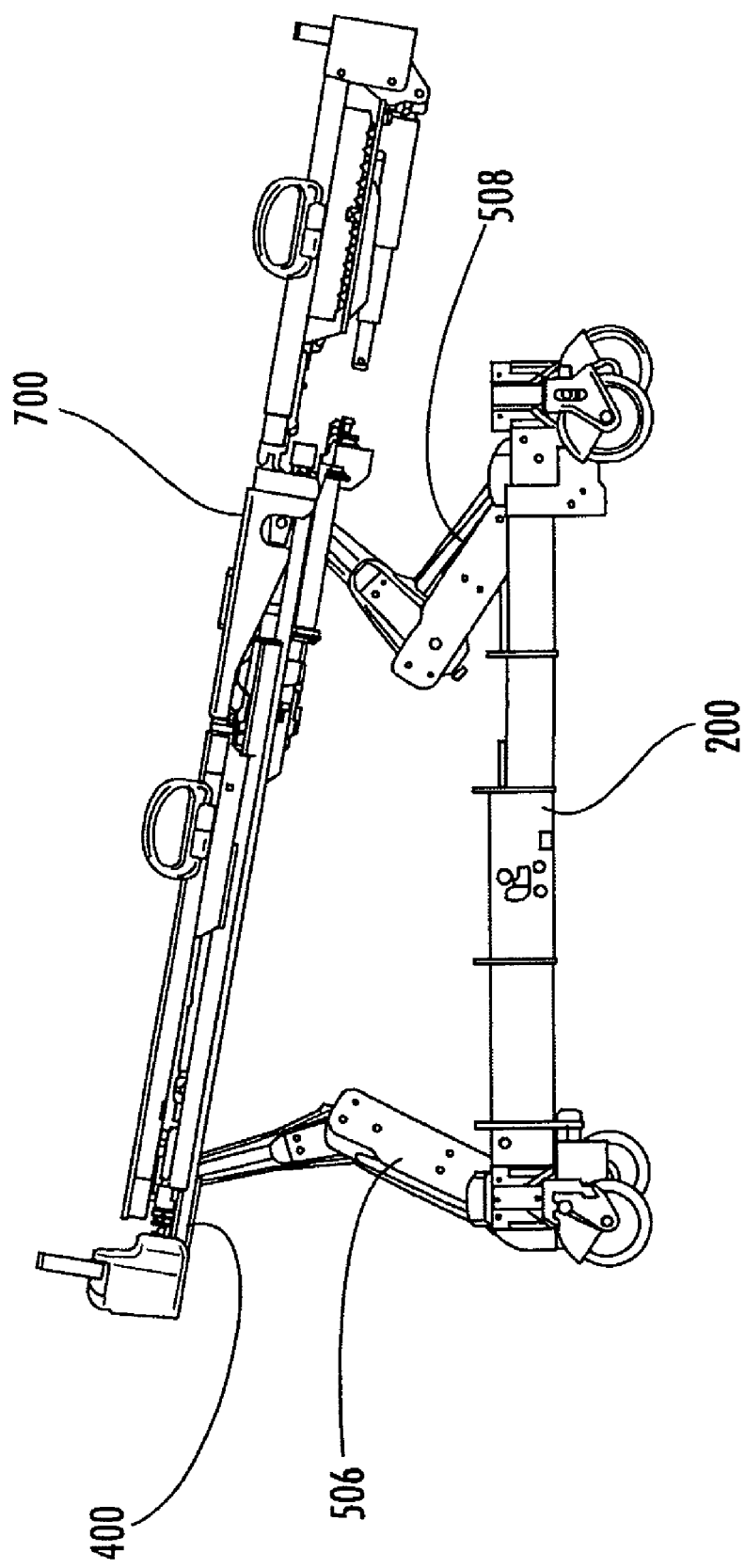
Figure 20C:
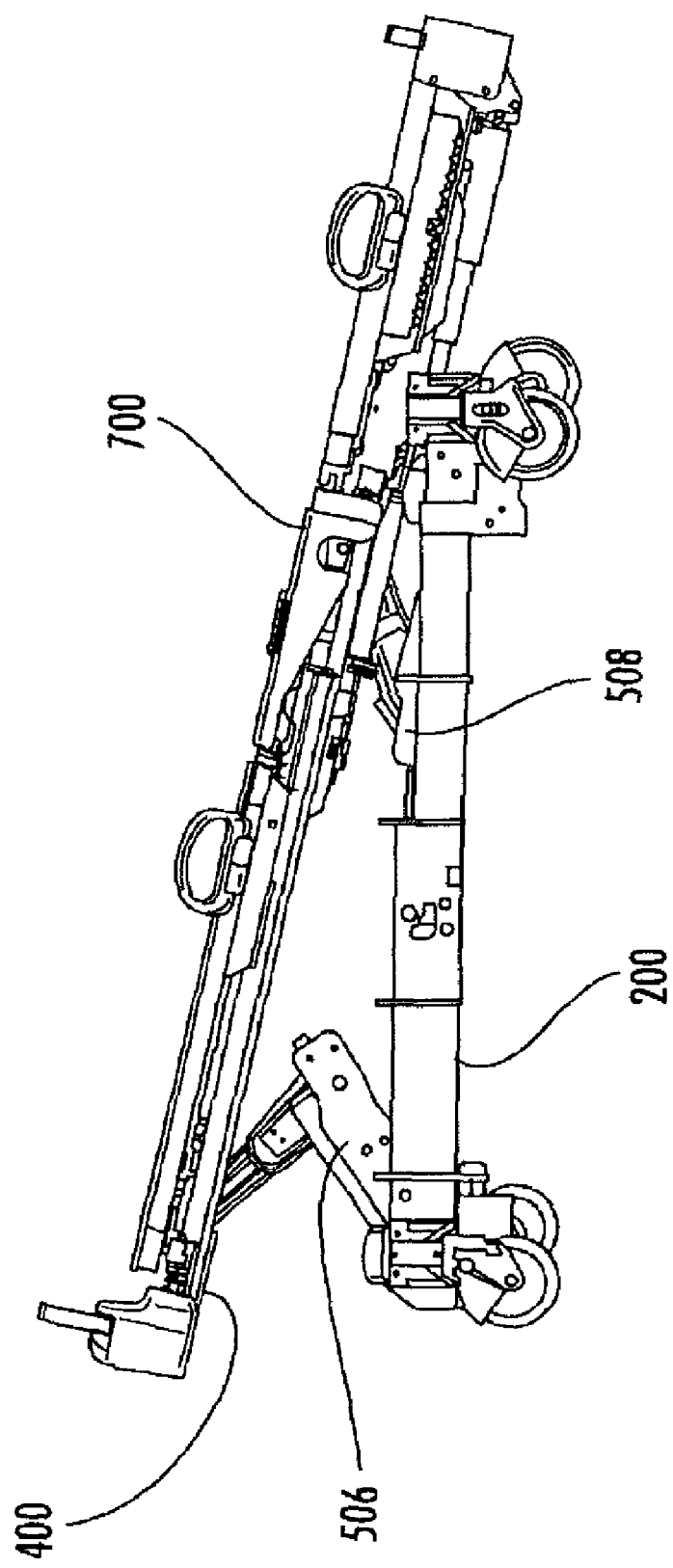

The elevation system 500, which generally comprises lift arms 502 interconnecting the base frame 200 to the intermediate frame 400, comprises in one embodiment, a series of linear actuators 504 configured to provide power to actuate the lift arms 502 and in turn raise and lower the intermediate frame 400 relative to the base frame 200. As explained in more detail below, lift arms 502 and linear actuators 504 are configured to position the intermediate frame 400, and ultimately the deck support 700 and lying surface 800 mounted thereon, in at least some of the following positions: a raised or upper substantially horizontal position wherein the intermediate frame 400 is at least partially raised above the base frame 200 (e.g. see FIGS. 1 to 8, 17A, 18A and 20A); a Trendelenburg position wherein a head-end 402 of intermediate frame 400 is lower than a foot-end 404 thereof (e.g. see FIGS. 17B and 18B); a Reverse Trendelenburg position wherein the foot-end 404 of intermediate frame 400 is lower than the head-end 402 thereof (e.g. see FIGS. 17C, 20B and 20C, wherein the bed 100 in FIG. 20C is in a lowered Reverse Trendelendburg position); and a lowered substantially horizontal position wherein the intermediate frame 400 is lowered adjacent to the base frame 200 (e.g. see FIGS. 17D and 18C). One skilled in the art will appreciate that the positions shown in the above-referenced Figures are exemplary positions and that the intermediate frame 400 may be positioned in a wide variety of positions relative to the base frame 200.

Figure 55:
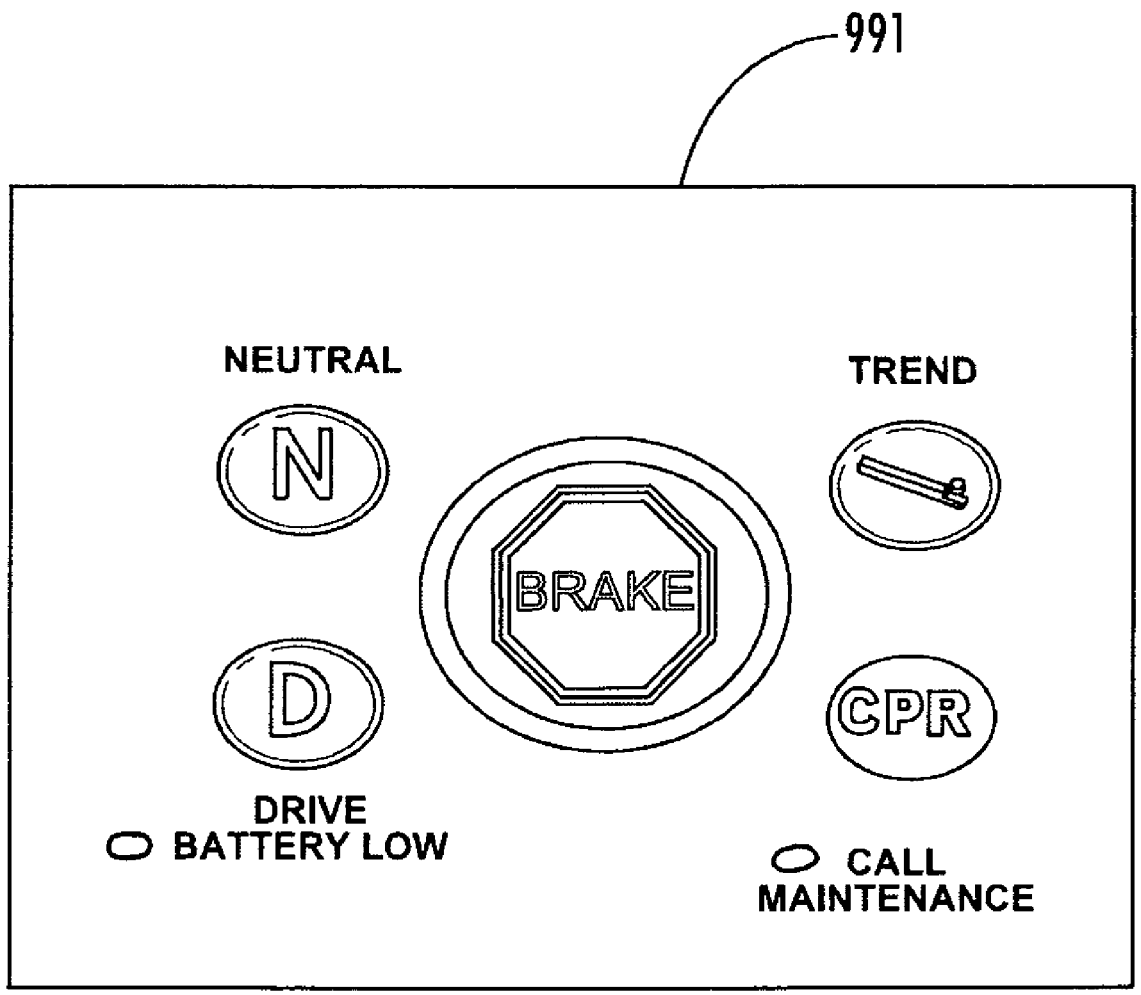
FIG. 55 is a diagrammatic view of an outer control interface provided by one of the head-end side rail control panels of FIG. 43.

As presented above, the various sections of the deck support 700 and lying surface 800 may be moved relative to the intermediate and/or load-bearing frames 400, 600 to move a user on the bed to various positions. For example, it may be required to configure the lying surface 800 of the bed 100 in a configuration that is designed to assist a caregiver in providing CPR to the patient supported thereon. In one example, a CPR configuration is defined by placing the head, seat and foot sections 702, 704 and 706 of the deck support 700 in a generally linear relationship. In one embodiment, the bed can be placed in this pre-defined CPR configuration via the control system 1000, which can comprise one or more control panels (e.g. see FIG. 55) configured to control a number of linear actuators operatively disposed to actuate the various sections of the deck support 700 to achieve the CPR configuration.

Other positions may also be considered useful in providing care to a patient positioned on the bed 100. For instance, with reference to FIG. 8, the head section, seat section and foot section 702, 704 and 706 may be positioned in a substantially linear relationship to provide a substantially flat lying surface 800. In one embodiment, the head section 702, seat section 704 and foot section 706 are placed in this linear relationship by the control system 1000 in response to a single user actuatable device, such as a button, being depressed on one of the control system's various control panels (e.g. see FIG. 55).

With reference to FIGS. 5 to 7 and 33 to 35, the head section 702 can be rotated about pivot 708 such that a head-end 710 of the head section 702 is raised relative to a foot-end 712 thereof. For example, the head-end 710 may be raised by the control system 1000 controlling an actuator 714 (FIGS. 34 and 35) to further extend a cylinder 716 of this actuator 714 and thereby raise the head-end 710. In one embodiment, the head section 702 is raised by the control system 1000 in response to a first user actuatable device, such as a button, being depressed on one of the control system's various control panels (e.g. see FIG. 57), and lowered by the control 1000 system in response to a second user actuatable device, such as a second button, being depressed on this same panel.

Furthermore, with reference to FIGS. 4 to 7, 33 and 36, the seat section 704 can be similarly rotated about pivot 718 such that its foot-end 720 is raised relative to its head-end 722. The seat section's foot-end 720 may be raised by the control system 1000 controlling an actuator 724 (FIG. 33) to further extend a cylinder 726 of the actuator 724 thereby raising the seat section's foot-end 720. In one embodiment, the seat section 704 is raised by the control system 1000 in response to a first user actuatable device, such as a first button, being depressed on one of the control system's various control panels (e.g. see FIG. 57), and lowered by the control 1000 system in response to a second user actuatable device, such as a second button, being depressed on this same panel.

Also, with reference to FIGS. 4 to 7 and 34, the foot section 706 can be similarly rotated about pivot 728 such that its foot-end 730 is lowered relative to its head-end 732. The foot section's foot-end 730 may be lowered by the control system 1000 controlling an actuator 734 to retract a cylinder 736 of the actuator 734 (FIG. 34) thereby lowering the foot section's foot-end 730. In one embodiment, the foot section 706 is lowered by the control system 1000 in response to a first user actuatable device, such as a first button, being depressed on one of the control system's various control panels (e.g. see FIG. 57), and lowered by the control 1000 system in response to a second user actuatable device, such as a button, being depressed on this same panel.

The Base Frame

Figure 8:
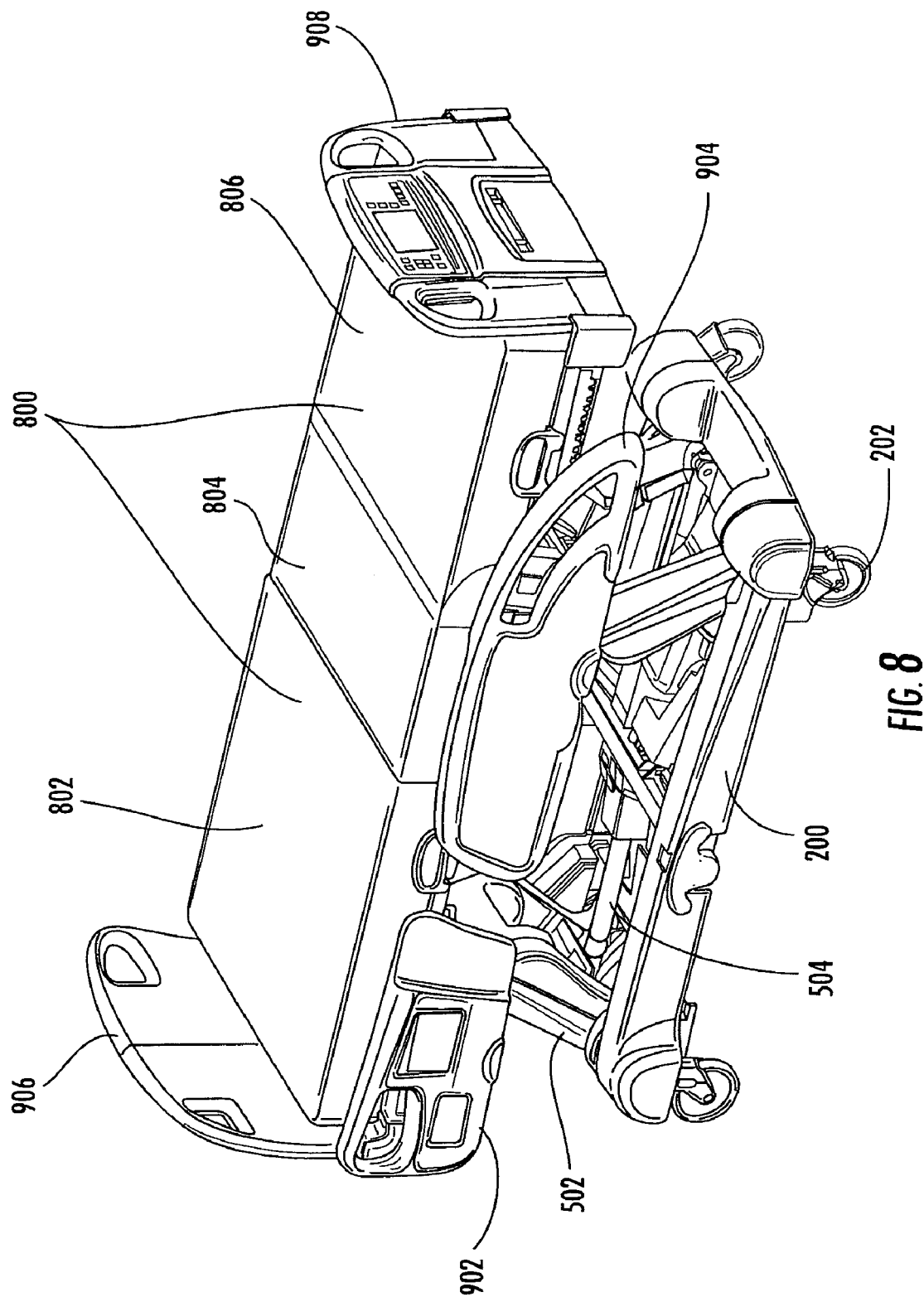
FIG. 8 is a right perspective view of the patient support apparatus of FIG. 1, further comprising a lying surface and wherein head-end and foot-end side rails are in respective retracted positions.
Figure 9:
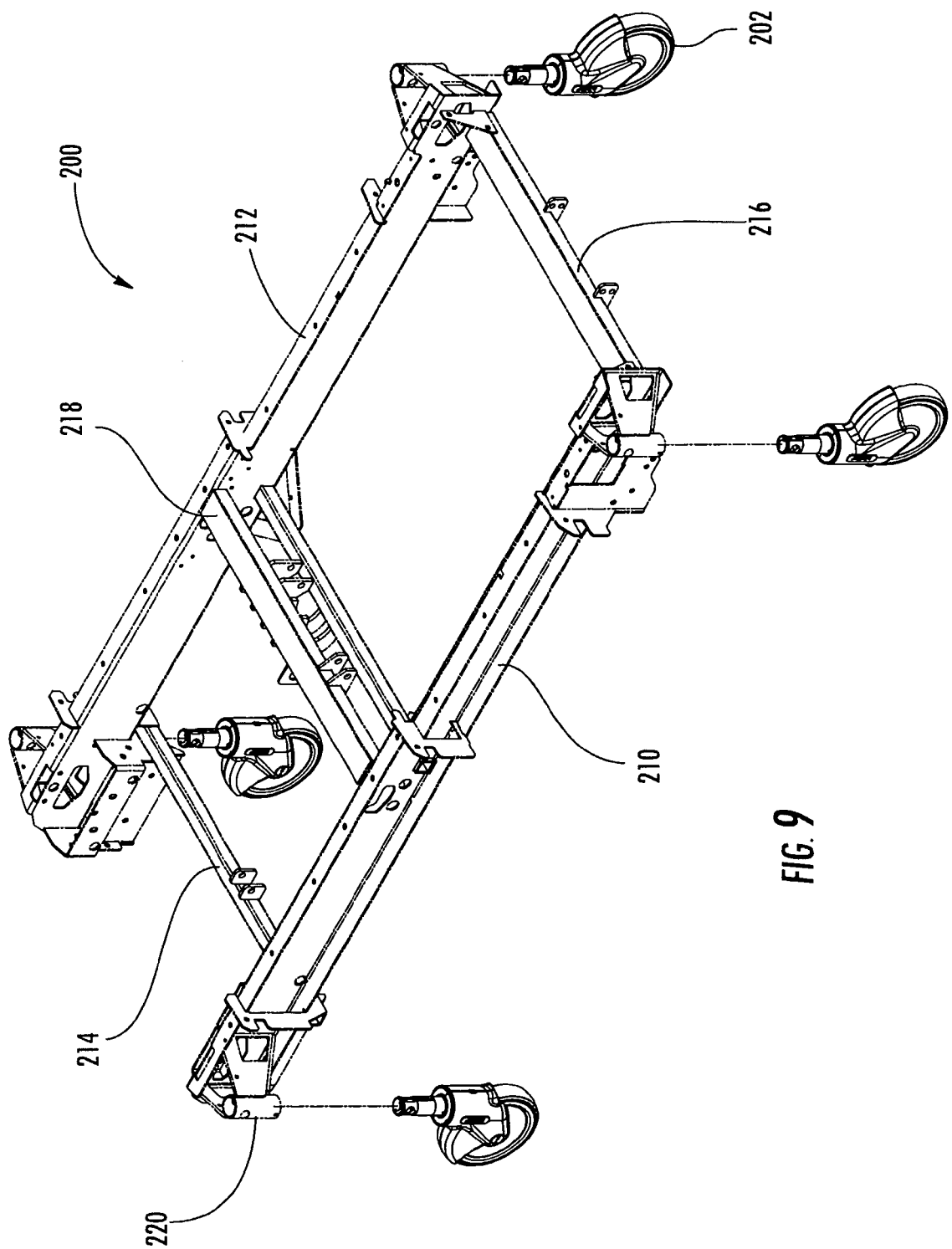
FIG. 9 is a right perspective view of a base frame assembly of the patient support apparatus of FIG. 1, showing attachment of a wheel system thereto.

With reference to FIG. 9, the base frame 200 generally comprises a pair of side frame rails 210, 212 and two or more transversal frame rails, as in rails 214, 216 and 218 connected to, and extending between, the side frame rails 210 and 212. For example, in the embodiment illustrated in FIG. 8, the base frame 200 includes right and left side frame rails 210 and 212 respectively, a head-end rail 214, a foot-end rail 216 and an intermediate rail 218. These rails generally provide the foundation upon which the bed 100 is built. In addition, base frame 200 may include a base frame cover 200a, which may be molded from a polymeric material or cast aluminum, for example. Base frame cover 200a covers and protects one or more the various components supported or mounted to the rails. In addition, base frame cover 200a may be formed as a monolithic part to facilitate cleaning and disinfection, as described more fully below.

In order for the bed 100 to be mobile to enable transport of the bed 100 and/or patient from one location to another, a plurality of bearing members, such as wheels or caster devices, including casters or caster wheels 202, may be provided to enable bed mobility. In this particular embodiment, four casters 202 are provided and pivotally mounted to the base frame 200 by means of respective mounting brackets 220 secured in a conventional manner to the corners of the base frame 200. Further, each caster includes operatively associated therewith a brake, which are well known in the art and available, for example, from Tente.

In one embodiment, the base frame 200 further comprises a sensor 203, such as an inclinometer or the like (e.g. see FIG. 11), for detecting and/or monitoring an inclination/orientation of the base frame 200. As will be described in greater detail below, data acquired using this and other such sensors disposed on various parts of the bed can be used in calculating and monitoring various characteristics of the bed 100 and/or of a patient lying thereon. As will be apparent to the person skilled in the art, the sensor can be mounted elsewhere on the base frame 200 without departing from the general scope and nature of the present disclosure.

Optional Drive Wheel Mechanism

Figure 10:
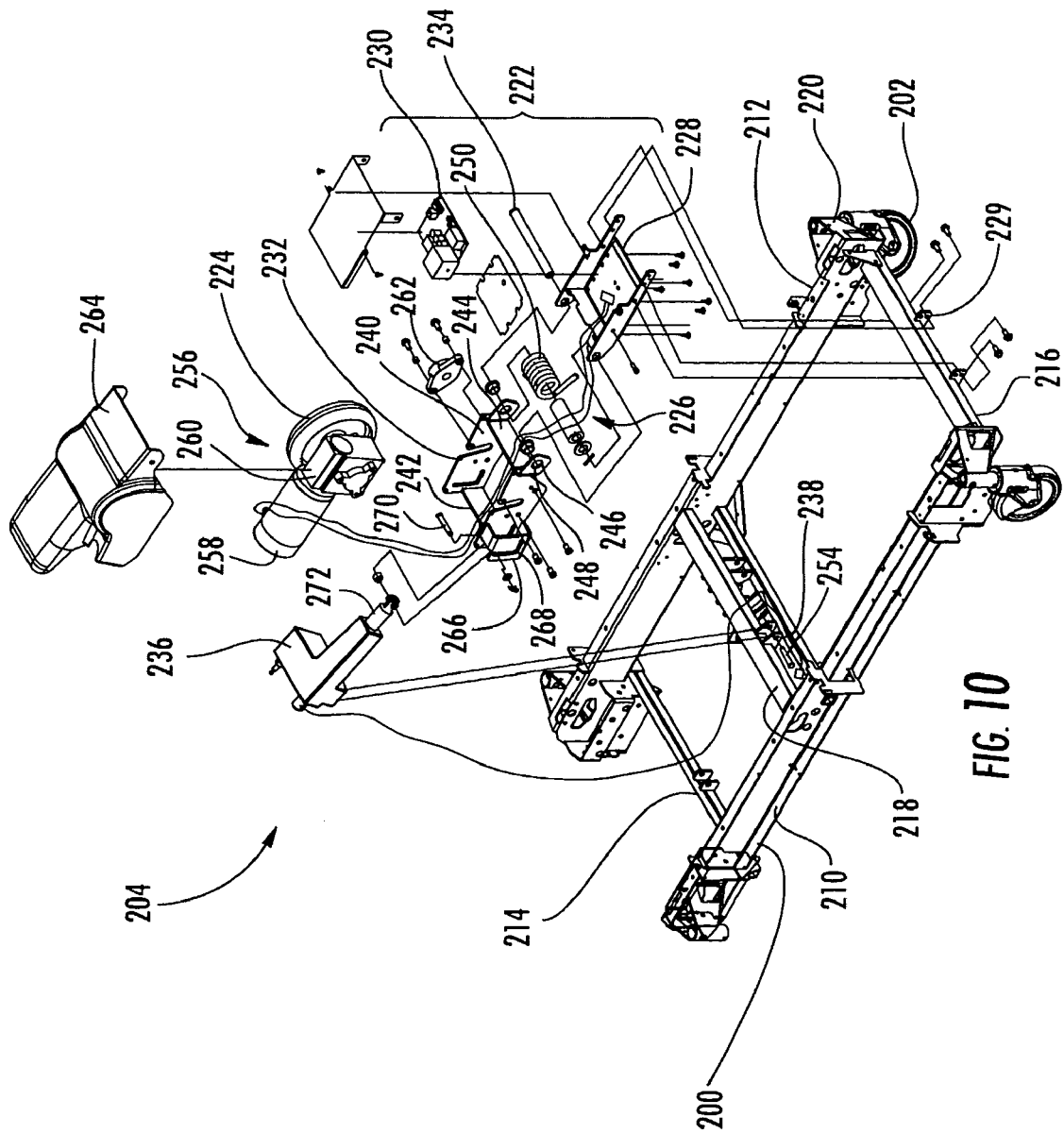
FIG. 10 is a right perspective view of the base frame assembly of FIG. 9, showing attachment of a further drive wheel system thereto.

In one embodiment, for example illustrated in FIG. 10, the bed 100 further comprises an optional motorized system for driving the bed 100. For instance, the bed 100 may be equipped with a drive wheel system 204 to enable motorized driving of the bed 100 from one location to another. According to this embodiment, a drive wheel support assembly 222 is provided and configured to enable a drive wheel 224 to move between a retracted position, wherein the drive wheel 224 is tucked within the base frame 200, and a driving position, wherein the drive wheel 224 is lowered for engagement with the floor to facilitate movement of the bed 100. In particular, the drive wheel 224 may be urged by a spring mechanism 226 into engagement with the floor with sufficient force to accommodate undulations in the floor surface, namely to maintain sufficient frictional engagement with the floor to provide a substantially continued and smooth driving of the bed 100 along the floor surface.

FIG. 10 illustrates the drive wheel support assembly 222 as it is mounted on the base frame 200 of the bed 100. In this illustrative embodiment, the support assembly 222 comprises a housing 228, which is secured to the head-end rail 214 via mounting brackets 229 thereof and is used for housing the drive system's control circuitry 230 (e.g. the Zoom drive circuitry described below, or any other such drive system circuitry), a drive wheel support bracket 232 pivotally coupled to the housing 228 via a torsion spring-loaded axle 234, i.e. providing the spring mechanism 226 introduced above, and a drive wheel actuator 236 pivotally mounted to the intermediate rail 218 via mounting bracket 238 thereof and drivingly interconnecting the support bracket 232 thereto.

The support bracket 232 generally comprises a pair of substantially parallel longitudinal side flanges 240 each oriented in a plane parallel to a longitudinal axis of the base frame 200, interconnected by wall members 242 and 244. Coupling ears 246 extending longitudinally toward the foot-end rail 216 provide coupling holes 248 configured to receive the axle 234 therein and thereby couple the support bracket 232 to the housing 228. A torsion spring 250 having oppositely extending legs encircles the axle 234 with one leg of the spring 250 bearing on wall member 244 and with the other leg bearing against the housing 228. The state of the spring 250 when the wheel 224 is deployed is tensioned and is configured to continually urge the support bracket 232 counterclockwise about the axle 234.

The mounting bracket 238 generally comprises a pair of parallel extending plates projecting upstandingly away from the intermediate rail 218 and including remote from the intermediate rail 218 a pair of axially aligned holes for receiving a coupling pin 254, bolt or the like therein. If desired, crosswise extending members (not illustrated) can be provided between the plates in order to rigidify the bracket 238.

A drive mechanism 256 for driving the wheel 224 comprises a reversible drive motor mechanism 258 and a right angle transmission mechanism 260 configured to connect the output of the motor 258 to a drive axle on which is fixedly secured the drive wheel 224. The drive mechanism 256 is secured to the support bracket 232 between longitudinal side flanges 240, the right-angle transmission mechanism 260 being fixedly attached along one of the flanges 240 whereas the drive axle and drive wheel 224 are rotatably secured to the other via a bearing mechanism 262 or the like. As a result, when the motor 258 is activated, the output thereof will effect, through the right angle drive transmission 260, a driving of the drive wheel 224. A housing 264 may be used to cover the drive mechanism 256, being disposed over same and secured to the support bracket 232, as shown in FIG. 10.

In this particular embodiment, one of the support bracket's side flanges 240 further comprises a bracket 266 configured with an L-shaped slot 268 for supporting a pin 270 used to couple the actuator 236 to the support bracket 232. In particular, the actuator 236 is connected at one end to the bracket 238, as described above, and at the other end to the pin 270. More specifically, the actuator 236 is configured to extend and retract to effect a driving of the support bracket 232 about axle 234 to cause the drive wheel 224 to move toward and away from the floor, namely between drive and retracted positions. In this particular embodiment, the actuator 236 includes a reversible motor having a rotatable output shaft which, upon being rotated, effects an extension and a retraction of a driven member 272. As such, the rotating output of the motor can be converted into a reciprocal motion of the driven member 272 by conventional means well known in the art. In this particular embodiment, the distal end of the driven member 272 comprises a hole in which is received the pin 270.

When the driven member 272 is moved to the retracted position, the pin 270 engages an uppermost end of the L-shaped slot 268 to draw the support bracket 232 in a clockwise manner about the axle 234 and against the urging of the torsion spring 250. Upon operation of the motor to effect an extension of the driven member 272, the pin 270 is moved to down the L-shaped slot 268 as drive wheel 224 engages the floor. When the drive wheel 224 reaches a recess in the floor, that is a region of the floor that is lower than a region engaged by one or more of the casters 202, the torsion spring 250 will effect a counterclockwise movement of the support bracket 232 to maintain an engagement of the drive wheel 224 with the floor with sufficient force so as to permit the drive wheel 224 to maintain a driving movement of the base frame 200. Simultaneously, the pin 270 will move up in the L-shaped slot 268. Alternatively, when the drive wheel 224 reaches a bump or protuberance in the floor, that is a region of the floor that is higher than a region engaged by one or more of the casters 202, a clockwise movement of the support bracket 232 will be effected against the torsion spring 250 such that an engagement of the drive wheel 224 is maintained with the floor with sufficient force so as to permit the drive wheel 224 to maintain a driving movement of the base frame 200. This motion will thus provide a relatively smooth transition over the bump or protuberance. As above, the pin 270 will move down the L-shaped slot 268 to accommodate for the motion of the support bracket 232. As a result, the spring 250 acts as a type of shock absorber for the drive wheel mechanism to provide a smoother ride.

The person of skill in the art will understand that other drive wheel mechanisms can be considered to provide similar results. For instance, the above L-shaped slot 270 may be linear, curvilinear, or other such shapes conducive to provide shock absorbing give and extendibility to the drive wheel 224.

Also, it is to be recognized that the drive wheel actuator 236 could be connected in a reverse manner to that illustrated in FIG. 10, such that the driven member 272 is connected to the bracket 238 via pin 254 while the other end of the actuator is coupled to the L-shaped slot 268 of bracket 266 via pin 270.

It is to be also recognized that the actuator 236 can comprise a drive motor having a rotatable output shaft rotatable in a single direction of rotation. In this case, the output shaft of the drive motor, when rotated, would rotatably drive an elongate double flighted screw shaft on which would be provided the driven member 272, here a traveling nut also having a double flighted internal screw thread operatively connected to the threads on the screw shaft. Upon the nut reaching an end of travel in both lengthwise directions along the length of the screw shaft, a continued rotation of the screw shaft will effect an automatic crossover of the operatively mated threads to cause a movement of the nut (and driven member 272) in the opposite directions.

As will be described further below, activation of the drive wheel mechanism may be achieved using a number of controls provided on or around the bed 100. For example, in one embodiment, activation of the drive wheel mechanism is controlled using a same control interface or panel (e.g. see FIG. 55) used to activate the breaking system 206, described below. For example, the controls may be configured to provide three operating states: a brake state, wherein the casters 202 are locked (e.g. both from turning and from pivoting), a neutral state, wherein the casters 202 are free to move and driving and maneuverability of the bed 100 is achieved manually, and a driving or steering state, wherein the casters 202 are again free to move and wherein the drive wheel mechanism is actuated to bring the drive wheel 224 in operative engagement with the floor and the drive controls (discussed below) are activated. It will be understood that a variety of other methods and systems can be used, as described below, to activate and operate the above and other such drive wheel systems 204, and that such alternative methods and systems should not be considered to depart from the general scope and nature of the present disclosure.

Also, operation of the drive wheel system 204 when activated by the above controls, may be provided via push handles 451 described further below, or other such devices as will be readily understood by the person skilled in the art. For instance, in one embodiment, the drive wheel system 204, once in drive/steer mode, may be responsive to a forward and/or backward pressure applied to these handles 451 to impart a corresponding drive to the drive wheel 224. These and other such drive activation systems will be further described below, in particular, with reference to the illustrative and optional Zoom drive algorithm.

Braking System

The bed may further comprise a braking system 206 to selectively immobilize the bed from moving, or again to selectively immobilize an orientation of one or more of the bed's casters 202. In general, each caster 202 can be associated with a common braking mechanism operated either manually or by control means provided by the control system 1000. Alternatively, each caster 202 may be associated with a respective braking mechanism, or again grouped and associated with respective group braking mechanisms to be operated individually, or via a common activation system, as will be readily understood by the person skilled in the art. The caster braking system 206 generally provides simultaneous braking of each caster 202, however, less effective braking systems wherein only some of the casters 202 are immobilized may also be considered, as will be apparent to the person skilled in the art.

In one embodiment, illustrated for example in FIGS. 11 to 16, the braking system 206 generally comprises a low force braking system for reducing the force needed by a user to activate and deactivate the braking system 206. For instance, the bed 100 may comprise a power-assisted or actuated breaking system 206 (e.g. as described below) to facilitate an operation of the bed 100 using various available steering and/or braking features of this mechanism. In addition, such systems may further comprise one or more hand and/or foot actuated manual override mechanisms (e.g. see FIGS. 14 to 16) in the event of a power failure, for example. Contemplated brake system control means may include, but are not limited to, power-assisted hand and/or foot brakes, such as handles or pedals, user actuatable devices, such as a button, a touch screen, and/or a switch, on one or more control panels provided on or near the bed 100, and other such controls powered electrically, hydraulically, pneumatically and/or magnetically, as will be readily understood by the person skilled in the art.

Figure 2:
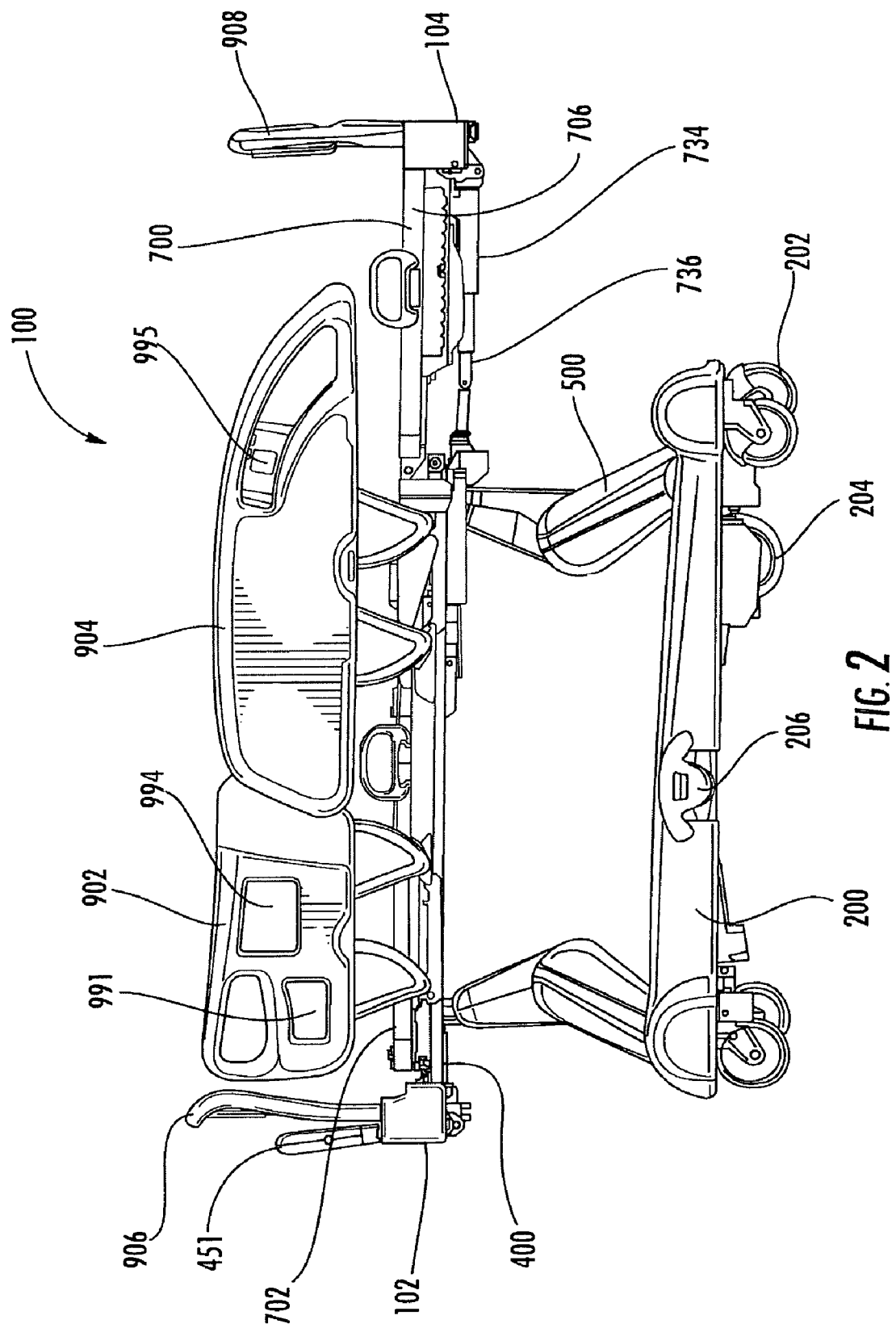
FIG. 2 is a right side view of the patient support apparatus of FIG. 1.
Figure 3:
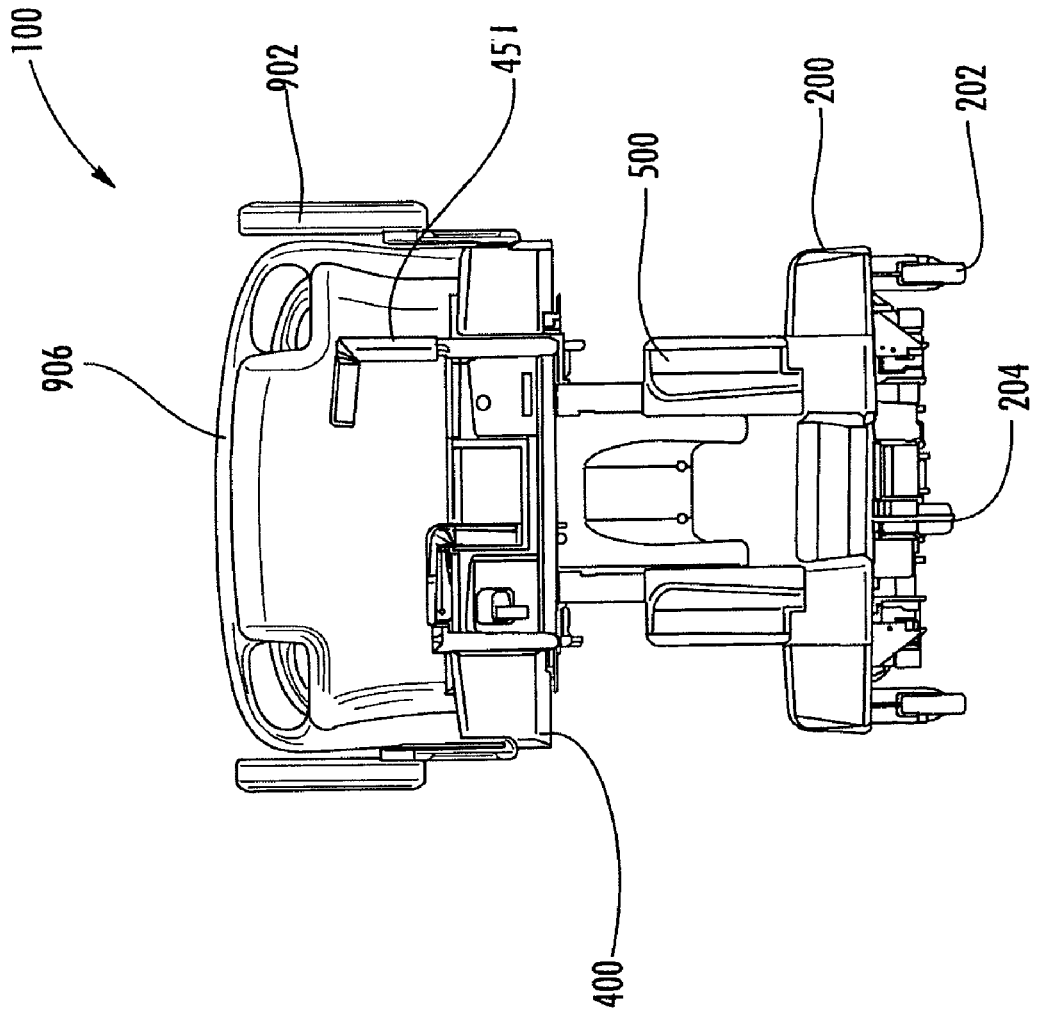
FIG. 3 is a front side view of the patient support apparatus of FIG. 1 wherein a right push handle is in a working position and a left push handle is in a stored position.
Figure 52:
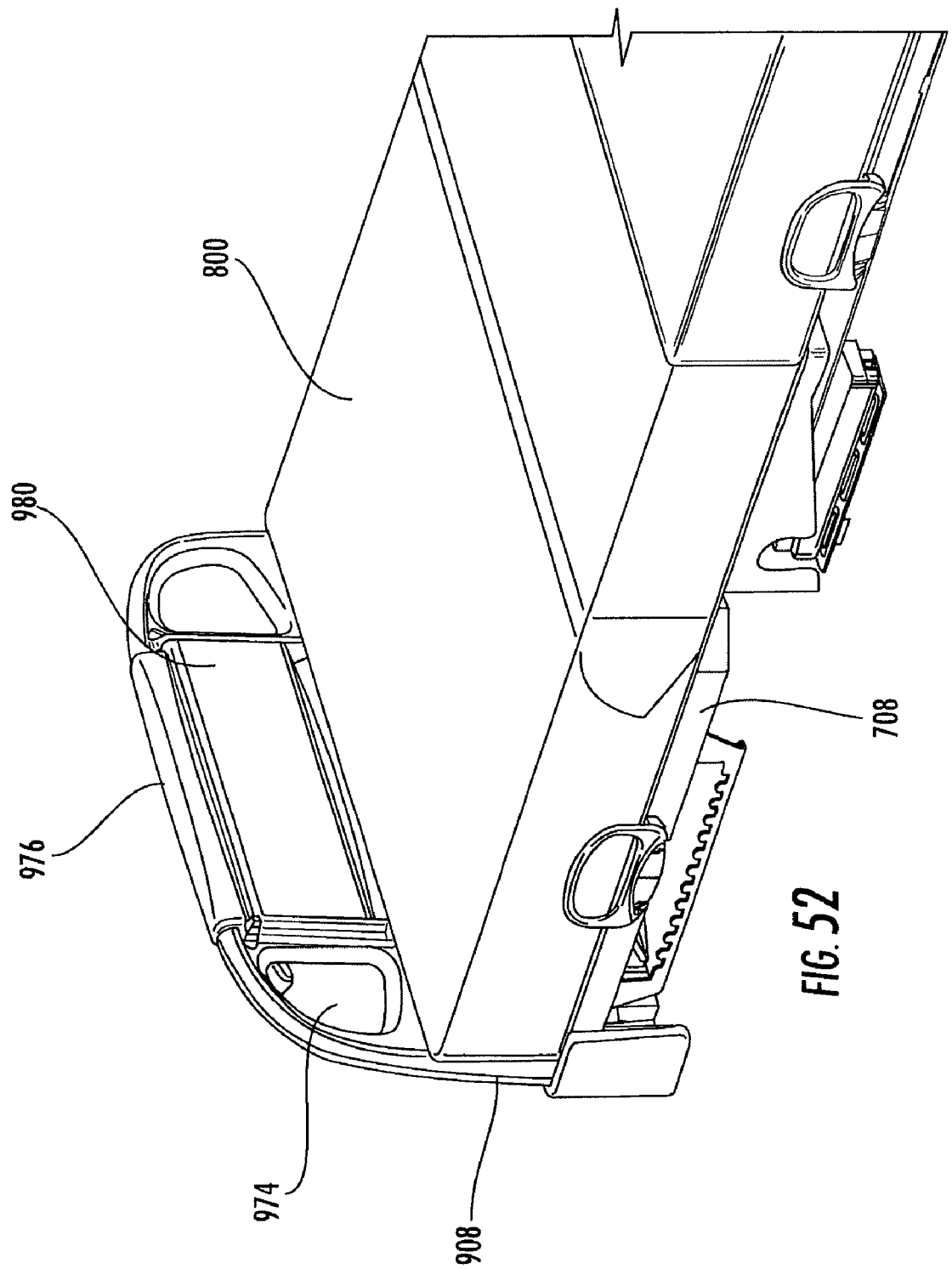
FIG. 52 is an inner perspective view of the footboard of FIG. 40 showing the footboard control console in the tilted position shown in FIG. 51B.
Figure 53:
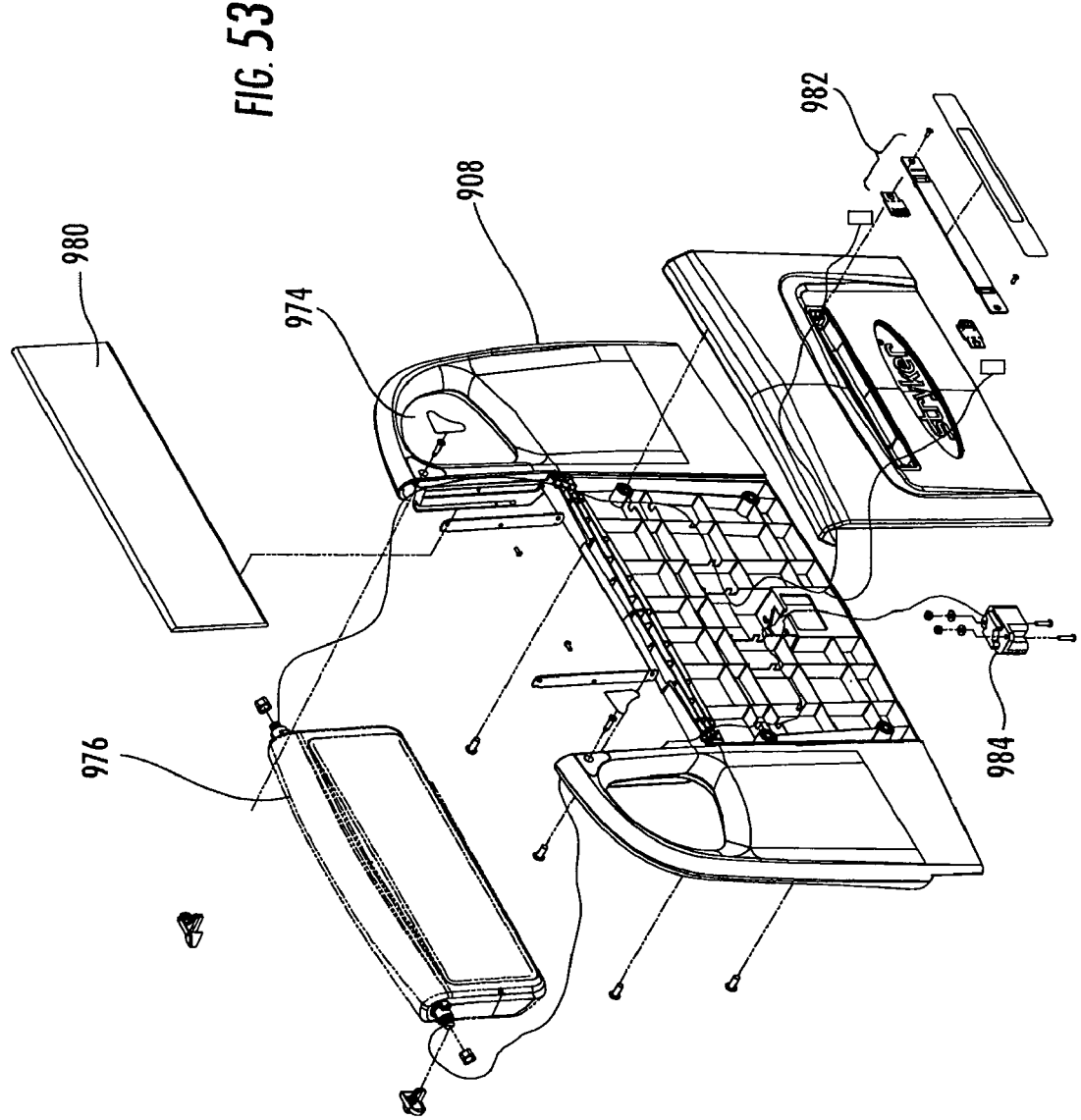
FIGS. 53 and 54 are respective exploded views of an assembly of the footboard of FIGS. 50 to 51 and an assembly of the footboard control console coupled thereto, respectively.

For example, in one embodiment, the user can activate the brakes on one or more control panels (e.g. see FIGS. 55, 58) located, for example, on the exterior of the head-end or foot-end side rails 902, 904 and/or on the head-end structure 450, within the vicinity of the push handles 451, as depicted for example in FIGS. 2 and 3. Access to the brake activation can also be available on other control panels, including for example, a footboard control console (e.g. see control console 976 in FIGS. 51 to 53, and an exemplary interface thereof in FIG. 58), a removable panel, and the like. The positioning of the brake controls on one or more control panels allows the user to more easily access and activate the braking system 206. For instance, in some embodiments, the positioning of the bed's side rails and/or the positioning of the bed itself (e.g. when the bed is in a lowered position) may impede access to a manual brake activation pedal or handle (e.g. brake pedal 290 of FIGS. 14 to 16). Using controls disposed on one or more control panels, however, the braking system 206 may still be readily accessed and controlled.

Furthermore, automatic brake control via the control system 1000 can also provide a safety feature when the system is in a motion lockout, further discussed below. In a total lockout of motion, a lock mechanism prohibits movement functions from being controlled on the control panel(s), located for example on the side rails, footboard, pendant and headboard, etc. The brake can be set during the lockout but, for safety reasons, preferably cannot be removed at any point during a total lockout.

In one embodiment, the brake control(s) is located proximate the push handles 451 and can be engaged or disengaged without removing the user's hands from the handles 451. For example, the bed 100 generally rolls in the direction guided by the user who is controlling one or more of the push handles 451. When force is not exerted on the handles 451, the drive wheel 224 decelerates, and eventually comes to a halt, usually within 4-10 seconds. While the braking system 206 may be used to assist in bed deceleration, it is usually not required, given the bed's slow speed. Furthermore, if a patient is in the bed 100, use of the brake during bed displacement may be jerky and uncomfortable. As such, the braking system 206 is typically used to secure an immobile bed, similar to a vehicle's hand brake.

When in use, the user engages the braking system 206 which imparts a braking force directly on the casters 202. The brake can be a cam that pushes on the tire or brake on the axle or separate disk or the wheel itself. The brake system is usable on heavy beds and is adaptable to different braking system (ring, wheel, or direct floor pressure).

Furthermore, the casters 202 may comprise brake casters, selectively operated in free rotation and brake modes, or steer/brake casters selectively operated in free rotation mode, pivotally locked mode and brake mode, wherein actuation of the braking system 206 can implement either immobilization of one or more casters from rotating (e.g. prohibit displacement of the bed) and/or immobilization of one or more casters from pivoting (redirecting a displacement of the bed).

For instance, in one embodiment where a drive wheel mechanism is provided (e.g. such as the drive wheel mechanism 204 described above), the bed 100 may be operated in three states, a braking state wherein the casters 202 are rotatably and pivotally immobilized, a neutral state where the casters 202 are free to move in either direction, and a steering state wherein the casters 202 are still free to move in either direction while a drive wheel mechanism is activated. In another embodiment where a drive wheel mechanism is not provided, the bed 100 may again be operated in three states, braking and neutral states as above, and a steering state wherein the foot-end casters 202 (or head-end casters if the bed 100 is commonly operated from the foot-end) are pivotally immobilized while the head-end casters 202 can move freely. Other combinations and permutations of the above breaking and steering options may also be considered, as will be apparent to the person skilled in the art. Selection of the brake mechanism's state may be implemented using conventional means, such as a manually operated handle and/or pedal, or again via electronic controls (e.g. provided via control panels or the like).

For example, in one embodiment, three push buttons corresponding to brake, steer and neutral modes are provided on one or more control panels (e.g. see FIGS. 55, 58) to selectively operate the braking system 206. These buttons may be operatively coupled to one or more actuators, as in actuator 280 of FIGS. 11 to 16, configured to activate or deactivate the braking system 206. A manual override system 208 may also be integrated into the braking system 206 and may include, for example, a manually actuated pedal, as in pedal 290 of FIGS. 14 to 16, or the like.

The exemplary braking system 206 depicted in FIGS. 11 to 16 will now be described in greater detail. The braking system 206 is generally configured to immobilize the casters 202 from rotating such that a displacement of the bed 100 is substantially mobilized, and/or from pivoting such that a direction of the caster 202 is stabilized to facilitate, for example, steering of the bed 100. In the latter case, pivotal braking may be limited, for example, to two of the four casters 202 such that an operator of the bed 100 may select an orientation of the bed displacement by pivoting two of the casters 202, while using the pivotally locked casters 202 to facilitate this directional displacement.

Figure 11:
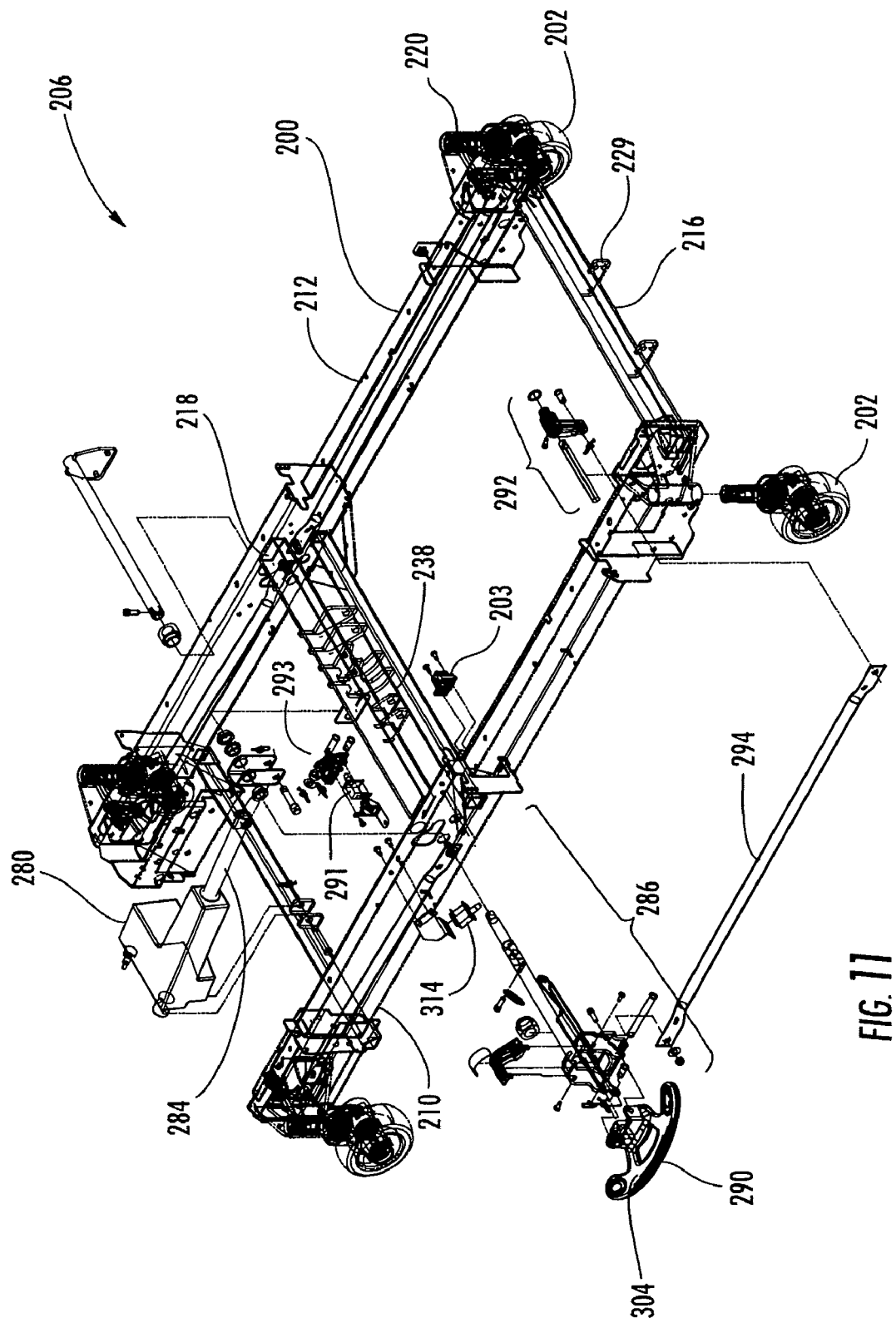
FIG. 11 is a right perspective view of the base frame assembly of FIG. 9, showing attachment of a further braking system thereto.

In the embodiment illustrated in FIG. 11, the braking system 206 is configured such that a motorized control of the system 206 is imparted via a single motor or actuator 280. In particular, the actuator 280, controlled or operated from one or more control means such as brake handles, user actuatable devices, such as push buttons and the like (discussed further below with reference to the control system 1000), is used to mechanically activate a locking mechanism on each of the casters 202. For example, a nurse may activate the brakes from the push handles. In an optimal form, the nurse may activate the brakes without removing his/her hands from the push handles. A person of skill in the art will understand that, although the present embodiment is described as including a single actuator 280, such as an electric, a pneumatic, a magnetic, or a hydraulic actuator, for all four casters 202, a similar braking system 206 could be designed to include one such actuator for each caster 202, or again, one actuator for each two casters 202 (e.g. an actuator to control the head-end casters 202 and a second actuator to control the foot-end casters 202). Other combinations of actuators for any number of casters may also be contemplated herein without departing from the general scope and nature of the present disclosure, as will be readily understood by the person skilled in the art.

The braking system 206 generally comprises a central levering mechanism 282 operatively interconnecting a driven member 284 of actuator 280 to lateral levering mechanisms 286 on each side of the base frame 200 via a transversal shaft 288. The lateral levering mechanisms 286, the right-hand side one of which is illustratively coupled to a manual override actuation pedal 290, are themselves configured to actuate the brake mechanism 292 on each caster 202 via longitudinally extending brake actuator bars 294 configured such that a substantially linear displacement thereof pivots respective brake actuating levers 295 configured to operate the respective brake mechanisms 292 of each caster 202. Contemplated brake mechanisms 292 may include, for example, a locking cam or the like configured to selectively immobilize a given caster 202 from rotating and/or pivoting, depending on the type of caster used. It will be understood that other braking mechanisms may be considered herein without departing from the general scope and nature of the present disclosure. As noted, commercially available braking mechanisms are available from Tente. Furthermore, different braking mechanisms 292 may be used for different casters 202, depending on the intended purpose and use of such brake mechanisms.

In particular, the central levering mechanism 282 comprises a sleeve member 296 that is slid toward the center of shaft 288 and coupled to the driven member 284 via flanges 297 extending radially outward therefrom. A bolt or pin 298 is further provided through the shaft 288 and biased within a notch 300 formed in through a periphery of the sleeve 296 by a spring mechanism 302, thereby operatively coupling the sleeve 296 to the shaft 288 when the pin 298 is so biased, such that a rotation of the sleeve 296 under a pivoting action applied to the flanges 296 by the driven member 284, induces a rotation of the shaft 288. As will be described below, when the override pedal 290 is deployed, the shaft 288 is shifted toward the right such that the pin 298 is released from the notch 300, thereby uncoupling the shaft 288 from the sleeve 296 and allowing for manual operation of the caster brake mechanisms 292.

The shaft 288 extends across the base frame 200 and through to the lateral levering mechanisms 292 such that a rotation of the shaft 288 imparts a substantially linear displacement of the bars 294. As recited above, displacement of the bars 294 generally translates into operation of each caster's brake mechanism 292 via respective brake actuating levers 295. A protective cover 299 may also be provided to hide and possibly protect the bars 294 and other elements of the braking system 206.

As introduced above, an override pedal 290 is provided on the right-hand side of the bed 100 and is operatively coupled to the lateral levering mechanism 286 on this side. In general, the override mechanism is practical in situations where the actuator 280 is in a given position and power thereto or to the control system 1000 is unavailable, thus preventing the actuator 280 from changing from one mode to another. In one embodiment, the pedal 290 is spring-biased in an upright and stowed position (FIGS. 12 and 13) such that a downward pivoting force is required to extend the pedal 290 to an operable position in which an operating surface thereof 304 is substantially parallel with the floor (FIGS. 14 to 16). Furthermore, the pedal 290 may be configured such that when it is stowed, a clearance of about five inches is maintained below the pedal 290 irrespective of the pedal's orientation. Although this clearance may be obstructed when the pedal 290 is engaged, the clearance is regained automatically as the pedal 290 is returned to its stowed position.

When such a force is applied to the pedal 290, a corresponding set of pivoting flanges 308 are configured to pivot and engage a bolt 310 transversally fastened through the end of the shaft 288 such that the shaft 288 is pulled toward the pedal side of the bed 100, thereby releasing the pin 298 from notch 300 and disengaging the actuator 280 from operative control of the braking system 206. As a result, control of the braking system 206 is then provided via the deployed pedal 290 rather than the motorized actuator 280 and controls thereof. When the foot or hand of the operator releases the pedal 290, the latter springs back to its upright position and the pin 298 is again urged toward the notch 300 by the spring mechanism 302.

In one embodiment, the release of pedal 290 is monitored by a switch 291 configured to report to the control system 1000, whether the braking system 206 is currently in override mode. For example, as shown in FIG. 11, as the shaft 288 is pulled toward the pedal 290, a levering mechanism 293 may be configured to release a user actuatable device, such as a switch 291, indicating that the braking system 206 is in override mode. When the pedal 290 is released to its upright position, the switch 291 is pressed and reports this event to the control system 1000, which may then activate the actuator 280 to pivot the central levering mechanism 282 through its course thereby rotating the sleeve member 296 to realign the notch 300 therein with pin 298 so to re-couple the actuator 280 with shaft 288. Alternatively, the pin 298 may be re-engaged with the notch 300 by manual rotation of the released pedal 290, or again by a control user actuatable device, such as a button or switch, provided therefor with the control system 1000.

In one embodiment, a visual indicator 312 is also provided above the pedal 290 and configured to indicate a status of the braking system 206 as the breaking system 206, and consequently the pedal 290, is moved through different positions (e.g. brake, neutral, steer), either manually or automatically via control system 1000. A sensor 314, such as a user actuatable device, such as a button or switch or the like, may also be provided to report a brake status to the control system 1000, which may be conveyed to the operator via one or more visual user interfaces, as described further below. In general, the brake status indicator(s) may help to avoid having the user inadvertently leave the bed without the brakes being set, which could result in inconveniences or safety concerns for the patient.

FIGS. 12A to 12C shows a change of the visual indicator 308 and a motion of the pedal 290, when stowed, as the braking system 206 is selectively moved from steer, neutral and brake positions respectively.

Figure 13A:
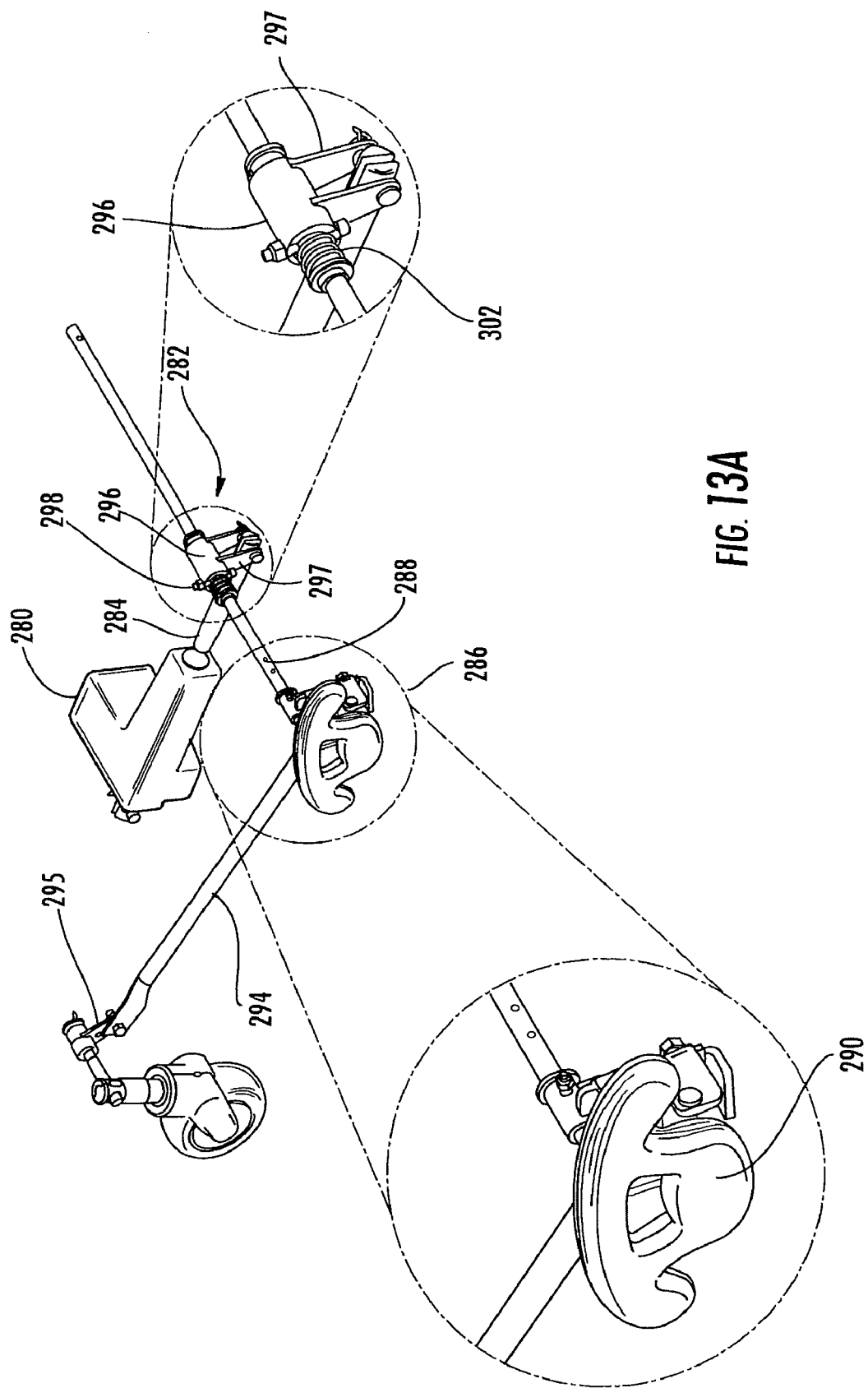
FIGS. 13A to 13C are right perspective views of the braking system of FIG. 11 in a steer, neutral and brake position respectively, showing in details A and B central and lateral levering mechanisms thereof respectively.
Figure 13B:
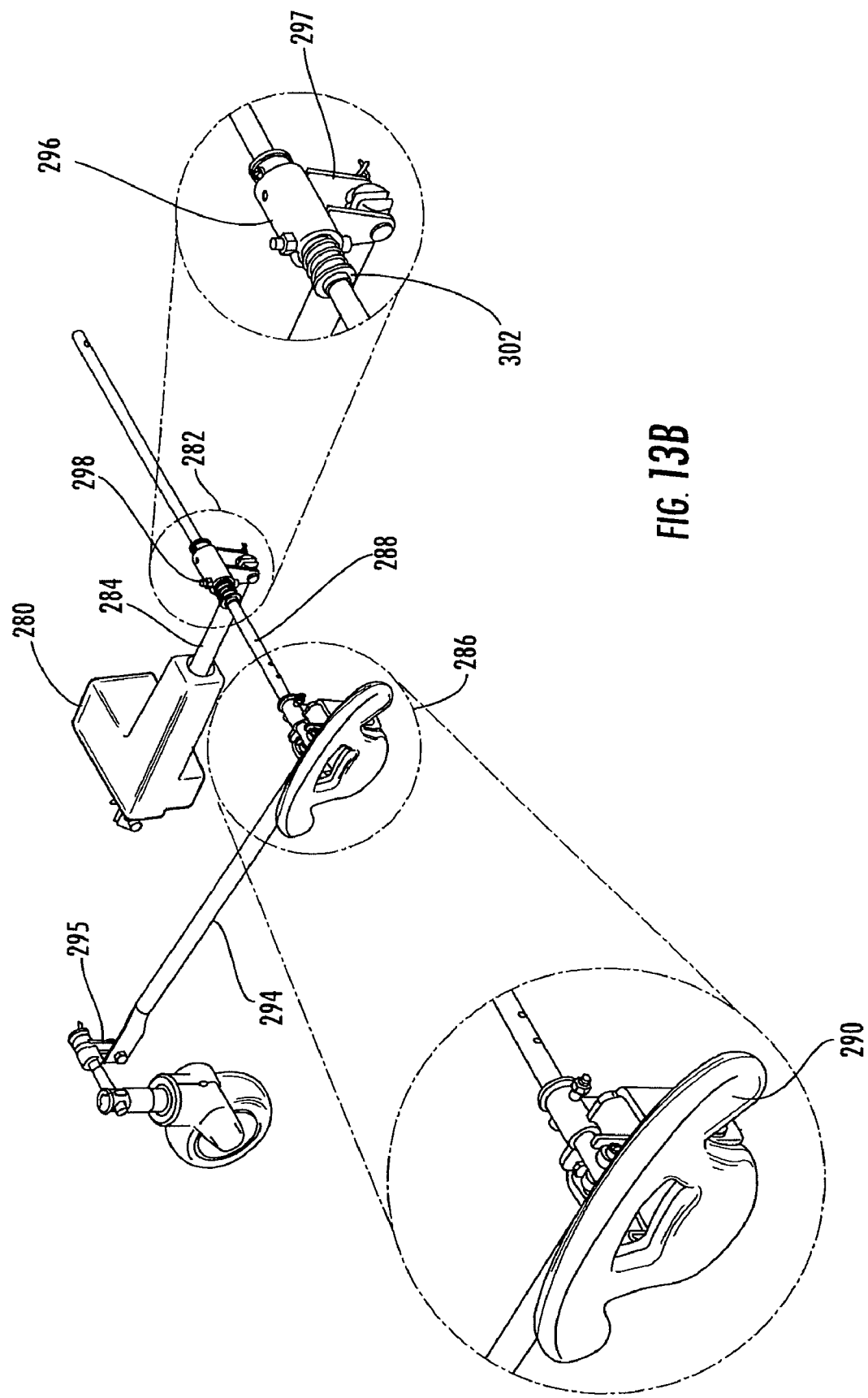
Figure 13C:
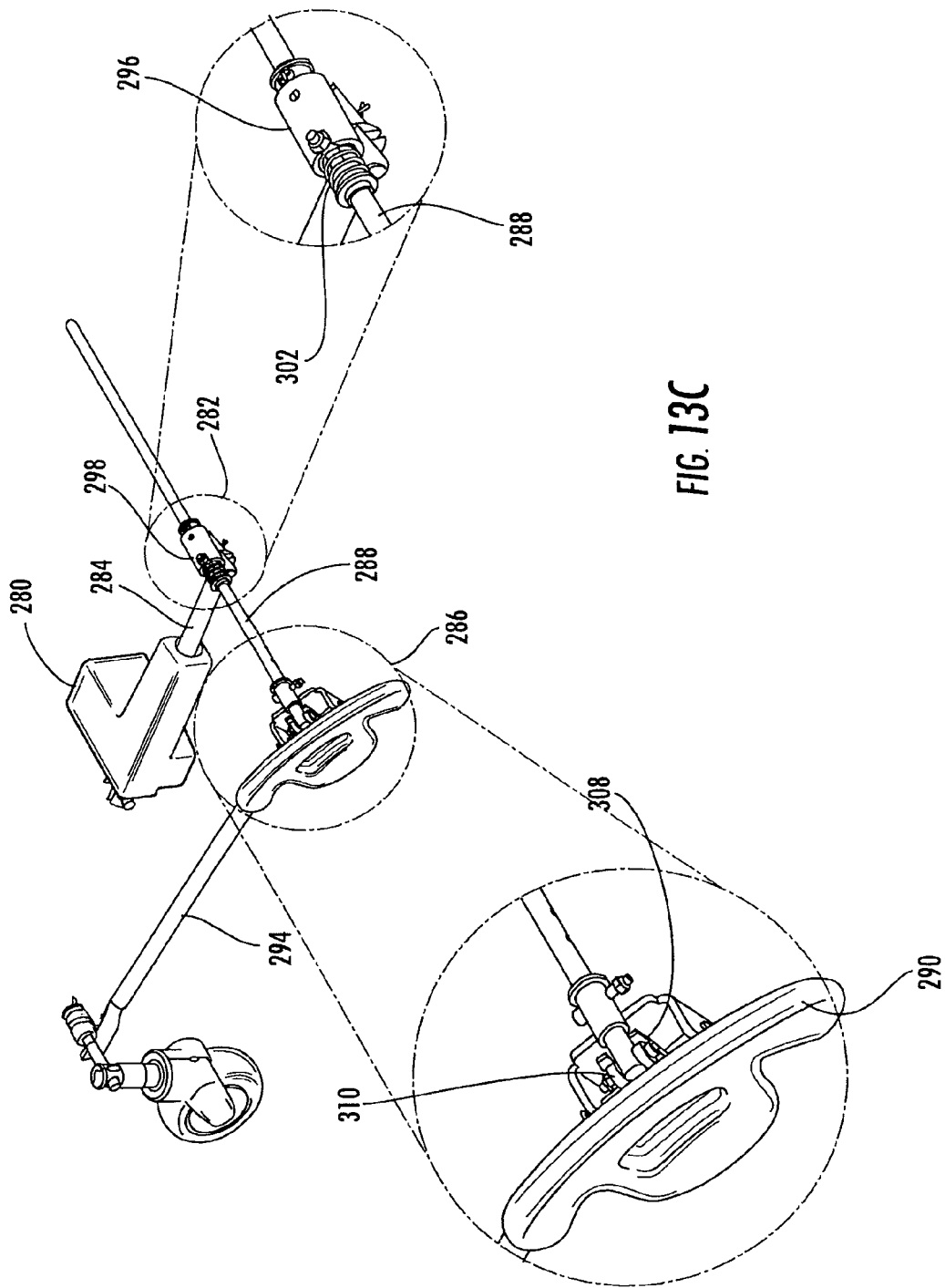
Figure 17A:
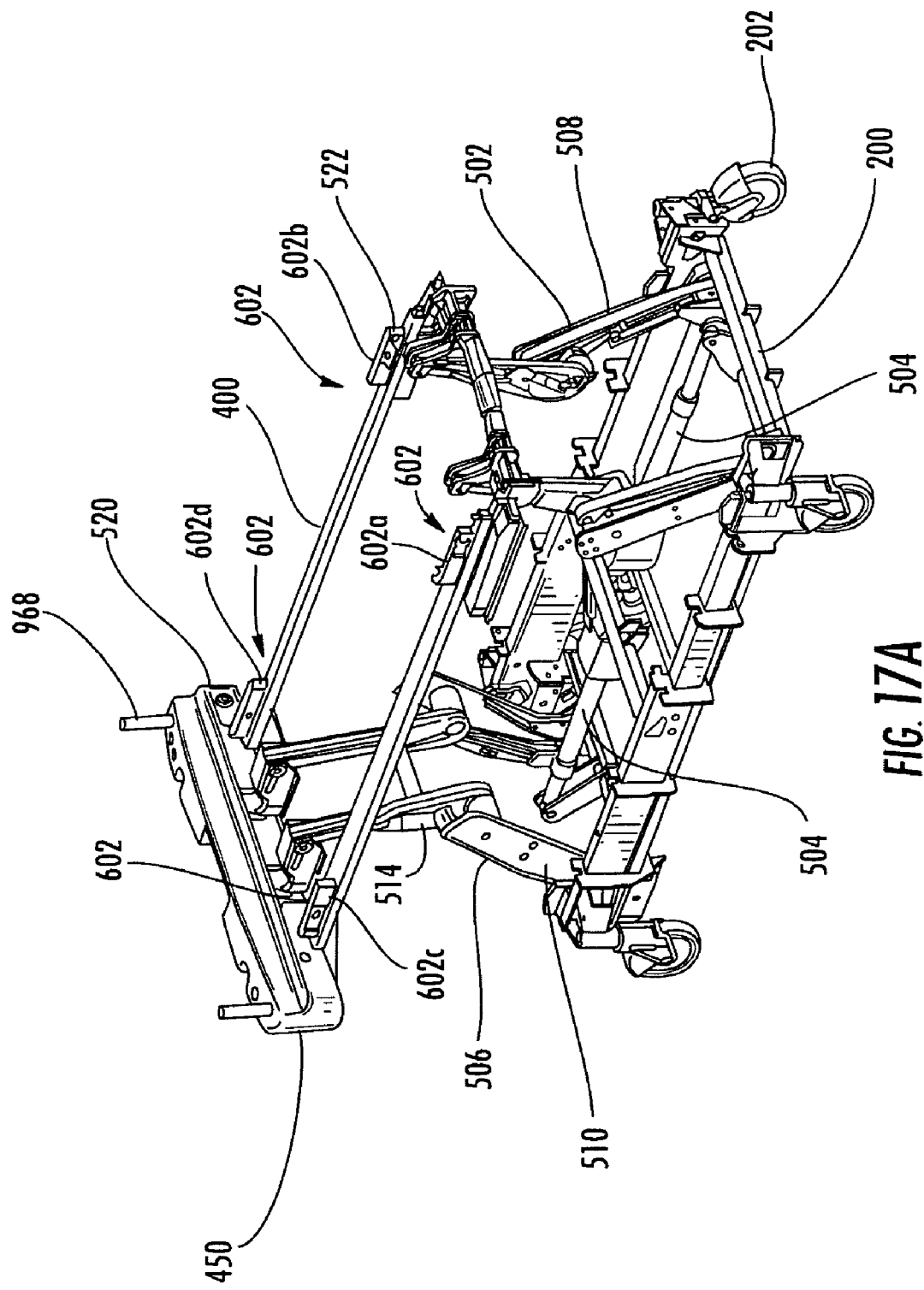
FIGS. 17A to 17D are right perspective views of an intermediate frame mounted via an elevation mechanism to the base frame of FIG. 9, wherein the intermediate frame is in a flat and elevated position, a Trendelenburg position, a reverse Trendelenburg position, and a flat and lowered position, respectively.
Figure 17B:
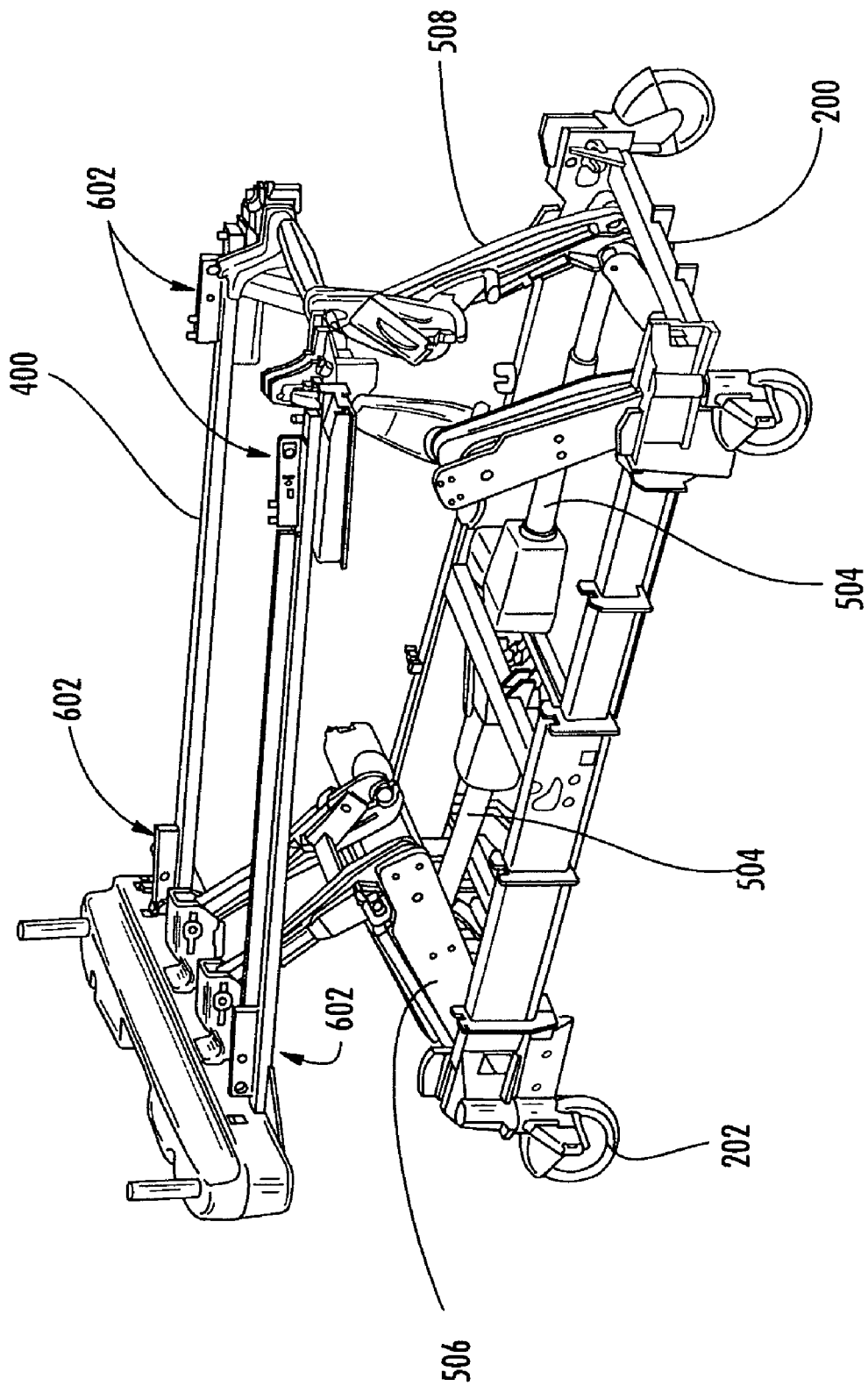
Figure 17C:
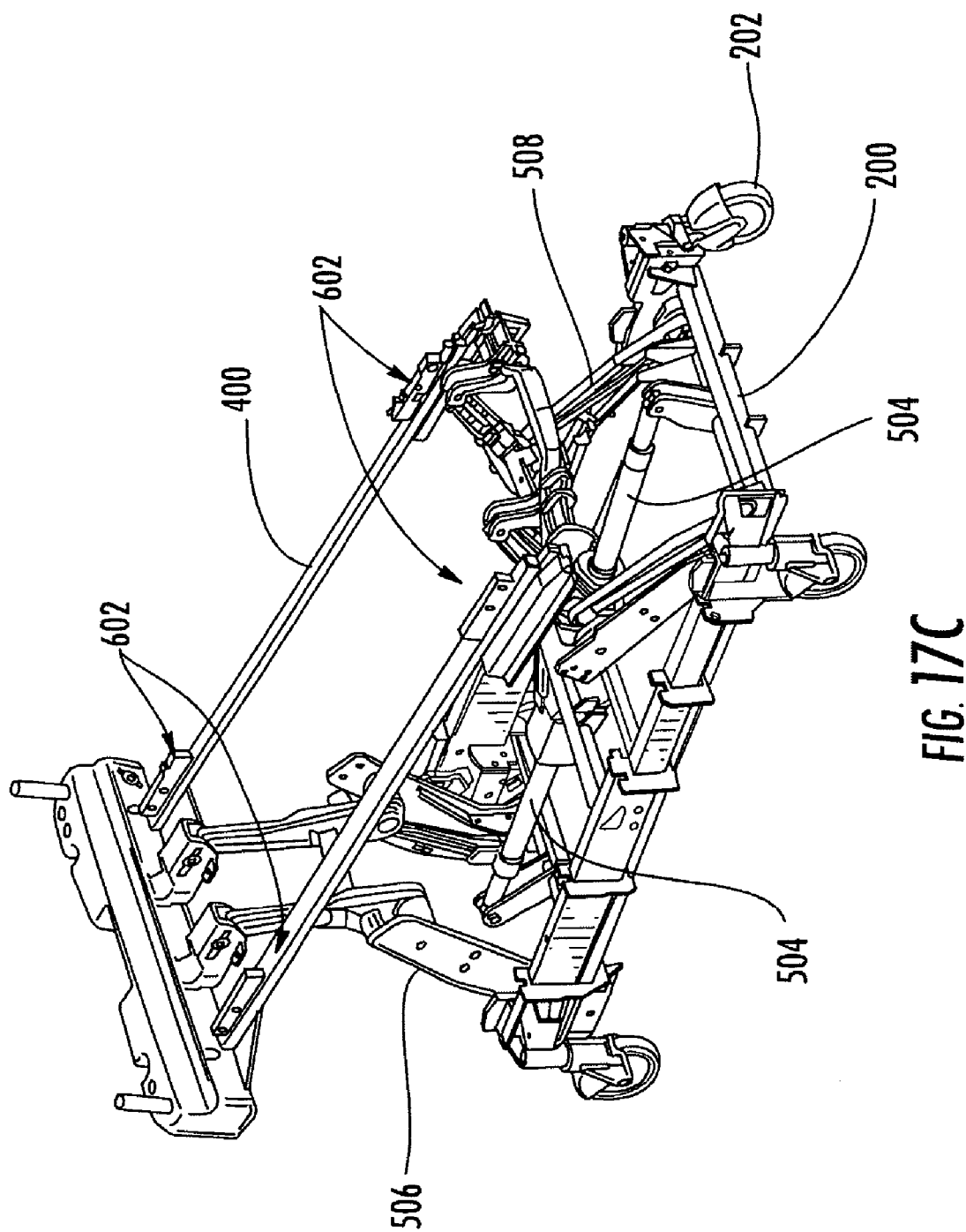
Figure 17D:
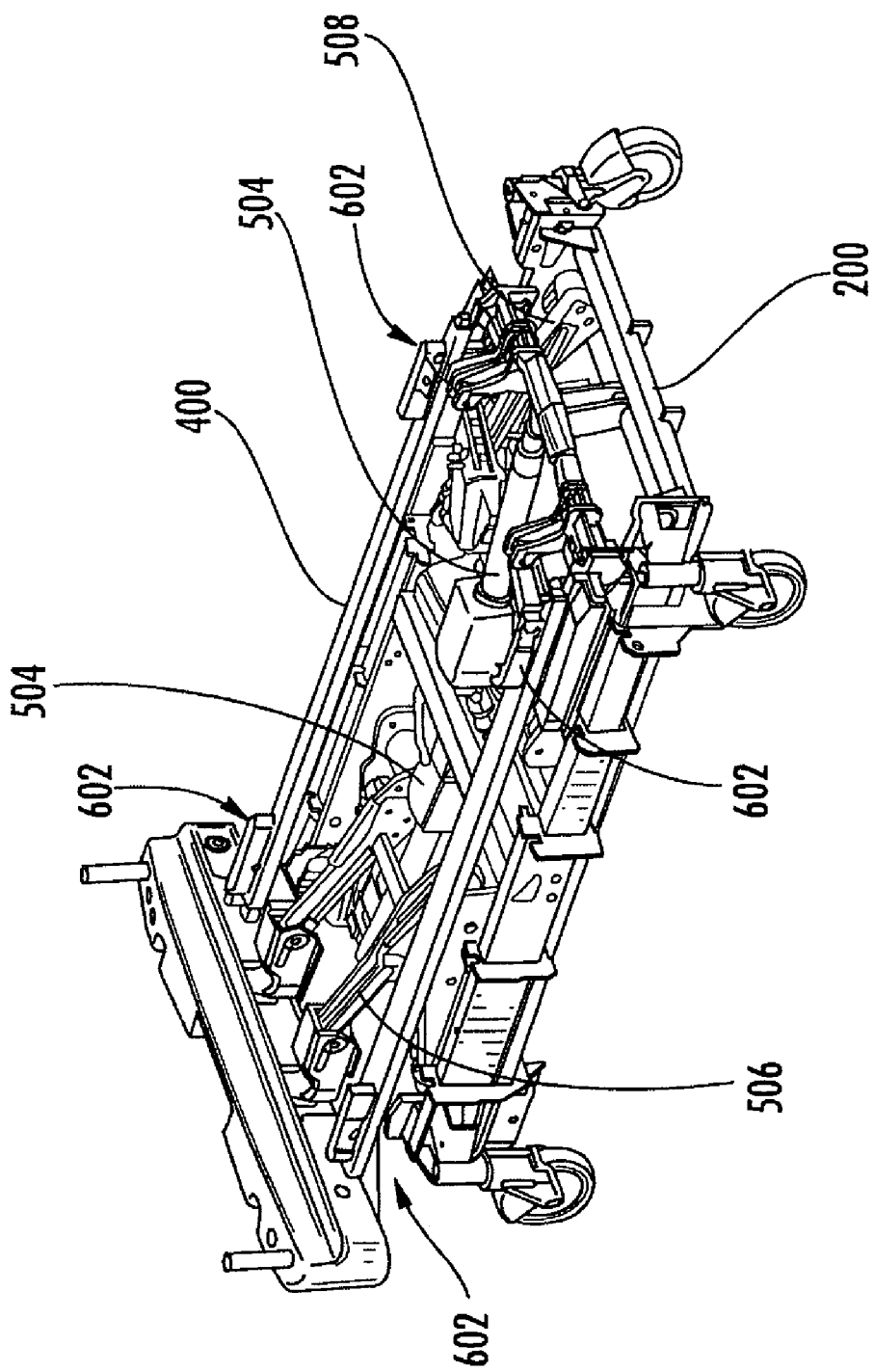
Figure 18A:
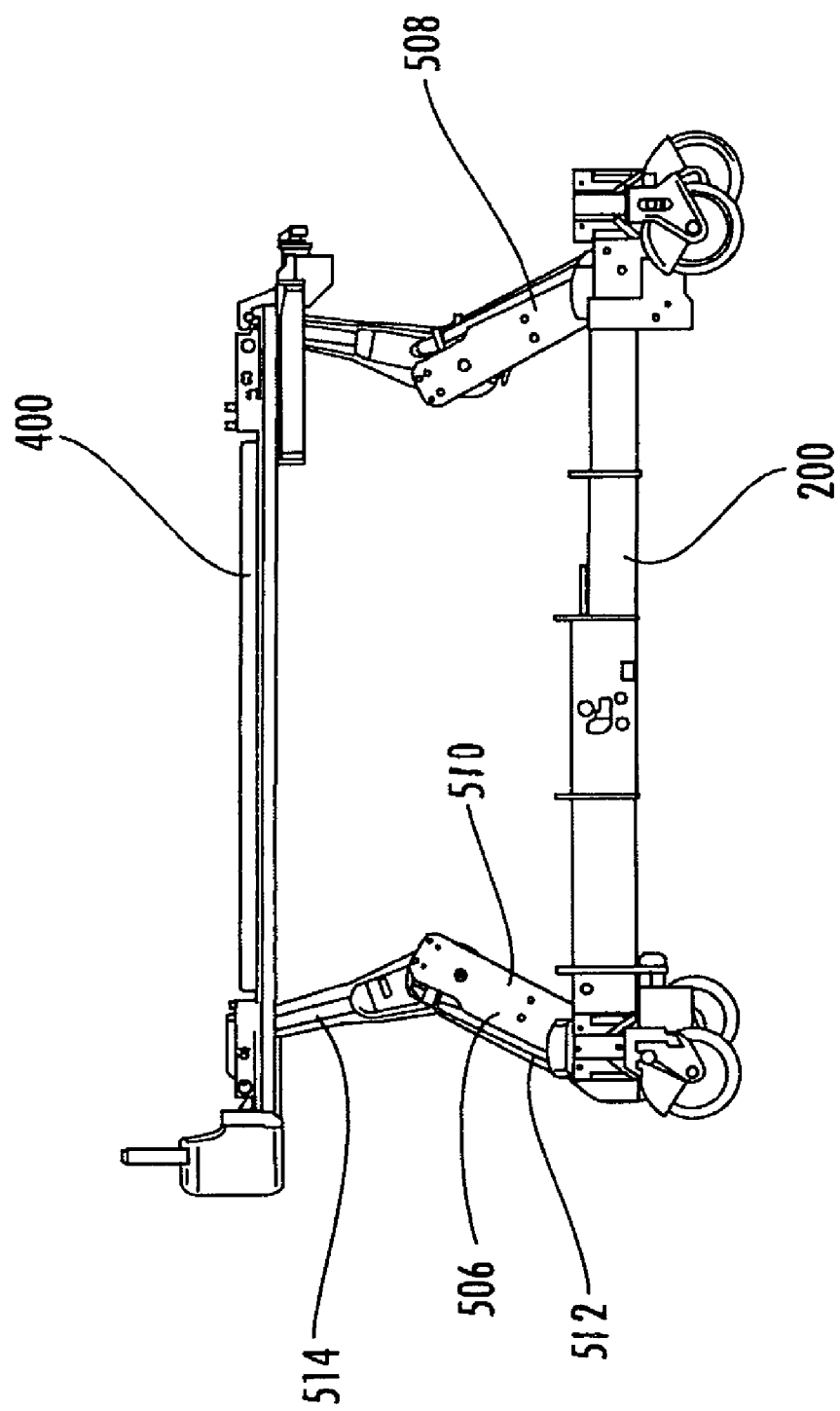
FIGS. 18A to 18C are right side views of an intermediate frame mounted via an elevation mechanism to the base frame of FIG. 9, wherein the intermediate frame is in a flat and elevated position, a Trendelenburg position, and a flat and lowered position, respectively.
Figure 18B:
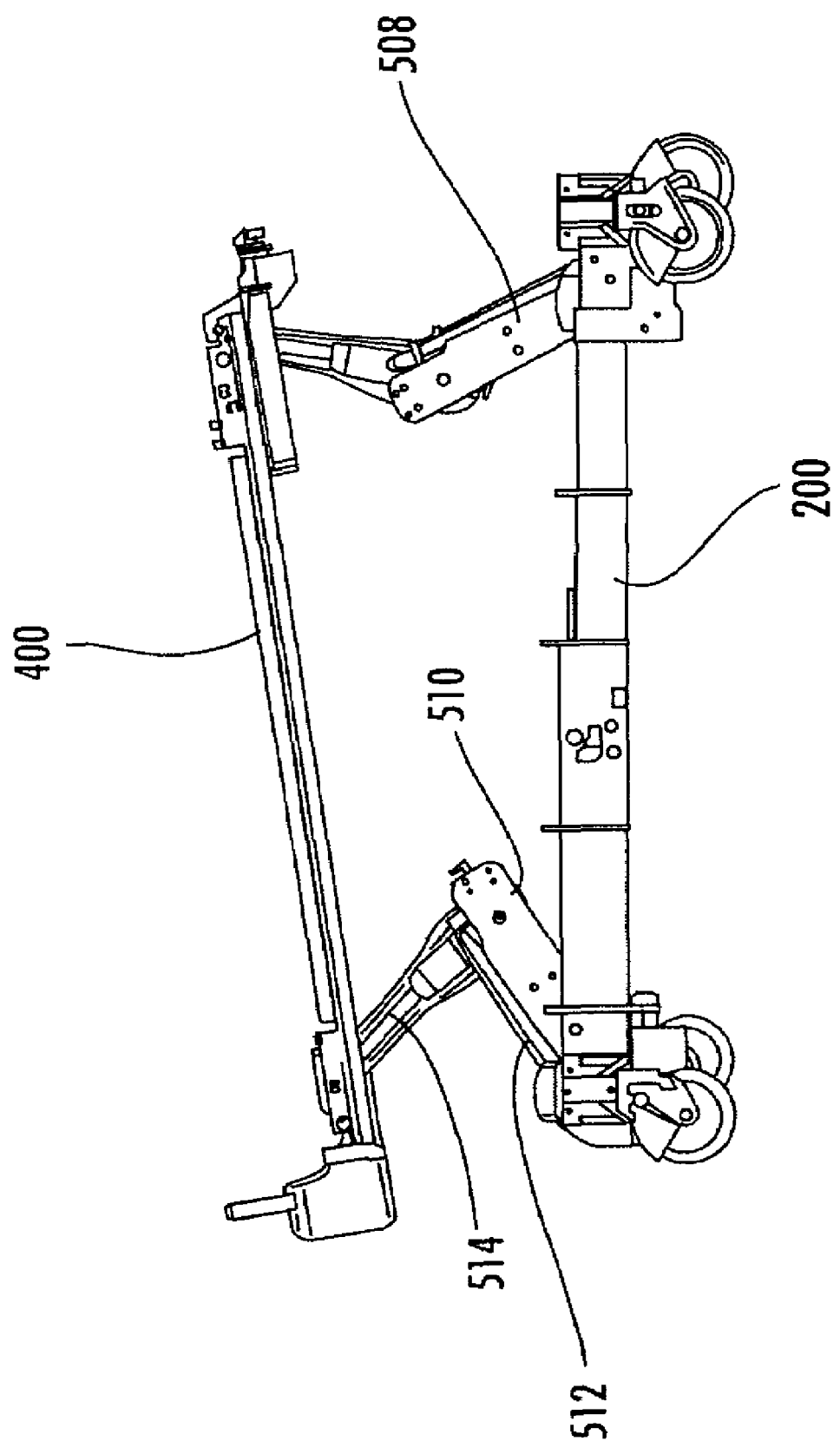
Figure 18C:
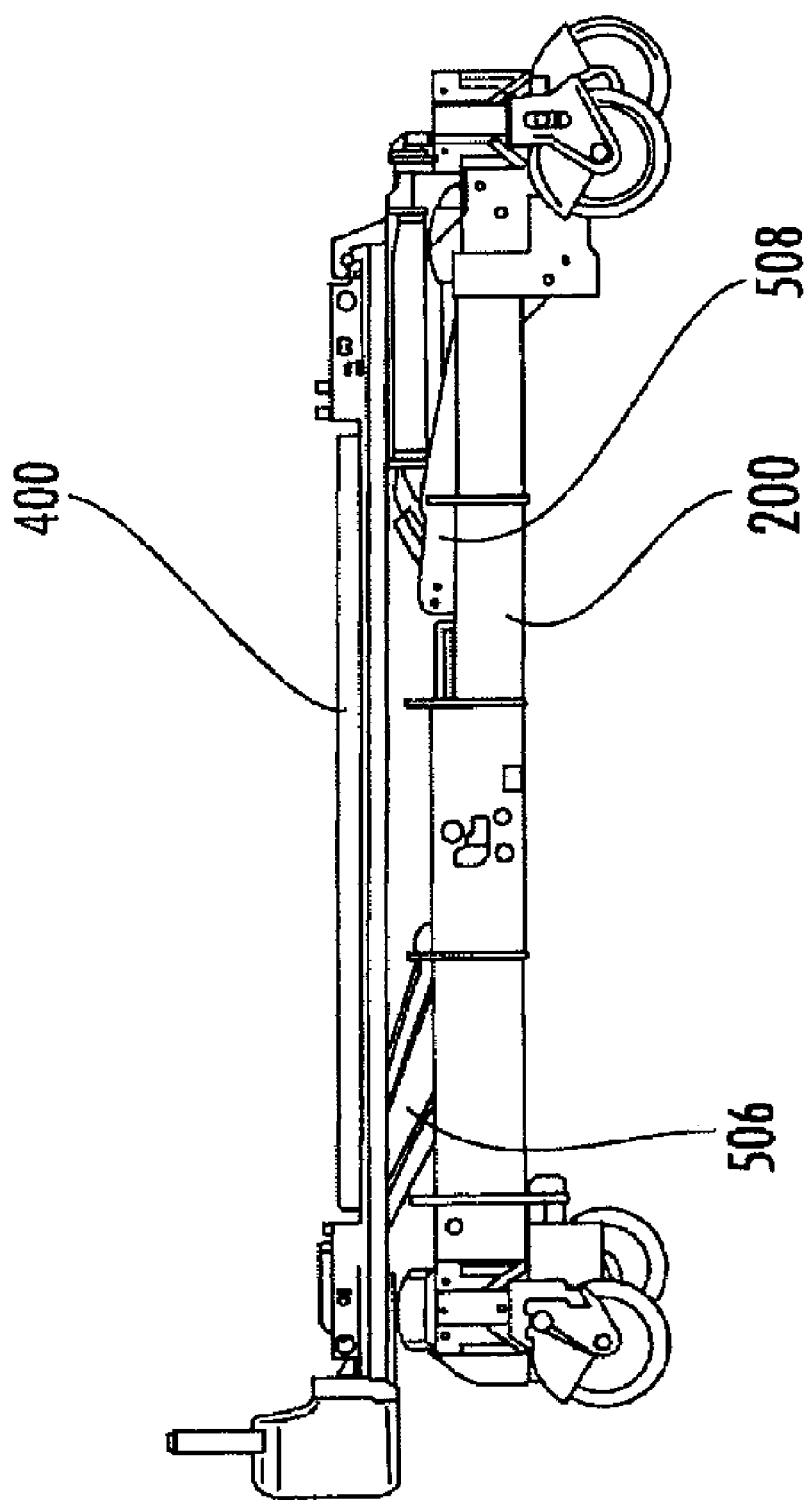
Figure 19:
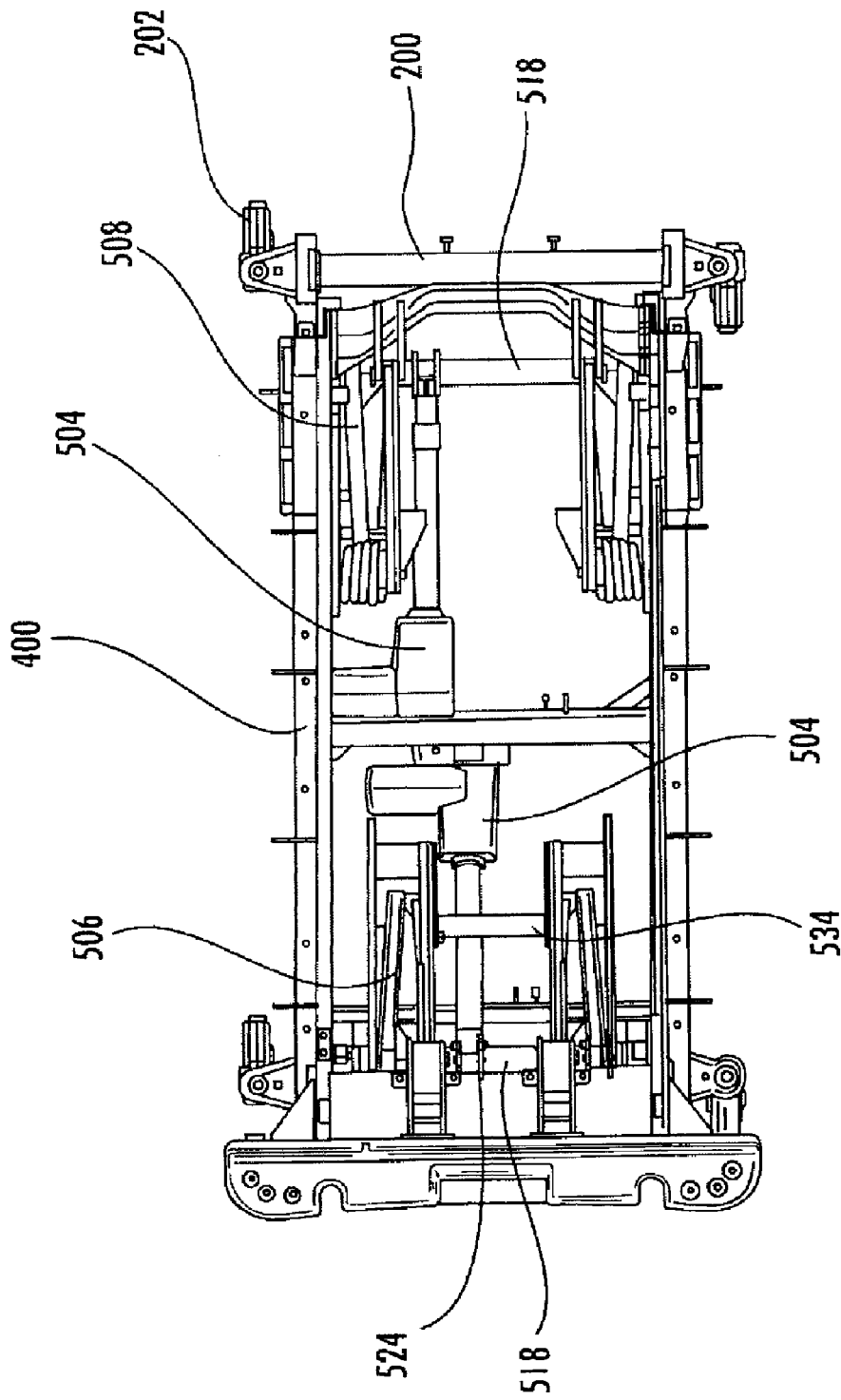
FIG. 19 is a top side view of an intermediate frame mounted via an elevation mechanism to the base frame of FIG. 9, wherein the intermediate frame is in a flat and lowered position.

FIGS. 13A to 13C show an automatic actuation of the braking system 206 in steer, neutral and brake positions respectively. For instance, in FIG. 13A, the actuator 280 fully extends the driven member 284 to pivot the handle 290 toward the head-end of the bed 100, thereby moving the bars 294 toward the foot-end of the bed 100, which in turn positions the caster breaking systems 292 in steer mode. In one embodiment, steer mode implies that all casters 202 are free to rotate and pivot, for example when a drive wheel mechanism is used. In another embodiment, steer mode implies that only head-end casters are free to rotate and pivot, while foot-end casters are pivotally immobilized. In the latter case, selecting the steer mode may pivotally immobilize the foot-end casters in their current orientation until a push or pull force is applied to the bed, at which point these casters will orient themselves with an axis of the bed and lock to maintain this orientation as they rotate.

In FIG. 13B, the actuator 280 partially extends the driven member 284 to level the handle 290, thereby centering the bars 294, which in turn positions the caster breaking systems 292 in neutral mode. In one embodiment, neutral mode implies that all casters 202 are free to rotate and pivot.

In FIG. 13C, the actuator 280 fully retracts the driven member 284 to pivot the handle 290 toward the foot-end of the bed 100, thereby moving the bars 294 toward the head-end of the bed 100, which in turn positions the caster breaking systems 292 in brake mode which immobilizes the casters 202. During operation when the bed 100 is not moving, users typically engage the braking system 206. Users can visually verify the status of the brake position with the status indicator 308, depicted in FIG. 12.

FIGS. 14 to 16 illustrate the manual override of the braking system 206, wherein the pedal 290 is deployed, generally by the foot of a user, though hand operation may also be contemplated. In general, as introduced above, when the pedal 290 is deployed, the pin 298 is released from notch 300 thereby uncoupling the actuator 280 and the shaft 288.

The pedal 290 can then be used to manually override the braking system 206 using foot or hand actuation. In FIGS. 14A to 14C, the actuator 280 coupling to the shaft 288 is released when in the steer position and remains in this position while the pedal 290 is moved from a brake position (FIG.

14A), through a neutral position (FIG. 14B), to a steer position (FIG. 14C). In FIGS. 15A to 15C, the actuator 280 coupling to the shaft 288 is released when in the neutral position and remains in this position while the pedal 290 is moved from a brake position (FIG. 15A), through a neutral position (FIG. 15B), to a steer position (FIG. 15C). In FIGS. 16A to 16C, the actuator 280 coupling to the shaft 288 is released when in the brake position and remains in this position while the pedal 290 is moved from a brake position (FIG. 16A), through a neutral position (FIG. 16B), to a steer position (FIG. 16C).

As stated above, when the pedal 290 is released, the pin 298 is again urged toward the sleeve member 296 such that as the sleeve 296 is rotated about the shaft 288 by activation of the actuator 280, the pin 298 eventually re-engages the notch 300 therein, thereby re-coupling the actuator 280 to the shaft 288 and caster braking mechanisms 292. Alternatively, the shaft 288 and pin 298 can be rotated manually using the stowed pedal 290 until the notch 300 is re-engaged by the pin 298.

The Elevation System

The bed 100 further comprises an elevation system 500 that allows the bed 100 to be raised or lowered relative to the floor. In certain embodiments of the invention, the elevation system 500 allows the bed 100 to be raised and configured into various positions. For example, as introduced above, the lift arms 502 and linear actuators 504 of the elevation system 500 may be configured to position the intermediate frame 400 of the bed 100, and ultimately the deck support 700 and lying surface 800 mounted thereon, in at least some of the following positions: a raised or upper substantially horizontal position wherein intermediate frame 400 is at least partially raised above the base frame 200 (e.g. see FIGS. 1 to 8, 17A, 18A and 20A); a Trendelenburg position wherein a head-end 402 of intermediate frame 400 is lower than a foot-end 404 thereof (e.g. see FIGS. 17B and 18B); a Reverse Trendelenburg position wherein the foot-end 404 of intermediate frame 400 is lower than the head-end 402 thereof (e.g. see FIGS. 17C, 20B and 20C, wherein the bed 100 in FIG. 20C is in a lowered Reverse Trendelendburg position); and a lowered substantially horizontal position wherein the intermediate frame 400 is lowered adjacent to the base frame 200 (e.g. see FIGS. 17D and 18C). Furthermore, the elevation system 500 enables raising and lowering of the bed 100 without any substantial longitudinal (or lateral) movement of the intermediate frame 400, and ultimately of the deck support 700 and lying surface 800 mounted thereon. As well, the elevation system can be driven by a motor, as illustrated herein, or be otherwise power-assisted, thereby minimizing the physical effort required to raise and lower the height of the bed 100. As will be described below, the elevation system 500 enables raising and lowering of the bed 100 without any substantial longitudinal (or lateral) movement of the intermediate frame 400, and ultimately of the deck support 700 and lying surface 800 mounted thereon. For example, the elevation system 500 enables raising and lowering of the bed 100 so that the support frame system remains substantially bounded between two parallel planes when raised or lower and further so that the maximum deviation along the longitudinal axis of the bed is less than 1 inch, more optimally less than ¾ inch, and more optimally less than ½ inch.

Figure 21:
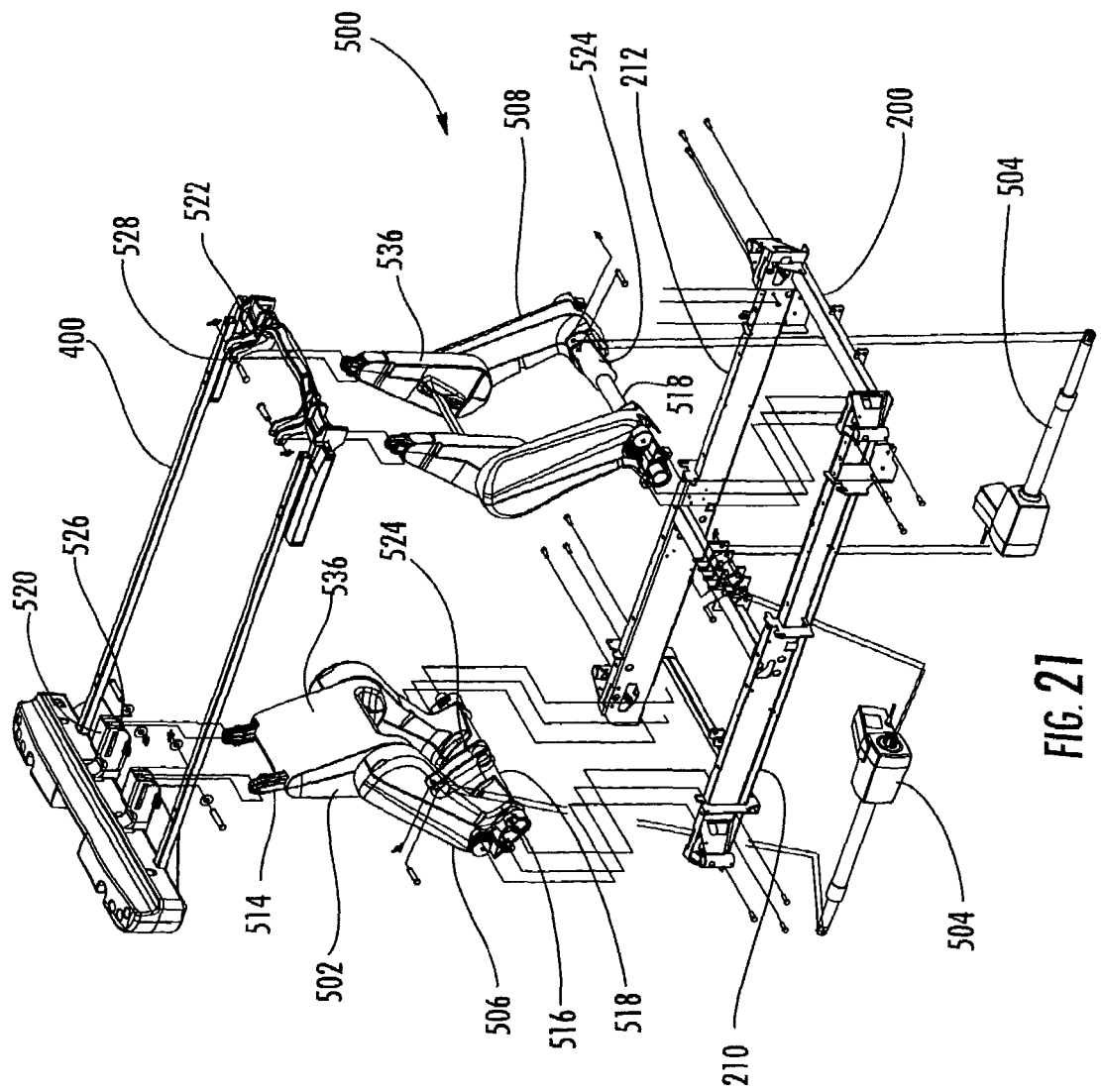
FIG. 21 is a exploded right perspective view of the intermediate frame, elevation mechanism and base frame of FIG. 17A, showing an interconnection of the elevation mechanism's elevation arms between the intermediate frame and the base frame.

With reference to FIGS. 17 to 23, and particularly to FIGS. 21 and 23, an illustrative configuration of the lift arms 502, in accordance with one embodiment of the elevation system 500 of the present invention, will now be described in greater detail. In this embodiment, the lift arms 502 are attached between the base frame 200 and the intermediate frame 400.

In particular, the lift arms 502 may comprise a pair of head-end lift arms 506 operatively coupled toward the head-end 102 of the bed 100, and a pair of foot-end lift arms 508 operatively coupled toward the foot-end 104 of the bed 100. Furthermore, each lift arm within pairs 506 and 508 comprises a pair of cooperating primary and secondary lower arm members 510 and 512, and an upper arm member 514, the combination of which being actuated by a linear actuator 504 respective to each pair 506 and 508.

Figure 22A:
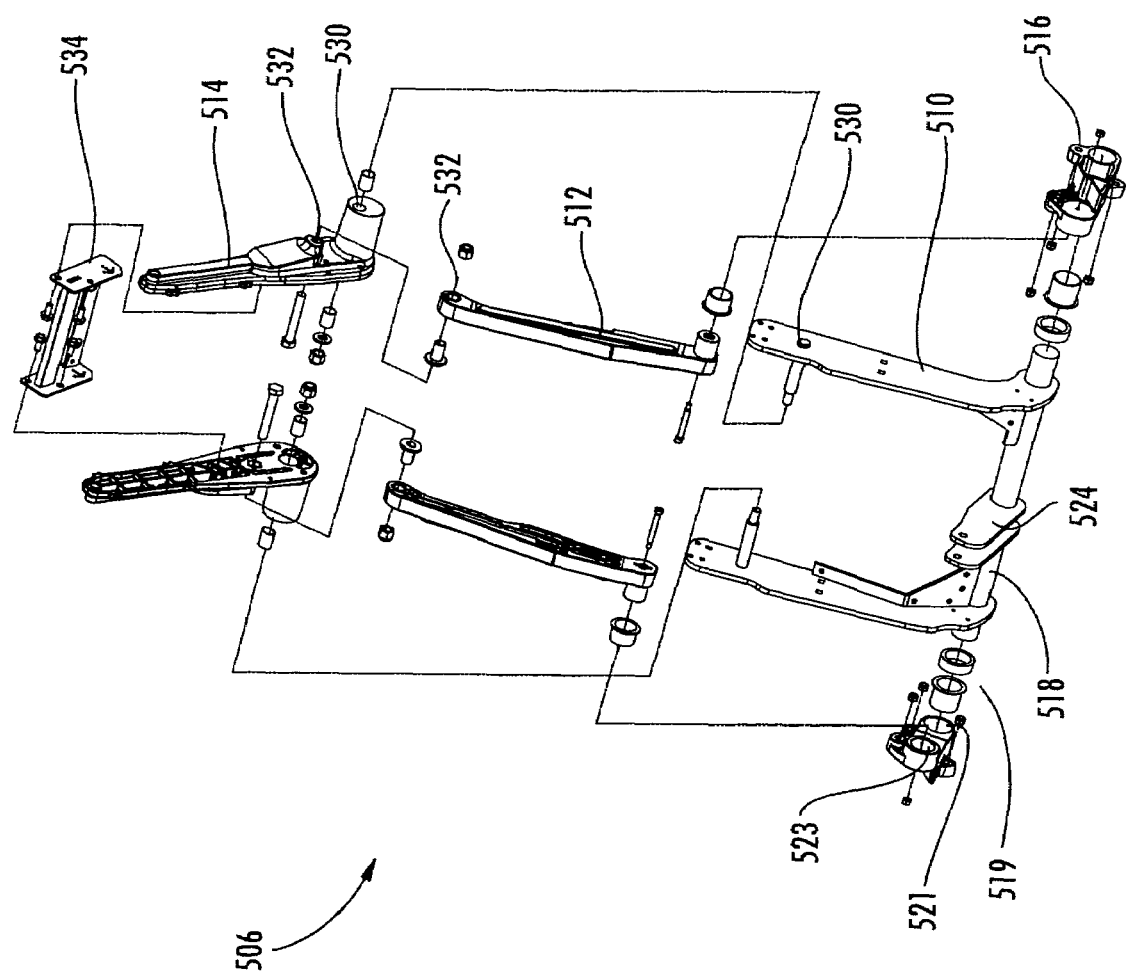
FIGS. 22A and 22B are exploded perspective views of the head-end and foot-end elevation arms of FIG. 21, respectively.
Figure 22B:
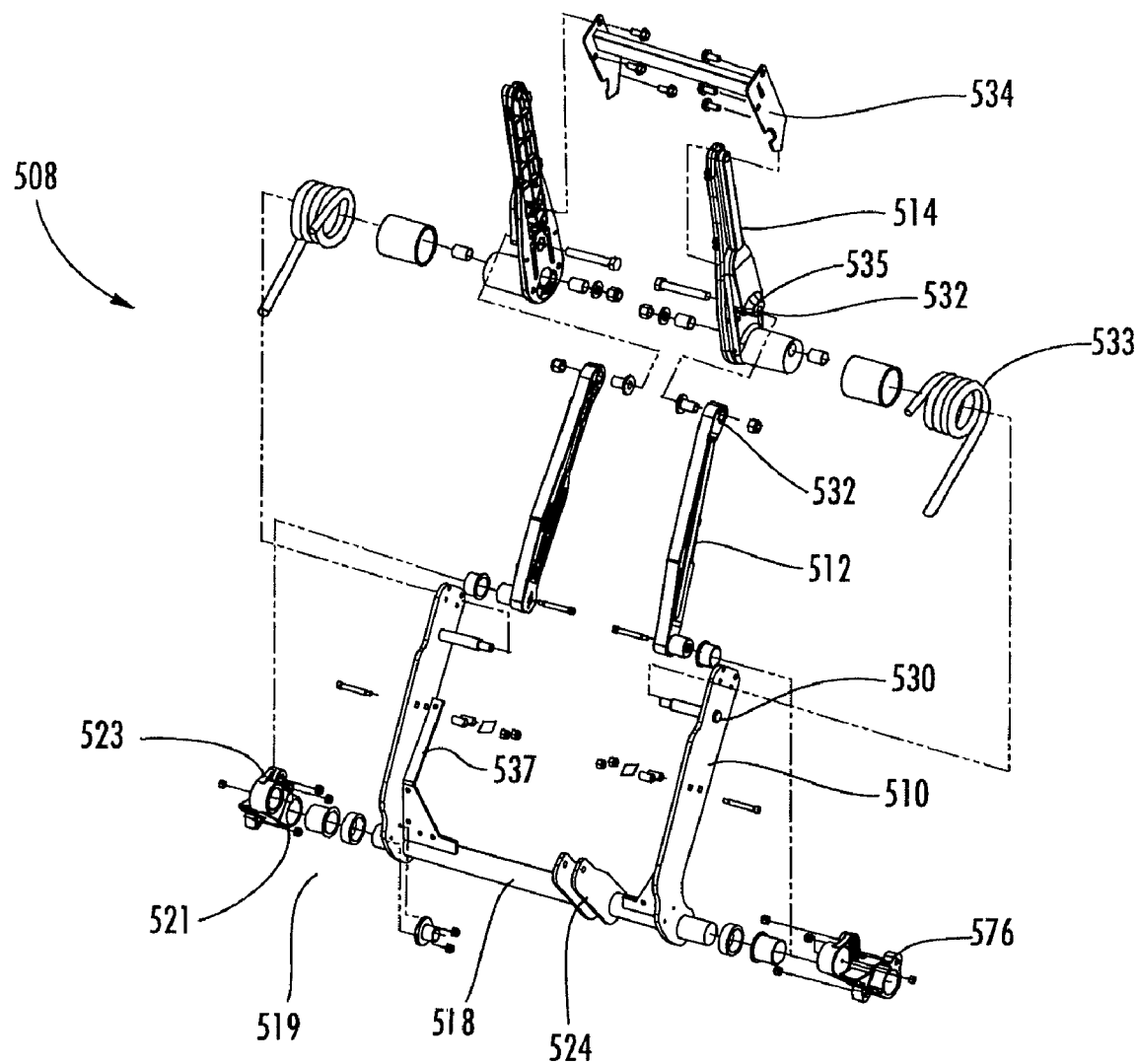

FIGS. 22A, 22B and 23 provide exploded views of an assembly of the head-end lift arms 506 (FIGS. 22A and 23) and foot-end lift arms 508 (FIG. 22B). As stated above, each lift arm 502 comprises a pair of cooperating primary and secondary lower arm members 510 and 512, and an upper arm member 514. In general, the lower arm members 510, 512 are coupled to the base frame via a coupling bracket 516 fixedly attached to the side rails 210, 212 of the base frame 200. In particular, the primary lower arm member 510 is fixedly coupled to an actuation shaft 518 that is rotatably coupled in a conventional manner (e.g. via a bushing assembly 519 or the like) within a cylindrical cavity 521 of bracket 516. A pair of levering flanges 524, fixedly disposed on the shaft 518, are used to couple the shaft 518 to one of the linear actuators 504 thereby configured to impart a rotation to the shaft 518 and to the primary lower arm member 510 thereabout. The secondary lower arm member 512 is also rotatably coupled in a conventional matter within a second cylindrical cavity 523 of bracket 516, and is generally not directly affected by a rotation of the shaft 518.

The upper arm member 514 is pivotally coupled at its upper end to the intermediate frame 400 via a coupling bracket 520 (or brackets 522 for foot-end pairs 508) and at its lower end to the lower arm members 510, 512. Note that the coupling bracket 520 for head-end arms 506 comprises a linear slot 526 to accommodate a relative longitudinal displacement of the upper ends of upper arm members 514 of the head-end and foot-end pairs 506 and 508 respectively, whereas the coupling brackets 522 for foot-end arms 508 comprise a single pivot point 528. This linear slot 526 is generally provided to accommodate such longitudinal displacements when the head-end or foot-end of the bed 100 is lowered relative to the other, for instance to achieve a Trendelenburg or reverse Trendelenburg position. The person skilled in the art will understand that a similar elevation system 500 could provide a linear slot at the foot-end of the bed 100, or again a combination of slots depending on the selected lift arm geometry.

The coupling of the upper arm member 514 to the lower arm members 510, 512 is provided via two distinct pivot points 530 and 532, respectively. Based on this geometry, as the primary lower arm member 510 pivots with shaft 518, the pivot point 530 is urged to revolve with the shaft 518 in its direction of rotation. Simultaneously, the secondary lower arm member 512 will impart a counteracting force upon pivot point 532 thereby urging the upper arm member 514 to pivot about pivot point 530 in a rotational direction opposite to that of the primary arm member 510.

For example, with reference to FIGS. 21, 22A and 23, when the head-end arm pair 506 is in a lowered position, the actuator 504 associated therewith may be activated to impart a counterclockwise rotation to the shaft 518, which imparts a counterclockwise rotation of the primary lower arm members 510, and consequently a counterclockwise revolution of the pivot points 530, about this shaft. Simultaneously, the secondary lower arm members 512 will urge, via pivot point 532, the upper arm members 514 to pivot about pivot point 530 in a clockwise direction, thereby raising the head-end 102 of the bed 100. As will be readily understood by the person skilled in the art, reverse operation of the actuator 504 will reverse the above process to lower the head-end 102 of the bed 100. It will also be understood that the foot-end lifting arm pair 508 may be operated in a similar fashion.

In one embodiment, the pivot points 530 between primary lower arm members 510 and upper arm members 514 of the foot-end lift arms 508 are upwardly biased by a torsion spring 533 disposed about these pivot points 530, a first leg of which being secured beneath outwardly extending pivot pins 535, and a second leg of which being secured above inwardly extending flanges 537. This spring-loaded embodiment may be useful, for example, to assist the lift mechanism 500 when most of the patient's weight is on the foot-end of the bed 100, for example in a seated or head-elevated position. Further, torsion spring 533 may reduce the load on the actuator and alleviate power to the actuator. Typically, the greatest forces on the actuator occur when the patient support is at its lowermost position relative to the base. Therefore, spring 533 reduces the load on the actuator for at least a portion of the range of motion of the actuator (or the patient support relative to the base). For example, the spring 533 may reduce the force for at least the 50% of the range of motion for the actuator (or for patient support). It will be appreciated that a similar spring-assisted system may be contemplated for the head-end lift arms 506 if needed, without departing from the general scope and nature of the present disclosure.

With reference to FIGS. 24A, 24B and 25A to 25D, in one embodiment, to achieve a substantially vertical elevation with minimal longitudinal deviation of the intermediate frame 400 relative to the base frame 200, the primary and secondary lower arm members 510, 512 are disposed to define an angle between them. By proper selection of the length and disposition of the lower arm members 510, 512, as well as the angle defined between them, a longitudinal deviation of the intermediate frame 400 relative to the base frame 200 as the elevation system 500 extends and retracts can be minimized. For example, a maximum deviation of 1 inch or less, more optimally of ¾ inch or less, and even more optimally of less than ½ inch.

As illustrated in FIGS. 22A and 22B, the upper and/or lower arm members of a given pair may be interconnected by a reinforcing member 534 to solidify and maintain a distance between such arm members. Also, as illustrated in FIGS. 21 and 23, lifting arm covers 536 may be provided to cover the lifting arm mechanism described above and thereby provide an aesthetic finish to the bed's elevation system 500. For example, the upper arm members 514 may be covered by a common cover that is formed by two cover halves 536a that when coupled together span across the upper arm members 514. Each of the pairs of lower arm members 510, 512 similarly may include a cover formed from two cover halves 536b, 536c. As best seen in FIG. 23, these covers have a split-housing construction, which are then fastened together about the respective arm components with a snap-fit or other similar connections. Covers 536 may be formed, such as by molding, including molding from plastic or from aluminum or magnesium or other moldable materials. Covers 536 may also be cast from, for example aluminum.

Figure 24A:
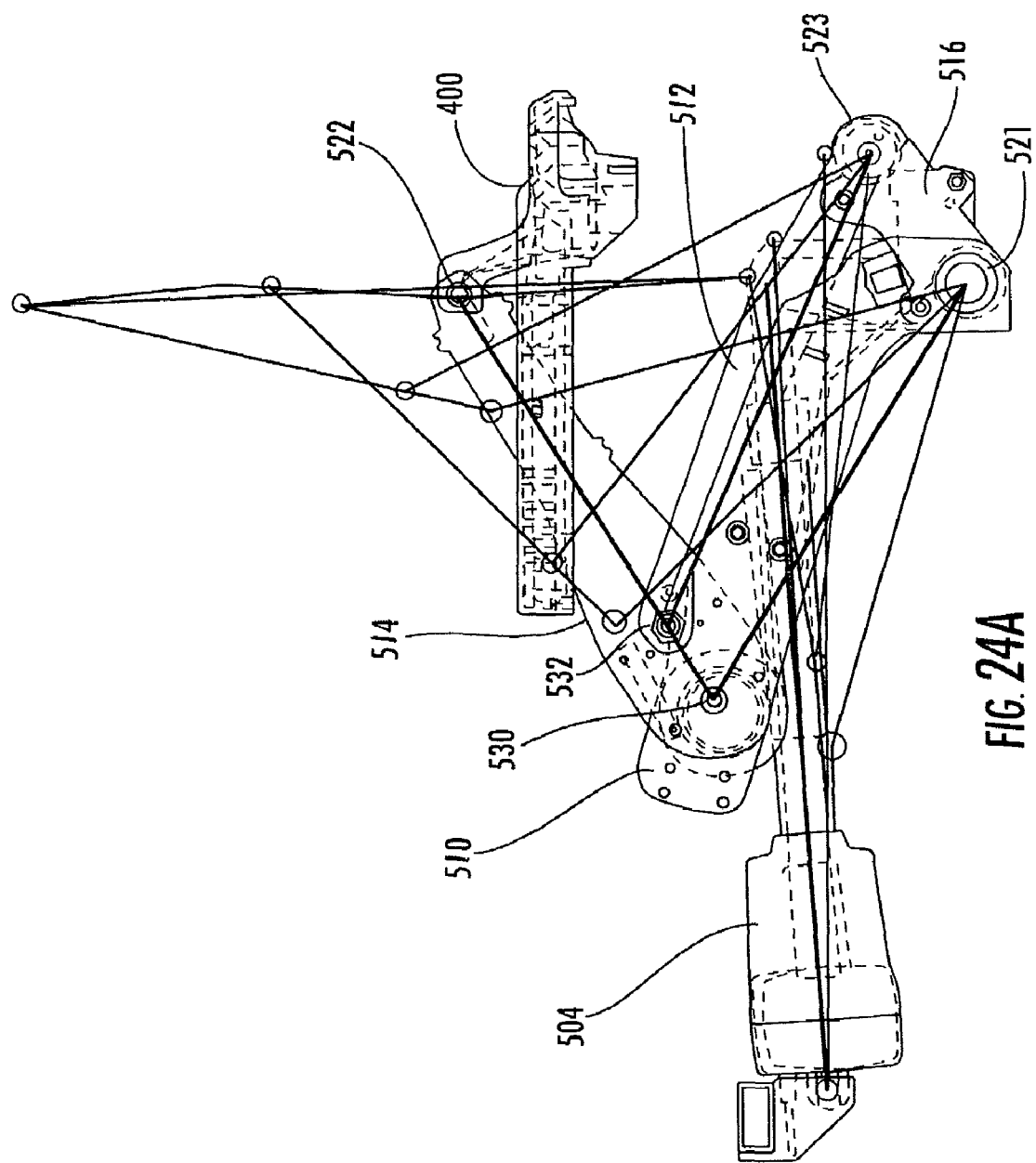
FIGS. 24A and 24B are side views of an elevation mechanism geometry in accordance with one embodiment of the present invention, wherein a progression of the elevation mechanism geometry is shown through various positions thereof, one of which being superimposed on an exemplary lift arm mechanism in FIG. 24A.
Figure 24B:
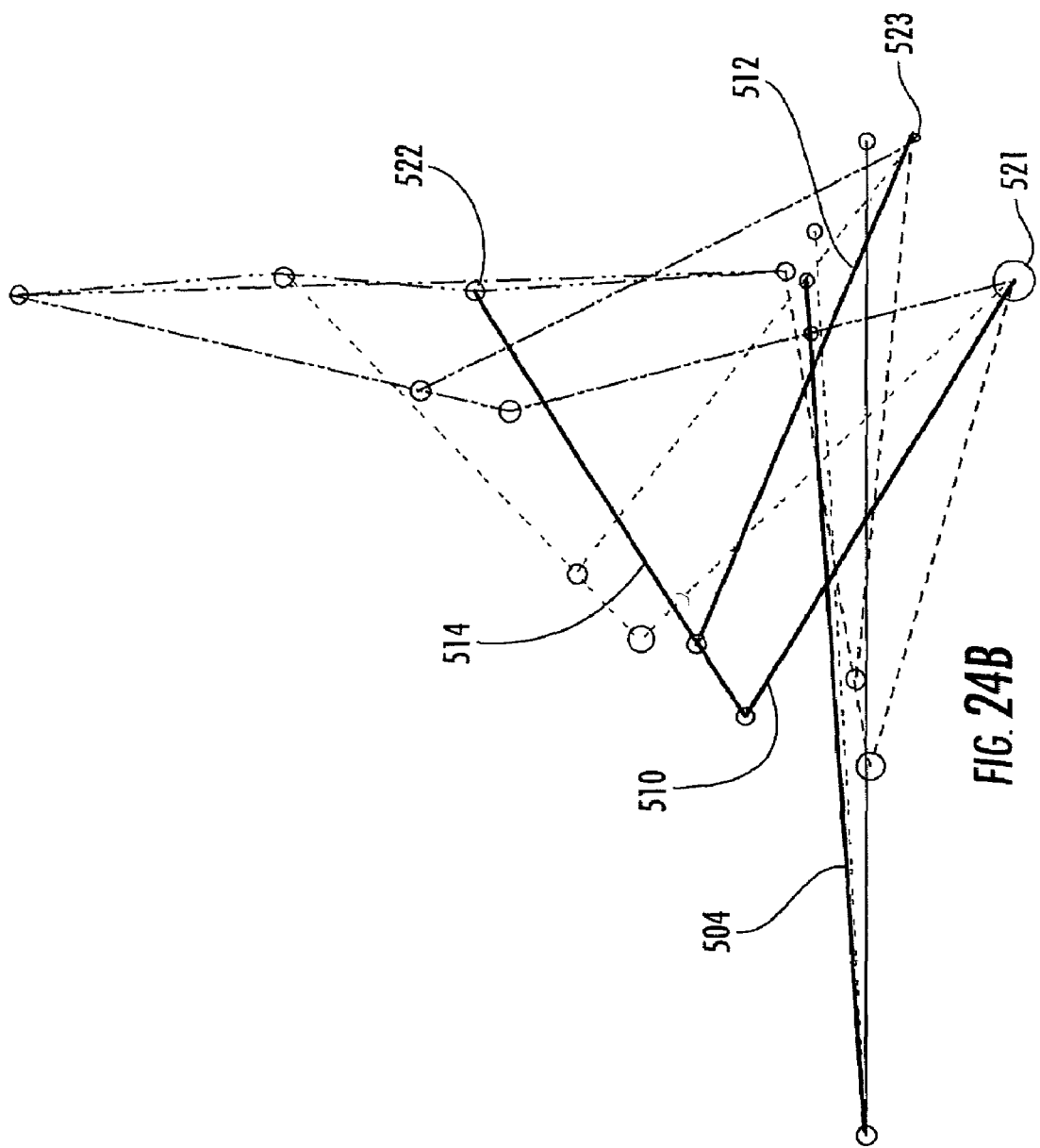

In FIG. 24A, the geometrical axes of the actuator 504, the primary and secondary lower arm members 510, 512, and the upper arm member 514 are shown for various elevations of the intermediate frame 400, the axes corresponding to the depicted components of the elevation mechanism 500 at a next to lowermost position being shown in bold. In FIG. 24B, the same axes are shown without illustration of the mechanism's components, reference numerals generally associated with these components being associated with their respective corresponding axes instead. As can be seen in these Figures, the respective axes of the primary and secondary lower arm members 510, 512 are angled relative to one another, which allows for the longitudinal travel of the intermediate frame 400 as it raises and lowers, illustrated by the displacement of the coupling bracket 522, to be minimized. For instance, the amplitude of the sinusoidal path or curve traced by the bracket 522 as it moves up and down under action by the lift arm 502 is kept relatively small. For example, the maximum amplitude of less than 1 inch, more optimally less than ¾ inch, and more optimally less than ½ inch. By adjusting the angle between the primary and secondary arm members 510, 512, this result may be improved to a desired setting.

Figure 25A:
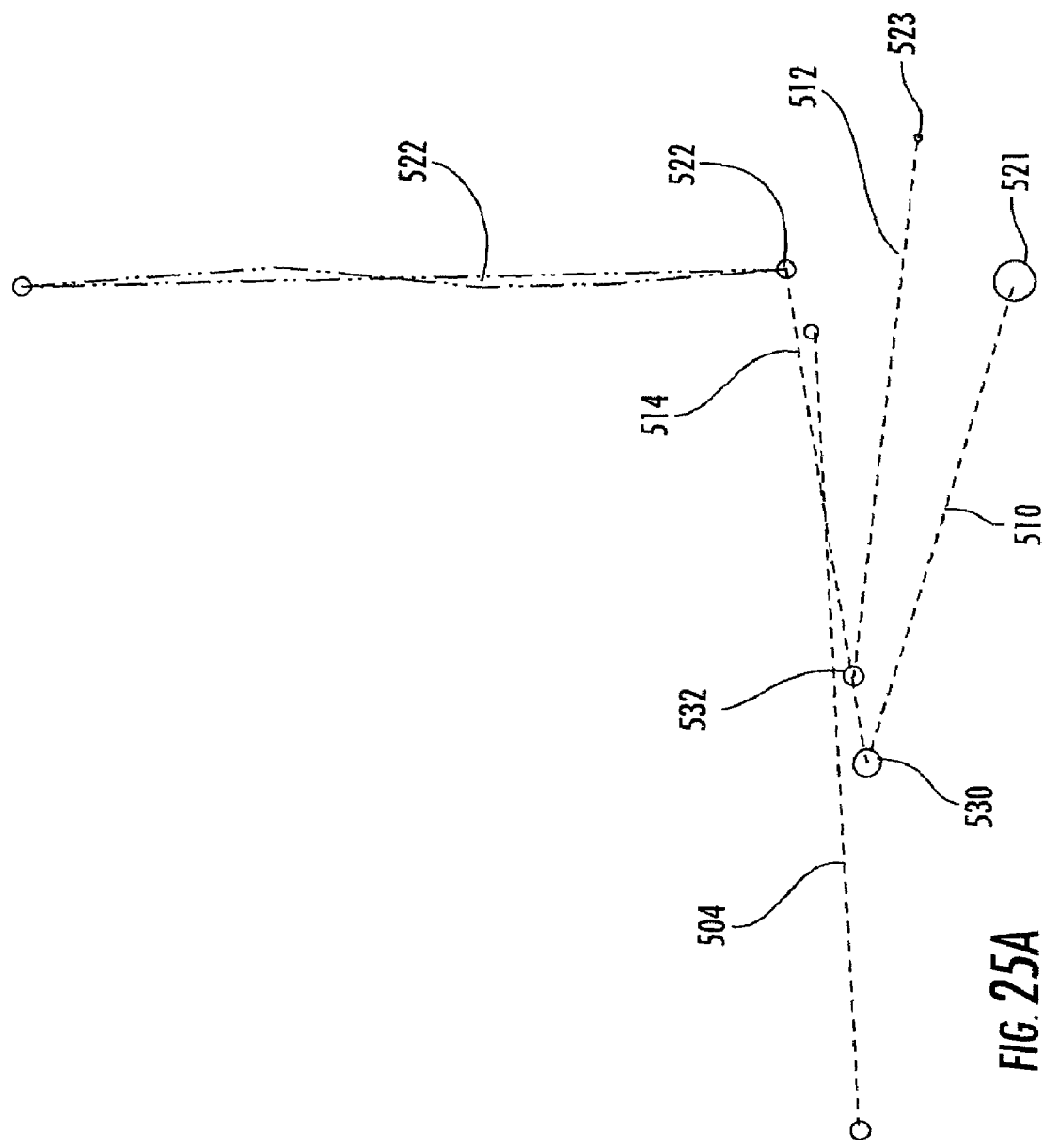
Figure 25D:
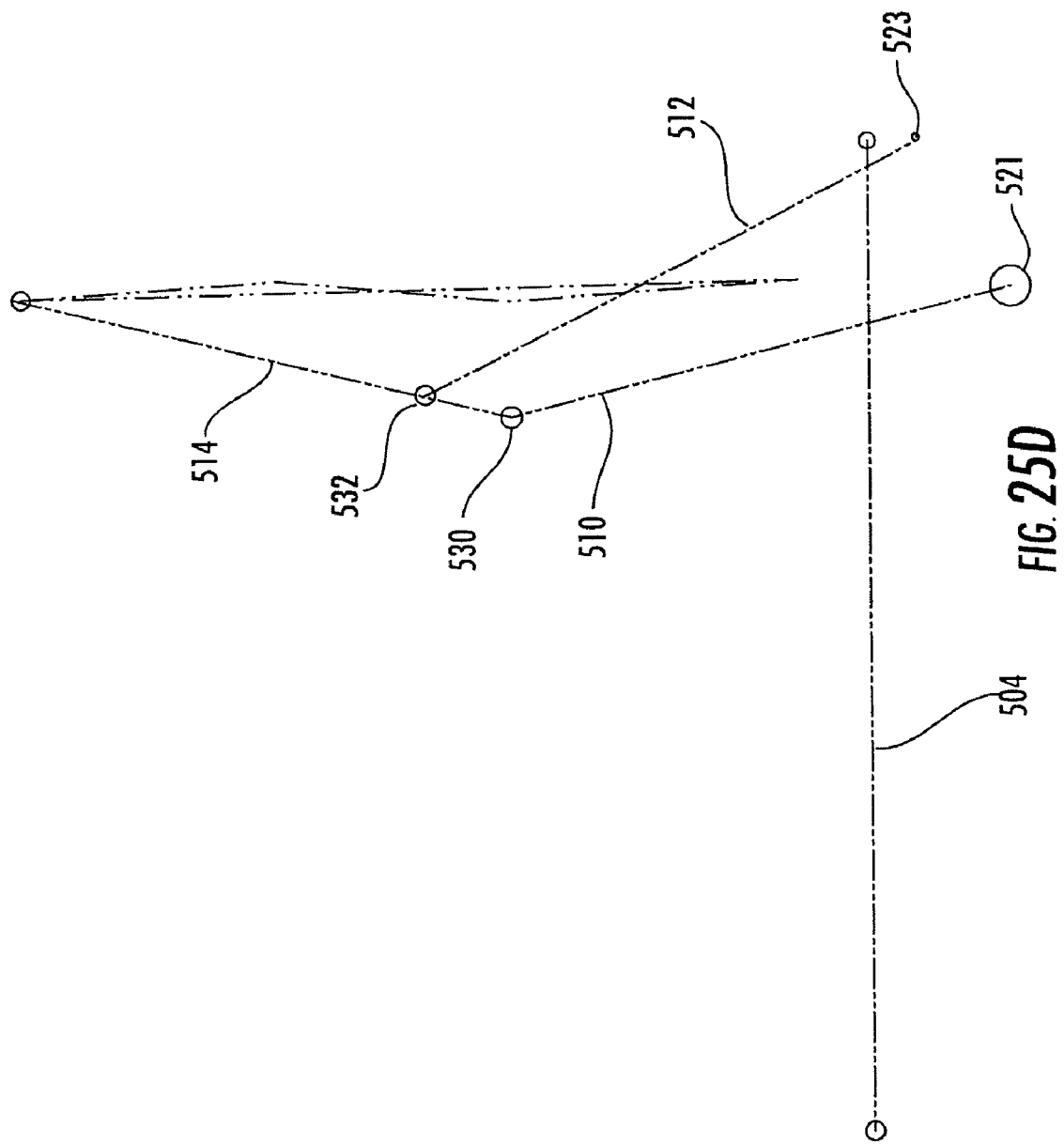

FIGS. 25A to 25D show a displacement of the aforethe axes from a lowermost position (FIG. 25A) to an uppermost position (FIG. 25D). Using this design, the bed 100 may be raised and lowered by the elevation system 500 with minimal longitudinal displacement. As will be readily apparent to the person of skill in the art, the characteristics described with reference to FIGS. 24A, 24B and 25A to 25D wherein the foot-end lift arms 508 are depicted, may apply equally to the head-end lift arms 506. As such, by minimizing a longitudinal travel of the intermediate frame 400 under action from both the head-end and foot-end lift arms 506, 508, an overall longitudinal travel of the intermediate frame when raised or lowered is minimized.

In accordance with one embodiment of the invention, the lifting mechanism 500 is governed by the control system 1000 introduced above and described in further detail below. For instance, actuation of actuators 504 may be controlled by one or more user actuatable devices, such as push buttons or interactive displays on one or more control panels 1004 such that a positioning and orientation of the bed's intermediate frame 400 (and deck support 700 and lying surface 800 mounted thereon) relative to the base frame 200 is governed electronically. These and other such considerations will be discussed further herein below.

The Intermediate Frame

Some aspects of the versatility and adjustability of the bed 100, in accordance with different embodiments of the present invention, are achieved by providing an intermediate frame 400 that is designed to allow a variety of adjustments to the foot-end of the bed 100, particularly of the foot sections 706 and 806 of the deck support 700 and lying surface 800 respectively. In one embodiment, the intermediate frame 400 allows the bed 100 to be configured into positions where a patient's legs are lower than the rest of the body (e.g. see FIG. 4), such as in a partially or fully seated chair configuration (e.g. see FIGS. 5 to 7). For instance, by providing an intermediate frame 400 whose length is at least partially reduced relative to the full length of the bed 100, actuation of the foot section 706 of the deck support 700 pivotally connected thereabove may be facilitated in a downward direction as a structural obstruction commonly produced by a full length intermediate frame is reduced and/or avoided completely. For example, the length of the intermediate frame 400 is less than the deck support 700 and optimally terminates at or near the pivot point of foot-end section 706 of deck support 700.

Such an intermediate frame 400 is useful in situations such as hospital environments, where it can alleviate the need to transfer patients from a bed to a chair and back for procedures which require upright positioning, or for allowing patients to sit up more comfortably for social or other personal purposes without requiring a chair transfer. In addition, certain medical positions require the patient to have his or her legs placed lower than the rest of the body. The intermediate frame 400 allows the patient to alternate positions from a chair-type configuration to the flat position, or any intermediary position therebetween.

Figure 4:
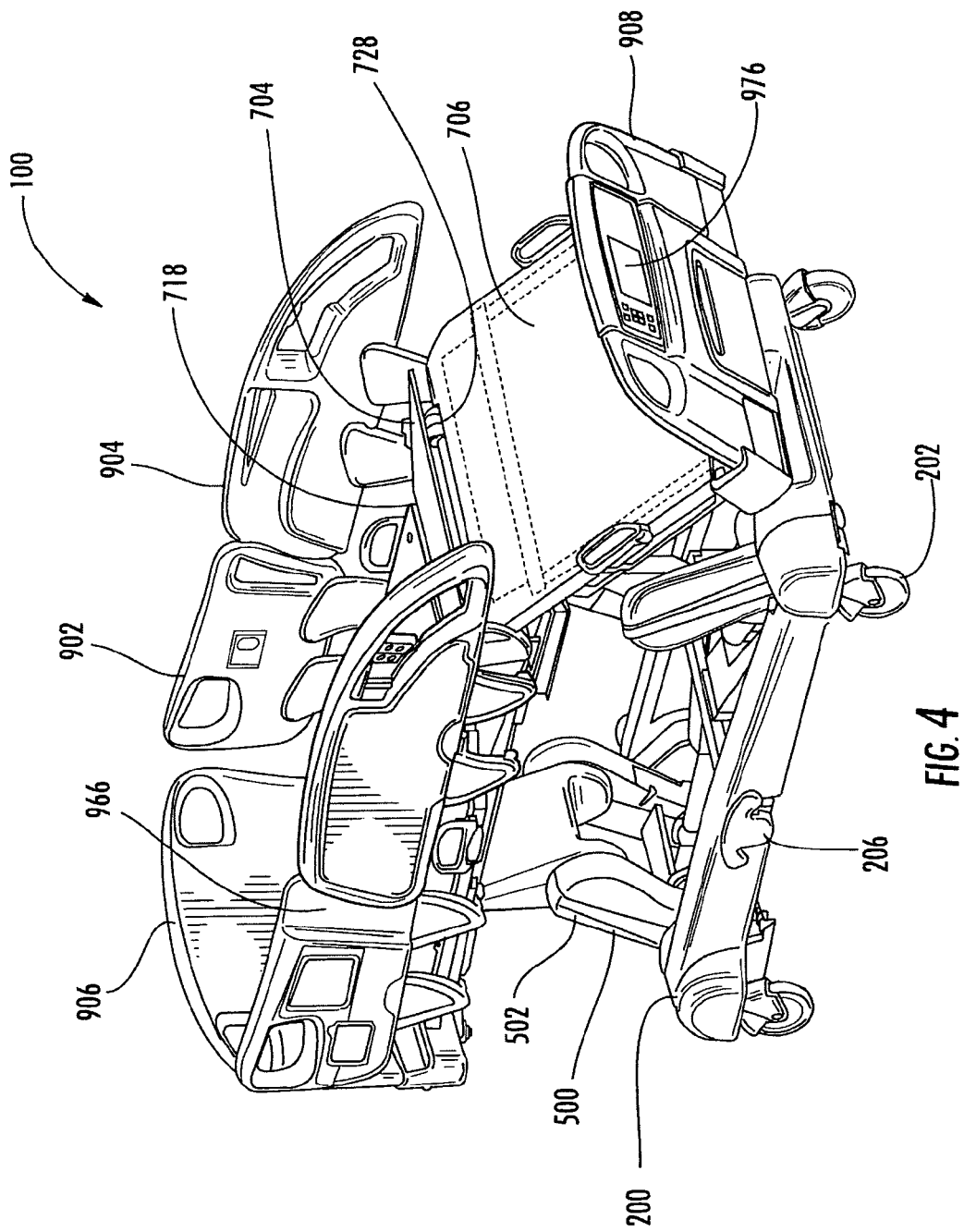
FIG. 4 is a right perspective view of the patient support apparatus of FIG. 1 wherein a seat and a foot portion of a support deck are articulated.

In one embodiment, the foot-end of the bed is designed to allow the foot section 706 of the deck support 700 to be lowered below the level of the head and seat sections 702, 704 (e.g. see FIG. 4). This is accomplished by means of a shortened intermediate frame 400 as noted above, upon which is mounted a load-bearing frame 600 and deck support 700, the foot section 706 of which being cantilevered or otherwise supported beyond the end of the intermediate frame 400. As depicted for example in FIGS. 34, 37 and 38, the foot section 706 projects or extends past the intermediate frame 400 so that it can be lowered without coming into contact with the intermediate frame 400.

Figure 26:
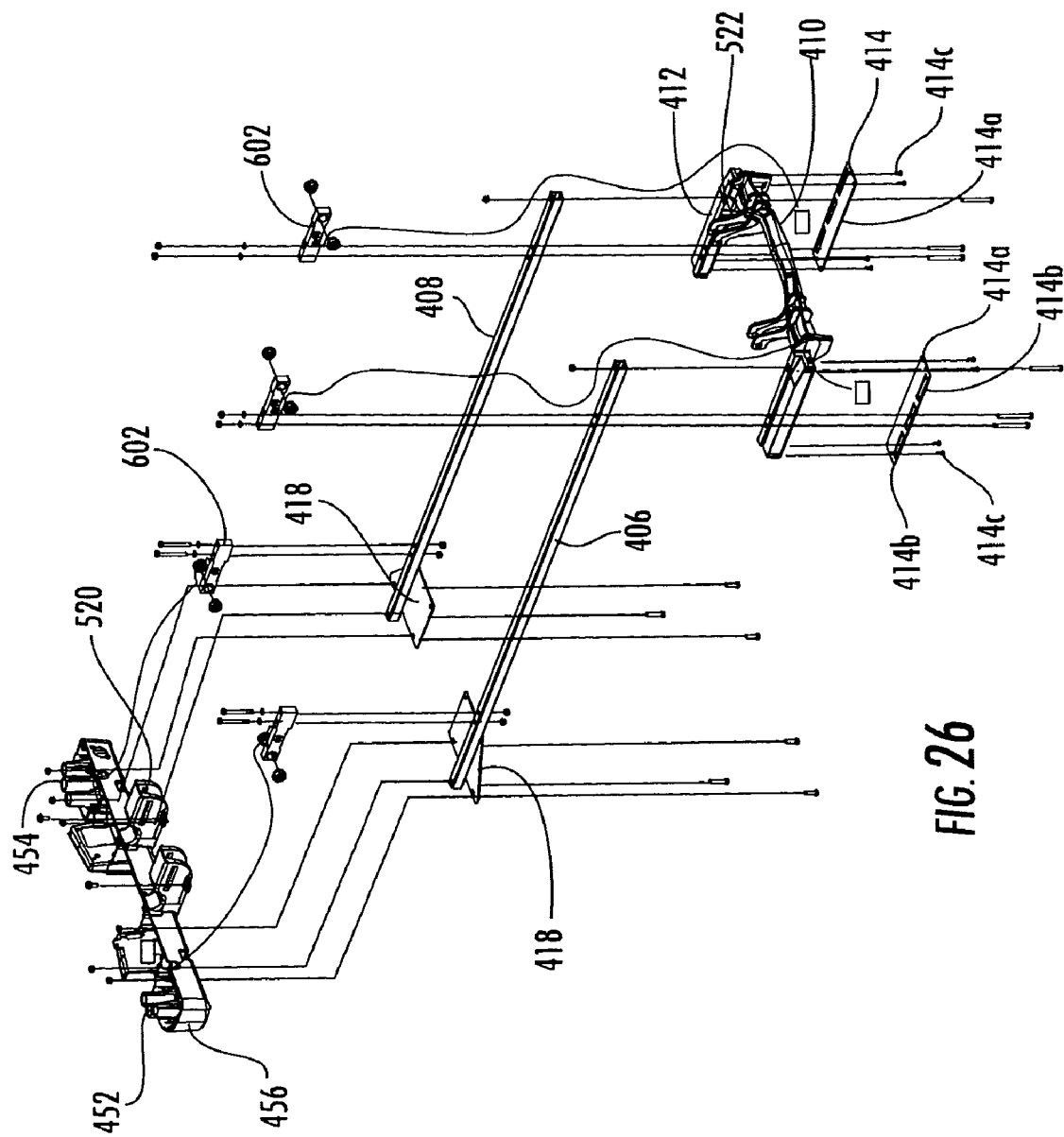
FIG. 26 is an exploded right perspective view of the intermediate frame of FIG. 21, showing attachment of load cells and partial attachment of a head-end operating console thereto.

An exemplary embodiment of the intermediate frame 400 is shown in FIG. 26. The intermediate frame 400 generally comprises opposing and substantially parallel longitudinal side rails 406, 408, (upon which are fixedly mounted the load cells 602, described further below), a head-end structure 450 disposed at a head-end 402 thereof, and a foot-end structure 410 disposed at a foot-end 404 thereof.

The Foot-End Structure

In general, the foot-end structure 410 comprises a substantially U-shaped structure that is fixedly attached below the side rails 406, 408 via longitudinally extending members 412 thereof. In one embodiment, the intermediate frame 400 may include one or more attachment means for mounting devices to the bed. In the illustrated embodiment, the members 412 of intermediate frame 400 may include the attachment means, such as support brackets 414, for fixedly or removably attaching various equipment, accessories and/or devices to the bed 100. Each support bracket 414 may be formed from a plate bracket 414*a* with a plurality of elongate openings 414*b* for receiving hooks, cables or the like for hanging or mounting the devices from the bed. Plate brackets 414*a* may be mounted to the frame, for example, by fasteners 414*c*; though it should be understood that they may also be welded or riveted or secured in place by other means.

Using these attachment means 414, which are coupled to the bed frame below the load cells 602, the weight of the attached objects will not influence the load readings acquired via the load cells 602. As such, adding and removing objects from these attachment means 414 does not require that the weight of these objects be taken into account by the load measuring and/or monitoring system, either manually, or via a recalibration of the system.

The foot-end structure 410 further comprises, in this embodiment, the foot-end coupling brackets 522 described above and provided to pivotally couple the upper arm members 514 of the foot-end lift arms 508 to the intermediate frame 400 in order to controllably lift and lower the foot-end 404 of the intermediate frame 400 relative to the base frame 200, as described above, for example, with reference to FIGS. 17A to 17D, etc.

The Head-End Structure

Figure 57:
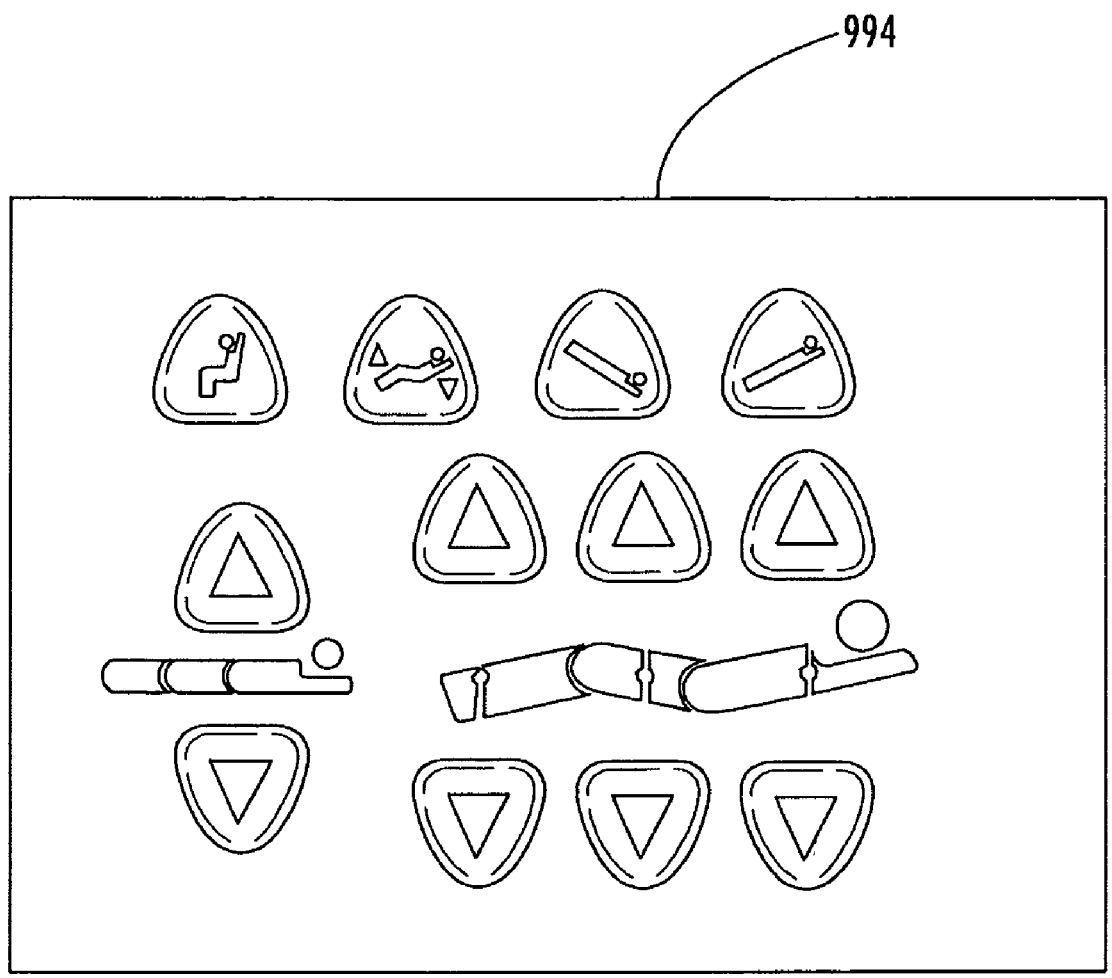
FIG. 57 is a diagrammatic view of an outer control interface provided by one of the head-end side rail control panel of FIG. 46 as well as by the head-end control panel of FIGS. 29A and 29B.

The head-end structure 450 is generally fixedly mounted to the side rails 406, 408, further supported by support plates 418 integrally coupled thereto. In general, the head-end structure 450 provides for the operative coupling of the push handles 451 to the bed 100, which may be used to control the optional drive wheel mechanism described above. The head-end structure 450 may further comprise one or more control panels and/or interfaces, as in interfaces 453, 455, and/or plug-ins, as in network plug-ins 457, input power plug-ins 459, or the like, for controlling, monitoring and/or operating the bed 100 and a patient lying thereon. For example, as illustrated in FIG. 57, a control interface 994 is shown for interface 453 providing a medical practitioner control of the bed's orientation and configuration, which are also illustratively provided by the head-end side rail panel 993 (discussed further below).

The head-end structure 450 may further comprise a number of structural components, such as for example, a pair of headboard sockets 452 for receiving therein headboard mounting post 968 for mounting the headboard 906 thereto, or other such sockets 454 for supporting therein various equipment, devices and/or accessories. As with the support brackets 414 of the foot-end structure 410, the sockets 454 allow for objects to be coupled thereto without a weight thereof affecting the load measurements acquired via the load cells 602. The head-end bracket 450 further comprises the head-end coupling brackets 520, comprising linear slot 526, described above and provided to couple the upper arm members 514 of the head-end lift arms 506 to the intermediate frame 400.

Figure 27:
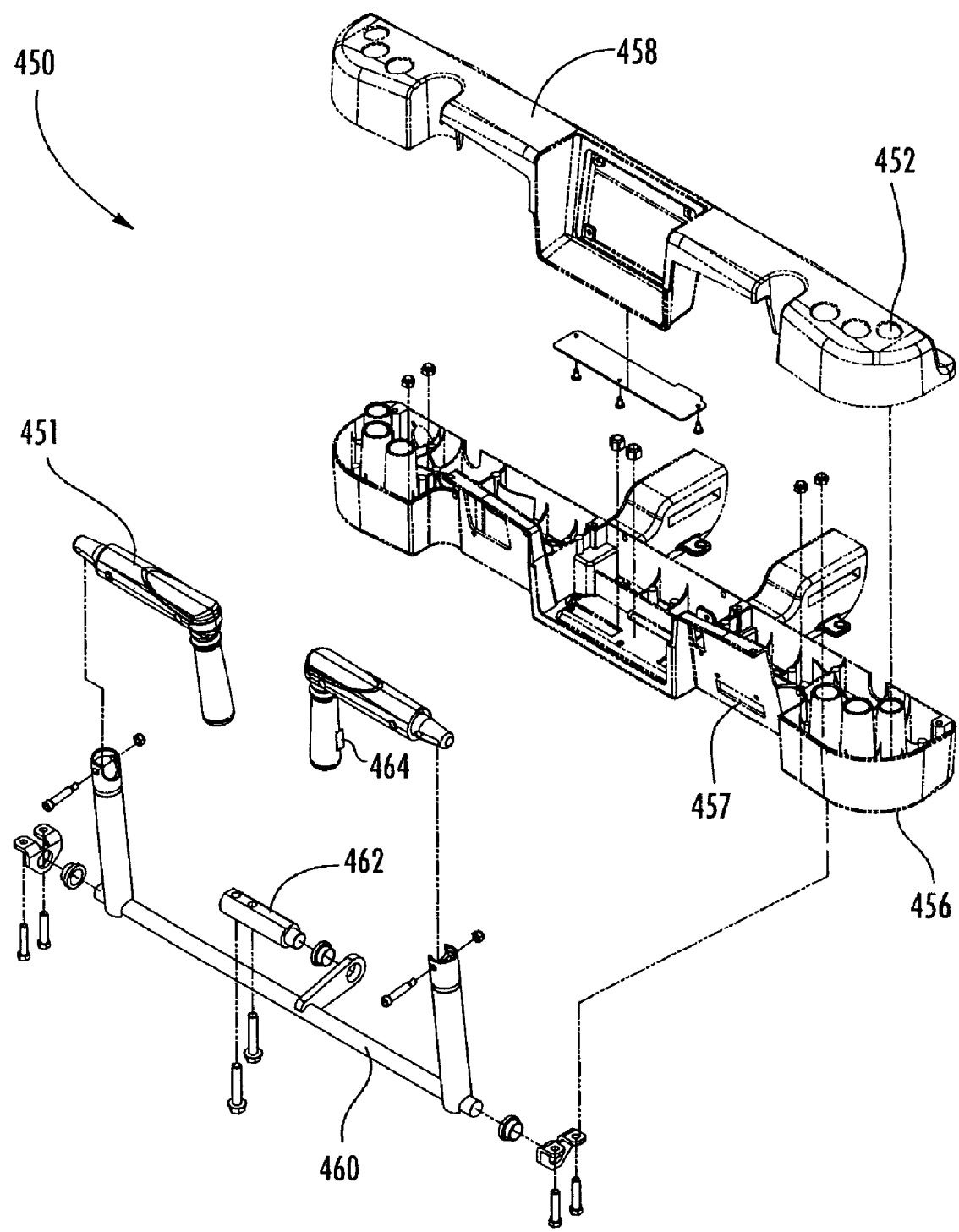
FIGS. 27 and 28 are partial exploded front perspective views of the head-end operating console of FIG. 26.
Figure 28:
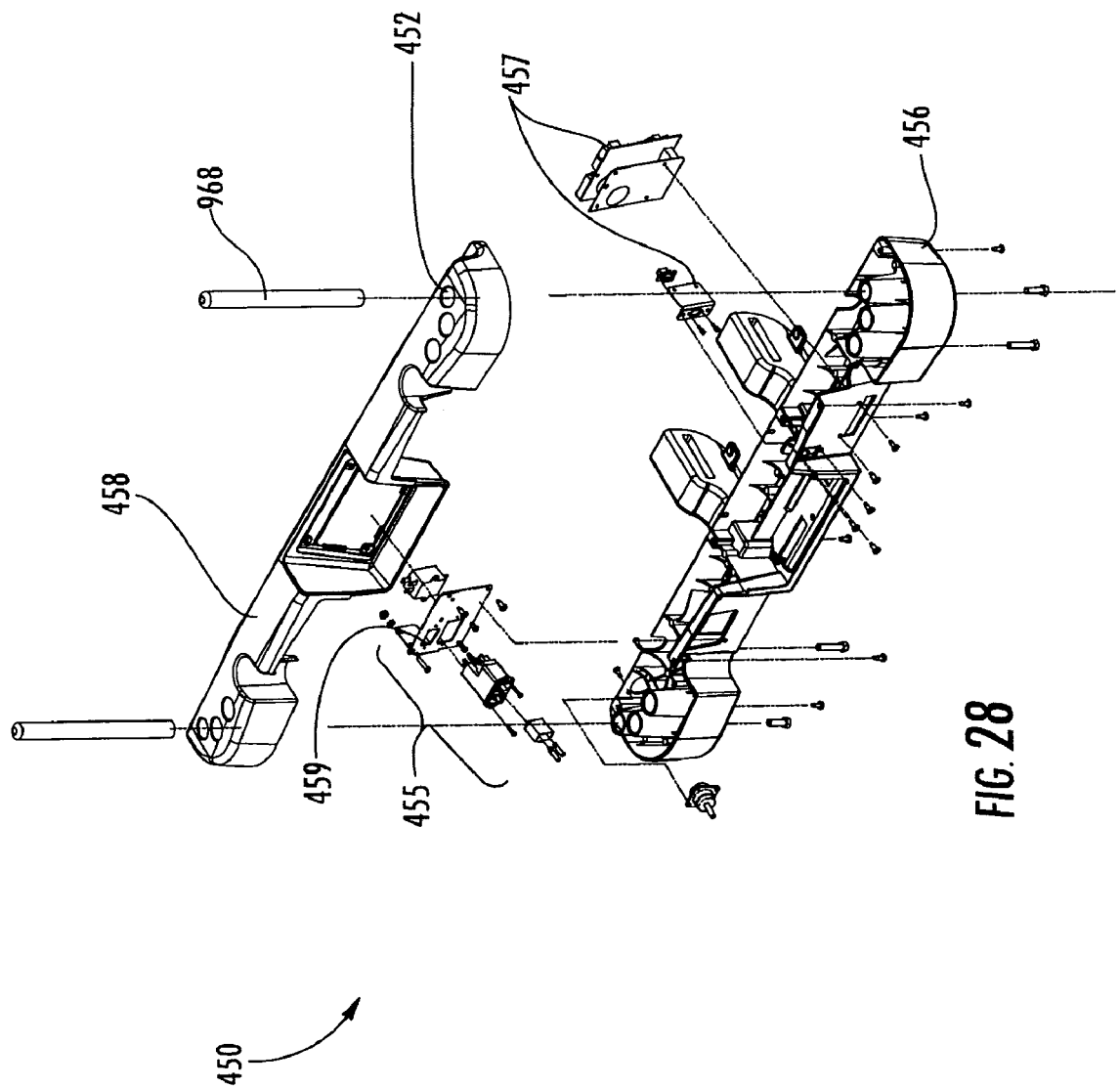
Figure 29A:
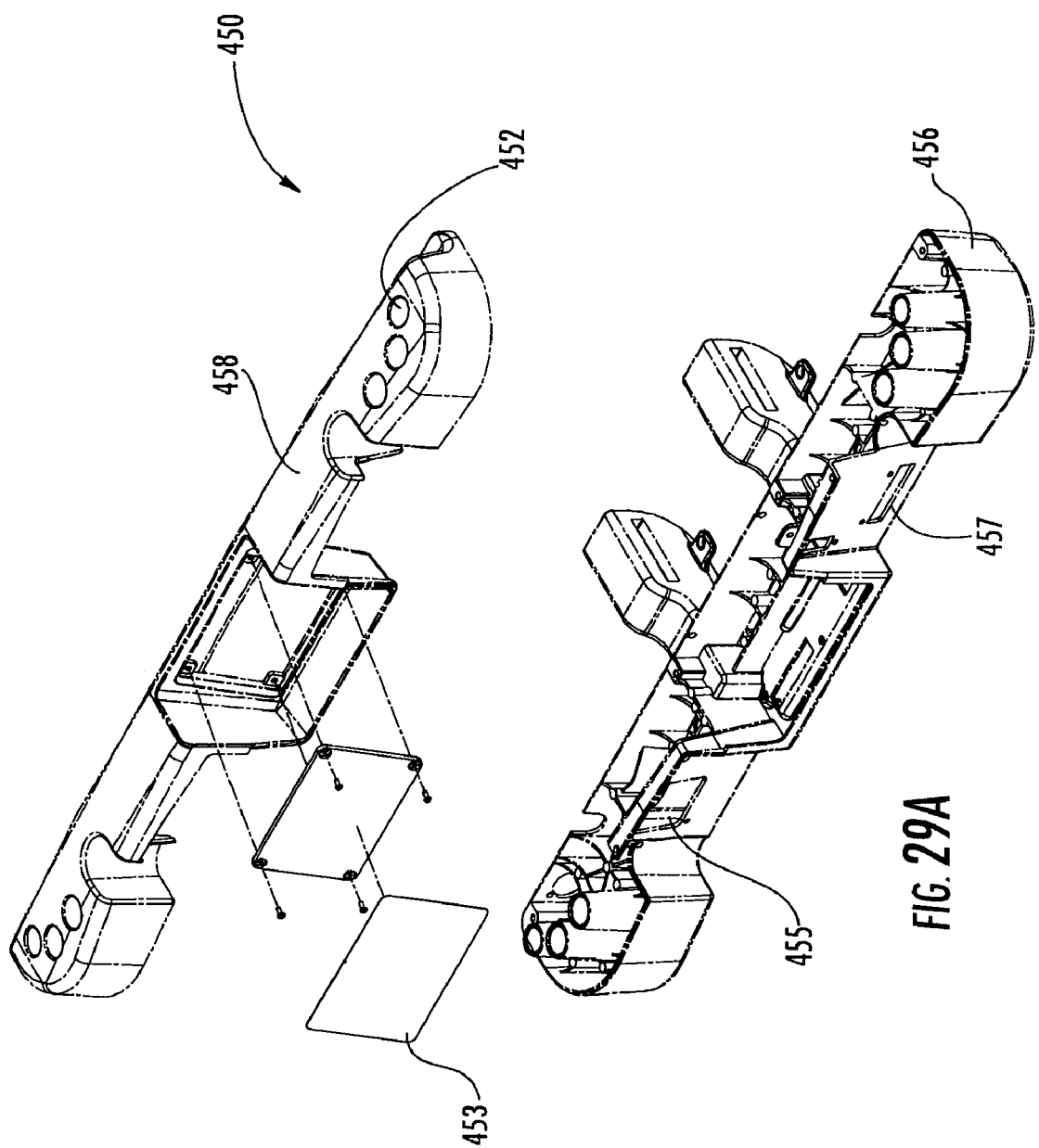
FIGS. 29A and 29B are respectively exploded and detailed exploded views of an assembly of a head-end control panel to the head-end operating console of FIGS. 26 to 28.
Figure 29B:
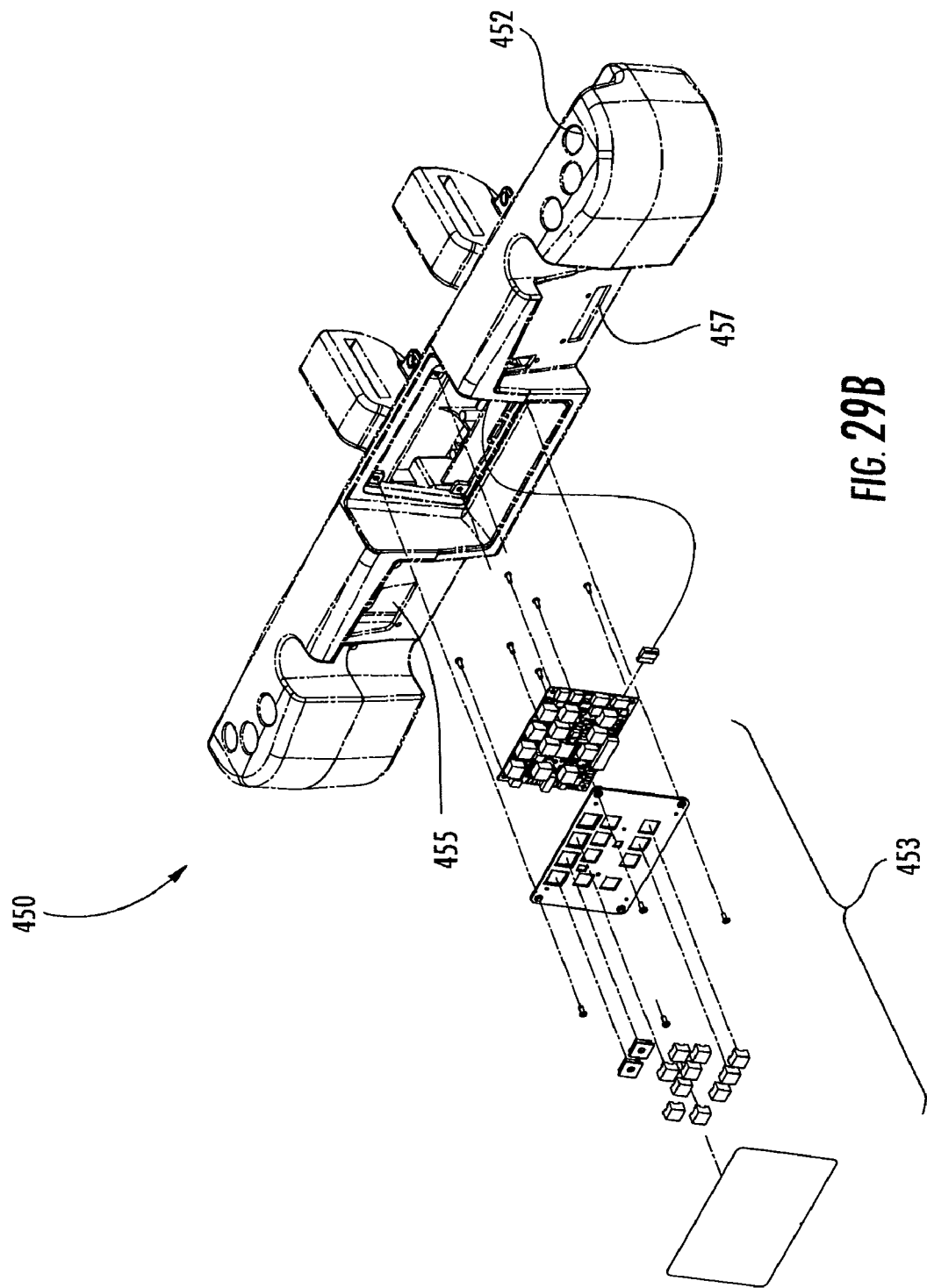

In FIGS. 27 to 29, a head-end structure 450, in accordance with an illustrative embodiment of the present invention, is depicted in greater detail. The head-end structure 450, is generally comprised of a lower module 456, comprising the coupling brackets 520 and configured for fixing to the side rails 406, 408, and an upper module 458 mounted atop thereof.

In general, the push handles 451 (FIG. 30) are operatively coupled to the lower module 456 via a levering support structure 460 pivotally coupled to load cell 462 (FIG. 27) which is fixedly attached to the bottom surface of the lower module 456. The handles 451 are themselves pivotally coupled to the support structure 460 and movable between a raised or deployed operative position (e.g. right handle of FIG. 3), and a lowered or retracted inoperative position (e.g. left handle of FIG. 3). For example, when not being used to displace the bed, one or both push handles 451 may be placed in a stored position such as by removing them from the bed or by folding them inwards, as depicted in FIG. 3. Typically it is convenient to access or remove the headboard when the push handles are stored.

A user actuatable device 464, such as an activation button, is further provided on the handles 451 such that even when a handle 451 is deployed, it remains inoperative until the button 464 is activated. In operation, when the support structure 460 is pivoted by a pressure applied to one of the handles 451, the load cell 462 registers and communicates the applied pressure to the control system 1000, which may then translate this pressure into an operational drive command to the optional drive system described above with reference to FIG. 9. In one embodiment, the drive command may be graduated as a function of the pressure intensity applied to the handle(s) 451.

As will be described in greater detail below, activation of the drive mechanism using the push handles 451 may be conditional on a prior activation of the drive mechanism. For example, as introduced above, selection of the drive or steer mode on one of the beds control panels, for instance via interface panel 453, may be needed for example, to release brakes previously applied, to lower the drive wheel in operative contact with the floor, and/or address a number of other possible restriction requirements associated with the patient resting on the bed in question. These and other such characteristics of the drive mechanism and push handle activation thereof will be described in greater detail below.

The Load Frame

The load frame 600 is generally provided to rest atop, and be operatively coupled to, the load cells 602 disposed on the intermediate frame 400, and configured to support the deck support 700 and lying surface 800 thereabove. As a result, any addition of weight, or any shift of weight applied to bed 100 from above the load frame 600, that is directly or indirectly to the lying surface 800 or deck support 700, can be monitored via the load cells 602. Figuratively, the load frame 600 vertically divides the bed 100 into a lower section below the load frame 600 comprising the intermediate frame 400, the elevation system 500, the base frame 200 and their respective components, and an upper section above the load frame 600 comprising the deck support 700 and lying surface 800 upon which a weight variation may be detected and/or monitored via the load cells 602.

FIG. 31 depicts an exemplary embodiment of the load frame 600. In general, the load frame 600 comprises two opposed substantially parallel longitudinal side rails 604, and a head-end cross bar 606 and intermediate and foot-end rails 608 and 610, respectively, each structurally coupled between the side rails 604. The side rails 604 comprise a substantially inverted U-shaped cross section sized to fit over the intermediate frame side rails 406, 408, and comprise four coupling holes 612 disposed and configured to be coupled to corresponding load cell apertures via coupling pins 614 such that any weight applied to the load frame 600 is communicated to the load cells 602 through these pins 614.

The intermediate and foot-end rails 608, 610, generally provide, as does the side rails 606 in some instances, a number of coupling brackets for pivotally connecting the various components of the deck support 700 to the load frame 600, as well as provide couplings for the various actuators and/or levers used to move these components relative to the load frame 600. In general, in order for all weight changes applied to the deck support 700 and lying surface 800 to be sensed and optionally monitored by via the load cells 602, the deck support 700 should, in most cased, be substantially isolated from the any component of the bed's framing operatively located below the load cells 602. That, as will be apparent to the person skilled in the art, the deck support components should be coupled to the bed such that substantially none of the weight of these components, or of any object or person resting thereon, be transferred to the intermediate frame 400, elevation system 500, or base frame 200 other than via the load frame's interconnection to the load cells 602. For reasons of clarity, the various coupling brackets provided by the load frame 600 for mounting the various components of the deck support 700 thereto will be described in the following section dealing specifically with the deck support 700.

Figure 44:
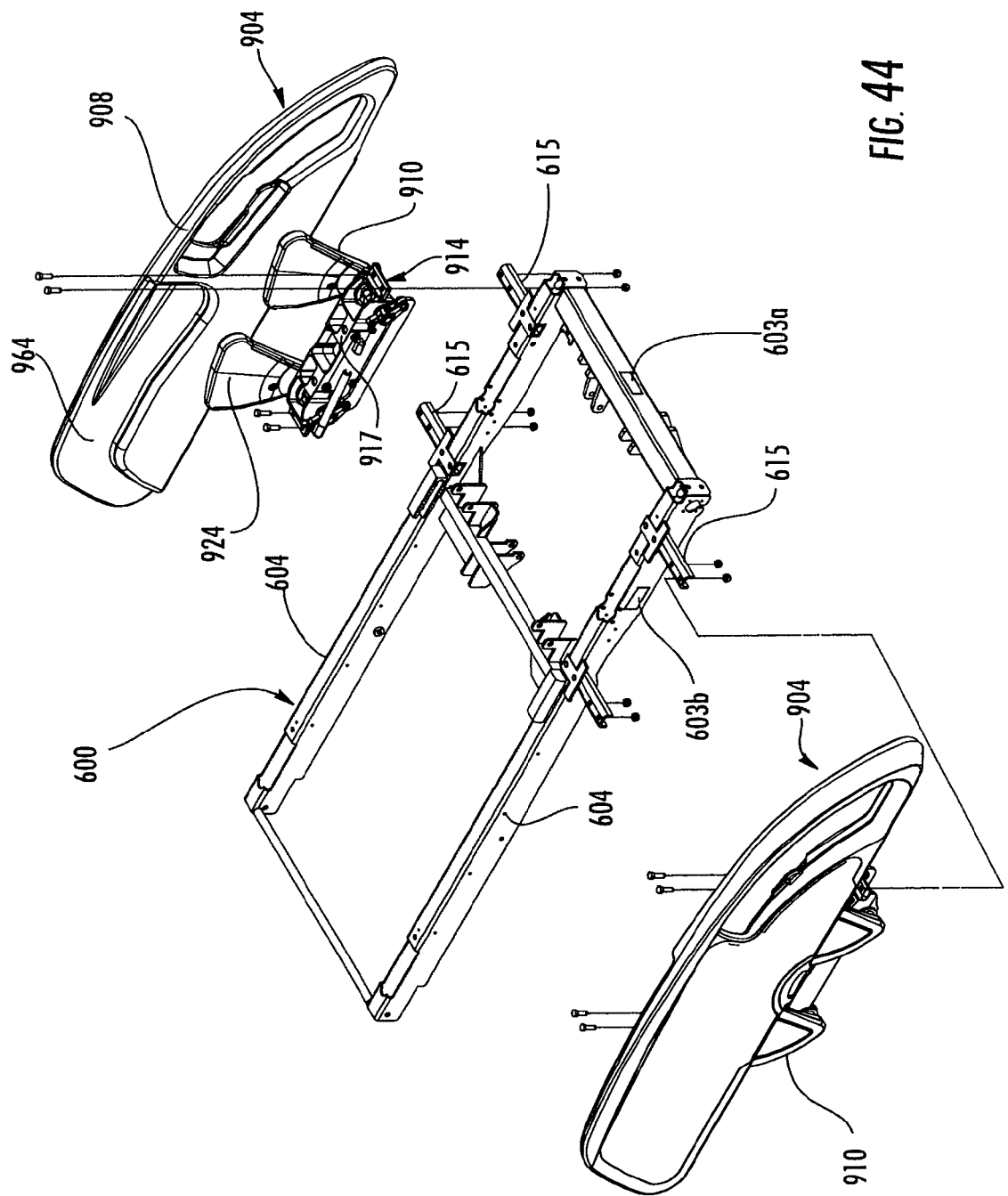
FIG. 44 is an exploded right perspective view of an assembly of the foot-end side rails of FIG. 40 to the load bearing frame of FIG. 31.

In one embodiment, the side rails 604 further comprise laterally extending support members 615 for securing the foot-end side rails 904 thereto (e.g. see FIG. 44). By coupling the foot-end side rails 904 to the load frame 600 rather than to a movable component of the deck support 700, as is the case for the head-end side rails 902, the foot-end side rails 904 will not move with the deck support 700 but will rather maintain their orientation independently of the deck support's orientation. The person of skill in the art will understand that in other embodiments, the foot-end side rails 904 could also be coupled to the deck support 700, for instance to the seat section 704 thereof which does not traditionally comprise a wide angular range.

In one embodiment, the load frame 600 further comprises a pair of guide channels 616 (FIG. 31) for guiding wires, cables, or other conduits, including tubing for delivering fluid, such as air. Each guide channels 616 includes a first substantially J-shaped rail 618 fixedly mounted to a side rail 606, and a staggered rail 620 having an upwardly extending flanges for coupling this rail 620 to the side rail 606 through the J-shaped rail 618. The outwardly and downwardly extending flanges of the staggered rail 620 are so formed as to cooperatively define with the bottom section of the J-shaped rail 618 the guide channels 616. As noted, these guide channels 616 can be used to guide a number of wires, cables and or other such conduits therethrough without impeding with the load-bearing functionality of the load frame 600. As noted, these conduits may be used to channel tubing through the bed for supplying fluid, such as air, to the various components on the bed. For example, should an air bearing pallet be needed to transfer a patient from bed 100 to another patient support device, the tubing may be used to inflate the pallet.

Furthermore, in one embodiment, the load frame 600 comprises a sensor 622 (mounted to one of the side rails 606 in the embodiment of FIG. 31), such as an inclinometer or the like, to detect variations in the inclination/orientation of the load frame 600. As will be described in greater detail below, data acquired using this and other such sensors disposed on various parts of the bed can be used in calculating and monitoring various characteristics of the bed 100 and/or of a patient lying thereon. As will be apparent to the person skilled in the art, the sensor can be mounted elsewhere on the head section 702 without departing from the general scope and nature of the present disclosure.

The Deck Support

Figure 32:
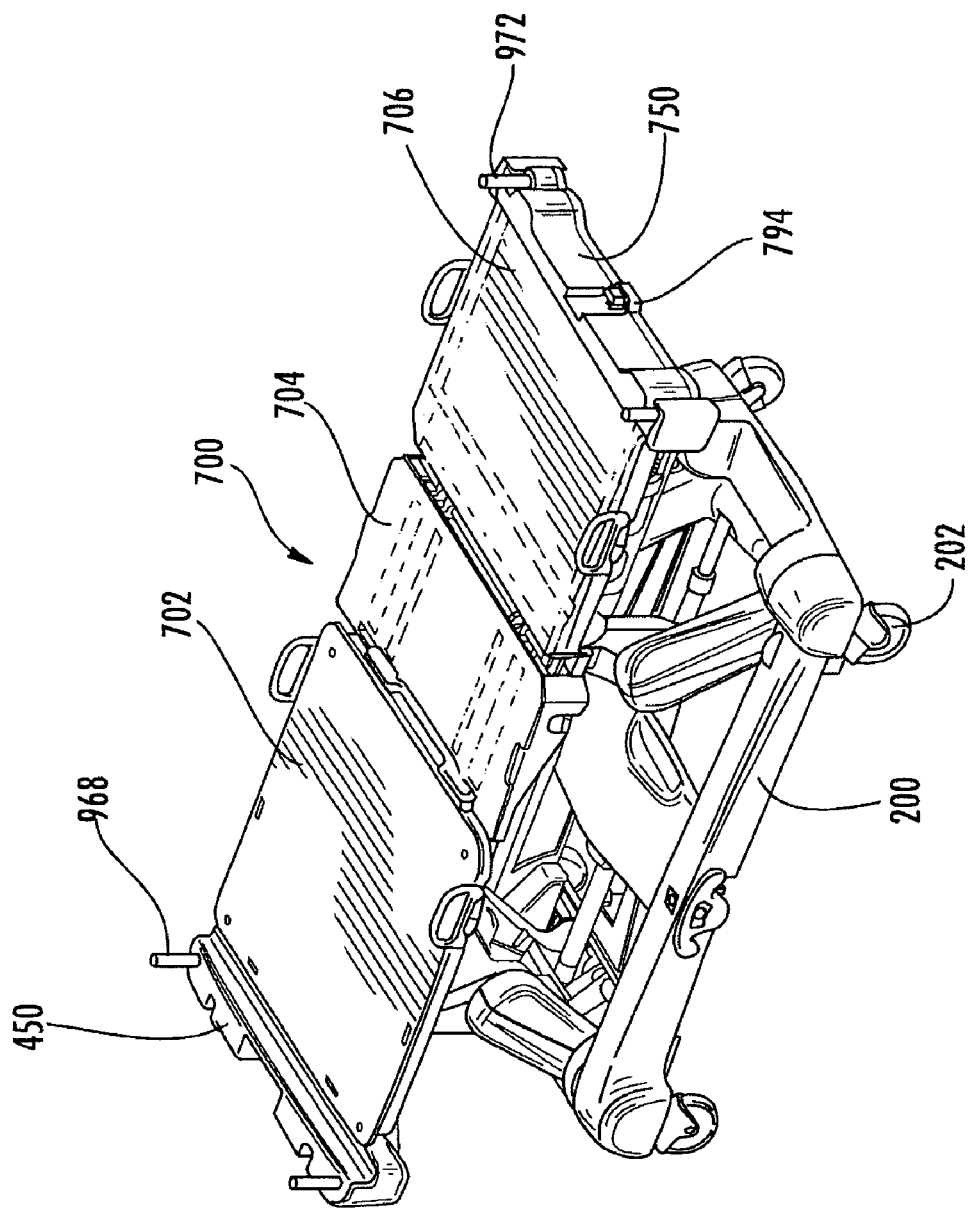
FIG. 32 is a right perspective view of a deck support mounted to the load bearing frame of FIG. 31, showing an assembled head portion, seat portion and a leg portion of the deck support.
Figure 33:
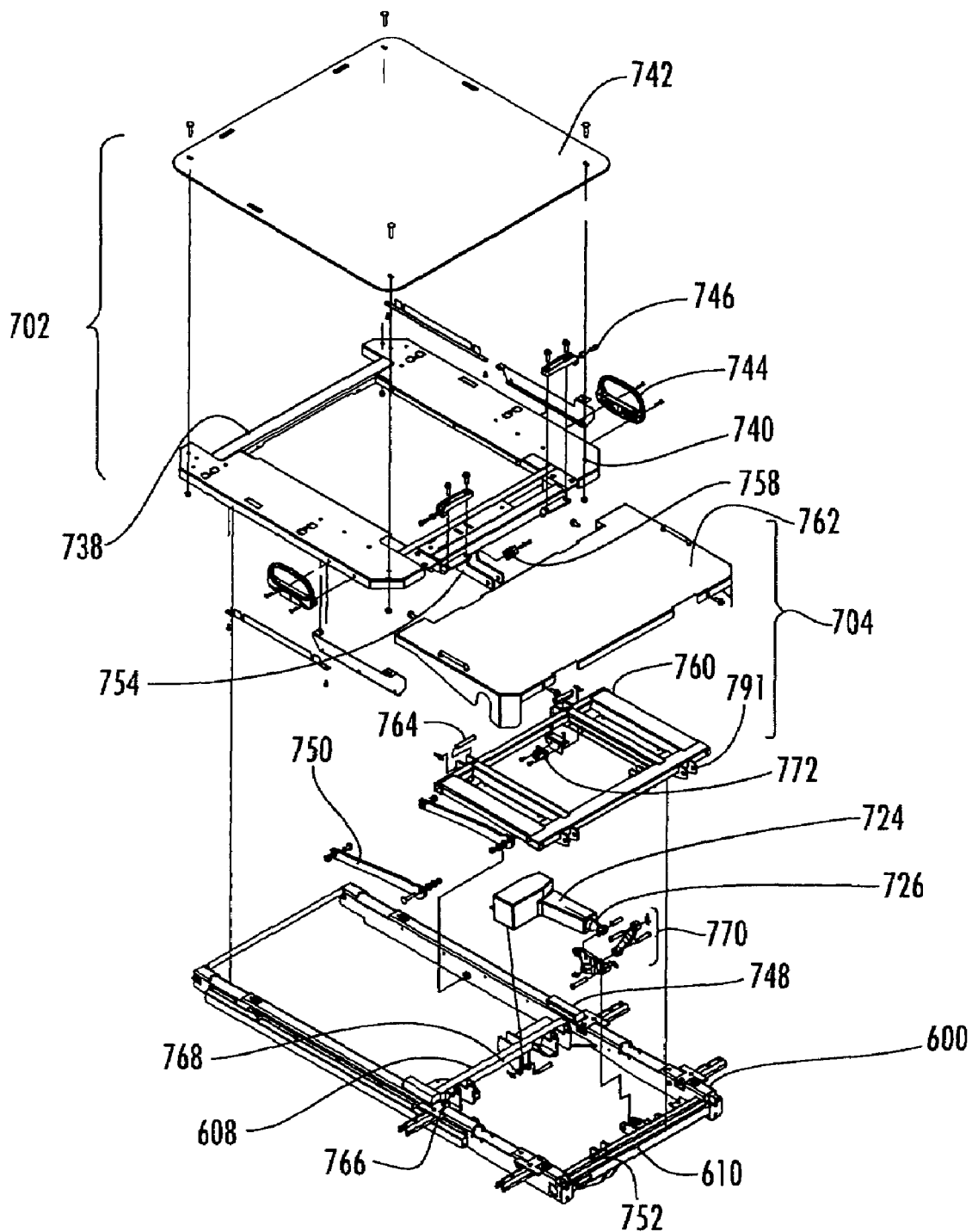
FIG. 33 is an exploded right perspective view of an assembly of the head and seat portions of the deck support of FIG. 32 to the load bearing frame.
Figure 34:
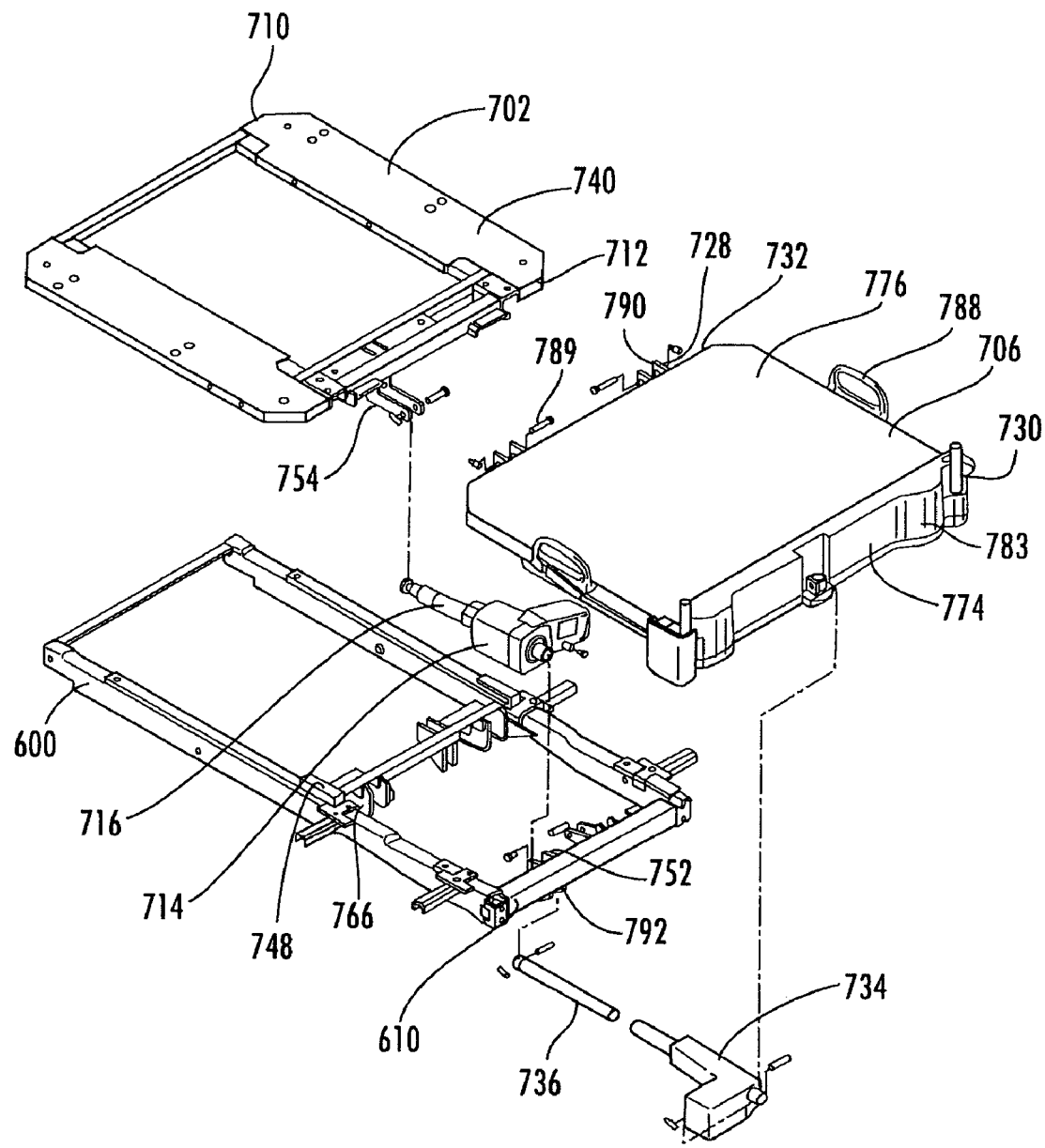
FIG. 34 is an exploded right perspective view of an assembly of the head and foot portions of the deck support of FIG. 32 to the load bearing frame.

Referring to FIGS. 32, 33, and 34, the deck support 700 is generally comprised of a head section 702, a seat section 704 and a foot section 706. As presented above, the various sections of the deck support 700 and lying surface 800 may be moved relative to the intermediate and/or load-bearing frames 400, 600 to move a user on the bed to various positions. For example, it may be required to configure the lying surface 800 of the bed 100 in a configuration that is designed to assist a caregiver in providing CPR to the patient supported thereon. In one example, a CPR configuration is defined by placing the head, seat and foot sections 702, 704 and 706 of the deck support 700 in a generally linear relationship (e.g. see FIG. 32). In one embodiment, the bed can be placed in this pre-defined CPR configuration via the control system 1000, which can comprise one or more control panels configured to control a number of linear actuators operatively disposed to actuate the various sections of the deck support 700 (e.g. see FIG. 57).

Other positions may also be considered useful in providing care to a patient positioned on the bed 100. For instance, with reference to FIG. 8, the head section, seat section and foot sections 702, 704 and 706 may be positioned in a substantially linear relationship to provide a substantially flat lying surface 800. In one embodiment, the head section 702, seat section 704 and foot section 706 are placed in this linear relationship by the control system 1000 in response to a single user actuatable device, such as a button, being depressed on one of the control system's various control panels (described below).

With reference to FIGS. 5 to 7 and 33 to 35, the head section 702 can be rotated about pivot 708, such that a head-end 710 of the head section 702 is raised relative to a foot-end 712 thereof. For example, the head-end 710 may be raised by the control system 1000 controlling an actuator 714 (FIGS. 34 and 35) to further extend a cylinder 716 of this actuator 714 and thereby raise the head-end 710. In one embodiment, the head section 702 is raised by the control system 1000 in response to a first user actuatable device, such as a button, being depressed on one of the control system's various control panels (e.g. see FIG. 57), and lowered by the control 1000 system in response to a second user actuatable device, such as a second button, being depressed on this same panel or another panel.

Furthermore, with reference to FIGS. 4 to 7, 33 and 36, the seat section 704 can be similarly rotated about pivot 718 such that its foot-end 720 is raised relative to its head-end 722. The seat section's foot-end 720 may be raised by the control system 1000 controlling an actuator 724 (FIG. 33) to further extend a cylinder 726 of the actuator 724 thereby raising the seat section's foot-end 720. In one embodiment, the seat section 704 is raised by the control system 1000 in response to a first user actuatable device, such as a button, being depressed on one of the control system's various control panels (e.g. see FIG. 57), and lowered by the control 1000 system in response to a second user actuatable device, such as a button, being depressed on this same panel.

Also, with reference to FIGS. 4 to 7 and 34, the foot section 706 can be similarly rotated about pivot 728 such that its foot-end 730 is lowered relative to its head-end 732. The foot section's foot-end 730 may be lowered by the control system 1000 controlling an actuator 734 to retract a cylinder 736 of the actuator 734 (FIG. 34) thereby lowering the foot section's foot-end 730. In one embodiment, the foot section 706 is lowered by the control system 1000 in response to a first user actuatable device, such as a button, being depressed on one of the control system's various control panels (e.g. see FIG. 57), and lowered by the control 1000 system in response to a second user actuatable device, such as a button, being depressed on this same panel.

The Head Section

With reference to FIGS. 32 to 35, in accordance with an illustrative embodiment of the present invention, the head section 702 generally comprises a framework 738 on which is mounted a pair of side plates 740 configured to receive thereon, in one embodiment, a cover plate 742 translucent and substantially transparent to X-rays and/or other fluoroscopic beams conventionally used to evaluate a patient's condition. The use of such a cover plate 742 may be practical, for instance, when a patient cannot or should not be moved from the bed. In such a situation, fluoroscopic and/or radiometric tests on the patient's head and torso may still conducted through the bed's head section 702. Alternatively, if such a feature is not required or desired, a single cover plate may be used instead. Two or more mattress restraints 744 may also be provided to help restrain movement of the lying surface head section 802 on the deck support's head section 702, and optionally, to provide attachment points for patient restraints or the like.

The head section 702 is illustratively mounted to the load frame 600 via pivots 708, generally defined in this embodiment by the sliding and pivoting engagement of pins or protrusions 746 with slotted brackets 748. A set of guide arms 750 are also provided to guide a motion of the head section 702 as it pivots and slides within slotted brackets 748 to accommodate for the corresponding movement of the lying surface 800 disposed on the deck support 700. Referring to FIG. 34, the actuator 714, pivotally coupled to coupling bracket 752 of the load frame's foot-end rail 610, is operatively coupled to lever 754 configured to impart a pivoting action to the head section 702 about pivot 708 while the foot-end thereof 712 slides toward the head-end of the bed under action of the actuator 714.

In one embodiment, the head section further comprises an emergency handle 756 (e.g. see FIG. 35) configured to disengage the actuator 714 in the event of a power failure or an emergency when the head section 702 must be lowered rapidly, for example to administer CPR to a patient. For example, handle 756 includes a cable 756a that connects to a collar on the actuator, which is coupled to a clutch on the actuator and when pulled decouples the driving force of the actuator from lever 754. Where two handles are provided, the respective cables 756a of the handles 756 are directed to a junction box 756b where the two cables couple to a single cable that is then coupled to the collar on the actuator so that if either handle is pulled the actuator will be decoupled from the lever.

Furthermore, in one embodiment, the head section 702 comprises a sensor 758 such as an inclinometer of the like (mounted to lever 754 in the embodiment of FIG. 33), to detect variations in the inclination/orientation of the head section 702. As will be described in greater detail below, data acquired using this and other such sensors disposed on various parts of the bed can be used in calculating and monitoring various characteristics of the bed 100 and/or of a patient lying thereon. As will be apparent to the person skilled in the art, the sensor can be mounted elsewhere on the head section 702 without departing from the general scope and nature of the present disclosure.

As will be more full described below in Reference to FIG. 45A, optionally, to provide a quick reference to the angular or inclined position of the head-end section, bed 100 may be provided with one or more visual indicators 905 on foot-end side rail 904.

The Seat Section

Figure 36:
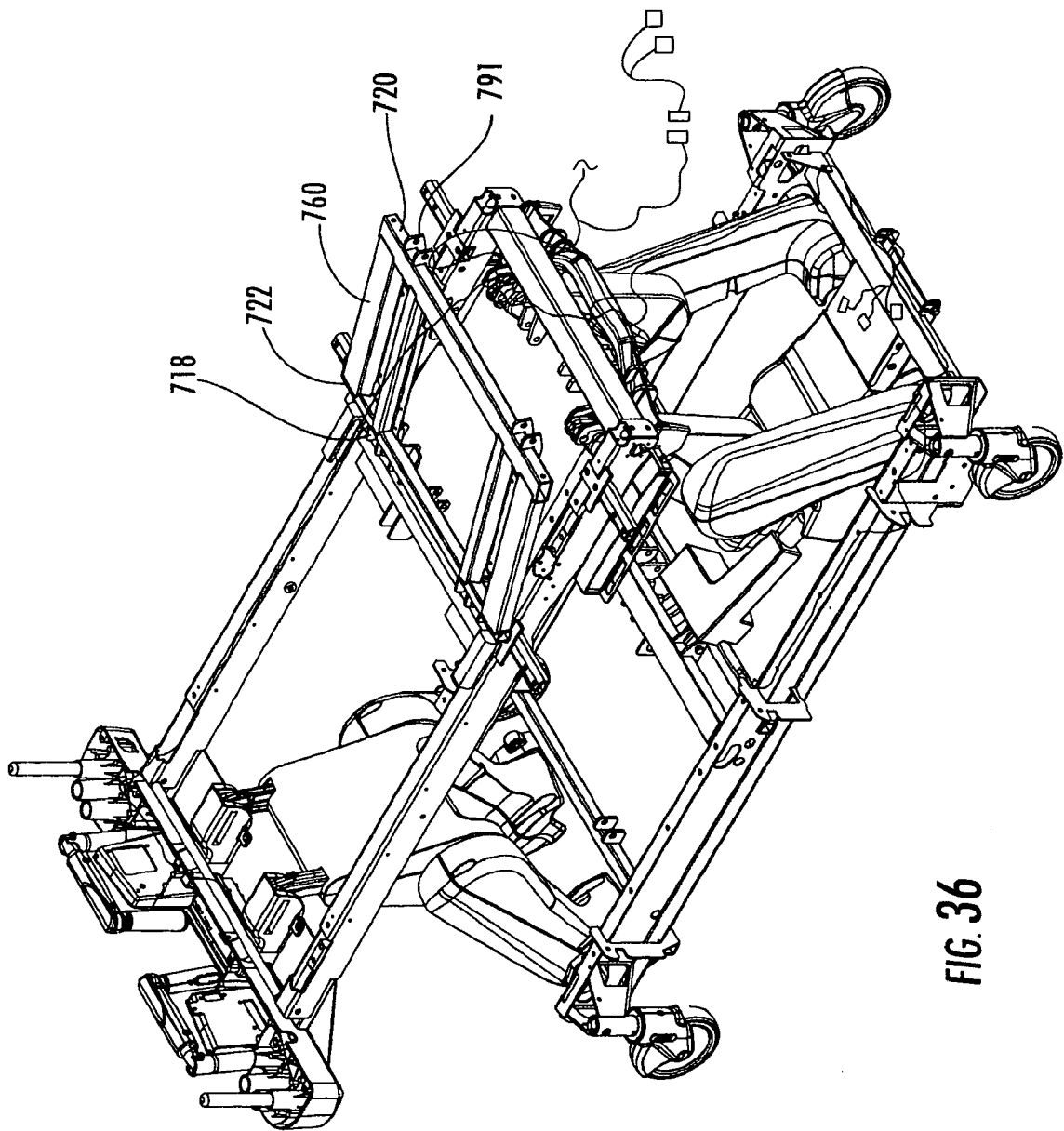
FIG. 36 is a right perspective view of an actuation of the seat portion of the deck support of FIG. 32 relative to the load bearing frame, a seat portion cover being omitted for clarity.

With reference to FIGS. 32, 33 and 36, in accordance with an illustrative embodiment of the present invention, the seat section 704 generally comprises a framework 760 on which is mounted a cover 762 to receive the lying surface 800 thereon. The seat section 704 is illustratively mounted to the load frame 600 via pivots 718, generally defined in this embodiment by the pivoting engagement of pins 764 with brackets 766. The actuator 724, pivotally coupled to coupling bracket 768 of the load frame's intermediate rail 608, is operatively coupled to lever assembly 770 configured to impart a pivoting action to the seat section 704 about pivot 718 under action of the actuator 724.

Furthermore, in one embodiment, the seat section 704 comprises a sensor 772 such as an inclinometer of the like (mounted to the framework 760 in the embodiment of FIG. 33), to detect variations in the inclination/orientation of the seat section 704. As will be described in greater detail below, data acquired using this and other such sensors disposed on various parts of the bed can be used in calculating and monitoring various characteristics of the bed 100 and/or of a patient lying thereon. As will be apparent to the person skilled in the art, the sensor can be mounted elsewhere on the seat section 704 without departing from the general scope and nature of the present disclosure.

The Foot Section

With reference to FIGS. 32, 34 and 37 to 39, in accordance with an illustrative embodiment of the present invention, the foot section 706 generally comprises a housing 774 on which is mounted a cover 776 to receive the lying surface 800 thereon. The housing 774 is generally configured to house therein a number of the power and control components of the bed 100. For example, in the illustrative embodiment of FIG. 38, the housing 774 encloses two batteries 778, a toroid 779 for converting input and output voltages as needed to operate the various electrical components of the bed 100 (e.g. 12/24V/120/240V/etc.), a mother board 780 and associated hardware and other such components as will be readily understood by the person skilled in the art.

Figure 37:
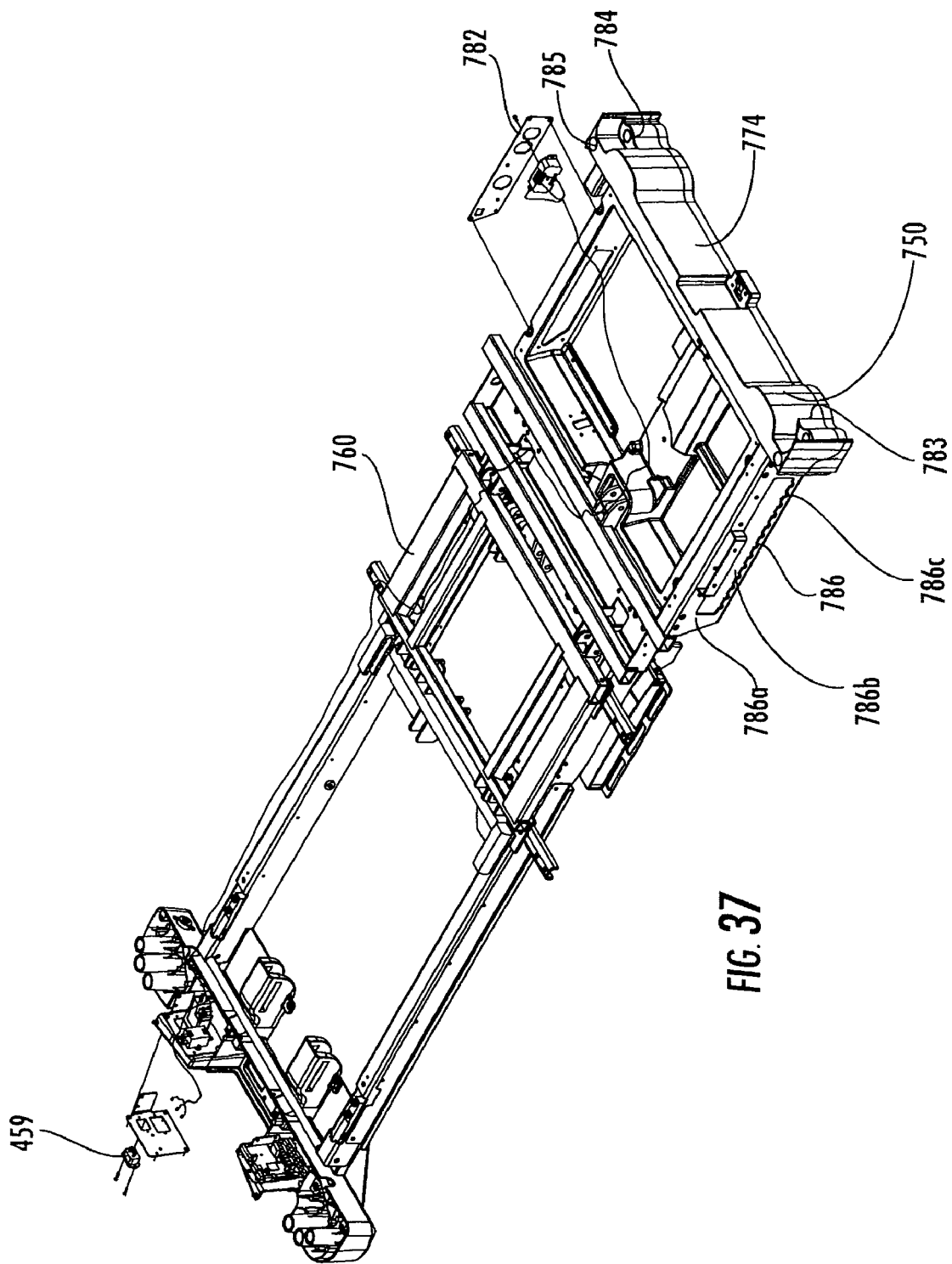
FIG. 37 is a right perspective view of an assembly of a leg portion housing of the deck support leg portion of FIG. 32 to the seat portion and load bearing frame.
Figure 39:
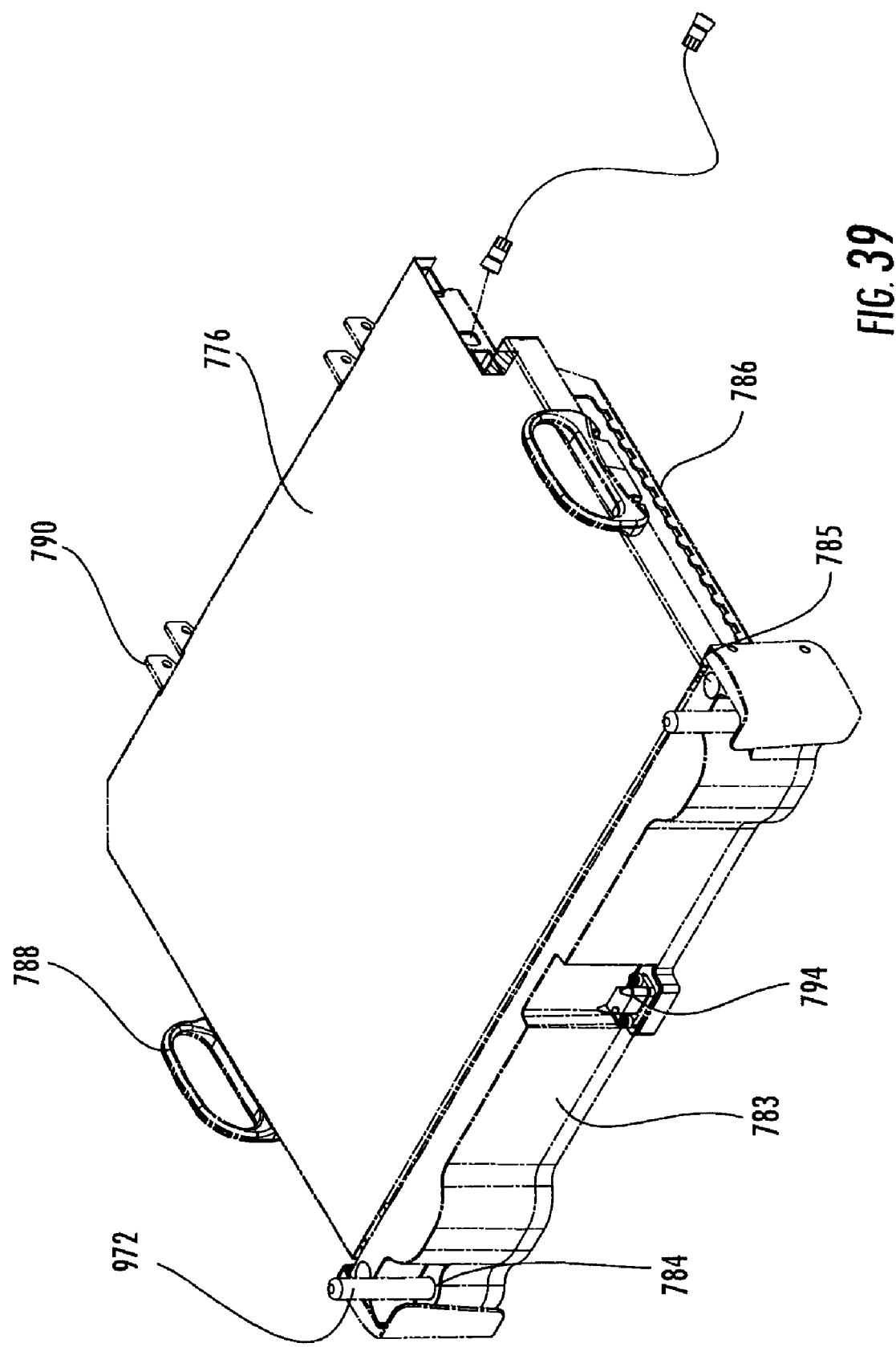
FIG. 39 is a left perspective view of the deck support leg portion of FIG. 32.

As illustrated in FIG. 37, power may be drawn from plug-in 459 and relayed to the foot section 706. Consequently, the foot section 706 may further comprise one or more optional power outlets 782 allowing various peripheral devices and/or equipment to be powered through the bed's internal wiring. Backup battery power may also be available. Power and/or control signals may also be communicated to various parts of the bed 100. For example, as shown in FIG. 39, a cable for communicating with an actuated lying surface 800 is provided to control this lying surface 800.

In this embodiment, the housing 774 further comprises a foot-end structure 783 configured to support, amongst others, the footboard 908 of the bed 100. In particular, a pair of footboard posts 972 may be fitted in coupling sockets 784 to support the footboard 908 thereat. Power and communicative links to the footboard 908, for example to power and communicate with the footboard's control console 976 and/or network/external plug-ins 982, may be provide by connector 794 configured to cooperate with a plug-in 984 of the footboard 908 (e.g. see FIG. 53).

The foot-end structure 783 may also comprise additional sockets 785 provided to support various accessories/equipment for use with the bed 100 or to treat or monitor the patient. In one embodiment, a switch (not shown) may be provided within one or more of these sockets 785 such that when a socket 785 is in use, the foot section 706 cannot be lowered. This may be useful when the lowering of the foot section 706 equipment with a given accessory would create an undesirable obstacle to medical practitioners attending to the patient.

The housing 774 may further comprise a support, such as a support rack 786 (FIG. 39), also configured to support various accessories/equipment used, for example, for treating or monitoring a patient. In the illustrated embodiment, the support rack includes a plurality of discrete holding locations for supporting a plurality of devices from the bed. As best seen in FIG. 37, support rack 786 is formed form a plate bracket 786a that includes an elongate opening 786b. Formed at the edge of the opening 786b are plurality of spaced notches 786 that form the plurality of discrete holding locations for devices to be hung from the bed, for example, pumps, bags or the like. Plate brackets 786a may be mounted to the frame, for example, by fasteners, though it should be understood that they may also be welded or riveted or secured in place by other means.

Note that as these accessories/equipment hang from a point operatively above the load cells 602, variation in the weight of these equipment/accessories should be accounted for when interpreting load data.

As for the head section 702, two or more mattress restraints 788 may also be provided on the foot section 706 to help restrain movement of the lying surface foot section 806 on the deck support's foot section 706, and optionally, to provide attachment points for patient restraints or the like.

Figure 35:
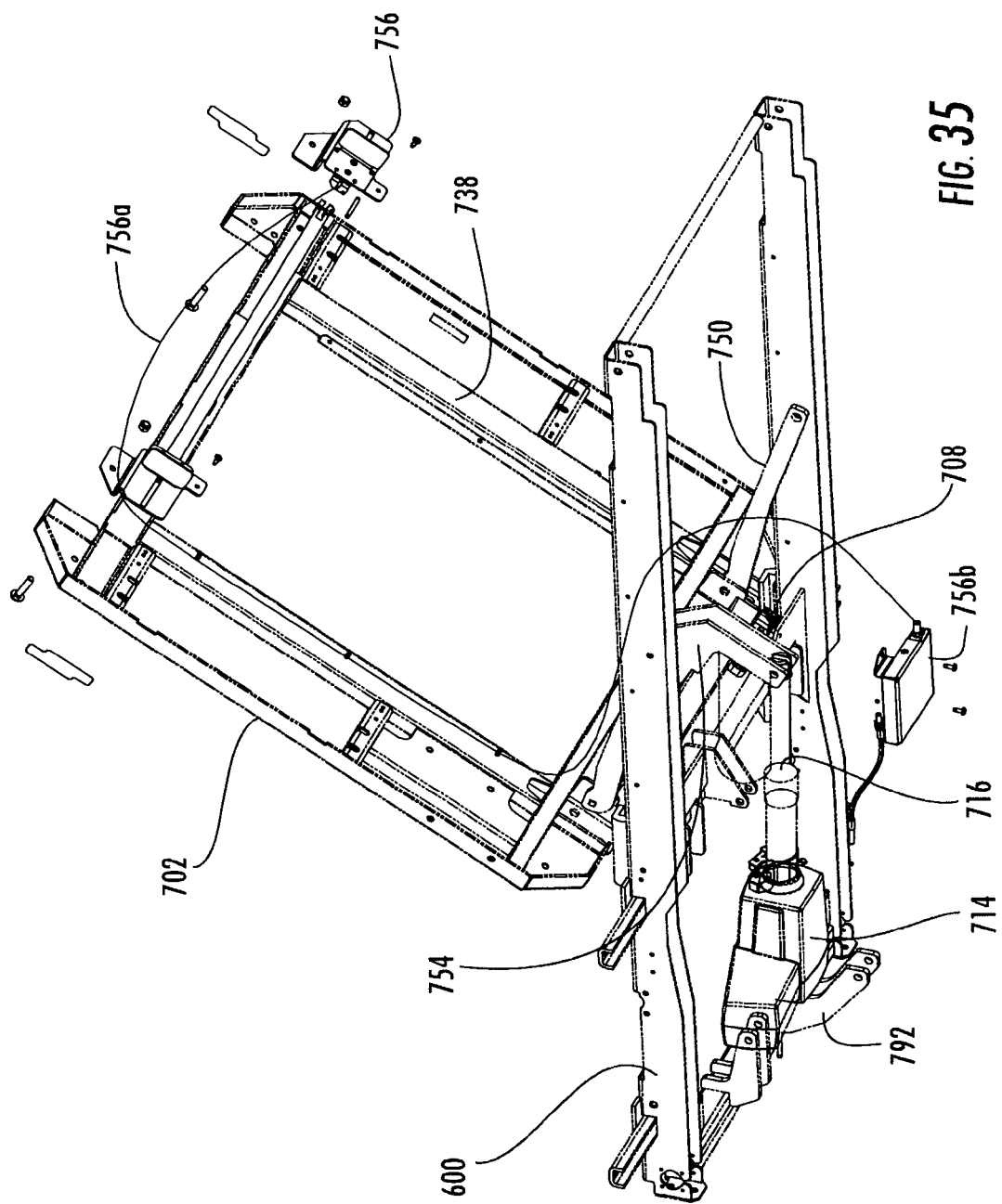
FIG. 35 is a rear left bottom perspective view of an actuation of the head portion of the deck support of FIG. 32 relative to the load bearing frame.

The foot section 706 is illustratively connected to the seat section 704 via pivots 728 (FIG. 34), generally defined in this embodiment by the pivoting engagement of pins 781 within brackets 790 (foot section 706) and brackets 791 (e.g. see seat section 704 of FIGS. 33 and 36). The actuator 734, pivotally coupled to coupling bracket 792 of the load frame's foot-end rail 610 (e.g. as seen in FIG. 35), is operatively coupled to a bracket (not shown) disposed under the housing 774 toward a foot-end thereof. As such, when the cylinder 736 is retracted, the foot-end of the foot section 706 is pulled down toward the floor, and vice versa. Note that despite the interconnection of the foot section 706 to the seat section 704, the motion of one does not significantly affect the position of the other. In fact, as the seat section is raised 704, the foot section 706 may remain substantially horizontal. The same applies to the seat section 704 as the foot section 706 is lowered.

Furthermore, in one embodiment, the foot section 706 comprises a sensor (not shown) such as an inclinometer of the like to detect variations in the inclination/orientation of the foot section 706. As will be described in greater detail below, data acquired using this and other such sensors disposed on various parts of the bed can be used in calculating and monitoring various characteristics of the bed 100 and/or of a patient lying thereon. As will be apparent to the person skilled in the art, the sensor can be mounted elsewhere on the seat section 706 without departing from the general scope and nature of the present disclosure.

The Lying Surface

Figure 7:
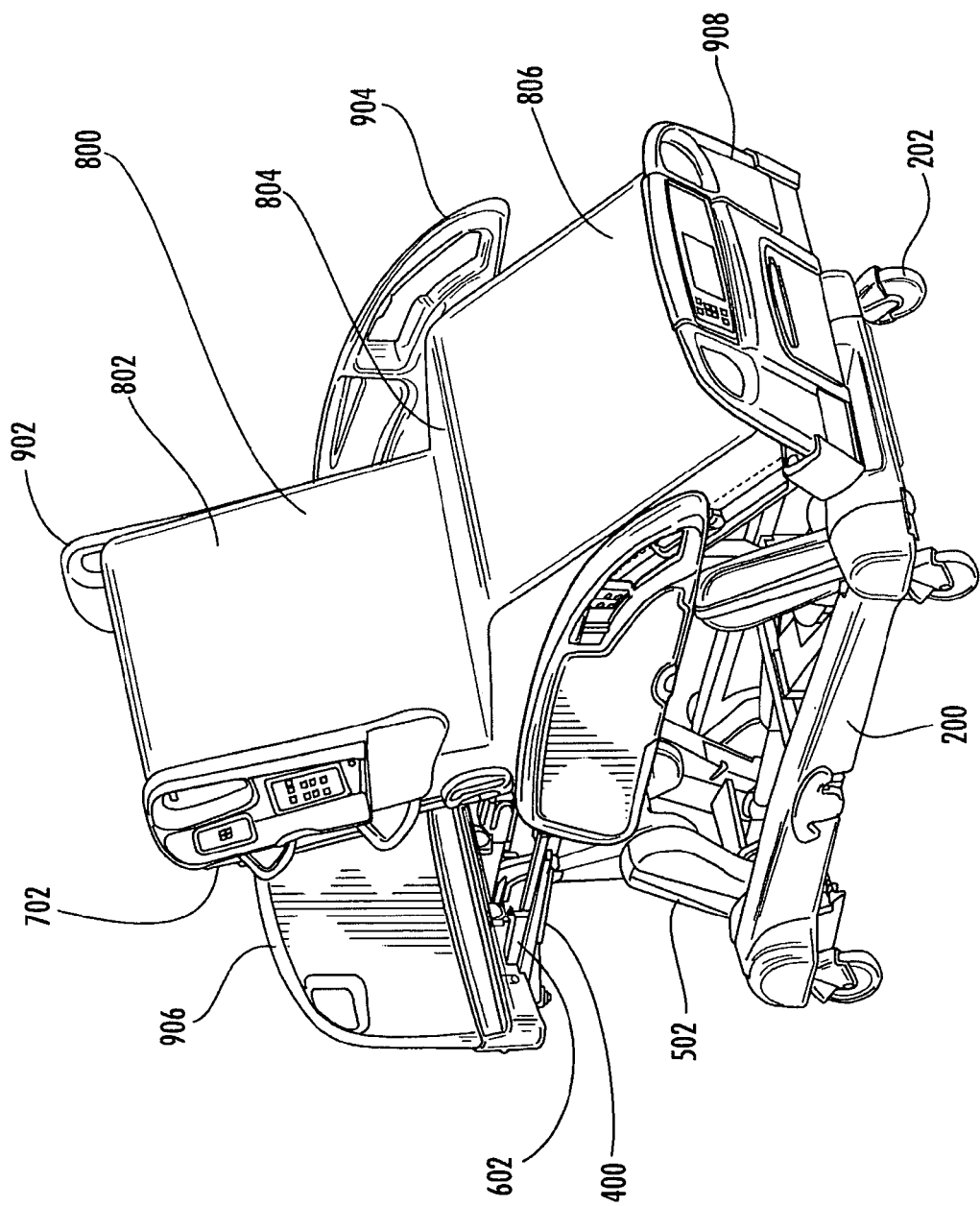
FIG. 7 is a right perspective view of the patient support apparatus of FIG. 6, further comprising a lying surface.

Referring to FIG. 7, a patient is supported on a lying surface 800, which can also be referred to as a mattress, a support surface, a lying surface, a patient surface, etc. For the purpose of this invention, these terms are used interchangeably to indicate the article upon which the patient lies, which is generally cushioned for patient comfort. The article may be cushioned with foam, air, springs, or any other cushioning means known in the art. For example, suitable mattresses include Gaymar mattresses or foam mattresses. In one embodiment of this invention, the lying surface 800 is a mattress, such as found in a hospital setting. For ease of discussion, the term mattress is used throughout, although another type of article defining a lying surface 800 may be used.

As described above, the bed 100 of the present invention is capable of being configured into a variety of positions so as to accommodate the patient. For example, the sections of the deck support 700, i.e., the head section 702, seat section 704, and foot section 706, can be adjusted to be raised or lowered into various positions. Consequently, the lying surface 800 also comprises a head section 802, a seat section 804, and a foot section 806, all three being articulated relative to the other to move and follow the contour defined by the deck support 700.

The person of skill in the art will readily understand that various static and/or adjustable lying surfaces 800 may be considered in the present context without departing from the general scope and nature of the present disclosure. For instance, adjustable mattresses comprising pneumatically activated compartments configured to provide an adaptable surface profile may be used for patients having reduced mobility and/or for patients generally difficult to move. These and other such mattresses may used with bed 100, the deck support 700 optionally providing power and/or control access to this type of lying surface 800 via integrated control and/or auxiliary power sources.

The Barrier System

The bed 100 generally further comprises a barrier system 900 comprised of structural barriers for ensuring the safety of a patient lying on the bed 100. Embodiments of the barrier system 900 may include any combination of a headboard 906, a footboard 908, a pair of head-end side rails 902, and a pair of foot-end side rails 904.

FIGS. 40A to 54 show an embodiment of the barrier system 900, illustrating therein the various components of this barrier system 900 in various positions. For example, FIGS. 40A and 40B show the full barrier system 900 when mounted adjacent the lying surface 800, wherein the side rails 902, 904 are shown in their fully deployed or extended position in FIG. 40A, and in their fully retracted position in FIG. 40B. FIGS.

Figure 45:
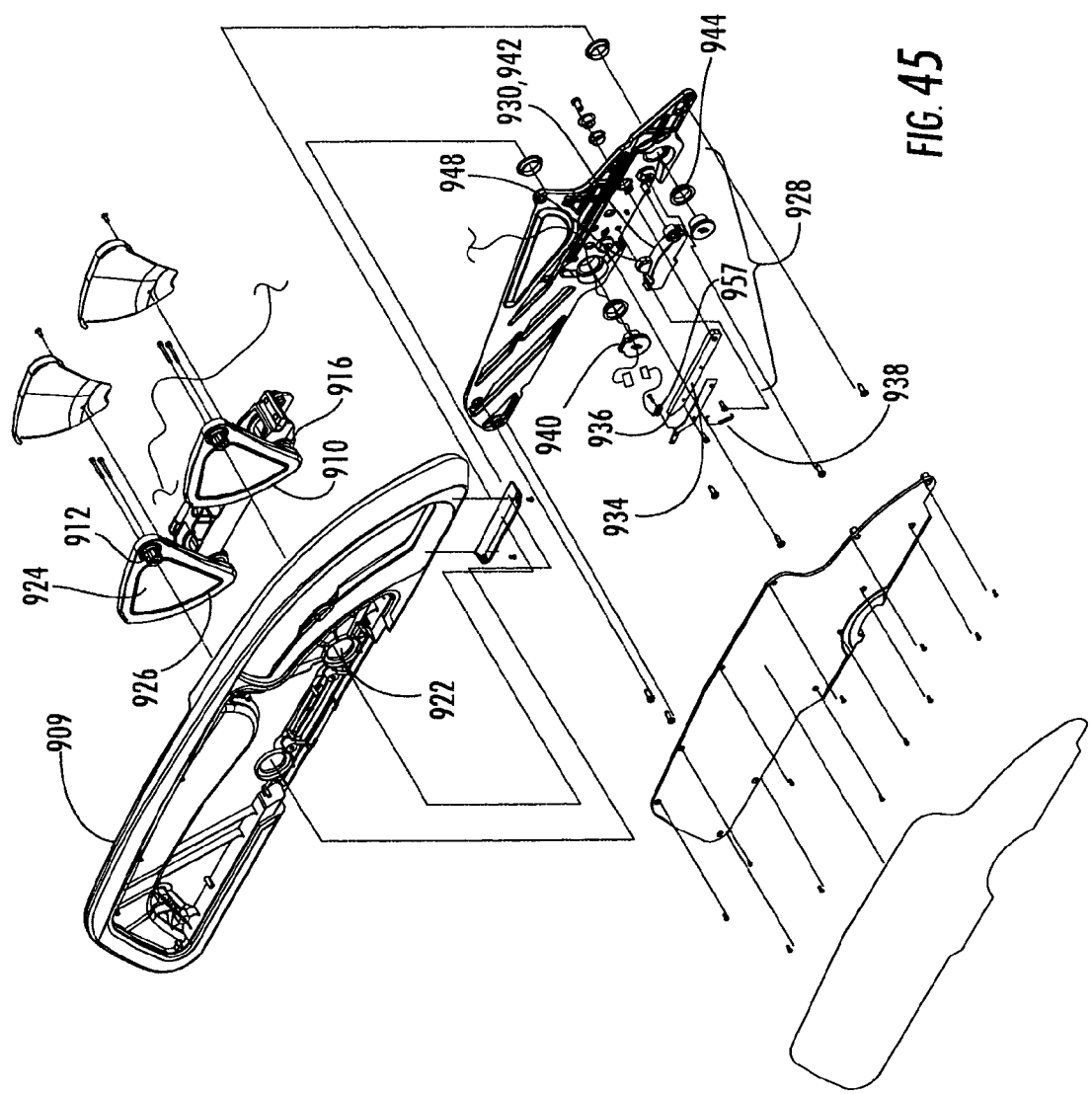
FIGS. 45 and 46 are respective exploded views of an internal assembly of the foot-end side rail of FIG. 44 and an assembly of a foot-end side rail control panel coupled thereto.
Figure 45A:
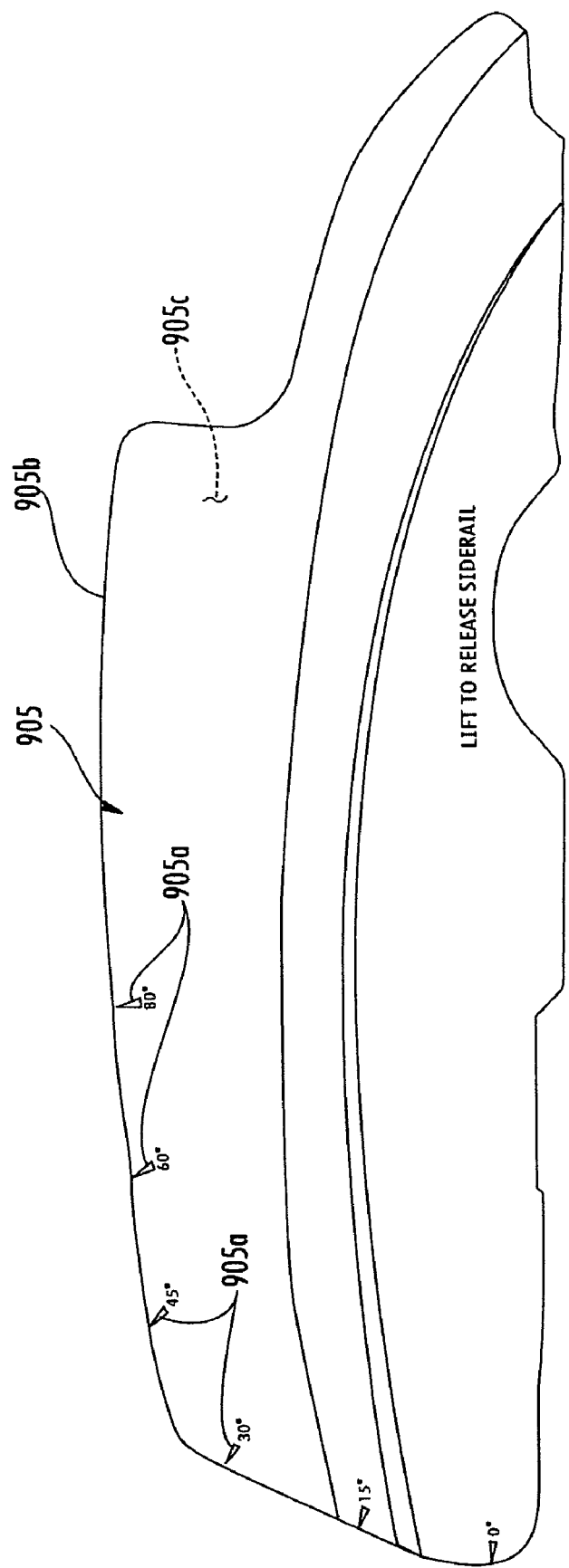
FIG. 45A is an elevation view of a visual indicator that can be provided or formed on a side rail to provide a visual indication of the angle of the head-end section of the deck frame when the head-end section is inclined.
Figure 46:
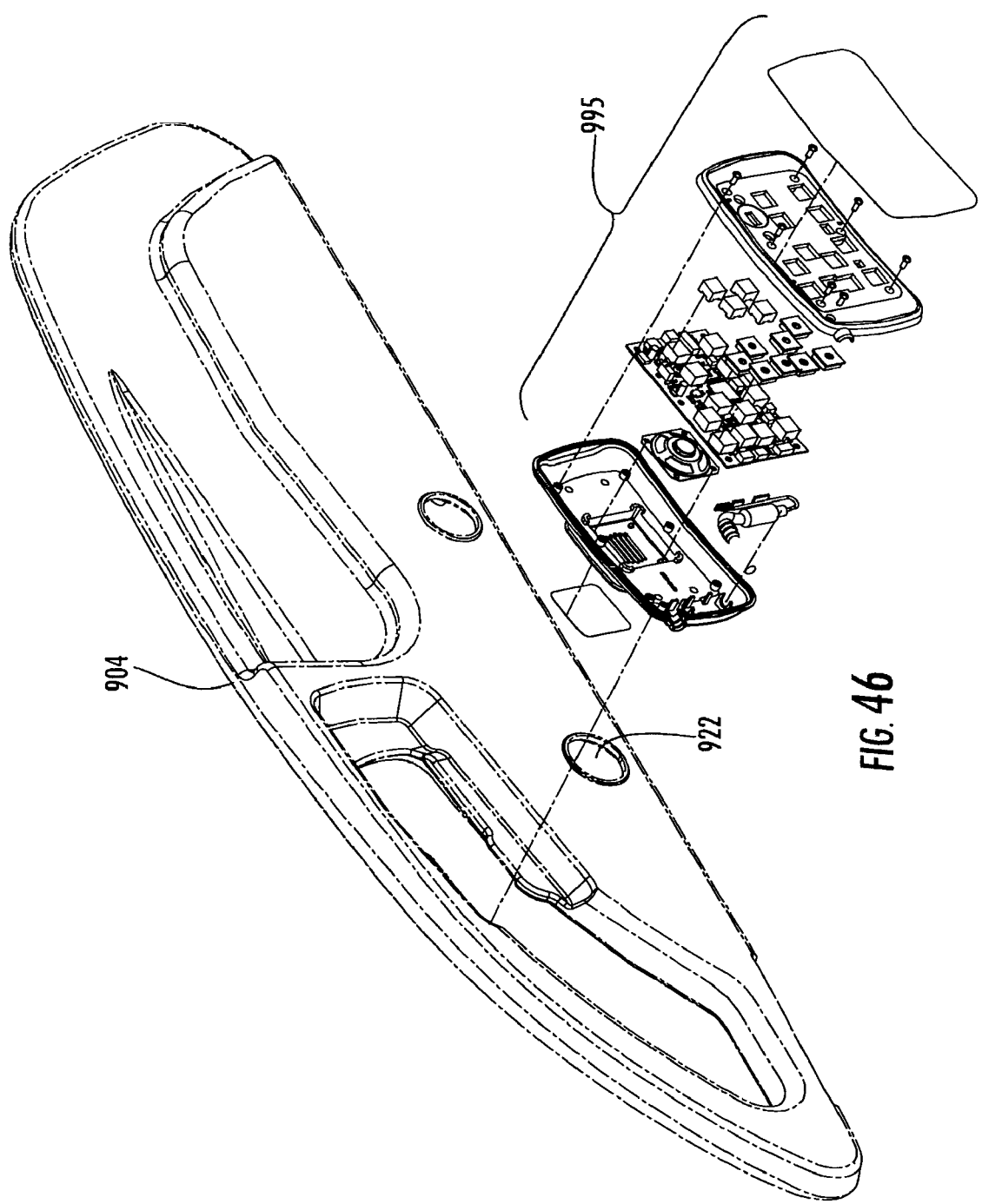

41 to 43 show an assembly of the head-end side rails 902 and their attachment to the head section 702 of the deck support 700, whereas FIGS. 44 to 46 show an assembly of the foot-end side rails 904 and their attachment to the load frame 600.

Figure 49:
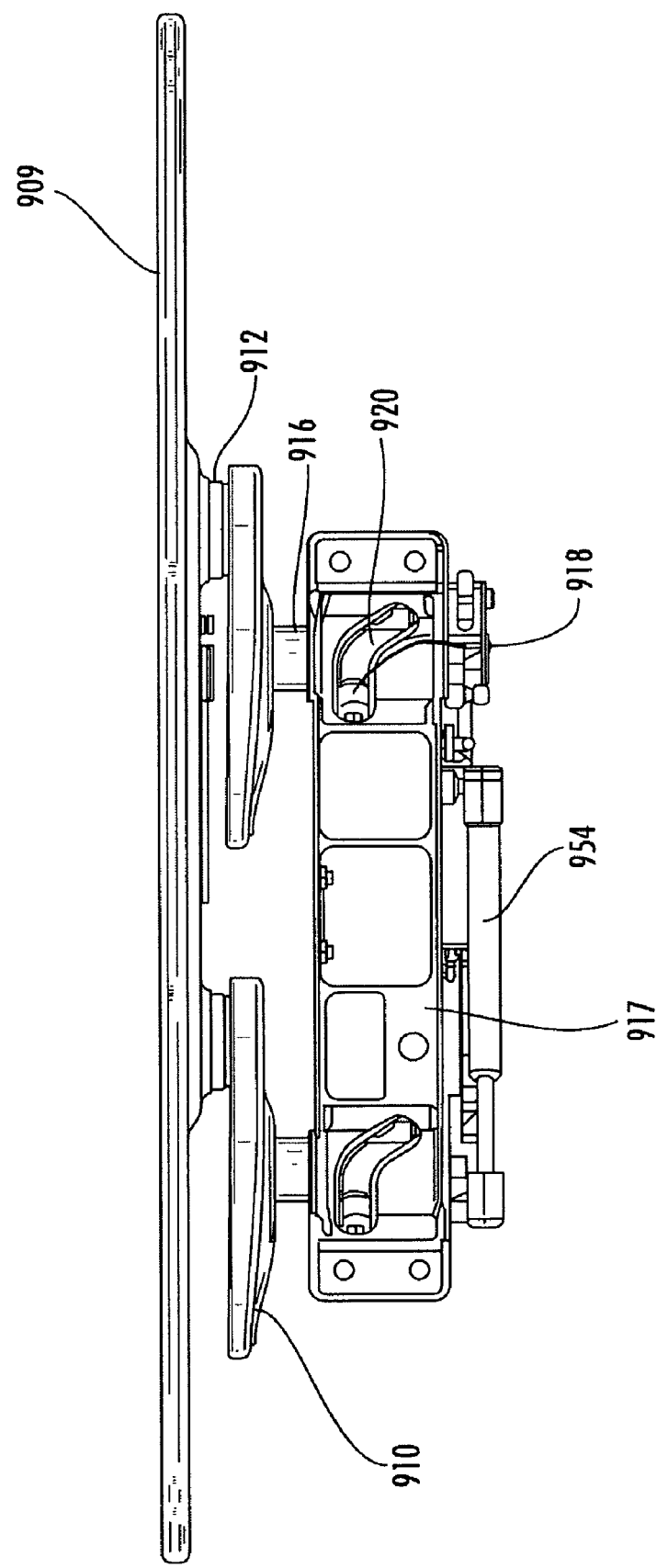
FIG. 49 is a top plan view of a side rail showing a guiding mechanism thereof in accordance with one embodiment of the present invention.
Figure 50:
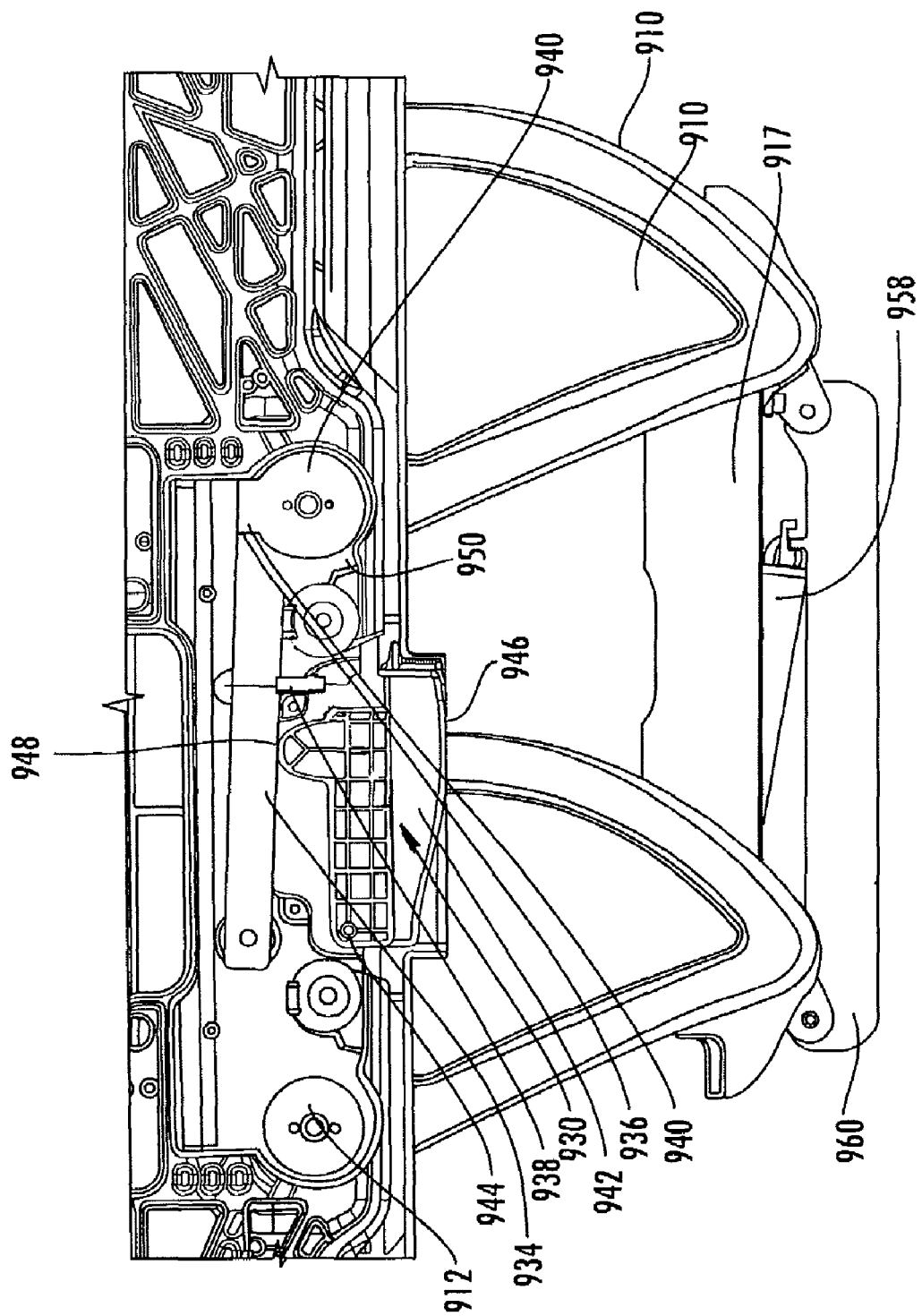
FIG. 50 is a side view of a side rail showing a locking mechanism thereof in accordance with one embodiment of the present invention.

In FIGS. 47A to 47D and 48A to 48D, an exemplary foot-end side rail 904 is shown in different positions, illustrating therein a damping mechanism applied to this side rail 904 as it moves from one position to another. In addition, FIGS. 49 and 50 show in greater detail of illustrative embodiments of a guiding mechanism 954 and a locking mechanism 928 (FIG. 45) for respectively guiding and locking a motion of the side rails 902, 904. FIGS. 51 to 54 provide various views of the footboard 908 and of an optional control console 976 pivotally attached thereto.

As will be understood by the person skilled in the art, the construction, configuration and operational mechanisms of the head-end and foot-end side rails 902, 904 are very similar in both design and operation. As such, sections discussing the actuation, damping and locking mechanisms of the side rails 902, 904, as well as various general discussions as to the fabrication and assembly of these side rails 902, 904, are cast with reference to various illustrations of an exemplary foot-end side rail 904. It will be appreciated that although referencing only one illustrative embodiment of the bed's foot-end side rails 904, the following description applies equally, unless otherwise indicated, to both the head-end side rails 902 and the foot-end side rails 904.

Side Rails

Referring now to FIGS. 40 to 50, an illustrative embodiment of the bed's side rails 902, 904 will now be described. In general, head and foot-end side rails 902, 904 are configured to move between raised or deployed positions, as shown for example in FIG. 40A and lowered or stowed positions, as shown for example in FIG. 40B to permit entry and egress of patients into and out of the bed 100. Head-end side rails 902 are illustratively coupled to the head section 702 of the deck support 700 (e.g. see FIG. 41) and may be moved between raised and lowered positions. Foot-end side rails 904 are illustratively coupled to the load frame 600 (e.g. see FIG. 44) and may also be moved between raised and lowered positions. As the head section 702 of the deck support 700 rotates relative to the load frame 600, head-end side rails 902 also rotate relative to the load frame 600. The foot-end side rails 904, however, remain unmoved irrespective of movement of the head section 702, seat section 704 or foot section 706 of the deck support 708.

With particular reference to FIGS. 41, 42, 44 and 45, each of the movable side rails 902, 904 for use with the bed 100 according to the present invention generally comprises a side rail body 909 and a side rail body support, the latter illustratively comprising two or more support arms 910 pivotally coupled between the side rail body 909 and a guiding mechanism 914 disposed within a cross member 917 configured for fixed attachment to the bed frame structure (e.g. to deck support 700 for head-end side rails 902 and to load frame 600 for foot-end side rails 904). A first end of each support arm 910 is pivotally connected to the side rail body 908 in a longitudinally spaced apart relationship using an upper pivot 912, and a second end of each support arm 910 is pivotally connected to a guiding mechanism 914 through a lower pivot 916 operatively engaged thereto in a longitudinally spaced apart relationship. The guiding mechanism 914 is coupled to a cross-member 917 connected to either the deck support head portion 702 (head-end side rails 902) or the load frame 600 (foot-end side rails 904).

With added reference to FIG. 49, each of the lower pivots 916 includes a radial protrusion 918 configured to engage with a groove 920 in the guiding mechanism 914. When the lower pivots 916 are rotationally moved, the radial protrusions 918 are guided by the grooves 920 thereby creating a transverse transitional movement of the pivots 916 along the pivot slots 922 of the guiding mechanism 914 resulting in the transverse movement of the side rail body 909 towards and away from the bed 100, during the lowering and raising movement, respectively, of the side rails 902, 904.

In one embodiment, each support arm 910 is configured to have a shape with a width greater at the first end 924 than at the second end 926 thereof. The side rail body 909 is movable between a deployed position and a stowed position through clock-type rotational movement in a plane substantially vertical and substantially parallel to the longitudinal length of the bed 100. As a result of the shape of the support arms 910, the side rail angle defined between each support arm 910 and the bottom edge of the side rail body 909 remains obtuse at all times during the rotational movement of the side rail body 909. This configuration eliminates pinch points created between each support arm 910 and the bottom edge of the side rail body 908, which typically occur when traditional support arms are used.

Side Rail Body and Support Arms

In FIGS. 41, 42, 44 and 45, showing one embodiment of the head-end side rails 902 and foot-end side rails 904, the side rail bodies 909 of head-end and foot-end side rails 902, 904 are each connected to two support arms 910 through two respective upper pivots 912. Two respective lower pivots 916 are used to connect the other ends of the two support arms 910 to a cross-member 917. The distinctive shape of the support arms 910 illustrated herein is an example of a configuration designed to avoid the creation of pinch points between the support arms 910 and the lower side of the side rail body 909 during movement of the side rail 902, 904. In this embodiment, the side rail body 909 is coupled to the support arms 910 in a manner allowing the side rail body 909 to be replaced or changed if damaged or to suit different needs, without having to change the complete side rail 902, 904.

In general, a locking mechanism 928 (FIG. 45) is provided (shown in greater detail in FIG. 50), in one embodiment to lock the side rail(s) 902, 904 in a deployed or raised position, and a release system 930 therefor is located on the side rail 902, 904 such that an operator may selectively lower the side rail(s) 902, 904 when needed. As will be appreciated by the person skilled in the art, the location of the release system may be designed according to its intended use. For example, where it is preferable to limit the use of the locking mechanism to the caregiver or someone else other than the person on the bed, the release system can be configured and located on the side rail body support (e.g. support arms 910) where it cannot be operated by the person on the bed 100. This configuration is useful for security and safety reasons. The side rail locking mechanism 928 (FIG. 45) will be described in greater detail below with reference to FIG. 45.

Figure 47A:
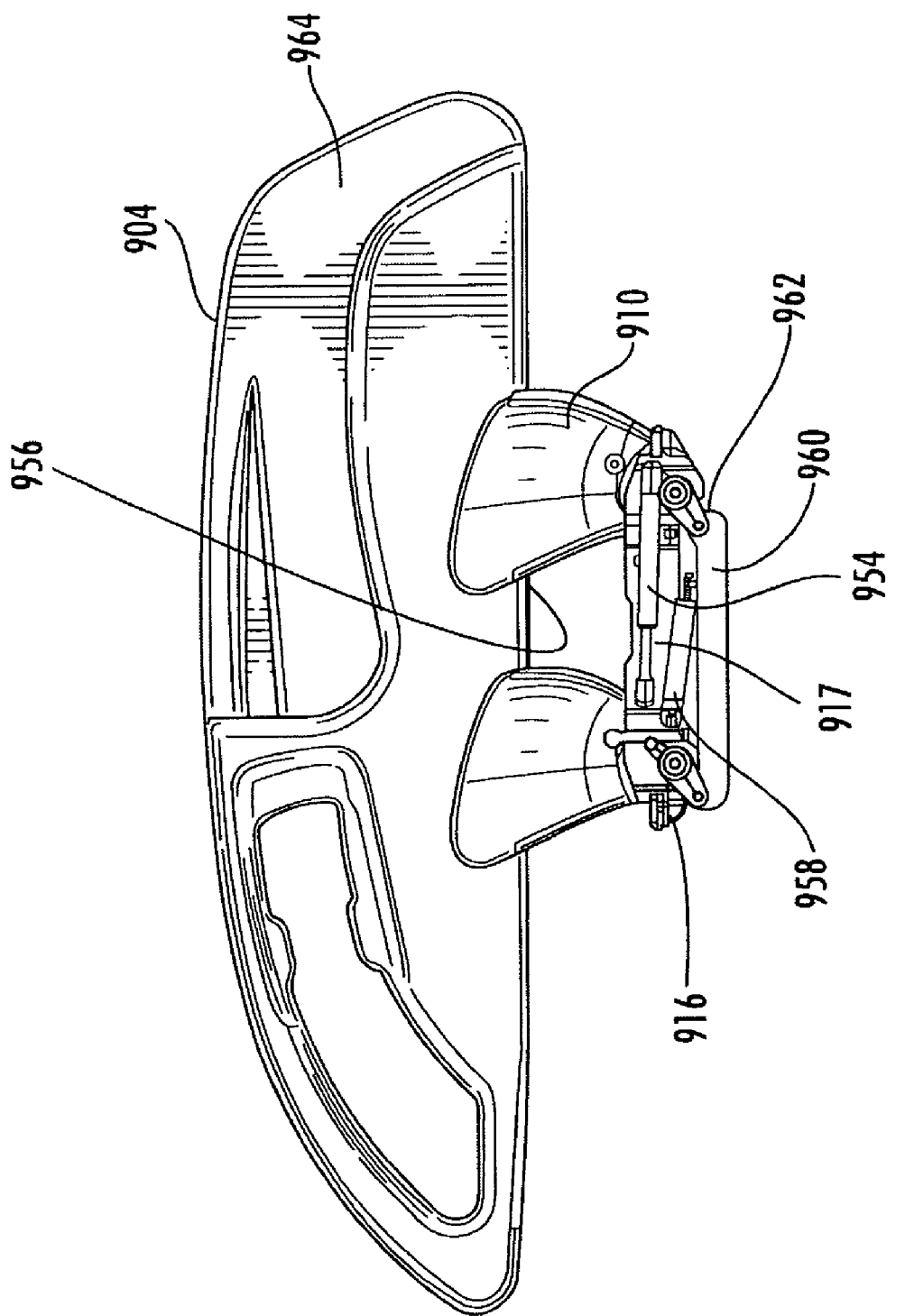
FIGS. 47A to 47D are inner side views of the foot-end side rail of FIG. 44 in positions ranging from a fully extended position (FIG. 47A) to a fully retracted position (FIG. 47D)
Figure 47B:
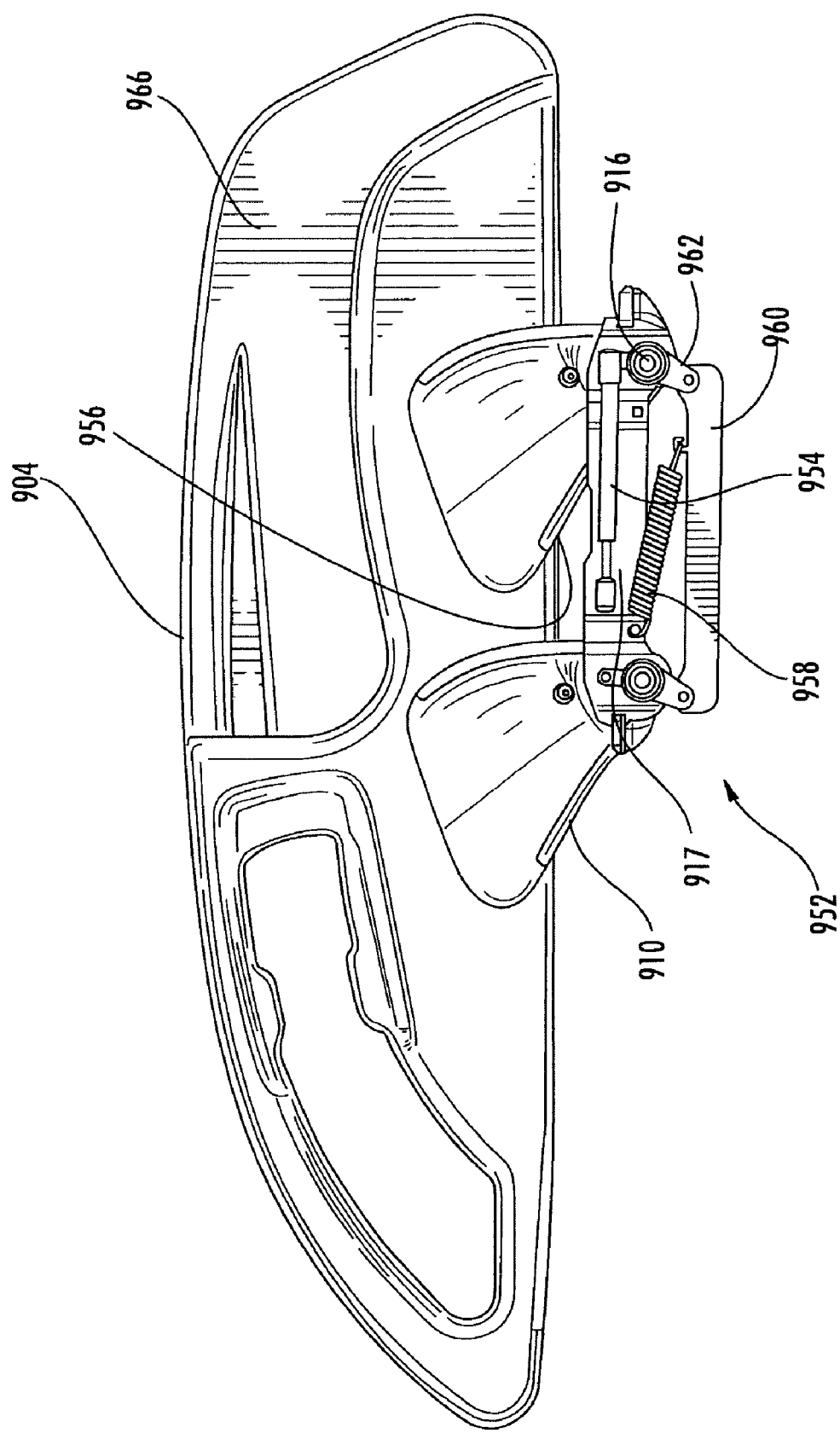
Figure 47C:
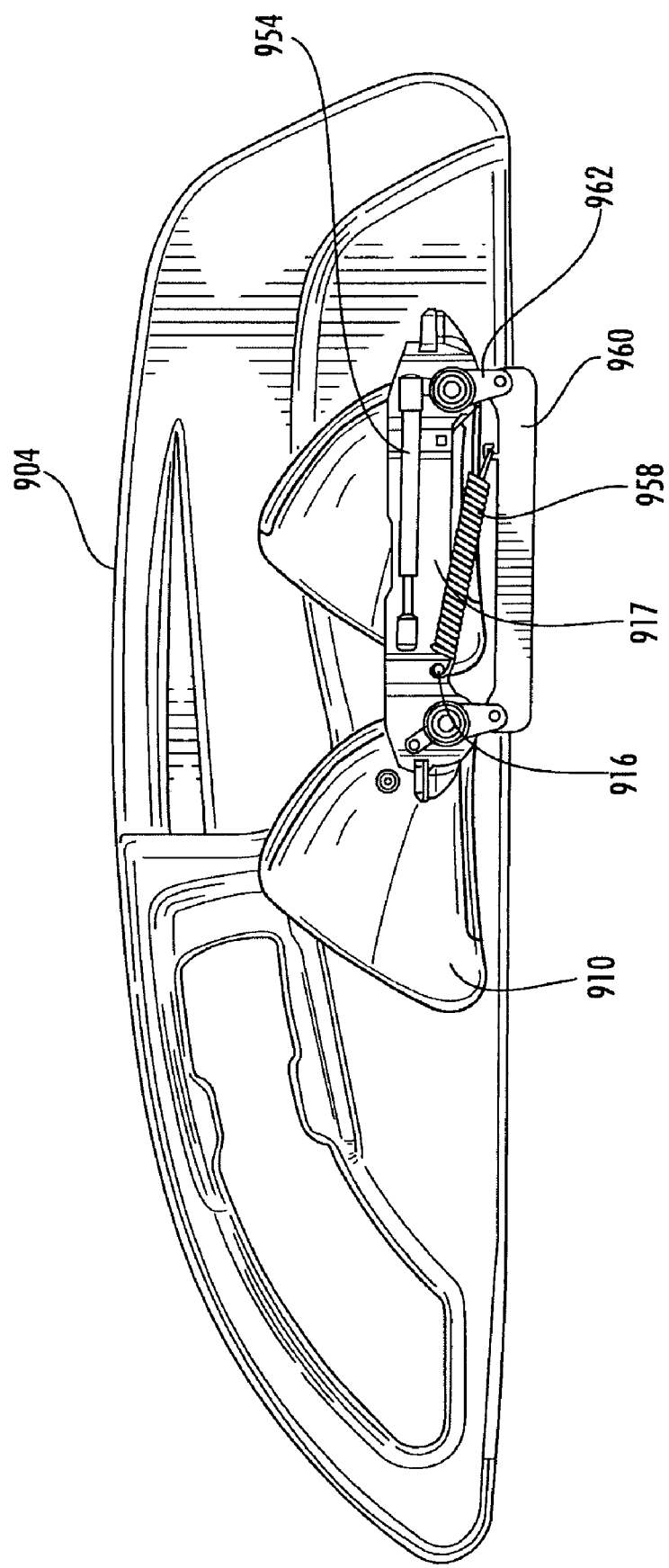
Figure 47D:
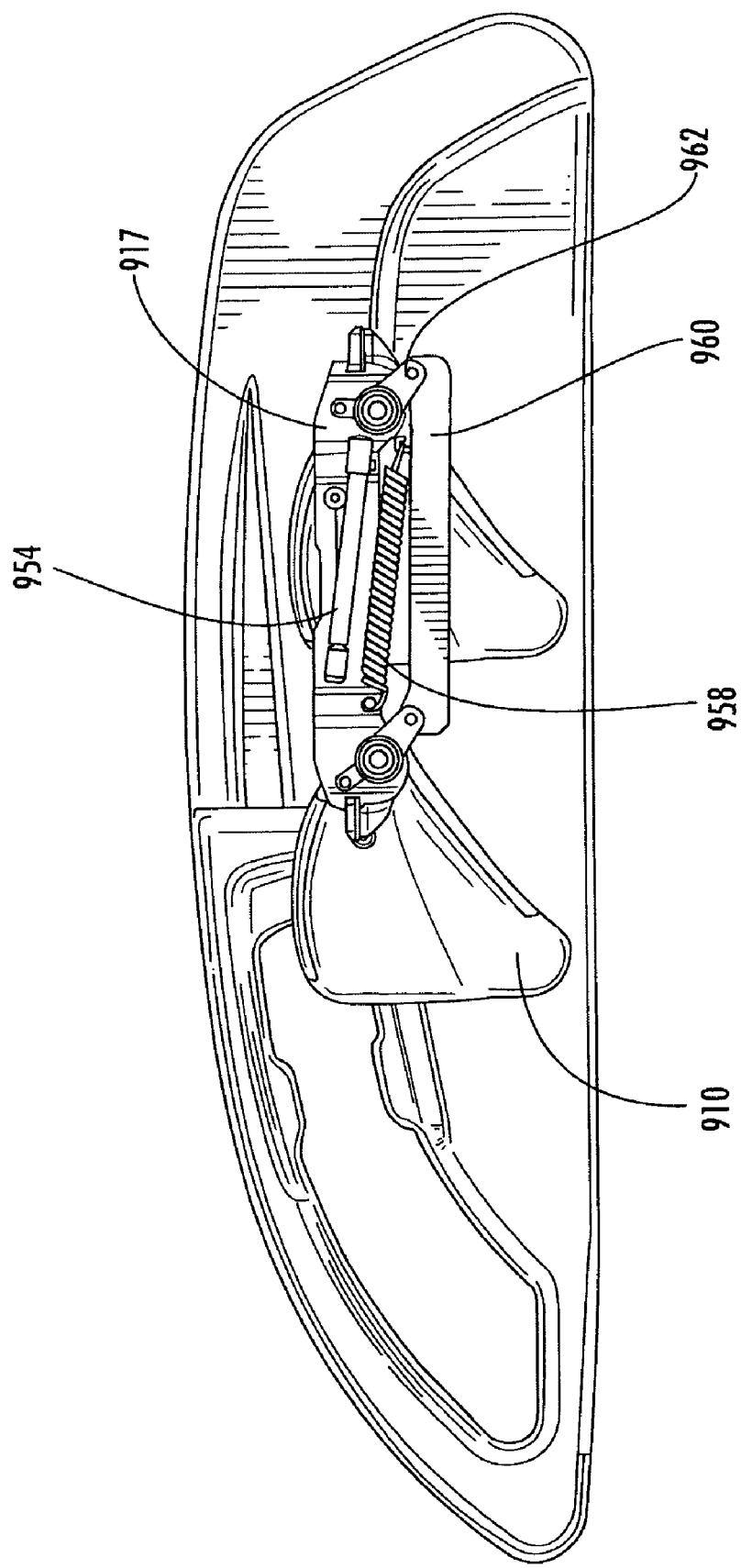
Figure 48A:
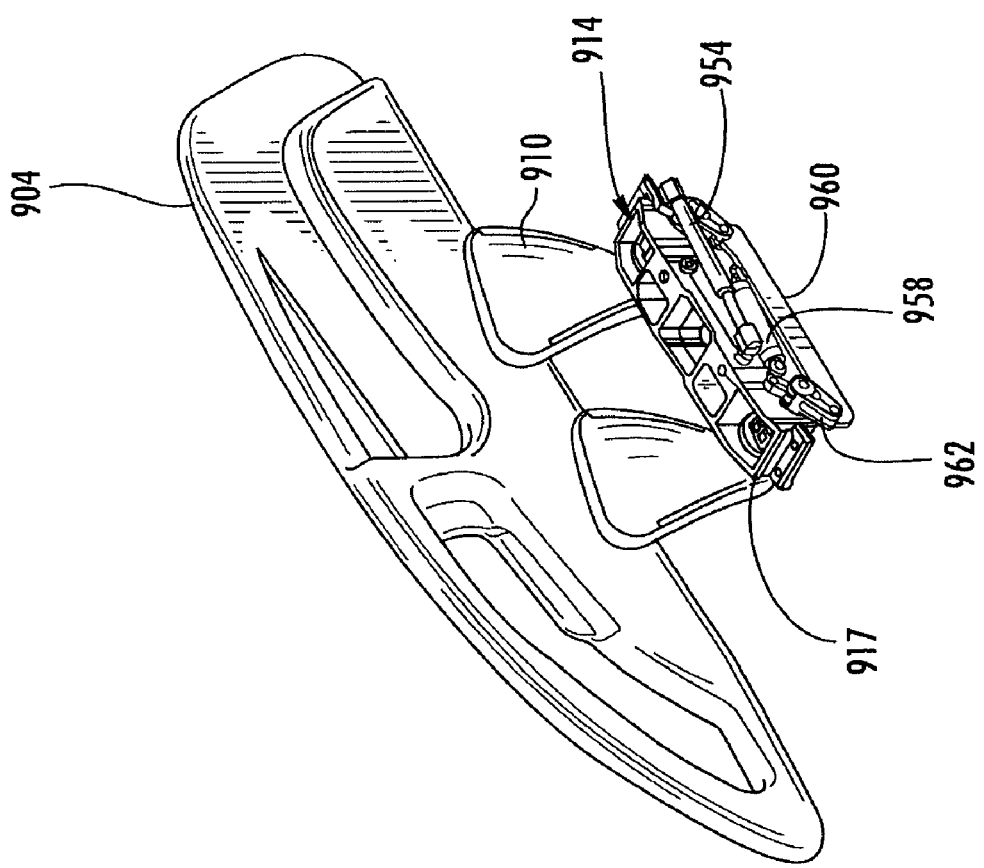
FIGS. 48A to 48D are inner perspective views of the foot-end side rail of FIG. 44 in positions ranging from a fully extended position (FIG. 48A) to a fully retracted position (FIG. 48D)
Figure 48B:
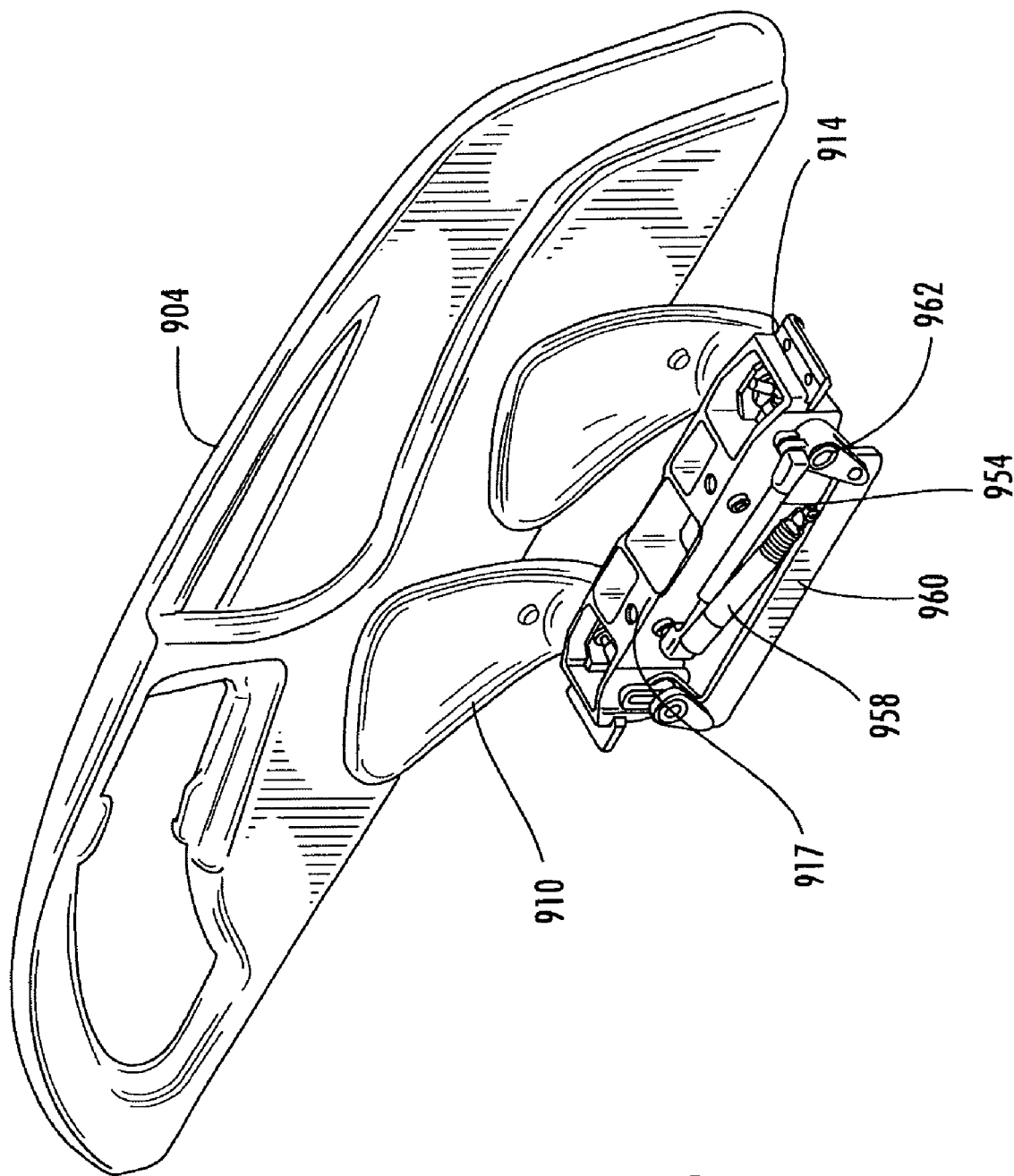
Figure 48C:
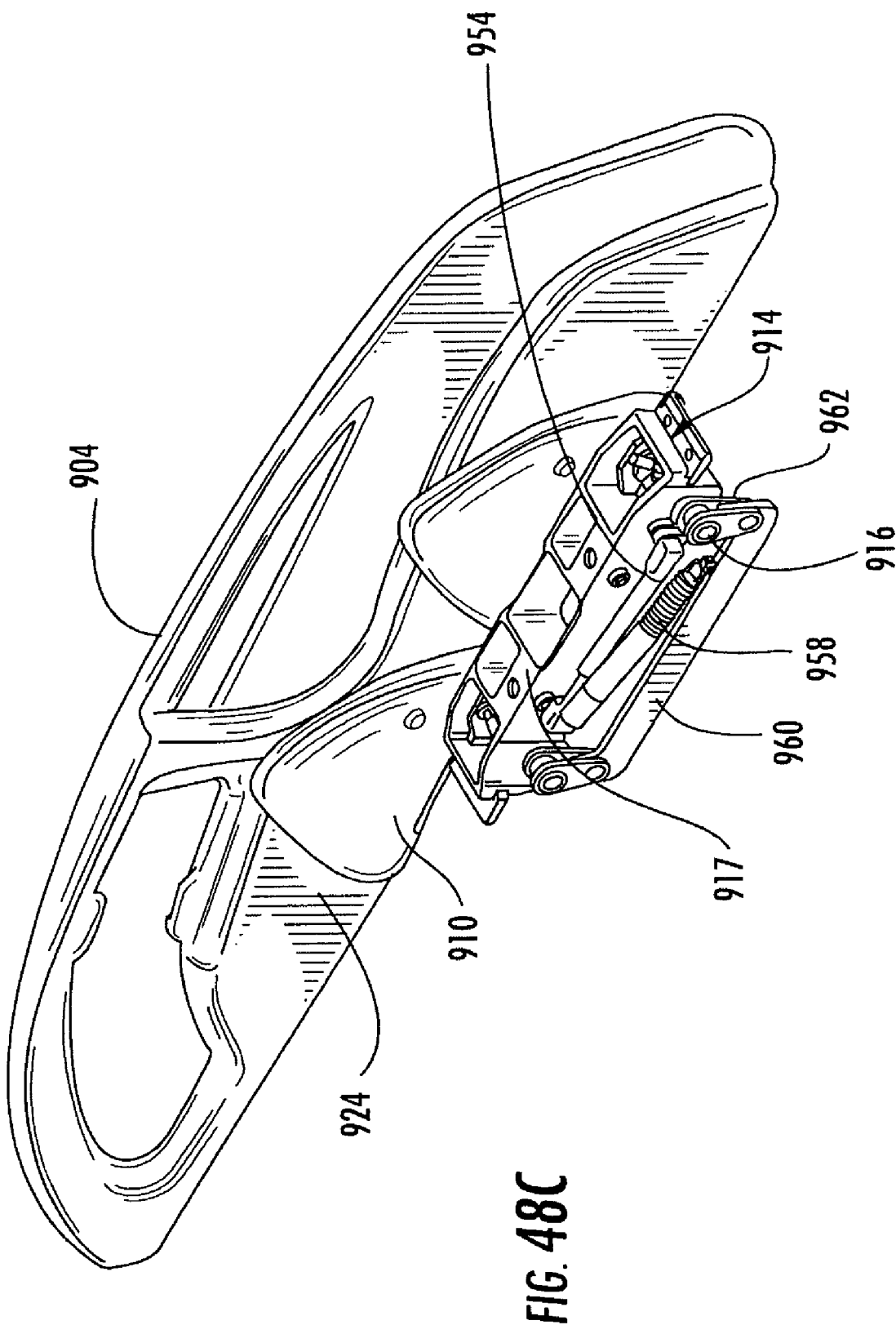
Figure 48D:
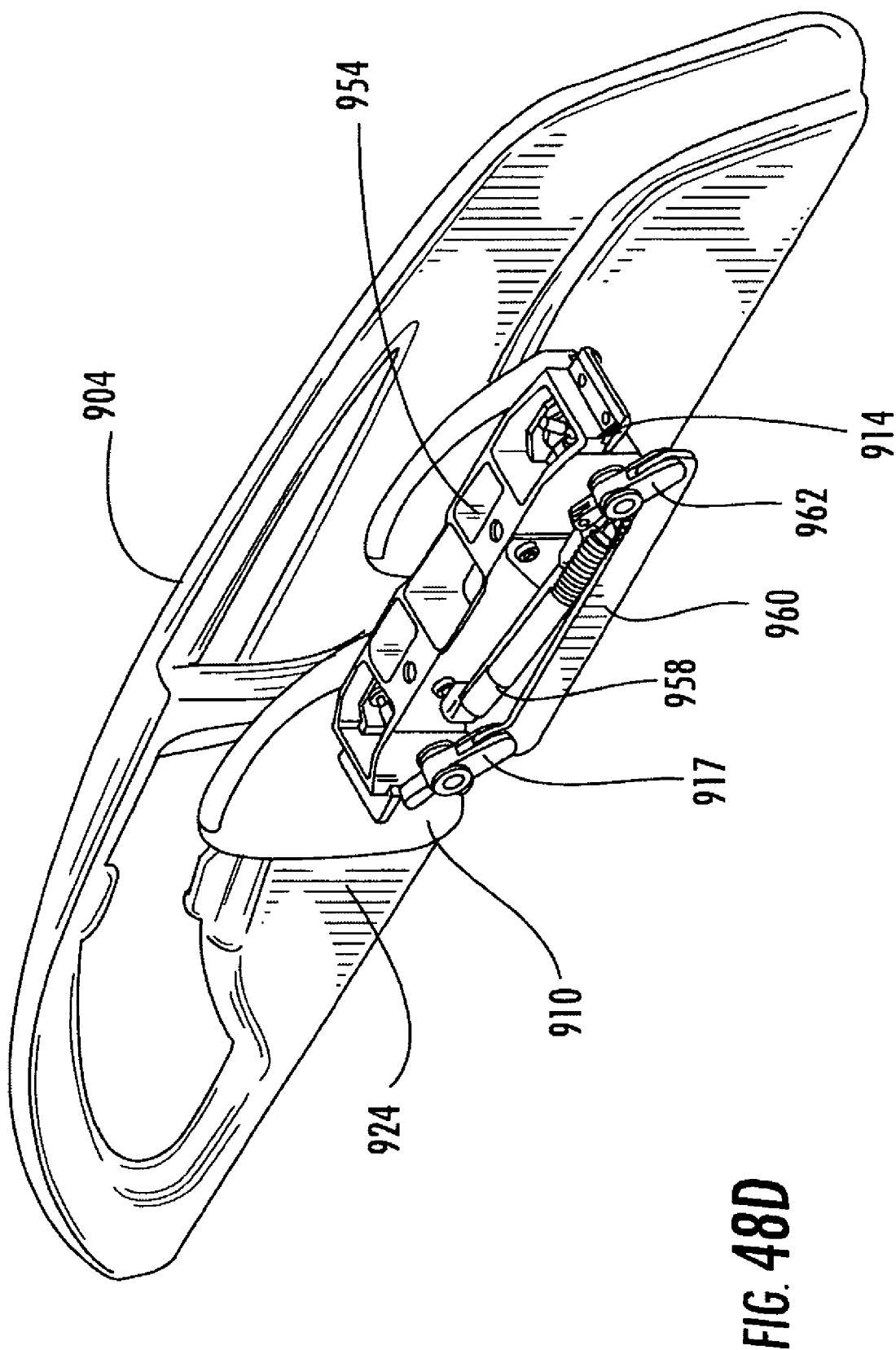

With reference to FIGS. 47A to 47D and 48A to 48D, interior side and perspective views of a foot-end side rail 904, in accordance with one embodiment of the present invention, are illustrated for different positions from a fully deployed position (FIGS. 47A and 48A) to a fully stowed position (FIGS. 47D and 48D). In this embodiment, it can be clearly identified that the angle formed between each support arm 910 and the bottom edge of the side rail body 909 remains obtuse at all times during the rotational movement of the side rail body 909. As discussed above, the person of skill in the art will understand that the above and following discussion applies equally to the head-end side rails 902. This obtuse angle increases as the side rail body 909 is lowered. Further, support arms 910 pivot in a counter-clockwise direction (as viewed in FIGS. 47A-47C) when side rail body 909 is lowered.

The side rail body 909 can be made for example from plastic or other synthetic materials, which can be molded, while the side rail body support 911 can be made for example of aluminum, aluminum alloys or any other material with a desired level of strength. These materials are provided solely as examples and the choice of materials used for these parts can vary according to various considerations such as weight, strength, appearance, durability and sturdiness for example, as will be readily understood by the person skilled in the art.

In the illustrated embodiments of the barrier system 900, the shape of the support arms 910 the characteristics of provides advantageous characteristics. The person of skill in the art will appreciate that several similar shapes for the support arms 910 can be used, these shapes sharing the common characteristic that the width of the support arms is greater at the upper ends 924 (operatively connected to the upper pivots 912) than the lower ends 926 (operatively connected to the lower pivots 916) so that the angle defined by the lower edge of the side rail body 909 and the support arms 910 remains obtuse at all times during the operation of the side rails 902, 904, thereby eliminating pinch points during operation of these side rails. For example, possible shapes for the support arms may include substantially triangular (e.g. as illustrated herein), trapezoidal, round, possibly comprising sides curved in a convex or concave manner, etc. To achieve the above-described effect of eliminating pinch points, the location of the connection between the upper ends 924 of the support arms 910 and the upper pivots 912 should be proximal to the rotational side of the support arms 910 which faces the rotational movement when the side rail 902, 904 is moved from the deployed position to the stowed position, as illustrated in FIGS. 47A to 47D and 48A to 48D for the foot-end side rails 904. Similar geometry also applies for the head-end side rails 902.

FIGS. 47B, 47C and 48B, 48C are detailed interior side and perspective views of a foot-end side rail 904 at intermediate positions. The angle formed by the bottom edge of the side rail body 909 and the support arms 910 remains obtuse until it is eliminated when the side rail body 909 is lowered to a point where the upper pivots 912 are substantially aligned horizontally to the lower pivots 916 (shown in FIGS. 47C and 48C).

Furthermore, as introduced above in accordance with one embodiment of the present invention, the side rail body 909 can be moved laterally towards and away from the center of the bed 100 as the side rail 902, 904 is stowed and deployed, respectively, in order to minimize the width of the bed 100 when one or more side rails 902, 904 are not in use and conversely maximize the patient's surface lying surface 800 when in use. In this embodiment, the vertical and lateral movement of the side rail body 909 takes place through a single movement during operation of the side rail 902, 904 thereby decreasing the effort and separate actions required for operation of these side rails.

Guiding Mechanism and Cross-Member

With reference to FIGS. 41, 42, 44, 45 and 49, the side rail body 909 is pivotally connected to two support arms 910 through a pair of upper pivots 912. The two support arms 910 are pivotally connected to guiding mechanisms 914 through a pair of lower pivots 916, the guiding mechanisms 914 operatively connected to a cross-member 917. A radial protrusion 918 located on each lower pivot 916 is operatively coupled to a bearing assembly 932 which is operatively engaged with a groove 920 of the guiding mechanism. The bearing assembly 932 operatively coupled to the radial protrusion 918 reduces the frictional coefficient during the operation of the side rail 902, 904 considerably diminishing the wear of the radial protrusion 918 and the edges of the groove 920. Any kind of conventional bearing assembly can be used for this purpose. The shape and size of groove 918 can vary depending on the desired lateral transitional movement of the lower pivots 916 along the pivot slots 922 of the guiding mechanism 914. The rotational movement around the lower pivots 916 which occurs during operation of the side rail 902, 904 results in the transverse movement of the lower pivots 916 and translates into a transverse movement of the side rail body 909 towards or away from the longitudinal centerline of the bed 100. In one embodiment, the distance between the side rail body 909 and the deck support 700 (head-end side rail 902) or the load frame 600 (foot-end side rail 904) is at its maximum in the deployed position.

The characteristics of the guiding mechanism 914 can be configured in several ways. For example, the guiding mechanism 914 can be cast in a single component, incorporating the cross-member 917. It can also be machined from a single piece of material. Some of the advantages of such embodiments are reduced costs of production, simplified installation and structural integrity of the guiding mechanisms 914 and the cross-member 917. The guiding mechanism 914 and cross-member 917 can also be formed from several parts. For instance, the areas immediately surrounding the grooves 922 of the guiding mechanism 914 can be made from parts distinct from the rest of the guiding mechanism 914. Given that these sections of the guiding mechanism 914 are the areas which will sustain the heaviest wear due to the friction between the radial protrusions 918 located on each lower pivot 916 or the bearing assembly 932 operatively coupled to the radial protrusions 918, it is desirable to have these sections separate from the rest of the guiding mechanism 914 and the cross-member 917 in order to replace only the damaged sections when needed instead of replacing the whole guiding mechanism 914 or cross-member 917. This aspect of the invention is also useful to replace the sections immediately surrounding the grooves 920 of the guiding mechanism 914 to change the configuration of the grooves 920 for different uses of the side rail 902, 904 with the same bed 100. The shape of the guiding grooves 920 themselves can vary to accommodate various needs and various lying surfaces 800 the side rail 902, 904 is to be used with. For example, the grooves 920 can be linear, curved, angled or a combination thereof, as long as the guiding grooves 920 of a same side rail 902, 904 are substantially identical and have the same orientation.

The embodiment illustrated in FIG. 49, for example, has guiding grooves 920 which have a substantially longitudinally linear portion followed by a curved portion. When a rotational force is applied to the side rail 902, 904, there is no lateral movement until the radial protrusions 918 engage with the curved portions of the guiding grooves 920. When the radial protrusions 918 reach the beginning of the curved portions of the guiding grooves 920, the top of the side rail body 909 is located lower than the side of the deck support 700 (head-end side rails 902) or load frame 600 (foot-end side rails 904) so that once the radial protrusions 918 engage with the curved portions of the guiding grooves 920, the side rail body 909 is free to translate laterally closer to the center of the bed 100.

Other embodiments where the radial protrusion 918 and bearing assembly 932 are in different positions during the lateral translation movement are also provided. The preceding is merely one example of possible configurations of the guiding grooves 920. The guiding grooves 920 can have curved portions curving towards or away from the cross-member 917, or any combination of curved and linear portions. For example, a guiding groove 920 can have two curved portions curving towards the cross-member 917 separated by a linear portion such that a rotational force applied to the side rail body 909 will result in a lateral movement translating in the side rail body 909 being closer to the center of the bed 100 when in a fully deployed position or fully stowed position and the side rail body 909 will be further from the center of the bed 100 when in transitional positions. It will also be appreciated that different groove configurations may apply to different side rails, for example, to head-end and foot-end side rails 902, 904 respectively.

In a further embodiment of the invention, the guiding grooves 920 are located on the pivot shaft to operatively engage with one or more protrusions coupled to a bearing assembly, extending from the inside of the pivot slot 922.

In one embodiment the guiding mechanism 914 and the cross-member 917, or the different components thereof, as the case may be, can be made of several materials. Characteristics such as weight-to-strength ratio, hardness, wear resistance and corrosion resistance (corrosion from airborne corrosive agents, air and cleaning solvents and bodily fluids usually found in a hospital/medical environment) should be given consideration when choosing the materials to be used in the manufacturing of the guiding mechanism 914 and the cross-member 917 or the different components thereof. One example of an appropriate material for the cross-member 917 is aluminum for its lightweight and resistance to corrosion. However, other parts such as the areas immediately surrounding the grooves 920 of the guiding mechanism 914 and the slots 922 for the lower pivots 916 can be made from other materials to accommodate the higher frictional abrasion on such parts and therefore being more prone to wear. Materials with a high resistance to wear, such as steel, stainless steels or ferrite alloys for example, can be used for making these parts. Other parts of the side rail mechanism can be made from further different materials and are not limited in any way to the materials used for the guiding mechanism 914. The various parts of the guiding mechanism 914 and the cross-member 917 can comprise interlocking mechanisms provided between the multiple parts to ensure correct alignment of these multiple parts during assembly. As mentioned previously, for example, the guiding grooves 920 within a same guiding mechanism 914 have to be substantially identical the side rail 902, 904 coupled thereto to function properly, requiring parts that are precisely operatively connected. Slots, grooves, apertures or fittings, for example, may be used to interlock the various parts of the side rail together precisely.

In one embodiment, the operation of the side rails 902, 904 is as described above and illustrated in FIGS. 47A to 47D and 48A to 48D, wherein an exemplary embodiment of the foot-end side rails 904 are illustrated in transitional positions between a fully deployed position (A) and a fully stowed position (D). In general, the distance between the lower portion of the side rail body 909 and the deck support 700 (head-end side rails 902) or load frame 600 (foot-end side rails 904) is generally at its minimum in the fully stowed position. In this embodiment, as shown, an angle between the support arms 910 and the lower edge of the side rail body 909 is generally maintained obtuse thereby eliminating pinch points.

In another embodiment (not shown), the pivot shafts of the lower pivots 916 engaging with the guiding mechanism 914 are screw-type shafts. In this embodiment, the guiding mechanism 914 is designed to have treads matching the radial extensions of the screw-type pivot shafts to operatively receive the radial extensions creating a lateral translation movement of the pivot shafts through a rotation of the pivot shafts. The lateral translation movement is away or towards the guiding mechanism 914 depending on the orientation of the rotational movement applied to the shafts. Using this type of screw-type pivot shaft, one or more lower pivot shafts can be designed to have radial extensions to operatively be coupled to a bearing assembly which can be operatively engaged with treads of the guiding mechanism 914.

In one embodiment pivot journals or journal bearings can be used between the pivot shafts and their corresponding pivot slots 922. The pivot journals or journal bearings help reduce significantly the wearing of the pivot shafts and the corresponding pivot slots 922 while also reducing high contact stresses and strain. Within the parameters of the embodiments of the present invention, this is especially useful when applied to the upper pivots 912 since they sustain the heaviest strain during operation of the side rail mechanism due to their relational position from the lying surface 800.

During operation of the side rail mechanism according to an embodiment of the present invention, a rotational force is applied to the side rail body. However, while operating the side rail mechanism, there will always be a certain amount of substantially longitudinal force applied to the mechanism possibly resulting in binding at the pivot points. This can happen as a result of the application of a force to the side rail that is not aligned with the rotation centered with the lower pivots 916. In order to address and minimize such a result, an embodiment provides a first upper pivot slot being slightly oblong-shaped while the second upper pivot slot is circular. This feature is particularly advantageous for one hand operation of the side rail where the force applied to the side rail 902, 904 will likely not be aligned with the rotational movement of the side rail 902, 904.

In one embodiment, a first upper pivot slot is an oblong slot or aperture for receiving a first upper pivot shaft. The oblong aperture has a minor vertical axis with a diameter substantially equivalent to the diameter of the first upper pivot shaft and a major horizontal axis having a diameter greater than the diameter of the minor axis and defined by a left extent and a right extent. The major axis of the oblong aperture is substantially parallel to a line drawn between the centers of the first and second upper pivot shafts. The side rail body 909 further includes a regular aperture, e.g., a circular slot, for closely receiving a second upper pivot shaft. As the support arms 910 rotate about the first and second lower pivots 912, the first upper pivot shaft shifts laterally within the oblong slot. As the side rail body 909 is further rotated to a zero point (e.g. shown in FIGS. 47C and 48C) the support arms 910 are nonparallel to each other to ease the passage of the side rail body 909 through the zero point. The oblong slot allows for this non-parallel arm geometry without binding. In the lowermost position, the first upper pivot shaft has shifted from the left extent of the oblong slot in to the right extent of the oblong slot (or vice versa depending on the orientation of the side rail and its direction of rotation).

A sequence of movement of the first upper pivot shaft within the oblong slot is generally as follows: in the uppermost side rail position, the first upper pivot shaft is at the left extent of the oblong slot. As the side rail body is moved from the uppermost position (e.g. FIGS. 47A and 48A) to the lowermost position (e.g. FIGS. 47D and 48D), the first upper pivot shaft shifts from the left extent toward the right extent of the oblong slot. The distance between the first upper pivot shaft and the second upper pivot shaft thereby decreases as the side rail body 909 is moved from its uppermost position to its lowermost position. This movement further acts to ease any binding that might occur.

As noted above, foot-end side rail may be provided with a visual indicator that provides a quick reference to the inclined angle of the head section when the head section is pivoted. Referring to FIG. 45A, the visual indicator 905*b* comprises a static or stationary indicator without any moving parts that includes a plurality of references marks 905*a* that correspond to selected angles. As shown, those angles may include 0, 15, 30, 45, 60 and 80 degrees, for example. The indicator 905 may be formed, such as by molding or marking on the outer surface of the side rail body or may be applied thereto by a cover, such a thin sheet or membrane 905*b*, which may be applied and secured to the body of the side rail by, for example an adhesive. For example, membrane 905*b* may be in the form of a sticker that has an adhesive rear surface 905*c*. In addition to being formed on a membrane, which is applied to the body, the visual indicator may be formed or provided on a plate, such as metal plate, including a steel plate, which is mounted to the body. For example, the plate may be magnetically mounted or adhesively mounted or mounted by fasteners to the body, or the plate may be insert molded with the body.

As would be understood, when the head-section of the bed is inclined the edge of the lying surface or an edge of the deck itself may be used as a reference line against the reference marks so that the angle of the head-section can be determined with a quick glance.

Locking Mechanism

As introduced above, and as illustrated the embodiments of FIGS. 42, 43, 45 and 50, each side rail 902, 904 may include a locking mechanism 928 configured to allow the side rail 902, 904 to be locked in a specific position. The locking mechanism 928 generally includes a locking arm 934 pivotally mounted on the side rail body 909 at a first end and having a locking tooth 936 at a second end. The locking arm 934 is biased downwardly by a spring 938 for the locking tooth 936 to engage with a locking cog 940 that is mounted on the shaft of one of the upper pivots 912. The locking cog 940 is affixed to this pivot shaft in a manner to be rotatably fixed with respect to its support arm 910. The position in which the side rail body 909 is locked is determined by the position of the locking cog 940. The locking mechanism 928 further includes a lock release handle 942 pivotally connected to the side rail body 909 by a pivot pin 944. The lock release handle 942 includes a contact pad 946 adapted for grasping by an operator and a locking arm engaging projection 948 configured to engage the underside of the locking arm 934.

In one embodiment, the lock release handle 942 and contact pad 946 are configured so that as the operator grasps the contact pad 946, the operator is applying the force in a centered position between the shafts of the upper pivots 912 and coinciding with the center of gravity of the side rail body 909. The operator is thus able to grasp and support the side rail body 909 in a balanced fashion, disengage the locking arm 934, and lower the side rail body 909, in a one-handed operation.

In one embodiment, the side rail body 909 is locked in its uppermost position, wherein the locking cog 940 is engaged by the locking tooth 936 of the locking arm 934. In this illustrated uppermost position, the support arms 910 are not fully upright, but are positioned at an angle from the vertical. In the alternative, the locking tooth 936 and the locking cog 940 can be configured to secure the support arms 910 in a vertical orientation. Furthermore, the side rail body 909 may include an integrally molded stop 950 adjacent to the locking cog 940 to prevent further rotation of the locking cog 940 from the lowermost position shown in FIGS. 47D and 48D, for example.

As shown in FIG. 50, the side rail body 909 is prevented from rotating to a lower position due to the interaction of the locking tooth 936 of the locking arm 934 with the locking cog 940. As will be understood by the person skilled in the art, as an operator draws upwardly on the lock release handle 942 by contacting the pad 946, the lock release handle 942 pivots about the pin 944 and the projection 948 engages the locking arm 934. The locking arm 934 is raised against the bias of the spring 938 so that the locking tooth 936 disengages the locking cog 940. This frees the side rail mechanism to rotate to a lower position.

In order to raise the side rail body 909, an operator can grasp the side rail body 909 at any convenient location. When the side rail body 909 is not in the locked position, the locking arm 934 is disengaged from the locking cog 940, the support arm 934 thereby being free to rotate. In one embodiment, any off-center force exerted by the operator does not cause binding due to the non-parallel configuration of the support arms and the oblong slot, discussed above.

In one embodiment, the locking mechanism 928 further comprises a sensor 951, such as an inclinometer or the like (e.g. see FIGS. 42 and 45), for detecting and/or monitoring an inclination/orientation of the locking arm 934. For instance, when the locking arm 934 of a given side rail 902, 904 engages the locking cog 940, a signal is provided to the control system 1000 to indicate that the given side rail is up and secured. When the locking arm 934 is released, the signal may change and indicate that the side rail 902, 904 is either down from its uppermost position, or that the side rail is still up but unlatched, and thereby not secured. As will be described in greater detail below, data acquired using this and other such sensors disposed on various parts of the bed can be used in calculating and monitoring various characteristics of the bed 100 and/or of a patient lying thereon. As will be apparent to the person skilled in the art, the sensor 951 can be mounted elsewhere on the locking mechanism 928 without departing from the general scope and nature of the present disclosure. A sensor may also, or alternatively, be mounted to the side rail body 909, support arms 910, etc. to provide similar or complementary data.

Damper Mechanism

In one embodiment, the movable side rail apparatus incorporates a damper mechanism 952 (FIG. 47B) to achieve a smoother movement of the side rail body 909, improve the feel for the user of the side rail 902, 904, eliminate noise and possible damage or injury caused when a side rail body 909 is dropped from the raised position, and improve the feel of quality of the side rail 902, 904.

FIGS. 47A to 47D and 48A to 48D illustrate various views of the damper 954 when the angle 956 between the support arm 910 and the cross-member 917 (also called the side rail angle) is 70, 30, 0 and −35 degrees respectively. As the angle 956 diminishes, the side rail body 909 lowers relative to the cross-member 917. The cross-member 917 is fixed to either the deck support 700 (for the head-end side rail 902) or the load frame 600 (for the foot-end side rail 904) and therefore may not move when the side rail body 909 moves.

The damper mechanism 952 comprises a spring 958, link member 960 and damper 954 operatively connected with the cross-member 917 of the side rail 902, 904. One end of the spring 958 is coupled to the cross-member 917 and the other end is coupled to the link member 960. The link member 960 is coupled to the cross-member 917 with links 962 that move proportionally to the rotation of the support arms 910. One end of the damper 954 is coupled to the cross-member 917 and the other end is coupled to a link 962.

The damper mechanism 952 facilitates the downward, lowering movement of the side rail body 909. The damper mechanism 952 prevents the side rail body 909 from descending to a lower position at an undesired fast rate due to the gravitational, force acting on the side rail body 909 and, therefore, acts as a counterbalance device. The skilled worker will appreciate that the tension in the spring 958 changes with movement of the side rail body 909 and damper 954. For example, as the side rail body 909 descends, the link member 960 displaces longitudinally, thereby increasing tension in the spring 958.

Based on the shape of the support arm 910 and the angle 956 it forms with the cross-member 917, the side rail angle 956 may vary at any given point. In this embodiment, as can be seen in FIGS. 47A and 48A, when the side rail body 909 is fully raised or deployed, the side rail angle is about 70 degrees and the damper 952 is fully open. At this point, there is minimal tension in the spring 958.

As the side rail body 909 lowers to a partially deployed position (see FIGS. 47B and 48B) the side rail angle 956 decreases to about 30 degrees, and the link member 960 is displaced horizontally. The damper 954 is partially open at this point.

FIGS. 47C and 48C depict a side rail angle 956 of about 0 degrees at which point the side rail body 909 is in a partially stowed position. The link member 960 has displaced even further and the damper 954 is partially closed.

FIGS. 47D and 48D depict the side rail body 909 in a fully stowed position. The side rail angle 956 is about 35 degrees past the horizontal and the damper 954 is fully closed. Since the link member 960 is at its maximum displacement, the tension in the spring 958 is at its highest.

The magnitude of effect on the lowering movement is called the damping coefficient. For the adjustability of the damping coefficient, the stiffness of the material in the damper 954 may be adjusted, thereby impacting the damper's degree of damping. The illustrated damper mechanism 952 can use elastomeric pads which may be identified by color coding corresponding to the desired damping coefficient. As the damper mechanism 952 of the illustrated embodiments are installed in the side rail mechanism to dampen the downward motion of the side rail body 909 (i.e. attenuating the force of gravity on the side rail 902, 904), the range of desired damping coefficients may not be large.

The damper mechanism 952 can further act as a shock absorber by decreasing the amplitude of the mechanical oscillations (up and down movement) of the spring 958. As such, the damper mechanism 952 eliminates or progressively diminishes the vibrations or oscillations of the side rail body 909, thereby resulting in a smooth movement from the fully deployed to the fully stowed positions.

For additional variations that may be incorporated into the side rails, reference is made to copending PCT Pat. Application No. PCT/CA06/01341, filed Aug. 16, 2006, which claims priority to U.S. provisional Application Ser. No. 60/760,564, filed Oct. 27, 2005 and to U.S. Pat. No. 6,721,975 to Lemire, issued Apr. 20, 2004, which are incorporated by reference herein in their entireties.

Relative Positioning of Side Rail(s)

In various embodiments, the side rail or side rails 902, 904 are positioned on a first side of the bed 100 and can be designed to operate in a mirror fashion to the side rail or side rails 902, 904 located on the other side of the bed 100, where the side rail 902, 904 on one side of the lying surface 800 would operate in the opposite rotational direction (clockwise/counter clock-wise) to the corresponding side rail 902, 904 on the other side of the bed 100 and where the longitudinal movement of the side rail bodies 909 along the length of the bed 100 would be in the same direction. Alternatively, a bed can have other configurations such as one side rail 902, 904 on one side and two side rails 902, 904 on the other. When a bed 100 comprises two side rails 902, 904 on a single side (as illustrated herein), the relative rotational movement of these two side rails 902, 904 should be opposite in order to avoid impact therebetween, for example when only one of the two side rails 902, 904 is moved between a raised and lowered position and vice versa. A single bed 100 can have side rails 902, 904 of different shapes and sizes (e.g. head-end side rails 902 and foot-end side rails 904).

Head/Foot-End Side Rail Assembly

As already discussed, the hospital bed 100 of the present invention can have a variety of side rail combinations. For example, the bed 100 can have side rails at the head-end of the bed (e.g. head-end side rails 902) or at its foot-end (e.g. foot-end side rails 904), or at both ends of the bed 100. As well, the bed can have side rails 902, 904 on the same side of the bed 100 or on both sides of the bed 100. In embodiments comprising a pair of side rails 902, 904, one at each end of the bed (i.e., the head-end and foot-end), the side rails 902, 904 are designed to allow movement of the bed 100 in its various configurations. In other words, the side rails 902, 904 are designed to allow relative movement of the components of the bed 100 (e.g. fowler 702, seat 704, and foot sections 706 of the deck support 700).

In one embodiment, the bed 100 comprises a pair of side rails 902, 904 on at least one side of the bed 100, that are designed to overlap at their mutually adjacent ends so that no gap exists between them in all positions of relative movement therebetween and while maintaining a generally uniform thickness between the head-end of the side rails and the foot-end thereof. In the illustrated embodiments described hereinabove, each of the side rails 902, 904 are contained in a plane that is parallel to a vertically upright plane containing a longitudinal axis of the bed 100. Furthermore, each of the side rails 902, 904 have a substantially uniform thickness extending over a majority of the length of each of the respective side rail components.

Figure 41:
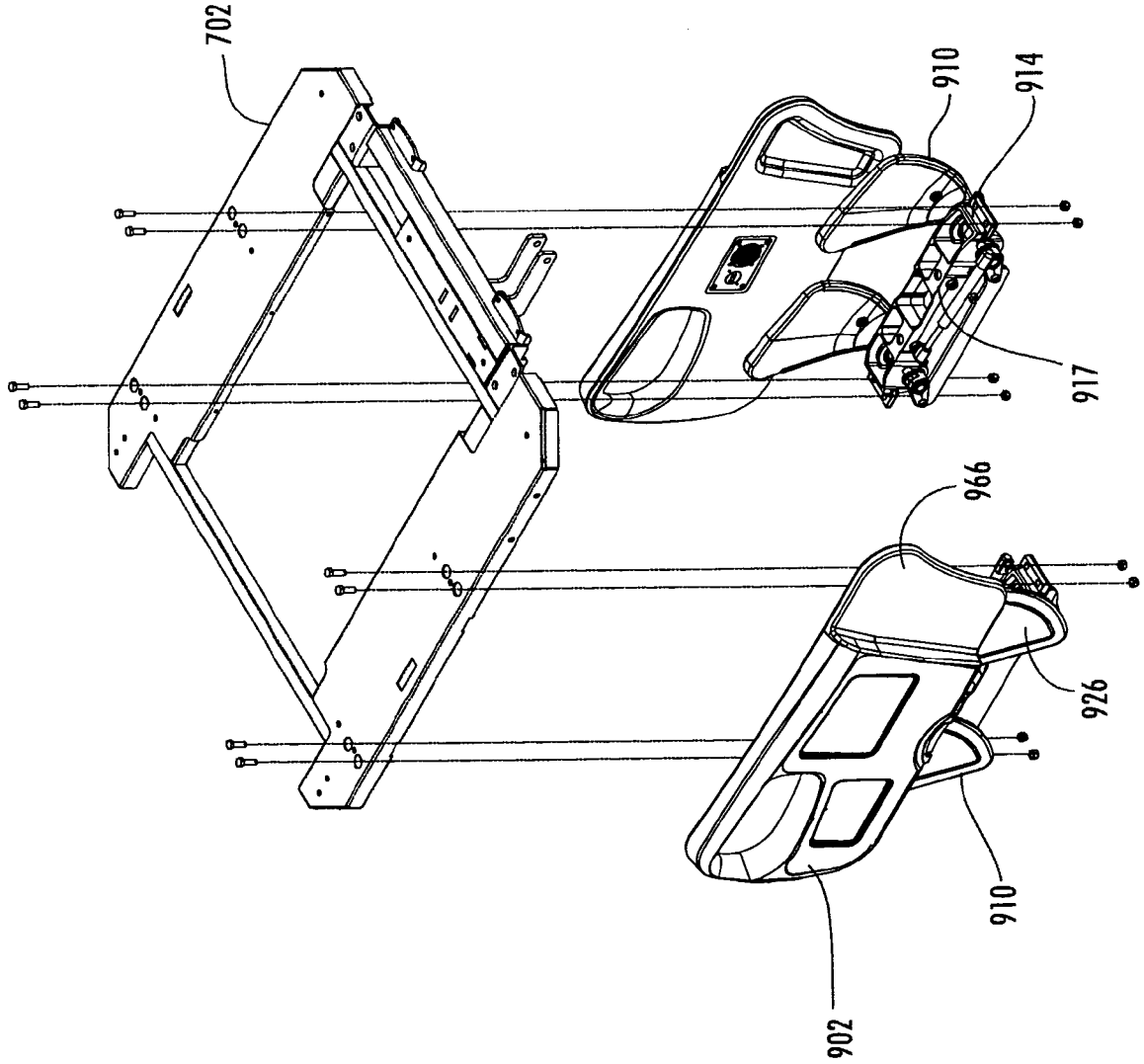
FIG. 41 is an exploded right perspective view of an assembly of the head-end side rails of FIG. 40 to the support deck head portion of FIGS. 32 and 33, the cover thereof omitted for clarity.

With reference to FIGS. 40A, 41, 44, the head-end of the foot-end side rail 904 has a region 964 of reduced thickness facing outwardly away from the plane. The outwardly facing surface of the region 964 extends in a plane generally parallel to the aforethe plane. Similarly, the foot-end of the head-end side rail 902 has a region 966 of reduced thickness facing inwardly toward the plane. The surface of the region 966 extends substantially parallel to the plane. As illustrated in FIG. 40A, for example, the opposing surfaces 964, 966 overlap and are in a side-by-side arrangement so as to prevent the formation of a longitudinal gap between the respective side rails 902, 904. In addition, the total thickness of the head-end of the foot-end side rail 904 and the foot-end of the head-end side rail 902 is of a thickness generally conforming to the overall uniform thickness of each of the respective side rails 902, 904. In embodiments comprising a pair of side rails 902, 904 on each side of the bed 100, the side rail configuration is duplicated on the other side of the bed 100.

In one embodiment, the region 964 of reduced thickness of the foot-end side rails 904 is generally L-shaped, the short leg of the L being provided at the head-end and the long leg of the L extending coextensively with the side rail 904 adjacent the upper edge thereof. The width at about the midlength of the side rail 904 is greater than the width immediately adjacent the short leg of the L of the region 964. The region 966 on the head-end side rail 902 is generally rectangular and has a generally uniform width in the horizontal direction over the lower half and another width over the upper half.

Figure 5:
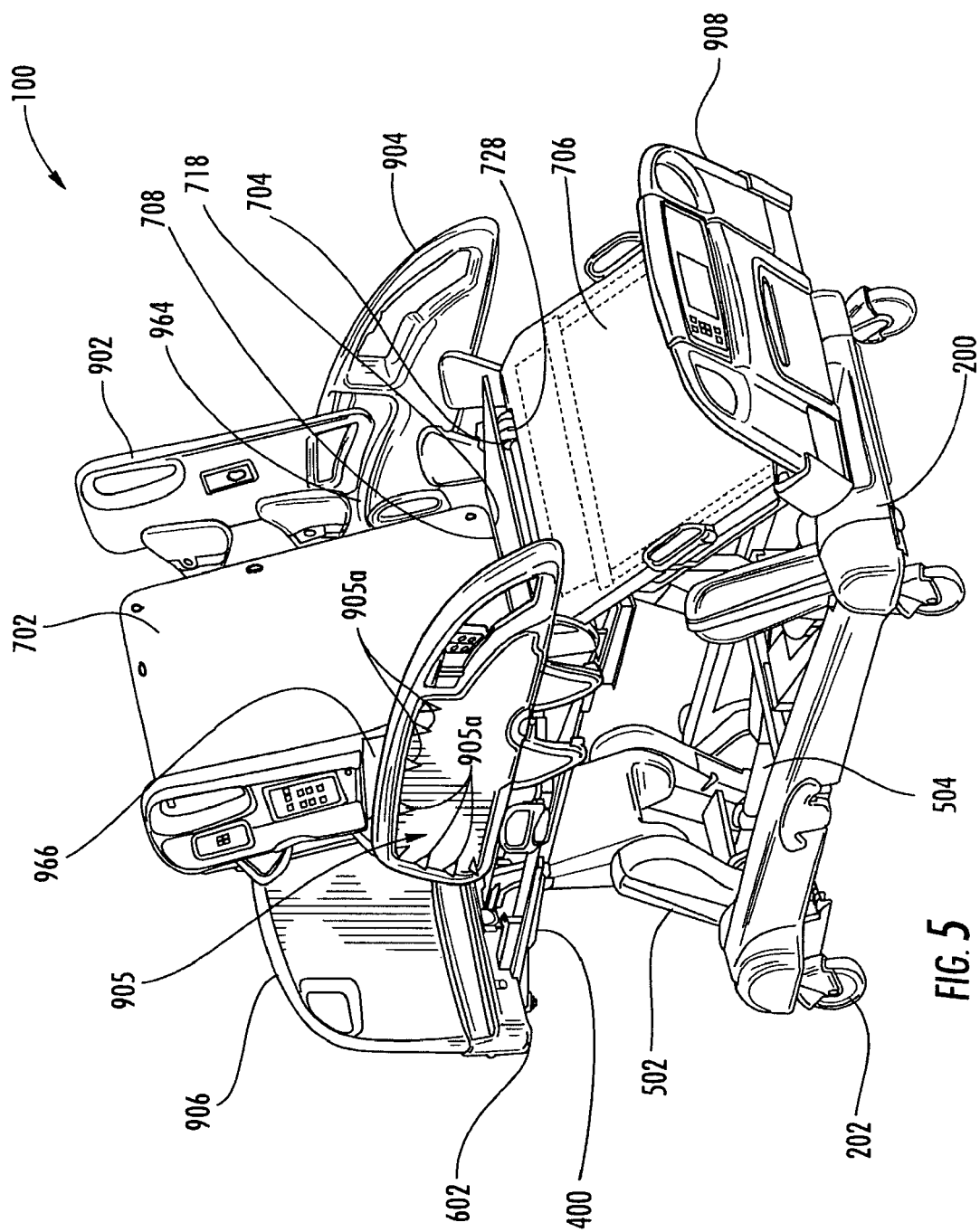
FIG. 5 is a right perspective view of the patient support apparatus of FIG. 4, wherein a head portion of the support deck if further articulated and wherein a load-bearing frame generally mounted atop an intermediate frame of the patient support apparatus via one or more load cells is not shown to reveal one of the load cells.
Figure 6:
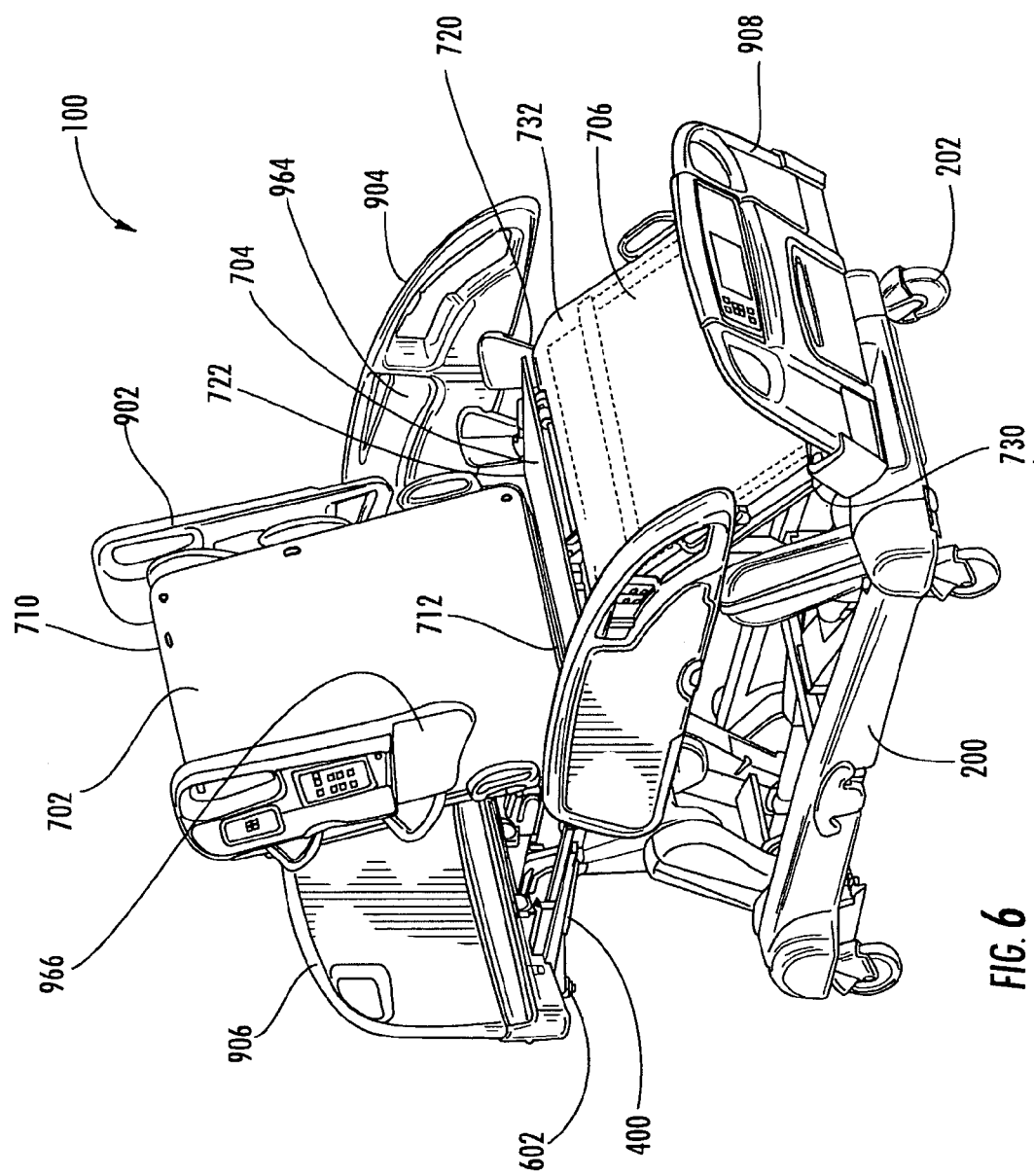
FIG. 6 is a right perspective view of the patient support apparatus of FIG. 5, wherein a left head-end and a right foot-end side rail are in respective retracted positions.

As would be apparent to a person skilled in the art, when the head section 702 and the seat section 704 of the deck support 700 are at about 0° relative to the horizontal, the foot-end of the head-end side rail 902 overlaps the head-end of the foot-end side rail 904, as illustrated in FIG. 40A, for example. As the head section 702 is advanced from the horizontal position to a raised position, the head-end side rail 902 is shifted toward the foot-end of the bed 100 relative to the foot-end side rail 904 while the overlapping regions 964, 966 remain overlapping. As the head section 702 advances through further inclined positions, as illustrated in FIGS. 5 and 6 for example, the foot-end of the head-end side rail 902 moves along the long leg of the L-shaped region 964 so that the foot-end of the head-end side rail 902 is received into the larger width section of the region 964. It will be noted that there may remain a gap between a top edge of the head-end side rail 904 and a head-end facing edge of the region 964 at the midlength portion of the foot-end side rail 904.

Side Rail User Interfaces

As introduced above, various user interfaces may be used to control different features of the bed 100, for example the bed's optional drive mechanism 204 (e.g. see FIG. 10), brake system 206 (e.g. see FIG. 11), deck support actuation mechanism(s) (e.g. see FIGS. 32 to 39), as well as provide various visual indicators as to a status of these and other systems operating in cooperation with the bed's structural elements (e.g. barrier system 900, networked components, peripheral devices, etc.). Other controls provided by such interfaces may include controls of various patient comfort, service and/or entertainment features, such radio, TV, nurse station calling system, phone, etc.

Figure 56:
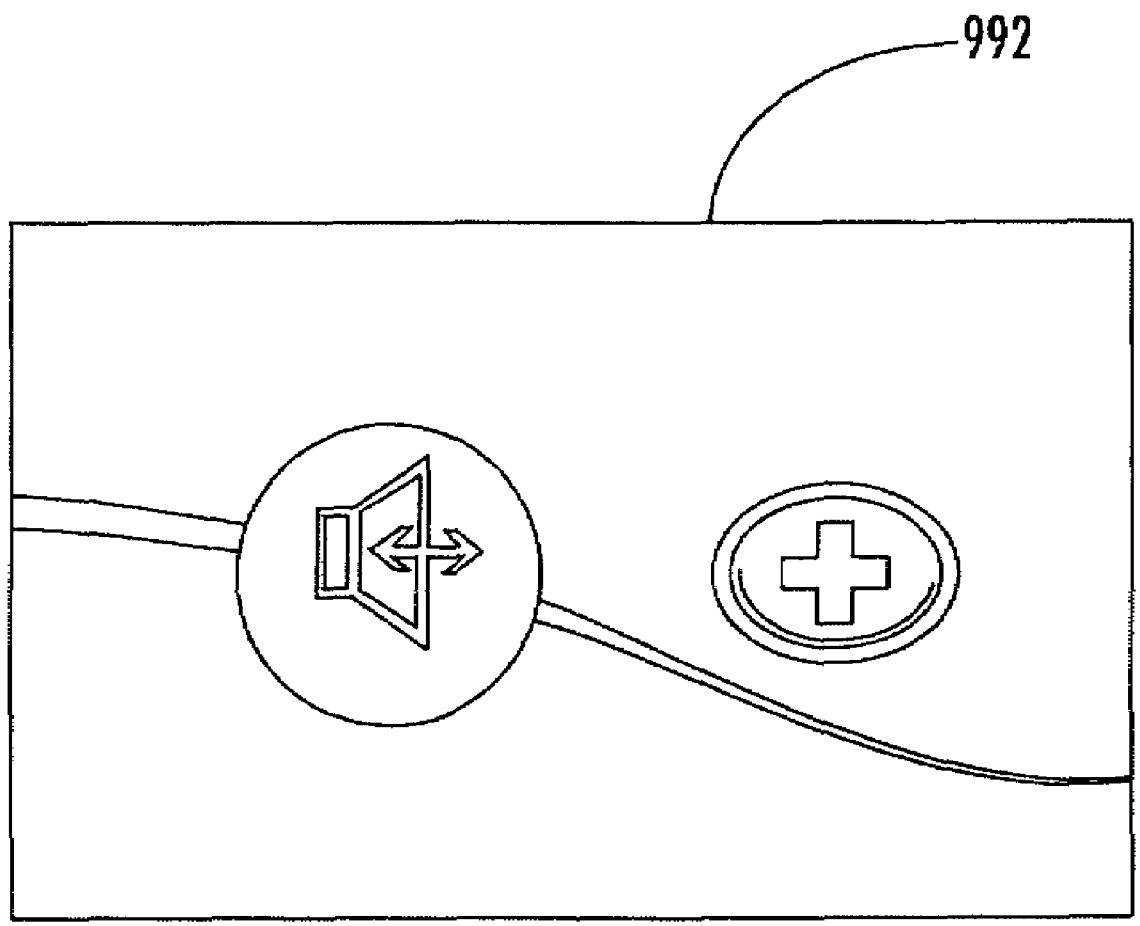
FIG. 56 is a diagrammatic view of an inner control interface provided by one of the head-end side rail control panels of FIG. 43.

With reference to FIGS. 40A, 40B, 43 and 46, showing an illustrative embodiment of the bed's barrier system 900, a number of user control interfaces are provided on or within the side rails 902, 904 to provide a user access to various controls and/or status indicators. For example, the head-end side rails 902 illustratively comprise a first interface panel 990 proving both an outer interface 991 for use by a medical practitioner, for example (e.g. see FIG. 55), and an inner interface 992 for use by the patient (e.g. see FIG. 56). The head-end side rails may further comprise a second interface panel 993 providing an outer interface 994 for used by a medical practitioner, for example (e.g. see FIG. 57). In addition, the foot-end side rails 904 may also comprise an interface panel 995 (FIG. 1), providing a further outer interface for use a medical practitioner for example, and providing similar features as illustrated in the FIG. 57 for the head-end outer interface 994.

Headboard and Footboard

The headboard 906 and footboard 908, illustrated for example in FIGS. 40A and 40B in accordance with one embodiment of the present invention, may be individually molded using a fluid injection molding process, such as gas-assist injection molding process or water injection molding process. Gas-assist injection molding is a well-known process that utilizes an inert gas (normally nitrogen) to create one or more hollow channels within an injection-molded plastic part. During the process, resin such as polypropylene is injected into the closed mold. It is understood that any other suitable material, such as ABS, nylon, or any other resin compatible with the process may be used. At the end of the filling stage, the gas such as nitrogen gas is injected into the still liquid core of the molding. From there, the gas follows the path of the least resistance and replaces the thick molten sections with gas-filled channels. Next, gas pressure packs the plastic against the mold cavity surface, compensating for volumetric shrinkage until the part solidifies. Finally, the gas is vented to atmosphere or recycled. Advantages to using such a process over other molding processes are known to a worker skilled in the art.

Headboard

The headboard 906 is illustratively made of one piece, as depicted in FIGS. 40A and 40B in accordance with one embodiment of the present invention. This mold is designed to produce a curved removable headboard 906 which is sturdy, very light, and easy to access and manipulate by the user. Further, headboard 906 may be removed and used as a CPR board. For example, the headboard may be removed from the bed and then inserted under the patient so that a medical professional can do CPR on the patient. For example, the nurse or medic may insert the headboard between the patient and the mattress, which provides a stiff surface so that the patient will not sink into the mattress and the medical professional can properly apply CPR.

Typically, medical professionals require access to the head section of a hospital bed 100 to position equipment proximate to the patient's head. In urgent situations, such as when the patient requires immediate medical attention, immediate access to the head section is often required. In both such situations, the headboard 906 is desirably moved away from the access area or completely removed from the bed 100. For a headboard 906 that is removed from the bed 100, it is desirable that such headboard 906 be as light as possible, while still maintaining sufficient structural integrity. Once removed from the bed 100, the headboard 906 is typically placed within the near vicinity, such as by leaning against a support surface such as a wall proximate to the bed 100.

Since the headboard 906 of the present embodiment is a one-piece unit, it is less costly to manufacture than headboards which have multiple parts and require assembly. With no additional parts to attach to the headboard 906, there are also fewer parts that are subject to mechanical failure. As will be apparent to the person skilled in the, other types of headboards may still be considered herein without departing from the general scope and nature of the present disclosure.

The design of the headboard mold of use in manufacturing the headboard 906 of the present embodiment is unique. The headboard 906 has a generally rectangular shape. A generally tubular channel 906a (generally shown in phantom in FIG. 38), which is hollow, borders the headboard 906 at both sides and the top, tapering inwards towards the bottom and ending in two ends which project below the generally rectangular portion of the headboard 906. Proximate to each end is a generally oval post 968 (e.g. see FIGS. 17A, 28, and 32) for removably mounting the headboard 906 into mounting sockets 452 provided in the head-end structure 450 of the intermediate frame 400 (described above).

Optionally, in order for the headboard 906 to avoid being damaged when it is resting on the floor against a wall for example, a cap, cover or plug made of a non-stick material such as rubber, can be fitted around each post. Additionally, the plug may ensure a snug fit into the mounting sockets 452 and minimize wear on the posts 968. The plug can be attached to or molded into the headboard 906.

The generally rectangular portion of the headboard 906 comprises a flat thin layer of resin or headboard skin 906*b*, which covers and joins the tubular channel, to form a hollow but rigid headboard with a substantially smooth joint-less surface to minimize areas likely to collect microorganisms and allow their growth as well as to facilitate cleaning of the headboard surface. In one embodiment of the present invention, the headboard skin has a thickness of about ⅛ inch. It will be appreciated that the thickness of the headboard skin and tubular channel is proportional to the amount of material required and the weight of the headboard 906. The headboard 906 can also be translucent or transparent for easier monitoring of the patient and better visibility.

In one embodiment, the headboard 906 has a gradual concave shape such that when the posts 968 are fitted into the mounting sockets, the center of the headboard skin is furthest from the bed's head section. Given that the headboard 906 is formed by a process, which uses a minimal amount of resin, the concave shape in addition to the integrated tubular channel provides additional stability to the headboard 906.

In operation, users, such as medical professionals, can seize the tubular channel at both sides of the headboard 906 and lift upwards for removal of the headboard 906. Installation requires lining up over and inserting each post 968 inside the mounting sockets 452. Optionally, one or more holes or transverse openings 970 of various shapes and sizes can be located within the skin to create handles allowing users to conveniently grasp the headboard 906 prior to removal or installation. In one embodiment the headboard comprises handles that can withstand at least 150 lbs. of force.

Footboard

FIGS. 40A, 40B and 51 to 53 depict a footboard 908 in accordance with one embodiment of the present invention. The footboard 908 is formed using a similar injection molding process as the headboard 906. The footboard 908 also has a generally rectangular shape. A generally tubular channel 908*a* (shown generally in phantom in FIG. 1), which is hollow, borders the footboard 908 at both sides and the top, tapering inwards towards the bottom and ending in two ends, which project below the generally rectangular portion of the footboard.

Proximate to each end is a generally oval 972 post (e.g. see FIG. 39) for removably mounting the footboard 908 into mounting sockets 752 (e.g. see FIGS. 37 and 39) provided in the foot-end structure 750 of the deck support's foot portion 708. Similar optional plugs as described above with reference to the headboard 906 may be used and fitted around each footboard post 972.

The generally rectangular portion of the footboard 908 has a thin layer of resin or footboard skin 908*b*, which covers and joins the tubular channel, to form a hollow but rigid footboard with a substantially smooth joint-less surface to minimize areas likely to collect microorganisms and allow their growth as well as to facilitate cleaning of the footboard surface. In one embodiment of the present invention, the footboard skin has a thickness of about ⅛ inch. Optionally, one or more holes or transverse openings 974 of various shapes and sizes can be located within the skin to create handles that allow users to conveniently grasp the footboard 908 prior to removal or installation. In one embodiment the footboard 908 comprises handles that can withstand at least 150 lbs. of force.

Figure 54:
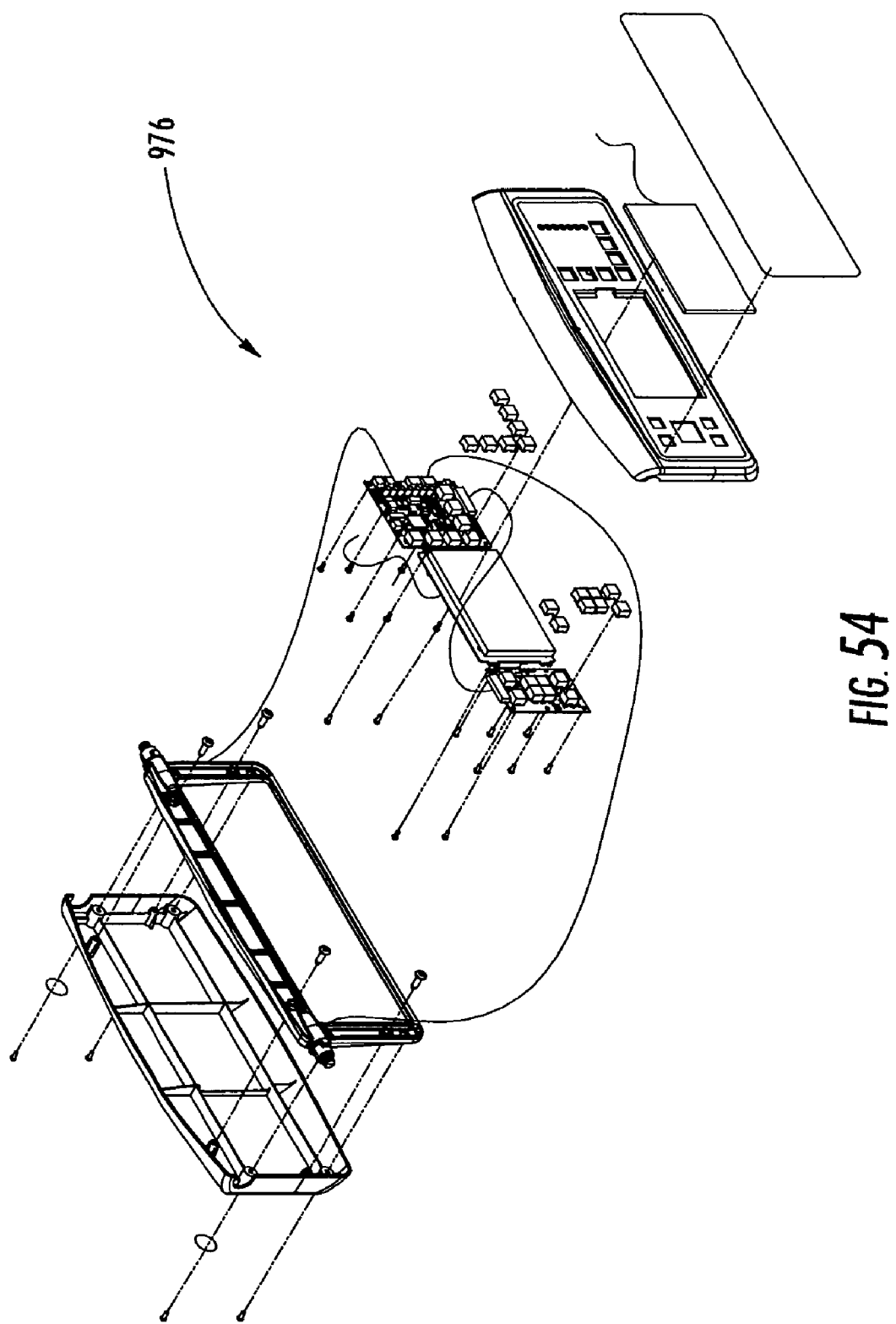

In one embodiment, as shown in FIGS. 1 to 8, and 51 to 53, the footboard 908 is molded so as to allow attachment of a control console 976 (e.g. see FIGS. 1 and 54). The console 976 has a display and/or interface 978 (FIG. 51A) with which the user can interact, as described further herein. When a control console 976 is attached to the footboard 908, the footboard 908 may further comprise a back panel 980 to secure and protect the control board's electronic components.

The console 976 can be of any shape or size. The board zone is generally structured to complement the interface. Users such as medical professionals, require an unobstructed view and access to the console 976. In one embodiment depicted at FIGS. 51 to 54, a generally rectangular control console 976 can be located at the board zone in the upper middle half of the footboard 908. The console 976 may optionally be positioned at an angle (FIGS. 51B, 52) relative to the vertical such that a user peering down at the console 976 from a position above is afforded an unobstructed perspective of the console 976.

In FIG. 58, an exemplary panel interface 996 is shown comprising a number of control user actuatable devices, such as a buttons, and indicators 997 and an LCD display 998, which may provide interactive control capabilities to a user thereof (e.g. touch screen functions, etc.). FIGS. 59A to 59D provide some exemplary screen shots provided by the LCD display 998.

Footboard Connector

Removable components of the bed of the present invention, such as the footboard 908 (and optionally headboard 906), may require electrical connection when attached to the bed. In one embodiment of the invention, the bed comprises male and female connector portions, where one portion is integrated inside the removable component and the mating portion of the connector is positioned within the bed. The connectors are configured in order that upon mechanical connection between the removable component and the bed, the male and female connector portions mate thereby forming the desired electrical connection. For example, a first portion of the connector can be positioned within a footboard mechanical support and the mating connector component can be positioned within the footboard support structure on the bed. When the footboard is connected to the bed, the footboard mechanical support is inserted into the footboard support structure thereby allowing complementary connector portions to mate thereby forming the electrical connection. For example, with reference to FIGS. 39 and 53, a first portion of the connector 794 is positioned on a foot-end structure 783 upon which the footboard 908 is mounted, and the second portion of the connector 984 (FIG. 53) is provided within a bottom portion of the footboard 908 such that, when the footboard posts 972 are coupled to the coupling sockets 784 of the foot-end structure 783, the first and second portions of the footboard connector 794, 984 are connected thereby provided a power and/or communicative link between the footboard 908 and the power/informatics housed within the foot section 706. It will be appreciated that a similar feature may be integrated within the headboard 906 and head-end structure 450 (e.g. see FIG. 31) to which it is mounted.

Integration of the connectors within the removable components (e.g. the headboard 906 and footboard 908) and the bed 100 allows the connectors and wires to be concealed within the footboard/headboard mechanical supports and the footboard/headboard support structures, thereby concealing the connection from view and protecting the connector from damage upon removal of the footboard/headboard. In this way, connector alignment is improved, as well as bed aesthetics. In addition, locating the connector internally also better protects the connector and attached electrical wires from misalignment, loss or damage.

Surfaces Enabling Ease Of Disinfection

There are different types of decontamination procedures for hospital beds (excluding mattresses, mattress covers and bedclothes) depending on the level of decontamination required. These decontamination procedures consist of two processes, cleaning and disinfection. Cleaning procedures do not destroy microorganisms, but physically remove microorganisms, organic matter and visible soiling through use of a general-purpose detergent and water. Disinfection procedures destroy microorganisms but not bacterial spores through the use of chemical disinfectants. Chemical disinfectants generally used on beds include iodophors, phenolics, quats, and chlorines.

Given the above, hospital beds of the present invention are designed to allow for efficient decontamination. For example, the surfaces of the bed are able to withstand frequent contact with disinfectants and cleaners used in the decontamination procedure. This is particularly true for high contact surfaces such as bedrails and adjustment knobs. As well, the surfaces of the bed of the present invention are designed to be smooth so as to minimize the surface areas likely to collect microorganisms and allow their growth as well as to facilitate drying. Furthermore the bed of the present invention are designed to minimize the number of openings into areas that are not easily accessible (i.e. joints, or hollow elements) into which microorganisms can enter and flourish. In one embodiment, the bed comprises modular side rails whereby the modules are sealed against the entry of microorganisms. In a further embodiment of the invention, the side rail modules are sealed off from the environment with a removable sealing means. Removable sealing means that are contemplated include, for example, covers, such as magnetic sided covers or reusable stickers. As well, the bed of the present invention is designed such that high contact surfaces, such as bedrails and adjustment knobs, are easily removable so that they can be subjected to more intensive decontamination procedures, for example sterilization, thus allowing for the removal of bacterial spores if necessary. Easy removal of mattresses and bedding materials is also contemplated by the present invention.

Referring to FIGS. 43A-43D, side rail 902 includes a rail body that is formed from a housing base, which houses most of the components forming the guide mechanisms for raising or lowering the side rail, and a housing cover 977 that mounts over the housing base 975 so that these components are generally not visible to the patient. Housing base 975 and housing cover 977 are optionally formed with transverse openings 902a that provided hand holds or gripping surfaces. As noted above, side rail 902 may incorporate one or more control interfaces, which are located in housing base 975 and located in openings provided in the housing cover 977 of the side rail body. In addition housing base 975 may house a speaker S, which is aligned with an opening provided in the housing base 975 and oriented to face the patient.

Optionally, the gaps formed between the housing cover 977 and the housing base 975, as well as the gaps that are formed between the interfaces in the surface of the housing cover 977 may be sealed by one or more sealing covers 979a, 979b, and 979c. Covers 979a, 979b, and 979c may comprise removable sealing covers, such as membranes or stickers that are applied by an adhesive, such as an adhesive layer that releases when pulled. As a result, the covers are flexible and further are easily contoured and shaped to fit and cover almost any surface of the bed. For example, sealing cover 979a may extend down to the lower edge of the side rail and follow the contour of the handgrip 902b provided at the lower edge of rail 902.

As best seen in FIG. 43C, housing cover 977 may include recessed areas around the openings for the control interfaces 990 and 993 with a rimmed surface that extends around each opening. In this manner when covers 979b and 979c are located and positioned over the control interfaces, the edges of the covers may be recessed such that the outer surfaces of the covers are substantially flush with the areas surrounding the openings. Similarly, the perimeter area around sealing cover 979a may be slightly raised so that the cover 979a is also slightly recessed in housing cover 977 and so that its outer surface is substantially flush with perimeter area surrounding cover 979a. This arrangement greatly enhances the cleaning of these surfaces and any of the other surfaces that have such sealing surfaces applied thereto.

In another embodiment, the bed is constructed from materials that do not favor the growth or adhesion of microorganisms. Exemplary materials would be known to the skilled person and can include, without limitation, materials that have been treated with an additive which can impede bacteria or other organism growth on this material, such as MICROBAN™.

II. Power and Control Systems

Powering Bed Electronics with or without a Battery

A means is provided for facilitating the operation of the electronics in a bed under conditions when it is not possible to rely on a battery to supply the required power for operation.

Figure 38:
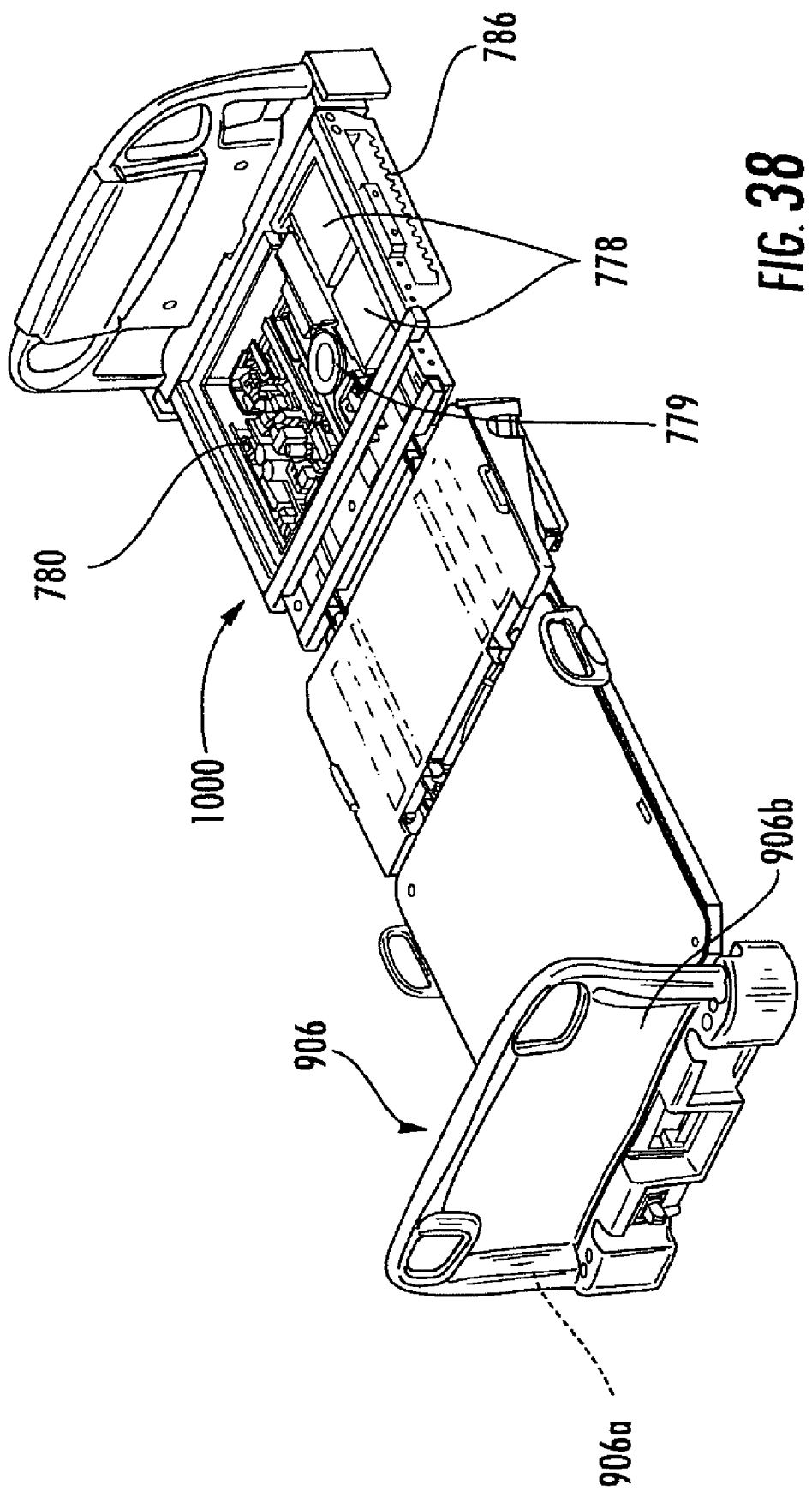
FIG. 38 is a right perspective view of the deck support of FIG. 32, a leg portion cover being omitted to show constituents of an internal housing thereof.

In one embodiment depicted in FIGS. 37 and 38, power from a remote or external power supply or source that is external to the bed, such as a conventional AC source, is fed into separate lines, one to recharge the battery and another to provide power to the electronic systems. In this manner, when the apparatus is connected to a power supply other than the battery, the battery can be recharged as needed and the electronic systems can operate concurrently with external power, which bypasses the battery. The battery may be located anywhere within the bed, however, in the illustrated embodiment of FIG. 38, two batteries are located in the foot section 708 of the deck support 700.

When the bed 100 is connected to an external power source, the electronic systems can be accessed immediately independent of the operability of the internal battery power. The power feed configuration of the bed 100 has the added advantage of preserving the life of the battery by avoiding problems that can arise when a battery is recharging and variable power demands are being placed on the recharging battery by the operation of the bed's electronic systems.

Button Activation for CPR and Trendelenburg on an Alternate Energy Source

The bed of the present invention provides a mechanism for quickly adjusting the Fowler configuration (e.g. head section 702 of the deck support 700) of the bed 100, for example, in situations where the fowler position needs to be quickly lowered or raised in response to a patient's state. A simple and convenient mechanism to quickly lower the Fowler section 702, while utilizing the motor-driven mechanism already in place, obviates the requirement for alternate mechanisms which may take up valuable room on the bed structure or that are complicated and/or cumbersome to activate.

Figure 60:
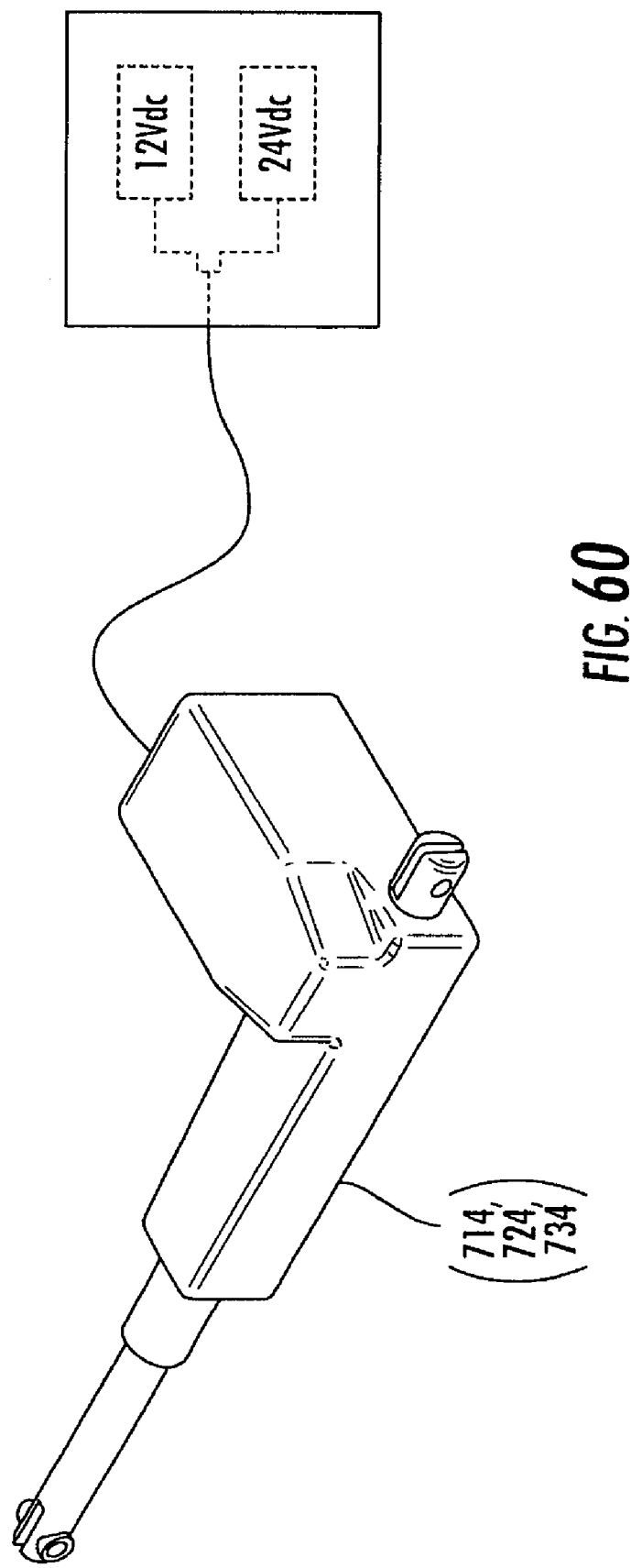
FIG. 60 is a diagrammatic representation of an emergency system for increasing a voltage applied to one or more bed positioning actuators, thereby increasing a velocity thereof, when a user selects a specific positioning function on a given control panel.

In one embodiment, the speed of Fowler movement can be increased by boosting the Fowler actuator voltage, thereby increasing the actuator speed. This is illustrated schematically in FIG. 60 where for example, the voltage to the actuator(s) for bed movement is increased from 12V DC to 24 VDC when the user selects a specific function on a control panel (e.g. see FIGS. 55, 58). The temporary increased voltage to the actuator(s) accelerates movement of the bed to the desired position.

One embodiment encompasses user actuatable device activation, such as button activation, for CPR and Trendelenburg on an alternate energy source, such as a battery, to transiently increase the voltage supplied to the motor, such that the motor speed is increased. The power needed to lower the head or Fowler section 702 is low and the relative load perceived by the motor is less than the actual load due to gravity. In addition, the motor can support the low duty cycle of the accelerated motion without risk of failure during operation at increased speed. In this way, accelerated movement of the Fowler section 702 is quickly and reliably actuated during an emergency with the press of the user actuatable device, such as the button, and is stoppable upon release of the user actuatable device. As discussed further herein, a convenient location for this function is on a control panel located on the exterior of the headboard 906. This location enables the caregiver immediate access to the patient while placing the patient in the desired position.

As one embodiment relies on a motor-driven mechanism which is already in place, it also provides a reliable back-up mechanism in which the position of the bed could be changed at a time and location in which normal movement would be impeded. The need may exist such as during a power outage or if the patient were to suffer cardiac arrest while in an elevator, with the bed detached from its conventional power supply.

Movement to the CPR or Trendelenburg positions may be enabled even under power failure. For example, a battery may be used to provide back-up, for example the CPR. The Trendelenburg positions, for example, may be provided with a manual override, which can be used in the power failure condition.

In one embodiment, in order to activate this movement, the corresponding user actuatable device (such as a button) on one of the control panels is pushed and maintained. As discussed further herein, a convenient location for this function is on a control panel located on the exterior of the headboard 906. This location enables the caregiver immediate access to the patient while placing the patient in the desired position.

Optionally, and in addition to increasing the speed of the Fowler movement by boosting the Fowler actuator voltage, thereby increasing the actuator's 714 speed, the speeds of the seat section movement and the foot-end section movement may similarly be increased by boosting the seat section actuator 724 and foot section actuator 734 voltage. The increased speed of the seat section and foot-end section, in addition to the increased Fowler movement speed, to a substantially horizontal position or a CPR or a Trendelenburg position, allows a user to quickly and reliably actuate all three deck support sections during an emergency with the press of a button, the movement being optionally stoppable upon release of the button.

A visual indication using lights may also provided which is viewable from several positions around the bed 100 in order to indicate low battery power.

Zoom Control Algorithm

An automatic control for acceleration and deceleration of the optional motorized auxiliary wheel 224 that is used to move the bed 100 is provided, thereby allowing for variable speeds during bed movement. The automatic control function provides movement assistance to users such as hospital personnel moving the bed, thereby reducing the perceived weight of the bed with or without a patient thereon. The zoom control adjusts the speed of the auxiliary wheels by comparing the drive signal of the auxiliary wheels with the force applied on the push handles by the user pushing the bed, and provides a level of feedback to the user relating to the natural deceleration of the bed due to frictional losses, for example. This results in the user having to use less force than is normally required to move the bed. Furthermore, when the user removes his or her hands from the push handles, the bed decelerates. Alternately, the headboard may include user actuatable devices that may generate signals to the zoom control. Either way, less force is needed to maneuver the bed when the patient is lying on it. As well, bed movement may be more intuitive since the speed of the bed during patient transport is controlled by the force applied by the user on the bed handles or on the bed headboard when pressure based actuatable devices are employed. Thus, the user does not have to push a user actuatable device or a pedal to adjust the speed of the bed. Furthermore, battery life is extended due to the bed slowing down from gravity and friction when the user removes his or her hands from the push handles or bed. Alternately, the automatic control may be responsive to other actuating input at the handle or at the headboard. For example, the handle or headboard may include one or more heat sensors, which detect heat at the handle or headboard, which generate actuating signals to the automatic control. Alternately, one or more handles or the headboard may include a switch, which when actuated generates the actuating input. Further, the automatic control may be based on displacement, such as a proportional displacement, of one or more of the handles.

III. Structural Informatics Systems

The hospital bed of the present invention further comprises structural informatics systems that enable the operation, control, monitoring, and evaluation, of the various electronic elements and conditions of the bed. The bed can comprise one or more of a plurality of electronic elements, for example, load sensors, tilt or angular sensors, linear sensors, temperature sensors, illumination sensors, humidity sensors, pressure sensors, electronic controls and keyboards, wiring actuators for adjusting bed angles and the like, in addition to other electronic elements.

Sensor and Detector Subsystems

A hospital bed of the present invention can include one or more sensors and detectors for sensing and detecting the status of structural or functional components of the bed as well as certain vital signs of a supported person. For example, sensors or detectors can be appropriately designed load sensors, angular movement sensors, pressure sensors, temperature sensors or any other type of sensor or detector that would be appropriate for integration into a hospital bed as would be readily understood by a worker skilled in the art. Each of these sensors or detectors can be configured to evaluate a desired piece of information relating to the supported person or the bed itself, for example the information can relate to the mass of the patient, the orientation of the bed in terms of position of the supported person or other characteristics.

In some embodiments of the present invention, there is provided a system for detecting the angular position of the supported person. The angular data collected can be applied in a number of ways in the overall operation of the bed, as will be discussed below. However, due to the dynamic nature of the bed, potential inaccuracies associated with mechanical sensors may arise. Gravitational accelerometers that rely on an inclinometry method to determine the angular position of a patient, can be used to improve accuracy. Although the accelerometers can provide an effective way to measure the inclination in the patient's position, the resolution of the gravitational accelerometers is restricted to a limited range of inclination angles. The resolution of the angular position of a patient can be improved by using dual axis (X-Y) accelerometers to sense the inclination angle with a higher degree of accuracy over a broader range of inclination. Advantageously, the gravitational accelerometers can be orientated in a variety of mounted angles, independent of any frame of reference. As a result, a particular accelerometer can be positioned such that its effective resolution specifically targets the anticipated range of inclination for a given application.

In one embodiment of the invention, the bed comprises a plurality of gravitational accelerometers located in various parts of the apparatus to provide a more complete picture of the patient's position. In some instances, the patient's angular location for a therapy may be important in relation to the gravity. For example, gravitational accelerometers can be located at the head section, Knee Gatch or seat section, foot section, elevation system and base frame. Output from the plurality of accelerometers can be compiled to provide a three-dimensional view of the patient's position. The angular inclination readings from the X-axis channel or the Y-axis channel of an accelerometer can be independently selected. Moreover, the sensed inclinations can be used to complement measurements from other sensors in the bed, such as load cells. Thus the floor angular effect may be effectively removed form the load cell reading.

In another embodiment of the invention, monolithic gravitational accelerometers are employed to further reduce the inaccuracies associated with mechanical sensors. In other embodiments, various types of sensors may be used such as angular solid state sensors or electronic angular sensors, wherein a change in angle of the sensor changes the impedance of the sensor which is measured.

In a further embodiment, there is an analog system (such as a potentiometer), which outputs a PWM signal with a good S/N ratio. This PWM signal is sent to a microcontroller wherein the period of the signal is measured and the on-time of the signals. A ratio of these results is proportional to the sine of the angle. The cosine of this angle is to calculate the desired angle. A microcontroller can also be used with reference to a look up table to determine the appropriate angle related to the collected data.

The positions of the angle sensors can be located anywhere on the bed and further comprise an integrated connection mechanism to enable attachment of the sensor to the desired location. For example, the angle sensors can be positioned at the: Fowler (head section), Knee Gatch (seat section/foot section), intermediate frame (to measure the Trendelenberg angle), elevation system at the head-end of the bed, base of the bed, or elevation system at the foot-end of the bed.

Angle sensors can also be placed in other bed locations, for example, the side rails or the footboard control panel. In the latter, a sensor determines if the angle of the control panel puts it outside of the footprint of the bed, which could result in damage. Such an event may trigger the non-disengagement of the braking system if requested. Sensors can also be coupled to bed accessories, for example sensors can be coupled to an IV pole coupled to the bed, such as on an accessory support, to determine the amount of fluid left in the IV bag.

Angular Data

There are a plurality of potential uses for the angular data collected by the structural informatics system of the present invention that can be applied to the functioning of the bed and overall patient care. For example, if predetermined patient positions are directed by a health care provider, a sensor can provide the true value of the position of the lying surface and consequently of the patient who is lying thereon. In another embodiment, an angle sensor can also provide a means to determine bed part interference. For example if a particular bed part is articulated at a certain angle, another part may be unable to perform its desired function. The detection of no change in an angle when an actuator is being operated to change the angle can indicate a blockage related to the actuator movement or an actuator malfunction. A sensor therefore provides a means for fault detection.

In other embodiments of the invention, the collection of angle changing data can be used by the health care provider to evaluate the patient's position over time (for example over a period of 44 hours). A desired positional change of the patient, for example with the inclusion of a timer, can indicate when to change the patient's position. Positional changes may occur automatically however the patient's movement is usually strictly monitored by the health care provider.

The collection of angular data can also aid in the maintenance of the bed. In one embodiment, the angle of a particular bed section and the period of time that that particular position was held as such can be determined to avoid undesired stress levels on the bed. For example, bed movement can be terminated based on measurements from a sensor, wherein once a particular bed position is reached, the controller prohibits further movement as it would result in undesired stress levels on the bed's components. In this way, especially when a particular position results in higher stresses on the lifting mechanisms and the bed's structure, maintenance of the bed can be facilitated. In a further embodiment of the invention, having a highly sensitive angle measurement system also enables the adjustment of a patient's angular position by a small variation such as 1 or 2 degrees, which can result in a desired change in pressure points noticed by the patient with minimal patient movement.

In addition to detecting angular changes relative to the length of the bed, other embodiments of the invention comprise sensors that are optionally oriented within the bed frame or mattress to determine torsional movement of the bed (rotation along the length of the bed). Such an angular sensor configuration can provide for rotational therapy of a patient. In other embodiments of the invention, angular sensors can also be used to detect positions which are dangerous for a patient and therefore the sensors can enable termination of bed movement if a particular position is achieved. In another embodiment of the invention, the mattress could also be configured with an angular sensor for the Fowler or head section of the mattress.

Calibration of the sensor is performed whenever a sensor is changed and can be conducted periodically, such as once a year, in order to verify the accuracy of the sensor. The calibration procedure can be bed specific and is directly related to the number of angle sensors in the bed. For example, the calibration can be performed using four positional orientations: Bed flat in low position, Bed flat in Trendelenberg position, Bed flat in reverse Trendelenberg position, and Bed surface at highest location with foot at lowest, seat at highest and Fowler or head at highest. The angle is calculated using the angle sensor and also the true angle is measured in order to determine the desired calibration of the sensor. Since at least one sensor is positioned on the elevation system, as sections of the elevation system rotate, the height of the bed surface can be calculated.

In one embodiment of the invention, the sensors are intelligent sensors, for example, sensors containing embedded processing functionality that provide the computational resources to perform complex sensing and actuating tasks along with high level applications. As such, the sensors enable the patient support apparatus of the present invention to perform tasks such as its own diagnostic evaluation and its own calibration. In another embodiment of the invention, the sensors are connectable to a sensor network. In a further embodiment of the invention, the sensors are connectable to a wireless sensor network.

In one embodiment, angular data is used to monitor and, when applicable, adjust an operation of the elevation system 500. For example, as illustrated in the embodiments of FIGS. 17A to 23, the elevating mechanism 500 may comprise a pair of lift arms 502 disposed between the base frame 200 and the intermediate frame 400 and configured to be actuated by respective actuators 504 to selectively raise and lower each end of the intermediate frame 400, either independently or simultaneously, relative to the base frame 200. The respective actuators 504, or other such drive mechanisms known in the art, may be capable of operating at variable speeds for selectively adjusting an elevation of the intermediate frame 400. In general, the respective drive mechanisms/actuators 504 may be configured to initially operate at respective, substantially equal, maximum operating speeds. As the intermediate frame 400 is raised, at least one angle sensor located thereon or on another frame or structural module mounted thereon (e.g. sensor 622 mounted to the load frame in the illustrative embodiment of FIG. 31) may be provided to determine an angle of inclination of the intermediate frame 400 (or load frame 600 in the illustrative embodiment of FIG. 33). A control module of the control system 1000 for selectively controlling the elevation of the intermediate frame 400 can thus assess this inclination during a change in elevation of the intermediate frame 400 as compared to a starting angle of inclination thereof and adjust the operating speed of one of the respective drive mechanisms/actuators 504 to compensate for any undesired change in intermediate frame inclination.

In another example, angular data may be used to maintain an angle of inclination of the intermediate frame 400, and of other frames and/or structural modules mounted thereon, when this frame is subject to an uneven distribution of load. This load can optionally be detected and monitored by load cells disposed between the intermediate frame 400 and the deck support 700, for example, as provided by load cells 602 illustratively depicted in FIGS. 26 and 31. In general, the control system 1000 may be communicatively connected with one or more inclinometers, as in sensor 622 of FIG. 31, as well as with the respective drive mechanisms/actuators 504 of the elevation system 500, the latter configured to selectively raise or lower each longitudinal end of the intermediate frame 400 relative to the base frame 200. In a first step, the starting angle, generally the desired angle, is first acquired by the control system 1000. The drive mechanisms/actuators 504 may then be activated to change an elevation of the first and second ends of the intermediate frame 400 respectively associated therewith, each initially operating at substantially equivalent maximum speeds. As the intermediate frame 400 is raised or lowered, a current angle of inclination of this frame may be monitored, for example via sensor 622 disposed on the load frame 600. When the control system 1000 observes that the current angle of inclination differs from the starting angle of inclination (e.g. possibly within a given tolerance), the speed of one of the drive mechanisms/actuators 504 may be adjusted to compensate for this change of inclination. This procedure may be repeated and maintained until a desired elevation is reached, at which point the elevations mechanism 500 is stopped.

Similar applications are disclosed in US Patent Application publication No. 2006/0021143 A1, the entire contents of which are incorporated herein by reference. The person skilled in the art will appreciate that the features disclosed in the above Application may also be applicable in the present context, without departing from the general scope and nature of the present disclosure.

The person of skill in the art will appreciate that other such control subsystems may be implemented using angular data acquired by the one or more inclinometers disposed on or within the structural elements of the bed 100, in conjunction with the various actuation controls discussed above, without departing from the general scope and nature of the present disclosure.

Diagnostic and Control Subsystem

The hospital bed of the present invention can comprise a diagnostic and control system that enables the specific control of each of the electronic elements of the bed, discussed above, for desired operation thereof and monitoring of the operating conditions of these electronic elements and additional bed conditions. The diagnostic and control system further enables the evaluation and determination of the existence of one or more faults relating to the operation of the bed. For example, the existence of a fault can be conveyed to an operator in the form of an error message. The diagnostic and control system can subsequently evaluate the detected fault and can determine, for example, a cause thereof and a potential remedy. In this manner the diagnostic and control system can provide the evaluation of the detected fault and subsequently provide the operator or technician with a remedy for the detected fault, thereby reducing the downtime of a bed that comprises the diagnostic and control system.

Control Subsystem

The diagnostic and control system can comprise a single monolithic subsystem or one or more modular subsystems enabling the control, monitoring, and, if required, calibration of the electronic components of the bed. In this manner the functionality of each of the electronic components, for example load sensors, temperature sensors, tilt sensors, actuator position sensors, actuators and the like can be evaluated and assessed for functionality within a desired set of parameters.

The diagnostic and control system can further monitor or query the functionality or status of the electronic elements, including for example, actuators, load sensors and the like. The system can monitor the current status of the operational parameters of these electronic elements and cross-reference the collected data with a set of standard operational characteristics. In this manner the system can be provided with a means for detection of a potential fault or error when a specific electronic element is not operating within a desired and/or predetermined range. For example, if a load sensor is being monitored and an extraneous load reading is detected, the system can re-query the load sensor to evaluate if it was merely an inaccurate reading or if a potential problem exists. This extraneous reading may be for example a reading that may be outside of normal operating conditions of the load sensor or may be evaluated as extraneous upon comparison with other load sensors in the vicinity, for example. Each of the electronic elements associated with the bed can be monitored in this manner as would be readily understood by a worker skilled in the art.

The diagnostic and control system can perform the monitoring of the bed system components in a continuous manner, periodic manner or on-demand manner. The frequency of the monitoring of these components can be dependent on the electronic element being monitored. For example, the format of the monitoring can be dependent on the level of computation that is required to determine if a component is operating within desired and/or predetermined parameters. Constant monitoring may include querying the sensors for current readings for comparison with operational parameters. Periodic monitoring may be performed when evaluation of the orientation and angular position of the bed frame is desired and on-demand monitoring may be performed on the diagnostic and control system itself wherein monitoring thereof would typically comprise a more extensive computation of current status.

In one embodiment of the present invention, the diagnostic and control system initializes or calibrates the operation of each of the electronic elements, for example actuators, load sensors and tilt sensors, in order that these electronic elements can provide the desired level of accuracy and desired functionality to the bed. For example, calibration of a load sensor may be performed when a lying surface is positioned on the bed and the load sensor can be zeroed under this condition. Furthermore, one or more of the actuators and tilt sensors can be calibrated or zeroed when a bed is in a known orientation, for example linearly flat in a horizontal orientation.

In one embodiment of the present invention, the diagnostic and control system, while providing control of the functionality of the bed, can additionally ensure that a procedure requested by a user is both possible and safe to be performed. In this scenario the diagnostic and control system can evaluate the current status of the bed, and subsequently determine if the selected function is possible. For example if an operator requests the elevation of the head-end of the bed, the system can determine if the head-end can be elevated, and if this procedure is possible, subsequently perform the desired function. If, for example, the head-end was fully raised, and the function was performed regardless, the actuator performing the requested function may be unnecessarily damaged due to overloading or over-extension, for example. This evaluation of the requested function can additionally be determined based on a current treatment being performed on a patient. For example, if a patient is to be oriented in a particular position, the diagnostic and control system can be configured to not allow any adjustment of the bed system until this particular position can be changed according to treatment procedures or requirements.

In one embodiment of the present invention, the diagnostic and control system can be designed using an interface-controller-model architecture. The interface can provide user access to functions of the bed, as well as a query or notification system that can provide access to bed functionality, or notify monitoring personnel of important status information about parameters of bed functionality in addition to certain vital information about the supported person. The model can provide an abstract description of the bed's operational parameters, for example desired operating conditions in the form of a virtual machine, data set or database. The interface and controller can also read information from the model and based on current detected status of the electronic elements associated with the bed, can determine if the bed is performing within desired parameters. For example, a representational model for a collection of load sensors can be provided which can provide operational parameters for the load sensors that can additionally be representative of the configuration of a load sensor web, thereby providing a means for evaluating the operational characteristics of the load sensors during operation.

In one embodiment of the present invention, the diagnostic and control system can include one or more monitoring sensors that can provide a means for independently monitoring the functionality of one or more of the functions of the bed. For example, a monitoring sensor can be associated with an actuator, wherein this monitoring sensor can be a temperature sensor that may enable the detection of overloading or overuse of an actuator due to an excessive temperature reading. The diagnostic and control system may optionally comprise redundant sensors for example, which may be activated upon detection of extraneous readings for a typically used sensor. This form of redundancy can additionally provide a means for evaluating the operational characteristics of the electronic elements associated with the bed.

In one embodiment, an interface associated with the diagnostic and control system can provide one or more different classes of functionalities to one or more different categories of users. For example functionalities can be categorized into functions accessible to a supported person, functions accessible to a monitoring person, and functions accessible to maintenance personnel for accessing diagnostic functionality. Consequently, there can be user interface subsystems that are available and intended for use by a specific user group. Functions of the patient support can also be grouped according to a person's physical accessibility to the bed and can be accessible on-site or remotely or both. As a result, the control system can interact with two or more physical tangible human-machine interface subsystems such as for example a console embedded in the bed. Another important aspect of the present invention is the ability to connect to the bed's control subsystem and diagnostic subsystem and transfer information therefrom or instructions thereto via a suitable number of user interface subsystems, for example communication systems using wired or wireless devices. Therefore, the diagnostic and control system according to one embodiment of the present invention provides the ability to obtain diagnostic information from the bed via wireless devices or by connecting a computer or other wired communication device to the bed. This provides an end user or a technician a means to access constructive information about the bed for any repairs or maintenance that could be required. In a similar fashion, the monitoring personnel or health care provider can have access to information about the supported person without being in close proximity to the bed incorporating the diagnosis and control system.

Upon the detection of a fault or error, the diagnostic and control system can activate an alarm setting that can be a visual, audible or other form of fault indication. For example, the interface associated with the bed can have an error message displayed thereon. In one embodiment, this error message can provide a means for a technician to evaluate and correct the identified fault.

In one embodiment of the present invention, upon detection of a system fault during the monitoring of the functionality of the bed, the diagnostic and control system can initiate a full diagnostic subsystem which can perform a more complete system diagnostic evaluation and, in turn, evaluate and identify one or more sources of the detected system fault.

In one embodiment of the present invention, the diagnostic and control system can collect specific information relating to the current status of particular components of the bed that are directly related to the detected fault, for example one or more sensor readings or the like, for subsequent use by the diagnostic subsystem for analysis of this fault.

Diagnostic Subsystem

The diagnostic and control system of the present invention comprises a diagnostic subsystem that can collect and evaluate the collected information relating to an identified fault and perform an analysis thereof in order to determine a source of such fault and a potential remedy to the detected fault. The diagnostic subsystem can indicate malfunctions of the bed's control system which can be due to a number of reasons such as for example an actuator break-down, an unacceptable deviation between a parameter of the bed and the control system's parameter's desired value as, for example, caused by overload or lack of calibration of an actuator, or any other condition of the bed's control system. A diagnostic program may be applied in order to make a distinction between any critical or non-critical function of the bed's control system when diagnosing a malfunction.

In one embodiment the diagnostic subsystem can also record a number of events including system data and user commands into one or more log records, for example one or more files in an embedded or a remote controller or computer system. Furthermore, essential information regarding any form of treatment administered to the supported person can be securely recorded which could be used in the future. The log records can also contain information from other subsystems of the bed. Information in the log records can be categorized; time stamped, and can contain human or machine-readable data describing the event. The data can be encoded, encrypted or clear text messages. Each subsystem can have its own logging mechanism for logging events specific to that subsystem, accessible only through an interface of the subsystem or accessible through interaction with a central controller. Events can be categorized into groups according to a severity or other schemes and, depending on the categorization, include varying degrees of detailed information relevant to a particular category.

In one embodiment of the present invention, the diagnostic and control system has a movement counting device (data logger) which is used to produce a diagnostic that can be used to improve the design of the system for specific uses or to perform preventive maintenance on the system. For example, it will be possible for an establishment utilizing such a diagnostic and control system to use the data logger in order to determine the different ways in which the bed is being manipulated and therefore provide information in a very constructive manner for any future designs. The information gathered by the data logger could also used in preventive maintenance such that more attention is given to any parts of the bed that is involved in more motion or manipulation.

In one embodiment the diagnostic subsystem can analyze the detected information relating to the functionality of the bed associated with the detected fault, and subsequently evaluate one or more indicators that can be compared with known indicators of known problems relating to bed functionality. In this manner, based on a comparison with the indicators of known problems, the diagnostic subsystem can determine the specific problem. Once a specific problem has been identified, a possible corresponding remedy for this problem can be identified, thereby providing a means for the remediation of the identified problem. The correlation between a calculated indicator defined by information relating to the present status of the bed system may not precisely match an indicator of a known problem. In this instance a probability of correlation between the evaluated indicator and the known indicator can be determined thereby providing a means for assigning a confidence factor with the identified problem.

In one embodiment of the present invention, the diagnostic subsystem can evaluate the identified fault through the analysis of previously detected readings, thereby providing for a correlation between the current readings at fault detection and previous readings. This manner of analysis may provide a means for identifying a malfunctioning component, for example a sensor through the correlation with previously detected values.

In one embodiment of the present invention, the diagnostic subsystem can be directly integrated into the bed. Optionally, the diagnostic subsystem can be electronically coupled to the bed upon the issuance of an error notification. Moreover, the bed system architecture can comprise a diagnostic interface providing access to the bed system such that a diagnostic subsystem can be separated or detached from the physical bed and provide the same set, a subset or superset of diagnostic tools than an integrated diagnostic subsystem.

In one embodiment of the present invention, the diagnostic and control system comprises a communication system that can provide a means for transmitting information relating to the evaluated functionality of the bed to another location. In this embodiment, the communication system can enable wired or wireless communication. For example, this form of connectivity of the bed may enable the remote monitoring of bed functionality at a location removed from the location of the bed. For example, in a hospital setting, this remote monitoring can be performed at a nursing station or optionally can be provided at a remote location removed from the hospital. The communication system can enable the transmission of monitoring and diagnostic results to a technician for analysis, for example if a more detailed diagnostic analysis of the bed is required in order to determine the source of the indicated error. This can provide a means for a detailed diagnostic to be performed and an appropriate remedy identified prior to the dispatching of a technician to the bed site. In this manner, time may be saved as the technician may be dispatched with appropriate replacement parts, thereby reducing the downtime of the bed.

The functionality of the diagnostic and control system according to the present invention can be provided by any number of computing devices, for example one or more microprocessors, one or more controllers or one or more computer systems that can be integrated into the bed itself in order to provide the desired computational functionality.

In one embodiment of the present invention, the diagnostic subsystem can be configured for coupling to the bed to subsequently provide the diagnostic capabilities. It would be readily understood how to couple the diagnostic and control system to the one or more electronic elements in order to data transfer therebetween, for example this connection can be a wired or wireless connection.

Scale Subsystem (Patient Surveillance and Monitoring Subsystem)

Sensed inclinations can be used to complement other measurements from other sensors in the bed. In some embodiments of the invention, there is provided a bed monitoring system, which comprises a scale and bed-exit system that can be based on a load cell measurement scheme including the evaluation of the patient's center of gravity. In this way, the patient's weight, as well as movement, can be continuously monitored.

Load Cell Measuring Scheme to Reduce Patient Motion on the Scale Measurement

A patient weight measuring system in a bed is provided to reliably quantify the weight of a patient independent of the patient's movements in the bed. The patient weight measuring system utilizes a system of sensors, which provide readings to a data acquisition controller. The weight measurements are processed and displayed, such as on an interface to indicate the patient's weight. Because of the physical characteristics of the bed, stable readings of the patient's weight during patient movements are obtained when the patient weight measuring system compensates for certain fluctuations in sensor readings which naturally occur during patient movement. The system models the physical characteristics of the bed and it embeds a compensation means for compensating sensor reading fluctuations, for example by time frequency filtering of sensor readings or by means of other data processing algorithms. The compensation means can process and provide a meaningful figure of the patient's weight, which does not fluctuate during patient movement conditions. The processing system may utilize a time averaging algorithm that can average fluctuating load cell readings to meet the stable patient weight reading requirement. Such an embedded or remote processing system can be manually or automatically calibrated.

Patient Movement Monitoring System

A patient movement monitoring system is also provided to detect and quantify patient movement as well as provide an indication when certain patient movement or lack thereof is detected. For example, an alarm may sound when movement of the patient exceeds predetermined spatial limits.

The movement monitoring system can be based on a load cell measuring scheme that can trigger an alarm if patient movement (e.g., relative to a predefined perimeter within the bed surface area) occurs or exceeds a predetermined threshold. Moreover, patient movement that is perpendicular to the bed's surface or vertical may also be detected and monitored. Parameters such as frequency and amplitude of patient movement may be monitored to provide an indication of irregular or abnormal patient movement. Such information may be used to trigger an alarm under lack or excess of patient movement which may indicate certain patient conditions. The monitoring system requires a suitable algorithm for the processing system to analyze patient movement. The algorithm may require considerable amounts of computational power depending on the complexity of the information required. In one embodiment, the system provides a means for reinitializing after each new position of the patient. In another embodiment, the system provides the time between the patient's movements to be preset in the program or can be programmed by the operator. This information may be displayed, for example, graphically or may be displayed by an indicator, such as a light, for example.

Scale and Bed Exit Information Available at Nurse Station and Through External Port The bed monitoring system, which can comprise a scale and bed-exit system, can provide information on the patient's weight, patient's bed location and other patient information, to a user such as a nurse or surveillance staff at a monitoring station. In particular, the position of the patient can be graphically displayed at a remote monitoring station wherein the position can be displayed in a color-coded position diagram. In one embodiment, based on the patient's bed position, the likelihood of a patient exiting the bed can be determined and an appropriate alarm can be initiated if bed exiting has occurred or is likely to occur. In a further embodiment, based on the ongoing evaluation of the patient's position, movement of the patient can be evaluated, thereby providing a means for issuing an alarm due to patient activity, for example when a patient in ICU is awakening, or patient inactivity, for example when a patient's physical state is degrading.

Depending on the design or architecture of the bed monitoring system, embedded or remote processing capabilities may be required which can have influence on the bed communication interface system (e.g.: an external port) by which the bed system can communicate information to the monitoring station.

Figure 62:
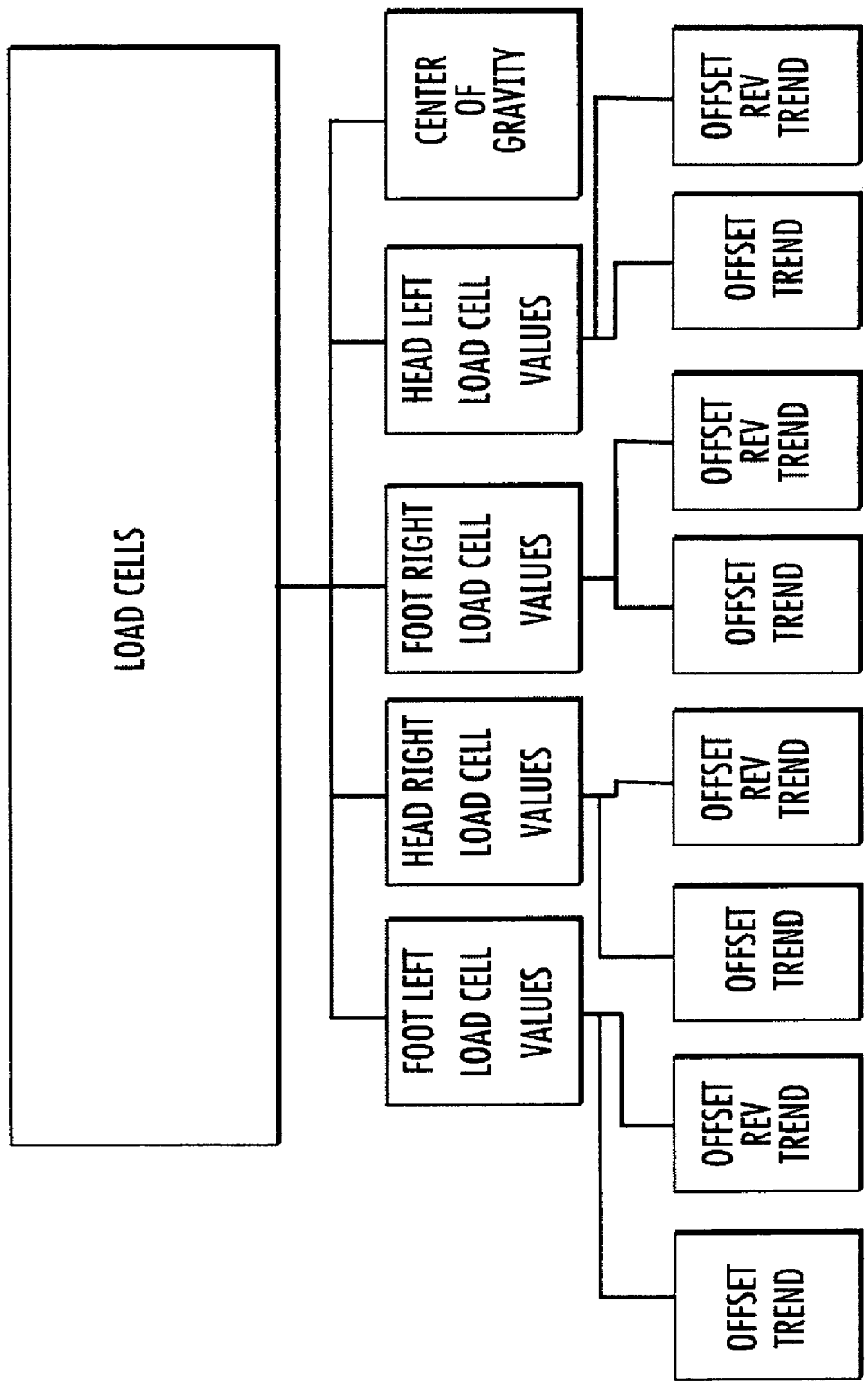
FIG. 62 illustrates a load cell system.
Figure 63:
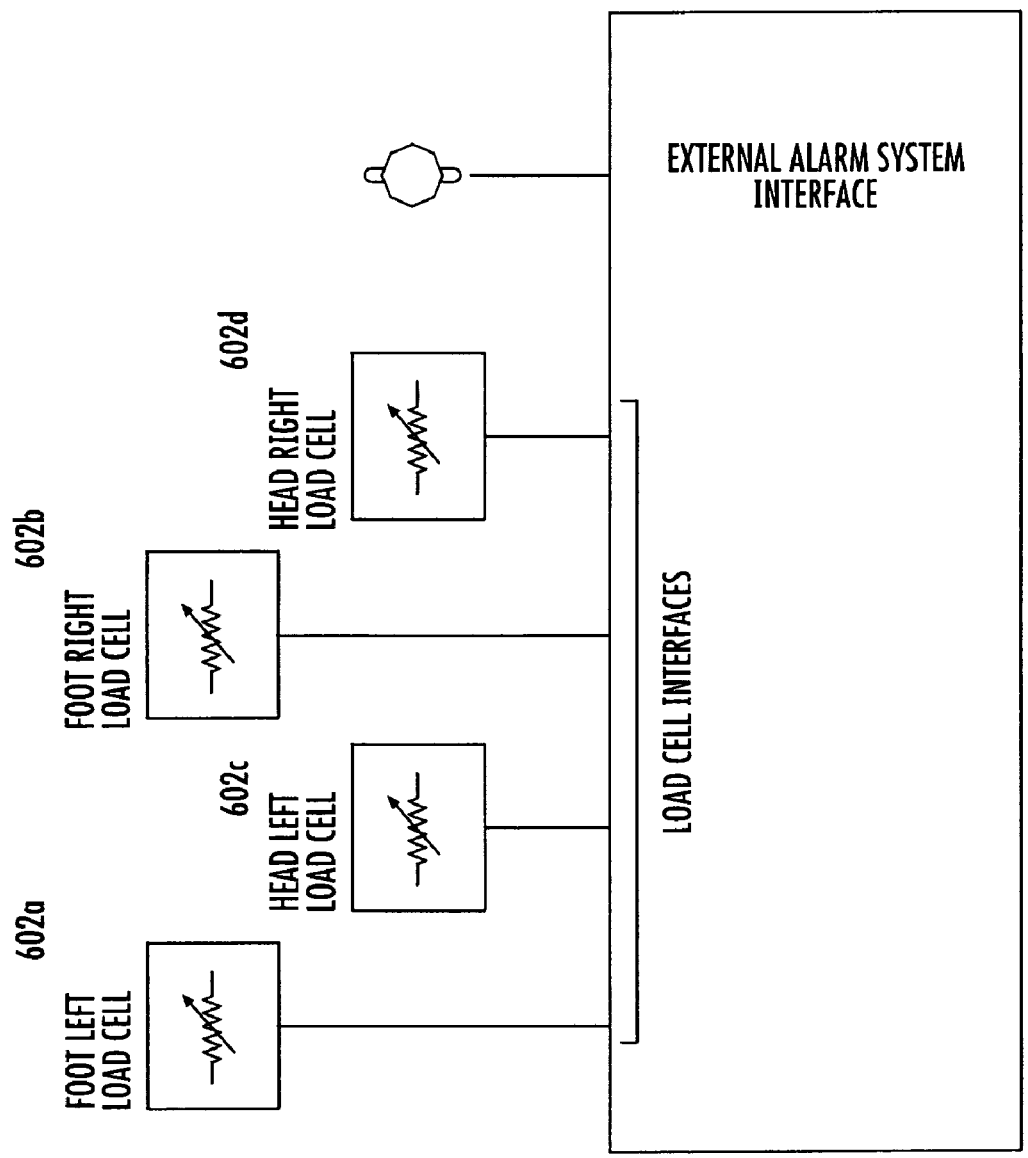
FIG. 63 illustrates an embodiment comprising a scale or weigh subsystem.

FIG. 62 illustrates an embodiment of a load cell system that may be used for monitoring movement of a supported person. The system can be integrated into the bed or can be part of a person support element such as a mattress. In addition, the load cell system can comprise a number of load cells or load sensors for example a load cell which can be embedded in the bed proximally positioned at each of a supported person's limbs and optionally at the center of the bed. The load cell system also can be comprised of a mesh of load cells for example. The signals from the load cells can be monitored and processed by a processing unit in the load cell system or a central processing unit capable of monitoring, processing, and controlling signals from the bed's subsystems. Instead of forming part of a support element such as a lying surface the load cell system can also be integrated into the surface of the bed for supporting the support element. The load cell system can provide a measure for the pressure, weight, or mass load of a certain load cell, for example foot left or right load cell values and head left or right load cell values and additional information about the location of the center of gravity.

In one embodiment the diagnostic and control system can comprise an additional scale subsystem providing a calibration process for calibrating the scale subsystem to provide accurate reading of a supported person's weight and subsequently to calibrate a motion detection system for monitoring movement of a supported person. It may be necessary to calibrate the load cell electronics in order to provide a match of the sensor signals with the scale subsystem electronics.

The scale subsystem can connect to a number of load sensors. The number of load sensors can be different from the ones illustrated. For example, four load sensors which are capable of sensing pressure and can be calibrated to provide a measure of force or weight applied to each sensor are attached to the scale subsystem control interface. The scale subsystem controller can process signals incoming from the load cells and can be used to detect the status of a supported person. The scale control subsystem can be configured to provide a messaging signal or to alert monitoring personnel through an external alarm system interface for example. If each load cell is properly calibrated, the scale control subsystem can also provide a measure of the weight of a supported person. The information can be utilized to determine a person's mass or weight or the respective mass or weight and can also be used to record this information in another subsystem of the bed that may be desired for patient monitoring for example.

In one embodiment, the scale subsystem may require occasional calibration depending on the nature of the chosen sensor technology. Access to the scale subsystem for calibration, monitoring or diagnostic purposes may be possible through the user interface.

It is understood that any kind of diagnostic procedure also includes inspection of the corresponding component and that each component may provide a hardware interface for connection to a special purpose diagnostic device for diagnosing the component.

Actuator/Motor Control System

Figure 61:
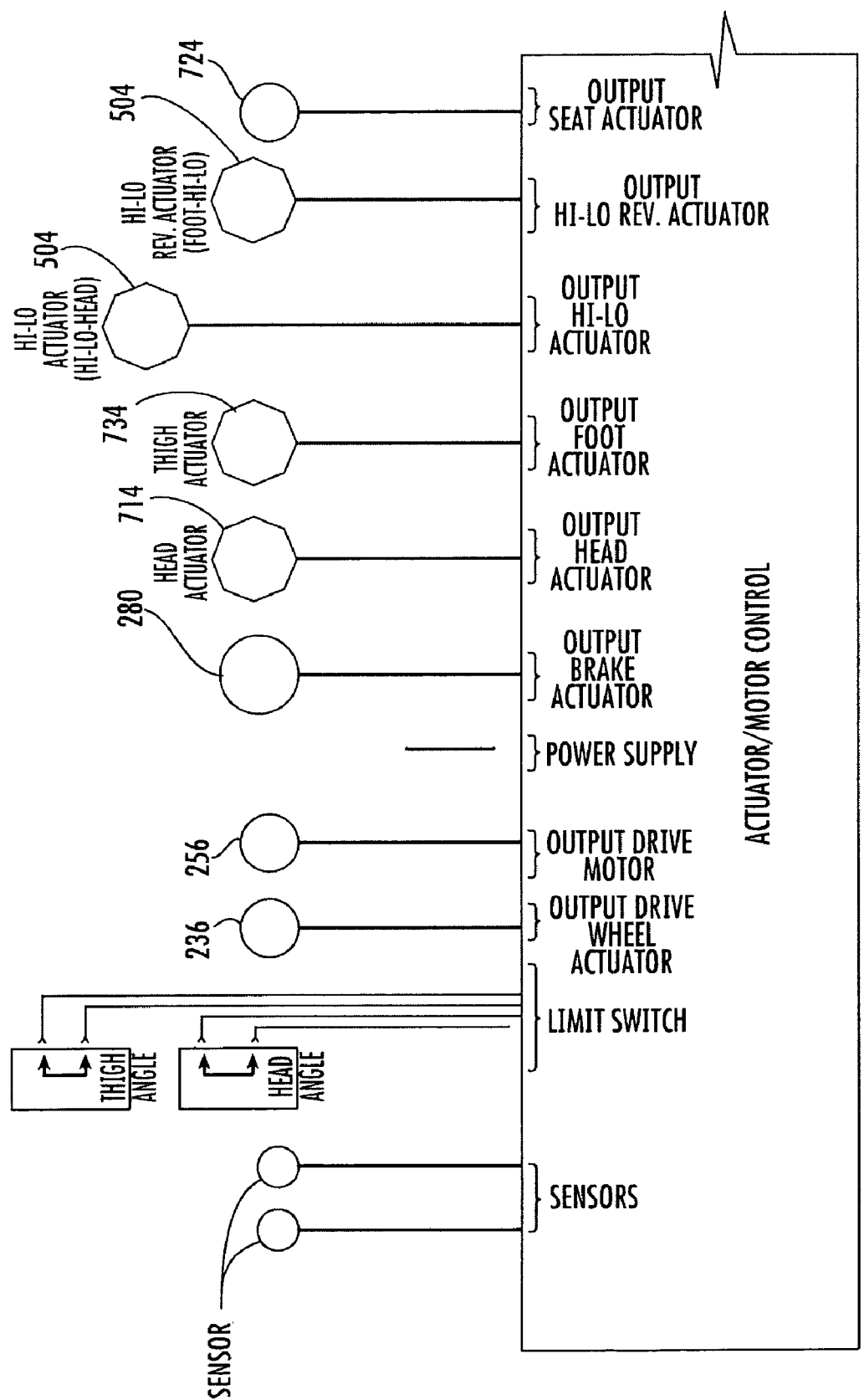
FIG. 61 illustrates an actuator/motor control system.

As discussed earlier, the bed of the present invention can be configured into various positions by orienting the head, seat, and foot sections of the bed into desired positions. The positioning of the various sections of the bed can be controlled by an actuator/motor control system. FIG. 61 schematically illustrates an embodiment of the actuator control system with a number of attached actuators and sensors, such as limit switches, which will be more fully described below. It is understood that, depending on the functionality of the bed, there can be different numbers of actuators and sensors than illustrated. In this embodiment the surface of the bed can be shaped by orienting a head, seat, and a foot section where the support surface for a supported person is intended to fold and provide an adjustable angle between the upper body and the seat as well as under the knee between the seat and the lower leg. The head actuator can position the end of the head section, and the thigh actuator can position the knee section of the bed surface relative to an even support structure. The HI-LO head actuator can position the head-end of the even support structure relative to the frame of the bed which is in contact with the floor. The HI-LO foot actuator can position the foot-end of the even support structure relative to the frame of the bed, for example. The two HI-LO actuators can pivot the support surface horizontally whereas the head and the seat or thigh actuator can shape the support surface by pivotally adjusting sections of the bed surface.

In one embodiment, the actuator control system is connected to a number of limit switch and/or angle sensors which ensures that the actuators do not move or position parts beyond predetermined limit angles or distances. When a part or section of the bed reaches a predetermined limit position while moving, the actuator control system can receive a status change signal via one or more limit sensor signals and/or angle sensor signals and can interrupt the respective movement. The actuator control system can have a safety control feature that does not allow any further continued movement in that same direction or orientation unless the limit condition indicated by the sensor system is resolved. Provided that no movement of other degrees of freedom of the bed takes place the limit condition typically can be resolved by reversing the original movement. For example, limits switches may be used to prevent, for example, the foot-end section of the deck from bumping into, for example, an IV pole.

As discussed previously, each component of the actuator control system including the actuators and sensors can provide diagnostic features or a diagnostic mode. The diagnostic features also can include a separate redundant diagnosis sensor subsystem for monitoring the state of the respective device or component for example a temperature sensor or a redundant parallel or serial sensor limit switch system to enhance the reliability of the positioning system. An important aspect of the diagnostic subsystem that is relevant to the actuator control system can regard the accurate calibration of sensors providing actuator position information. The actuator control system interprets actuator position sensor signals to be accurate representations, encoded in form of a suitable signal, of the real position of a respective part or section of the bed. The actuator control system may fail to execute a given command when the real position deviates from the actuator control system's perceived position as provided by or derived from an actuator signal. In such a case the diagnostic system can provide functionality to help avoid or diagnose a malfunction which can reach from functionalities such as automatic recalibration to alerting or messaging.

System Architecture

Figure 8A:
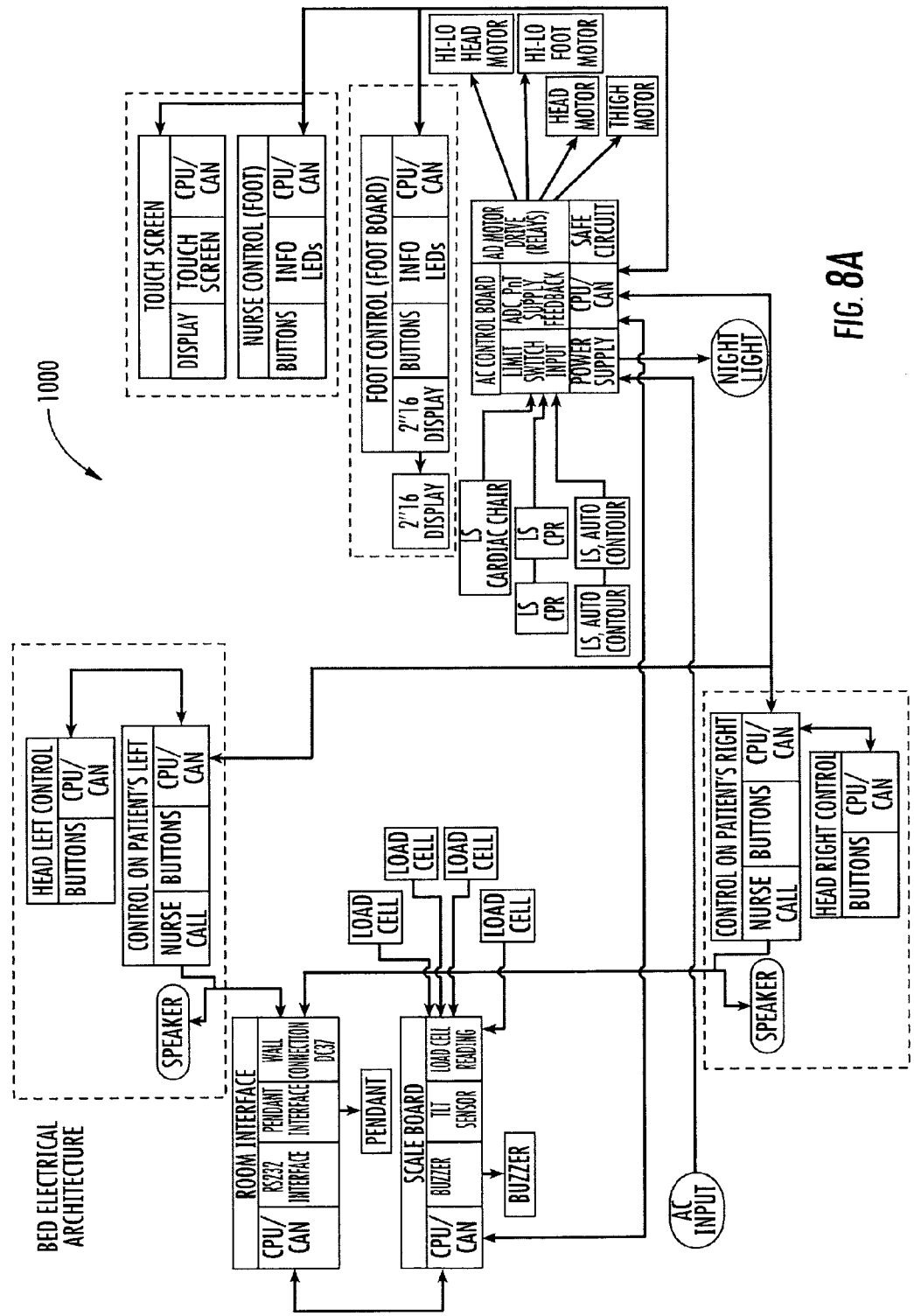
FIG. 8A is a schematic drawing of the control system architecture of the bed of the present invention.

FIG. 8A illustrates a schematic diagram of the system architecture of the control system with a diagnostic system of the present invention. The architecture can be divided into a number of user interface and control subsystem components. The system architecture comprises a power or AC control system for supplying electrical power, an actuator or motor control subsystem providing ability for positioning and orienting parts of the bed, a number of sensor and detector subsystems for sensing and detecting the state of parts of the bed, and a diagnostic subsystem as indicated. The diagnostic subsystem can interact with the sensor and detector subsystem or it can have its own redundant sensor and detector system. The user interface subsystem can comprise a number of control consoles comprising indication or display systems. The display systems can have a touch screen or a regular display with separate user actuatable devices, such as buttons. The sensor system can comprise a scale subsystem including a load cell system. The system architecture can further comprise a room or other interface for communicating information to and from the bed and a remote user interface system.

In one embodiment the bed system architecture further comprises a model subsystem or virtual state machine for representation of the state of the bed components for interaction with the controller and the user interface under operating conditions. Each control subsystem can comprise its own model and independent processor or the model of the subsystem can be integrated in a central program controlled by a central processing unit controlling the bed system.

In one embodiment the architecture may include a diagnostic subsystem for monitoring or querying the functionality or status of the bed components. The diagnostic subsystem can be separate from or simply an additional component of the one or more control subsystems. The diagnostic subsystem can monitor some or all of the bed actuators and can utilize an operatively required and already present sensor system or the diagnostic subsystem can have its own redundant sensor system for improved reliability of the bed control system. The diagnostic system may monitor the bed components on a continuous basis during the bed's normal or intended operation or it may be activated only when required to perform certain maintenance procedures. None, some or all of the functions intended for use during normal operation of the bed may be available during some or all of the diagnostic maintenance procedures. In addition, it may be safe for a person to remain in the bed during none, some or all of the diagnostic maintenance procedures.

In one embodiment the diagnostic subsystem can comprise sensors for the purpose of self-diagnosis of the bed control system sensing the status of actuating components for example. Such sensors may not be required to sense the status of the bed per se but rather provide access to important status information of the control system. Examples can include the temperature of actuator components or controller hardware.

In one embodiment of the present invention, the diagnostic subsystem can passively alert users through messaging systems, for example error messages displayed on the display system. The diagnostic subsystem may also provide procedures to actively query internal status information of the bed system not intended for use during normal operation. Examples of internal status information can include any kind of readings from sensors or results from self-diagnostic modes of employed digital devices. This information can be important, for example, when calibrating actuators and their respective motion sensor system to accurately scale sensor readings to provide positioning information that corresponds with the true physical position of the respective bed component. Other examples for internal status information include power supply voltages or current readings.

In one embodiment the diagnostic subsystem can also include a debug mode permitting the step-by-step execution of commands or procedures of the microcontroller or processing unit. For example, the diagnostic subsystem could be accessed via a general purpose computer for extensive debugging of such subsystem.

The communication between different components within the bed control and diagnostic system is achieved through network communication between components such as CAN-Open for example. This protocol utilizes the broadcast of information to the different electronic components (or module) within the bed. Information regarding any commands requested by the end user is thus transferred to every single electronic component within the bed and thereafter, action is taken by the component (or module) which is concerned by the information that has just been broadcast. Alternatively, the communication between different components within the bed control and diagnostic system can be achieved by a peer-to-peer network communication system or any other network communication protocol that would be known to a worker skilled in the art.

IV. User-Bed Communication Interfaces

The control interface allows for various adjustments to be made to the bed, such as adjustment of the relative position of the individual parts of the bed to position the patient on the bed, adjustment of the bed length and adjustment of the vertical position of the bed. As well, the control interface also allows for monitoring and control of various other functions, such as the communication capabilities of the bed with other apparatuses (e.g., vital care analytical apparatuses, heart monitoring apparatuses, etc.), the monitoring of the status of the bed, and the monitoring of the status of the patient, for example.

The bed of the present invention can comprise one or more control interfaces at various locations to facilitate operator use.

Control Apparatus

The bed of the present invention comprises a control apparatus that can be ergonomically and movably connected to facilitate operator use. The control apparatus comprises a control module which is operatively coupled to the bed and can provide a means for controlling the plurality of bed functions. The control module may be located in control console 976 and as previously described in reference to FIGS. 51A and 51B adapted for connection and is movably connected to the bed by a coupling device, such as described in copending application Ser. No. 11/588,726, filed Oct. 27, 2006, entitled Ergonomic Control Apparatus for a Patent Support Apparatus, which is assigned to Stryker Canadian Management of Canada and which is incorporated by reference herein in its entirety. The coupling device enables the relative movement of the control console 976 and as such the control module relative to the bed. In this manner access to the control module, and therefore to the functionality of the bed, can be provided independent of the configuration of the bed at any given time.

Figure 51A:
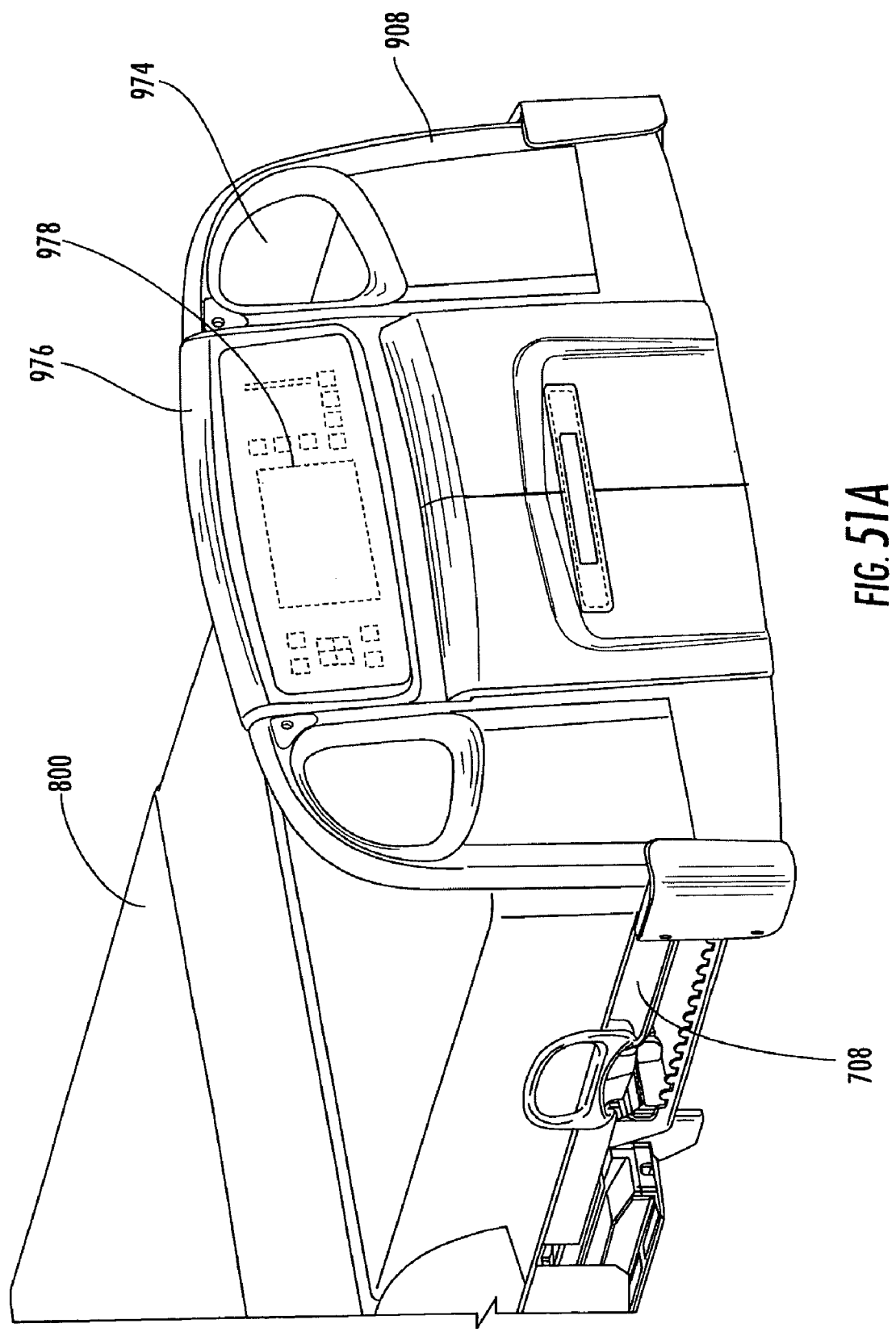
FIGS. 51A and 51B are outer perspective views of the footboard of FIG. 40, showing a footboard control console thereof in coplanar and tilted positions respectively.
Figure 51B:
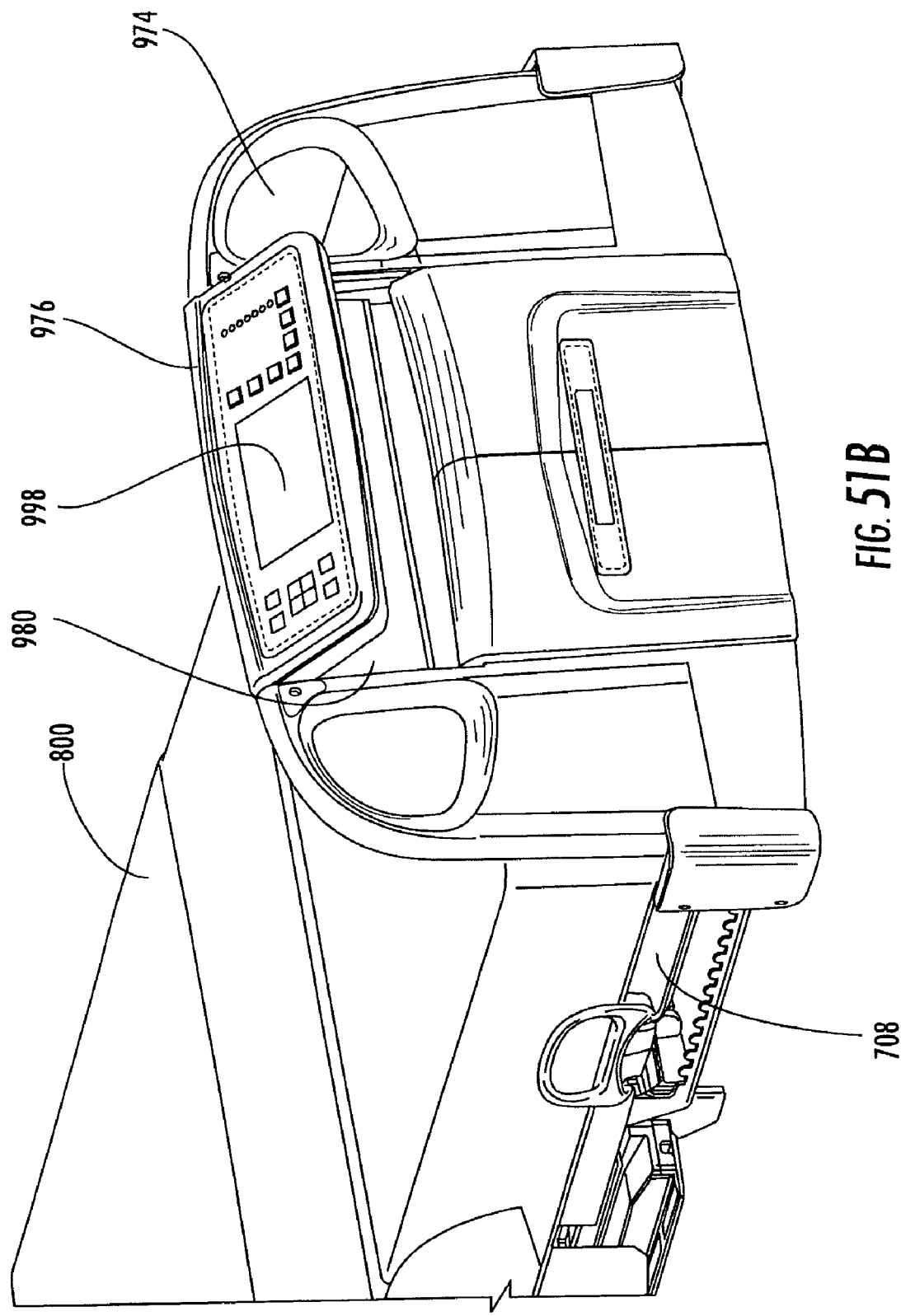

In one embodiment as illustrated in FIG. 51A, the control module is located at the foot-end of the bed, coupled to the footboard by console 976. The control console 976 is operatively and pivotally connected to the footboard and can pivot on at least one axis with an angle from 0 to 360 degrees so that the control console 976 may be angled to suit the nurse attendant or the like. As illustrated in FIG. 51B, the pivotal axis is shown to be substantially horizontally perpendicular to the length of the bed. In the stored position, as shown in FIG. 51A, user interface 978 of the control console is facing the exterior of the bed.

It would be readily understood that the illustrated embodiments can be modified in a manner in which the control apparatus would be located at either the head-end or foot-end of the bed, wherein a control module may be embedded in either the headboard or footboard or both or in other locations in the bed.

In another embodiment, the control module can be operatively connected to the deck support or the intermediate frame and positioned at any desired location along the length of the bed. In this embodiment, the control module is movably coupled to a coupling device, which is fastened to the deck support or intermediate frame. In these embodiments, the coupling device can be configured as an extension arm which can provide a desired level of movement of the control module relative to the deck support or the intermediate frame.

Housing

The housing of the control apparatus is configured to physically house the control module. The shape and construction of the housing is not restricted to a particular design but can rather be dependent on the attachment location, for example the footboard, headboard, deck support, intermediate frame, etc. The configuration of the housing can also be based upon the type of coupling device used for operatively connecting the housing to the bed. In addition the housing can be specifically designed for a desired level of impact resistance or strength, for example. As such, variations in the shape and construction of the housing which provide the desired functionality described herein may be design choices for both functionality, position and aesthetics.

The housing may have affixed thereto electronic cards, user actuatable devices, such as buttons, and other controls necessary to allow for the control of the operation of the features of the bed. The supports for these electronic cards can be made of transparent or translucent material to diffuse the light uniformly on the whole surface underneath the user interface. The transparent or translucent supports can be affixed from the outside of the module or housing. It may not be necessary to open the main control module to access the electronic components, which minimise the assembly time of the control apparatus.

In one embodiment of the invention, the user interface can be mounted on a metal plate through magnetic force. The control module can be equipped with a magnetised surface to receive the metal-based interface. The user interfaces can cover all of the joints between these components to eliminate cleaning and contamination problems caused at the physical joints between the various sub-components. These magnetised interfaces can be advantageous as they do not require adhesives to assemble all the components of the control module. They can further provide the possibility for the patient or the operator to quickly change the options of the control module without having to replace the interface which remains sealed and easy to clean.

Coupling Device

The coupling device of the control apparatus provides a connection between the housing and the bed. The coupling device can be configured in a plurality of different configurations in order to provide movement of the housing in one or more different planes.

The coupling device can be for example, without any limitations, a socket-type connection which may enable three dimensional movement, a rotational pivot, railings, and several operatively coupled rotational pivots. The coupling device can also be configured as one or more coupled link arms or flexible tubing. The coupling device can further comprise a combination of some of these elements among themselves or with an articulated support arm or a fixed support arm, for example.

In one embodiment, the control apparatus comprises a stopping mechanism positioned at intermediary angles between 0 and 360 degrees. This stopping mechanism can be either mechanical, electrical, hydraulic or magnetic. In one embodiment a mechanical stopping mechanism is a ratchet-type system. Alternately a frictional force may be used to bring the control module to a static stop position. For example this stopping mechanism can be configured using dampening grease, friction discs and springs or a Stabilus Hydro-Lift®-type cylinder. The Hydro-Lift®-type cylinder uses a gas spring which allows variable positioning of the element to which it is attached for example, the housing. The articulated support arm or fixed support arm can be adjusted by applying a defined manual force and subsequently locked in the new resting position. An advantage of integrating a Hydro-Lift®-type cylinder into the coupling device is that this cylinder does not require an actuation mechanism for adjustment.

In one embodiment, the control module can also comprise a motor that allows it to maintain a predetermined angle or position relative to the floor regardless of the angle of the intermediate frame, deck support, footboard or headboard relative to the floor. The operator can adjust it manually and then the control module can register the desired position in order to keep it constant until the next change. The operator can also adjust the angle of the motorised control module by using various controls on the user interface.

In another embodiment, the control module can pivot on three axes, allowing three-dimensional movement. The control module is connected to the bed though a coupling device. The wire linking the control module to the bed can pass though the coupling device thereby not limiting the movement of the control module.

In one embodiment, the control module via the housing can be linked to the bed by an articulated support arm or fixed extension arm. Such arms can be coupled to the intermediate frame or the foot-end frame to ensure it does not move if the lying surface is moved, for example through movement of the deck support. The arm can also be connected to the deck support, for example at the head, seat or foot sections.

In one embodiment, the support arm can be removable from the bed, thereby allowing for versatility in the positioning of the control module connected to the support arm via the housing. The receptors enabling this movability of the support arm can comprise adapters for the mechanical, electrical and electronic hook-ups required for the control apparatus. These receptors can move to accommodate the needs of the health care provider, for example. In one embodiment, the support arm may be coupled to the base frame of the bed.

In another embodiment, the control module is capable of sliding on straight or curved rails. Non-parallel rails provide various control angles depending on the relative position on the rails. A rail mechanism between the housing and a footboard of the bed is provided. The rail mechanism comprises a pair of rails disposed on each side of the embedded cavity. Each rail can comprise a single groove pattern to receive and guide one or more protrusions extending outwardly from each side of the housing of the control module. The groove pattern on one side mirrors the groove pattern on the other side and the protrusions are located on corresponding locations on each side of the housing of the control module. In one embodiment, bearings can be used between the protrusions and their corresponding groove patterns. The bearings can help reduce the frictional forces and thereby reduce wear of the protrusions and their corresponding groove patterns while also reducing high contact stresses and facilitating movements from one position to another.

In one embodiment, the coupling device can have features where the controlled movement of the housing relative to the movement of the bed is monitored by the control module and can be adjusted, in real-time or on command, in order to maintain a predetermined accessibility and visibility to the control module by a healthcare provider. To achieve this, the coupling device can have a motorised component operatively connected to the housing and the control module can comprise a positioning sensor.

Control Module

The control module is operatively coupled to the bed, as described above, and can provide a means for controlling the plurality of bed functions.

The power for the control module can be provided by the bed or from another power source. If it is provided by the bed, it can be from an alternating current or direct current. If it comes from outside of the bed, it can come from another medical apparatus having an auxiliary outlet or a battery pack (conventional or rechargeable), or directly from a power source such as a power outlet. The power source can also be a photoelectric cell to keep the memory and the processors' power or a high or low frequency radiation energy. A further possible source of power for the control module is through an electromechanical setting that will enable any mechanical motion to be used to generate current (electricity) that will, in turn, be used to recharge a battery which could be used to drive the control module. The electromechanical setting can be as simple as a coil with a magnet or as complex as Piezo™ sensors (generators) which convert mechanical energy into electrical energy. Depending on the other source(s) used to power a particular bed, simpler AC (alternating current) electromechanical generators, known as alternators, or DC electromechanical generators can be used.

The control module is linked to a bed network, which can be of any kind known in the art such as serial communication networks, CAN-based networks, Echelon™-based networks, peer-to-peer networks, etc. These types of networks do not represent limitations, as any type of known communication network can be used without departing from the present invention. The control module can also be wireless, based on various types of wireless communications networks such as, without limitations, RF (Radio Frequency field propagation) communications, Bluetooth® communications, Infra-red communications and ultrasound communications.

In one embodiment of the invention, the control module further comprises security features to ensure that only authorized personnel access the control module and thereby prevent misuse of the control module. For example proximity sensors can be included and can be in the form of a passive or an active RFID (Radio Frequency Identification) that signals the control module to deactivate and/or activate, based on preset operator proximity readings, for example. In another embodiment, the control module comprises a digital recognition system that positively identifies only pre-authorized individuals to operate the control module. Positive identification can be based on a variety of known features, for example fingerprints, an iris, or vein patterns, for example in a hand.

As discussed earlier, it is an aspect of the invention that the control module can communicate with apparatuses other than the bed. The control module can have an antenna to communicate with and control functions of the other apparatuses through wireless communication or through wired communication. As well, the control module can also communicate with other departments within the facility. For example, the control module can communicate with the radiography department to display the patient's radiography results and the notes from his or her medical file from this department.

In another aspect of the invention, the control module can also comprise a camera and a speaker and a microphone. As it can be oriented in all directions, it provides a continuous visual communication between the patient and the health care provider. It can also be used for communication from one health care provider to another, whether the latter is at a guard station, in another department, in front of another bed with similar equipment or even outside the facility where the control module is located.

LCD Panel/Touch Screen

The control apparatus includes a console interface or LCD panel with a touch screen, at least one processor, software and programmable or flash memory. In addition to providing the necessary algorithms to control and/or monitor the functions of the apparatus, the software provides a graphical user interface (GUI) to organize the multitude of functions of the apparatus. The GUI can display a set of symbols such as "icons" and buttons in any arrangement for a particular function, for example, bed motion. If another function is desired, the GUI can display another set of icons and buttons for that particular function.

The GUI can be configured such that the operation of each function is easy to understand for an attendant who may be unfamiliar with all of the functions of the apparatus. Examples of functions that can be operated or monitored from the LCD panel are: apparatus motion, mattress air pressure, patient motion, patient biometrics, scale, bed security, alerts, exit and event log/history, help screens, diagnostics, room lights or doors/windows, motion sensors, etc. The actual screen displays and menus of the touch screen for a particular bed will be determined by the functions of the bed and the needs of the operator.

In addition, the control apparatus may include a display that provides a status of the bed and displays data, for example in text format or the like, about the bed status collected in the data logger of the diagnostic system. For example, the status of bed sensors, software, and control output may be displayed. With this information, a maintenance person may diagnose the bed without needing special tools to remove covers or bed parts. This diagnostic tool, as noted, may be located at the bed, for example at a separate display or at the main control interface. Further, the diagnostic information can be transmitted by the bed network to a dedicated external interface, such as an external computer, or transmitted to a remote link via, for example, a modem, Ethernet, a wireless network, such as an RF network or the like. Further, this interface may be used to update the software.

For example, one embodiment of the invention comprising the following components and indicators:
A Touch Screen Display
B Bed Exit Detection Interface
C Mattress Interface
D Information Interface
E Modification of Intensity of Backlighting
F Lock Out System Interface
G System Message Indicator
H Indicator for detection of BED EXIT ON/OFF
I Weighing Scale Interface
J Motion Interface
K Brake Activation Indicator
L CPR Activation
M Steer Activation Indicator
N Neutral Activation Indicator
O Trendelenburg Activation In another embodiment of the invention, the touch screen is removable from its position on the bed. It is therefore possible to use the touch screen as a tool to explain the data stored in the control module or simply to show it to the patient at times such as to explain the patient's health status.

In another embodiment of the present invention, the touch screen can also be equipped with one or more speakers to give instructions to the hospital staff. Hospital staff can use the touch screen to facilitate the study of the data. A summary of the patient status can be communicated by the touch screen. For example, the touch screen will have the possibility to provide a weight summary of the patient and provide, as the case may be, variations in the patient's weight throughout a predetermined period of time. The touch screen can also assist the hospital staff for specific tasks such as calibrating the bed.

According to an aspect of the present invention, the control apparatus is highly adaptable in that its functionality can be changed or adjusted by updating the software stored in the flash or programmable memory. The software can be customized to the particular requirements of the user. With any change in function of the apparatus, the GUI of the control apparatus can be altered and adapted to accommodate such changes.

In a further embodiment, the control apparatus can be adapted for use in a computer network. In a hospital, for example, a number of hospital beds can be remotely monitored from a central location such as a nursing station. The software in a number of hospital beds can also be remotely updated or altered using a computer network. The ability to remotely operate the control apparatus is especially desirous where a patient has been quarantined and contamination to the patient, hospital staff or equipment, must be minimized.

Control Interface Location

As discussed, the bed of the present invention can include one or more control interfaces to facilitate the operator's use.

Head Control Location

In one embodiment, a control interface is located at the head-end of the bed. The head-end control interface can be an auxiliary to the other control interfaces of the bed, such as the interface located on or proximate to the footboard, which is typically more convenient to access to health care providers.

One of the advantages of this additional interface is that it provides for easy and rapid adjustment of the bed by the operator during transport of a bed. This is important in situations when, for example, the patient must be rapidly moved into a prone position to facilitate an emergency medical procedure such as CPR, or to alleviate the onset of a medical condition that occurs while the patient is in transit.

Installation of an auxiliary control interface at the head-end of the apparatus allows the operator to adjust the position of the patient without having to physically move around the bed to access another control interface. This feature is advantageous when the bed is in transit and when another control interface is not easily accessible, for example.

Other controls that are desirable to use when the head of the bed is accessible can also be incorporated into the head-end interface, for example, controls to peripheral devices. While the centered location of the head-end control panel is desirable, it can also be positioned to one side if required based on the design of the bed.

Duplicate Patient/Nurse Controls

In another embodiment of the invention, the bed comprises duplicate patient/nurse control interfaces to allow for easy access to the controls by both the patient and a nurse. The control interfaces can be touch pad control panels, for example, that can be installed in a location on the bed that is convenient for the respective users. In one embodiment, a first control interface is installed onto an inner surface of a head side rail, for access by a patient, and a second control panel installed on an outer surface of a foot side rail, for access by a nurse. In this way, should the foot side rail be lowered, for example, when a nurse is attending to the patient, the lying position of the bed may still be adjusted using the control panel at the head side rail. In another embodiment of the invention, the control interfaces are installed onto a side rail and a headboard, respectively. In a further embodiment, the control interfaces are installed onto a side rail and a footboard, respectively.

The duplicate control interfaces of the present invention can be embedded into and, therefore, flush with the side rails, footboard, and/or headboard to allow the hospital bed, side rails, and control panels themselves to be easily cleaned. As well, the control interfaces can be positioned slightly inside of the perimeter of the side rail, footboard, and/or headboard in order to prevent accidental activation of any of the features of the bed.

The control interfaces can be positioned in such a way as to facilitate viewing of the control panel. In one embodiment, the control panels are angled slightly, for example, upwards, to allow for ease of viewing of the control panel in the side rail device even when the side rail is in the lowered position.

Control Panel Functions

In one embodiment, the operation of any feature of the bed is initiated on a first come, first serve basis for a given actuator. For example, the same actuator cannot be simultaneously controlled from two locations. Upon initial activation at one control panel, all other controls for operating that actuator are locked until release or termination of the activation of the actuator.

Each location of the control panels can be used simultaneously to control different features of the bed. For example, a control panel located proximate the headboard may provide for the following bed movement:
  A Fowler up/down: Moves the head section about pivot
  B Knee Gatch up/down: Moves the seat section about pivot
  C Foot up/down: Moves the foot section about pivot
  D Bed Height Control Up: Raises the height of the bed from the surface
  E Bed Height Control Down: Lowers the height of the bed from the surface This same control panel configuration can be located on the exterior of the head side rails.

Another embodiment of a control panel located on the exterior of the head-end side rails may provide for the following bed movement:
  A Fowler up/down: Moves the head section about pivot
  B Knee Gatch up/down: Moves the seat section about pivot
  C Foot up/down: Moves the foot section about pivot
  D Reverse Trendelenburg: Raises the intermediate frame at the first (head) end and lowers the intermediate frame at the second (foot) end
  E Trendelenburg: Raises the intermediate frame at the second (foot) end and lowers the intermediate frame at the first (head) end
  F Bed Height Control Up: Raises the height of the bed from the surface
  G Chair Position: Places the bed in a chair position
  H Bed Height Control Down: Lowers the height of the bed from the surface
  I Flat Bed Position: Places the bed in a flat position.

One embodiment of a pendant control interface comprises the following functions:
  A Raise Fowler: Raises the head section about pivot
  B Lower Fowler: Lowers the head section about pivot
  C Raise Knee Gatch: Raises the seat section about pivot
  D Lower Knee Gatch: Lowers the seat section about pivot
  E Caregiver Call: Alerts a caregiver that assistance is required
  F Interactive Control Panel: Provides access to television, radio, lighting, other.

Another control panel may be directed to the brake mechanism, can also be located on the exterior of the head-end side rails, comprising the following functions:
  A Brake Activation: Raises zoom actuator, places brake actuator in Brake position
  B CPR Activation: Places the apparatus in the CPR position
  C Neutral Activation: Raises zoom actuator, places brake actuator in Neutral position
  D Steer Activation: Lowers zoom actuator, places brake actuator in Steer position
  E Battery Low Indicator: Indicates low battery power
  F Call Maintenance Indicator: Indicates an error that cannot be fixed by the user
  G Trendelenburg Activation Indicator: Indicates the bed is in Trendelenburg For this control panel, components A, C and D are also indicators of the brake status.

In other embodiments, the position of the control panels can be anywhere on the bed.

Message Indicators

The apparatus may have numerous system message indicators, optionally displayed on the control panels. For example, in reference to part G of FIG. 29, indicators include Total Lockout, Call Maintenance, Battery Low, Brake Not Set and Side rail Not Locked or Side Rail Down.

The Total Lockout lock mechanism blocks the control panel from the side rails, footboard, pendant and head panel. When the lock mechanism is activated, such as by pressing a user actuatable device, such as a button, the corresponding lock icon illuminates. In one embodiment the brake can be engaged during a total lockout but cannot be disengaged at any time during a total lockout. The lock mechanism does not affect the functions of the caregiver call, the scale system or the bed exit detection. In another embodiment, the control panels located on the footboard and the head panel may not be affected when the user activates the total lockout button. The different parameters for the lock mechanism are saved if there is a power outage and resume from their original state when the power is back to normal.

The Call Maintenance indicator is meant to indicate the need for repairs or support in regards to the proper functioning of bed system. This indicator is triggered by one or more monitoring sensors placed at various locations within the bed. The need to call maintenance can arise in situations where there are problems particularly associated with the electronics of the bed, including overheating of the motors/actuators, non-functioning tilt sensors, loss of network links or "SAFE" errors.

The Battery Low indicator apprises the user on the level of power remaining in the one or more batteries. It indicates the batteries are almost out of power and require re-charging soon.

In one embodiment, there are two batteries. The time needed to charge both batteries completely is approximately 8 hours. The approximate charge left on the batteries is determined by the amount of voltage that both of the batteries are able to provide to the system, according to the following table and graph:

| Voltage | Percentage |
|---------|------------|
| 27.60 | 100 |
| 27.00 | 80 |
| 24.00 | 20 |
| 22.10 | 0 |

From this graph, there are 3 linear graphs that are determined for which the amount of remaining charge on the batteries can be calculated. For example, if the batteries are currently providing a voltage of 27.2V, the following formula determines the percentage of charge left on the batteries:

$$\text{Percentage of charge left on the batteries} = (80 + ((27.2 - 27)/(27.6 - 27)) \times (100 - 80))$$
$$= 80 + 6.66\%$$
$$= 87\%$$

Similarly, if a voltage of 25.0V is detected from the batteries, the amount of charge left on the batteries is calculated as:

$$\text{Percentage of charge left on the batteries} = (20 + ((25.0 - 24)/(27.0 - 24.0)) \times (80 - 20))$$
$$= 20 + 20\%$$
$$= 40\%$$

Finally, if the voltage detected from the batteries is of the order of 23.0V, the percentage of charge left on the batteries is:

$$\text{Percentage of charge left on the batteries} = (((23.0 - 22.10)/(24.0 - 22.1)) \times 20)$$
$$= 9.47\%$$
$$= 10\%$$

The Brake Not Set indicator is used to apprise the user that the brakes are not engaged on the bed. Such an indication assists to avoid health care personnel's inadvertently leaving the bed without the brakes being set so as to avoid any inconveniences or injury to patients.

The Side rails Not Locked indicator is used to indicate if any side rails are not locked with the side rail locking mechanism. This indicator helps users prevent situations where patients are left unattended with their side rails not locked.

Apparatus Positions

Figure 59B:
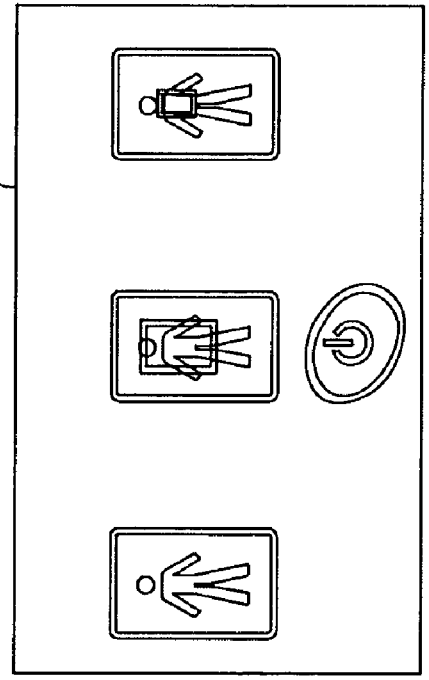
FIGS. 59A to 59D are diagrammatic views of exemplary screen shots provided by an LCD display of the control interface of FIG. 58.
Figure 59D:
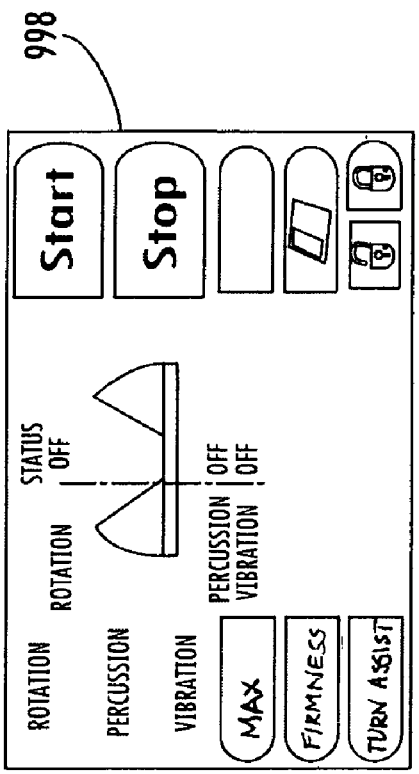
Figure 59A:
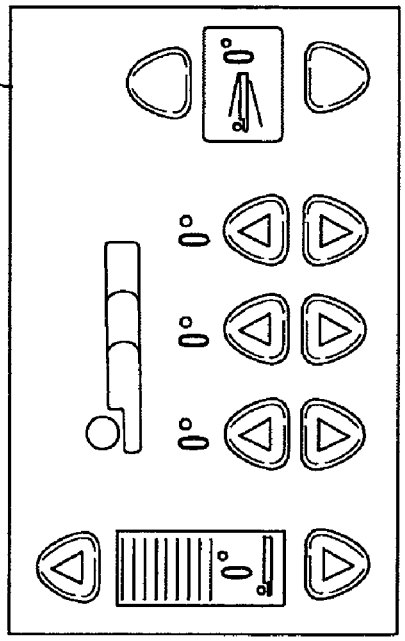
Figure 59C:
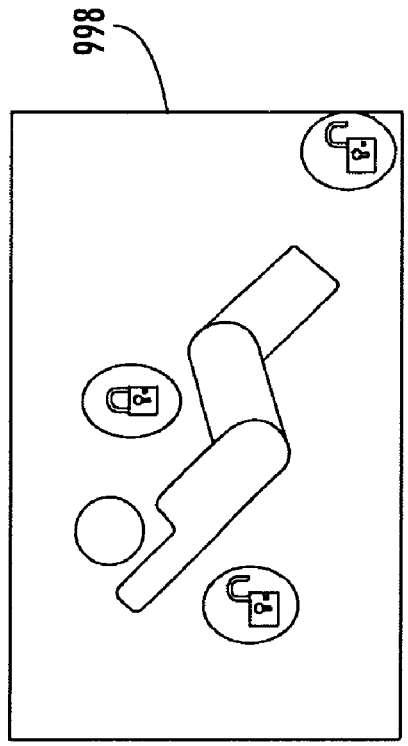

A would be understood, different positions can be achieved with the various user actuatable devices, such as the buttons display in FIG. 59A. In one embodiment, the desired angles for different positions can be:

| Deck support 20 Section | Flat | Standard Cardiac Chair | Enhanced Cardiac Chair |
|---|---|---|---|
| Fowler (Head) | 0 degree (State 0) | 64 degrees (State 1) | 80 degrees (State 2) |
| Foot | 0 degree (State 0) | 30 degrees (State 1) | 50 degrees (State 2) |
| Knee Gatch (Seat) | 0 degree | 13 degrees | 15 degrees |

When the user presses on the chair button, the sequence starts at the current height. If the bed is in the Trendelenburg or the Reverse Trendelenburg position, the elevation system which is in the lower position between the two, is raised to reach 0 degree of Trendelenburg. If the bed needs to be raised so that the foot section reaches 50 degrees without the interference of the foot panel with the surface, the bed is raised to a secure height to ensure no interference. In this embodiment, when two elevation motors function, the other sections of the bed do not move.

There is a "soft stop" of about 1 second between each chair position to make sure that the user wants to continue the sequence when button G (Chair) is still being pressed. When button G (Chair) is pressed, the state of each section of the bed is calculated. The state to be achieved is always superior to the state of the section which is in the lowest state. For example, if the head section of the bed is in the state 0.5 (between 0 and 64 degrees) and the foot section is in the state 1.5 (between 30 and 50 degrees), the state to be achieved is 1. Every single section of the bed will thus move to be able to reach this state. In this example, the head or Fowler section is raised. Consequently, each section of the foot can move in both directions with the same button. In one embodiment, the state of the Knee Gatch section is never used to determine the state that needs to be achieved but it is used to inform the system as to whether a given position has been completed.

If one of the three locks (Fowler, Knee Gatch or Total) is activated, no motion in regards to the Enhanced Cardiac and Cardiac chair sequences is allowed. This condition is independent of the position of the deck support. Consequently, the bed will not carry out any motion when buttons I (Flat) or G (Chair) are pressed.

When button I (Flat) is pressed, the state of each section of the bed is also calculated. The state to be achieved in this example is always lower than the state of the section which is the lowest. For example, if the Fowler section is in the state 0.5 and the foot section is in the state 1.5, the state that needs to be reached is 1. Consequently the head section is at 0 degree, Knee Gatch is at 0 degree and the foot section is at 0 degree.

In the event that button I (Flat) is pressed when the apparatus is in the Trendelenburg or Reverse Trendelenburg positions, the bed will be set into motion such that both the Fowler and the seat sections will move in order to achieve the flat position. In this example, the bed will settle itself at the height of the "point (axis) of rotation" of the apparatus.

It is possible to move the Knee Gatch, head and foot sections at the same time. In one embodiment, the motion of the bed stops if the user presses on button C (Foot Button Down) and there is a possibility that there might be contact of the foot-end section with the surface.

The commands that are activated from the control panel of the headboard and the footboard are commands that are typically attributed to a caregiver such as a nurse. The commands activated from the pendant are typically attributed to the patient. In one embodiment, the motions that are requested from the caregiver have priority over the motions requested by the patient. In the event that the caregiver inputs several simultaneous motions in the control panel and it is not possible to activate all the motors at the same time, the first requested motion will be carried out first. The system does not allow several motors to be put in motion at the same time. In one embodiment, other than the motors for the bed height, three motors can be put into motion simultaneously. The motors for the height work together and none of the other motors can work simultaneously with them. Also, the motors for the Fowler, Knee Gatch and foot sections can work together at the same time.

When two motions that are opposite to each other are requested by the user (for example, simultaneous raising and lowering the bed) on the same control panel, none of the requested motions are carried out. In such a case, the system stops all the motions. In one embodiment, the footboard control panel takes priority over the side rail and pendant control panels. If, for example, signals from the side rail control panel request to lower the apparatus while signals from the footboard control panel request to raise the apparatus, the system will raise the apparatus. It does not matter if the motion for the bed to be lowered has been initiated first before the footboard control panel function to raise is activated.

There are maximum angles with which the Knee Gatch section can be articulated in relation to the angle of the foot section and vice versa.

If there is a mechanical constraint that prevents a requested motion from being completed, the constraint needs to be removed to allow for the motion to occur. When the Knee Gatch section is raised and lowered, the foot section angle changes mechanically. Therefore the foot section needs to be moved in such a way that it is able to maintain its angle of inclination.

The Trendelenburg position is achieved when the Fowler (head) section is set to the low position while the foot section is set to the high position. This particular position can be achieved such as by pressing button E (Trendelenburg) until the desired position is obtained. In contrast to the Trendelenburg position, the Reverse Trendelenburg position occurs where the Fowler (head) section is set to the high position and the foot section is set to low. This is achieved by pressing button D (Reverse Trendelenburg). There is a maximum angle of inclination that can be achieved during the Trendelenburg and Reverse Trendelenburg positions. Typical angles of inclination for the Trendelenburg position and Reverse Trendelenburg position are 15 degrees.

With respect to the elevation system motors, the speed is decreased since the mass is not necessarily uniformly spread on the bed and the two motors do not necessarily have the same characteristics. Consequently, the angle of Trendelenburg is calculated when the motion is initiated and the speed of the fastest motor is adjusted so that the angle of inclination in the Trendelenburg mode is maintained during raising or lowering of the apparatus. In one embodiment, the amount of time needed for the bed to reach the highest position when it was initially at the lowest position is not more than 35 seconds.

During the Trendelenburg and Reverse Trendelenburg motions, there are minimum angles that need to be respected for the elevation system. In one embodiment, the elevation system for the head is not lowered to a height where the corresponding angle is less than 20 degrees during the Trendelenburg position. A similar restriction exists for the elevation system during the Reverse Trendelenburg position. Consequently, if the bed is in the lowest position and the user wants to move to a Trendelenburg position, the elevation system for the head is first raised (even if, under normal conditions, the elevation system for the head is lowered during the positioning for Trendelenburg) to avoid any interference. The elevation system for the head will sufficiently rise to avoid any possible interference, which at the limit is 15 degrees of Trendelenburg.

Similarly, if the bed is at a height with a low angle of Trendelenburg and the user wants to lower the bed by pressing the Bed Height Control Down button, the bed is lowered by keeping the same angle of Trendelenburg as explained above until the elevation system for the head reaches a minimum angle in the Trendelenburg position. At such an angle, the elevation system for the head will stop its motion and the elevation system for the foot will continue its decline if the user continues to press on button H. The same logic is applicable for the elevation system for the foot and the position is Reverse Trendelenburg.

In one embodiment, the angle between the Knee Gatch (seat) section and the Fowler (head) section are never less than 90 degrees. An angle smaller than degrees would eventually result with the patient being stuck in an uncomfortable position. If the user desires to raise the Knee Gatch section and the 90 degree limit is reached, the system will automatically lower the Fowler section to avoid such an acute angle situation. Similarly, if the user raises the Fowler section and the 90 degree limit is reached, the system will automatically lower the Knee Gatch section.

During Reverse Trendelenburg motion, the angle of the head section is monitored to ensure that the sum of the two angles is not more than 90 degrees. For example, if the head support is at 80 degrees, and the user wants to set the bed to the Reverse Trendelenburg position, there is a danger that the patient may be ejected from the bed if the sum of the two angles is above 90 degrees.

V. Bed-Network Communication Systems

A network connection is integrated into a plurality of hospital beds that provides an information or data link between each bed and the computing network of the care facility. This data link provides a means for the transfer of information between the bed and the care facility, thereby enabling patient information to be transferred to the bed, and bed diagnostic information to be transferred to the computing network. Data transfer is provided by a wired or wireless data link.

The information that can be transferred from the computing network to the bed can include patient data for example, test results, personal histories, or other patient related information. Furthermore, bed diagnostic information, current location, and patient information evaluated by the bed, for example can be transferred from the bed to the computing network. The transfer of information via the data link provides a means for remote access to the information determined and collected by the bed and remote monitoring of both the bed and the patient. In addition, the data link enables the remote updating of bed software and operational parameters when desired.

The data link enables the centralization of patient and bed monitoring, which assists in providing enhanced and more efficient patient care, bed servicing and maintenance, and efficient bed allocation based on patient requirements, for example upcoming procedures and required bed requirements for these procedures, thereby reducing patient transfers if an appropriate bed is originally allocated.

Multipoint Control Architectures

The network connection integrated into the hospital beds of the present invention is, in one embodiment, a communication network embedded in the bed having a multiple control point architecture. The network is based on Controlled Area Network (CAN). Several processors are connected to the network, each processor being capable of controlling various functions. Each function can be controlled by one processor or by several processors connected to the network. The types of functions to be controlled in this manner are button reading functions, motion decision functions, scale system functions, and functions related to the bed exit system. In this type of configuration, multiple functions can be computed simultaneously from different processors of the control points in the network. Where the same function is computed from two different control points, a priority mechanism decides which function will be performed.

One feature of the network is the multiple control points associated with specified functions allowing simultaneous computing of functions and the priority or conflict resolution mechanism. This improves the motion security of the bed, diminishes the impact of the processors' computing limitations, improves response time and reduces the length of the cables required in the network. Such multiple control point architecture is also compatible with any bed having a pre-existing CAN-based embedded communication network.

Universal Communication System

In one embodiment, the hospital bed is adapted to wirelessly communicate with a hospital network to transmit bed data between the bed and the hospital network. The network may comprise wired and/or wireless communication paths. In addition, communication can occur in a distributed manner, from bed to bed to bed from the beds to more than one available hospital network, or from the beds to more than one remote station. Also, communication can occur directly, using dedicated wired or wireless networks, from the beds to the remote station located on the hospital network.

The bed data may include information such as:
a bay location of the bed
a position of side rails of the bed
status of bed brakes, e.g., brakes set/brakes not set
housekeeping status of the bed, e.g., whether the bed is clean, dirty, or in the process of being cleaned
a height of the bed
an angle of the head-end of the bed, e.g., a fowler angle
a weight of a patient on the bed
a status of a bed exit system, e.g., is the bed exit system active or inactive
bed maintenance data and history
bed usage data and history
bed scale 'zero' status
patient location
patient movement
patient motion tracking
the patient's weight history
location of non-bed devices associated with the bed The information is transmitted either wired (e.g., Ethernet) or wirelessly (e.g., WiFi) by the bed, directly or indirectly, to a remote station (e.g., central nurses station) located on the hospital network where the data and/or information received is processed to configure or control the bed or other various systems. In one embodiment, the remote station is positioned at a central nurse's station in the healthcare facility and is implemented in a workstation, e.g., a personal computer, for use at the central nurse station. The workstation may include software configured to manipulate data and/or information received from the various systems or the hospital bed. For instance, the workstation may be configured to receive data and/or information from the communication module of the bed or to transfer data and/or information back to the bed.

Such data may originate from a bed exit detection system, a bed height detection system, a weight scale, a side rail sensing system that detects a position of the side rails, a therapy mattress, and the like. The remote station preferably includes a graphical user interface on a touch-screen display for reviewing and manipulating the data and/or information. It should be appreciated that the remote station may also be a stand-alone unit that is not located on the network, but includes the necessary hardware to link to the communication module of the bed.

Other systems on the hospital network may also have access to the information. These systems may include an asset management system, a bed management system, an admission/discharge/transfer system (ADT), patient throughput systems, eICU systems for the remote monitoring of critically ill patients, a nurse call system for facilitating patient contact with a healthcare professional, or any one of several existing or future information systems. The information can be presented at the bed, within the room, outside of the room or at any other location, including the remote station, or any other networked display, including any mobile devices or displays such as personal data assistants (PDAs), wireless badges, phones, and the like. The information can also be transmitted wirelessly from bed to bed (daisy-chained) until the data is received by a wired network node.

For instance, the control system may comprise multiple nodes arranged on a bus for acquiring, transmitting, and receiving the information. It should be appreciated that any number of configurations of the control system are possible to carry out the communication.

A bed exit node receives signals from multiple bed exit sensors to detect movement of a patient on the bed. A side rail sensing node receives signals from multiple side rail sensors to detect a position of each of the side rails. A bed articulation/height node receives signals from a bed height sensor to determine a height of the bed and from a fowler angle sensor to determine the fowler angle of the head-end of the bed. A brake set node receives signals from a brake set sensor to determine whether or not the bed brakes are set. Additional nodes could also be contemplated such as a scale node for monitoring a patient's weight and weight history, a patient node for monitoring a location of a patient and movement of a patient, and a non-bed node for monitoring the status or location of non-bed devices such as patient monitoring, diagnostic, or treatment devices. Each of these nodes may include a processor for processing the raw sensor signals and are adapted to broadcast the respective information for receipt by the remote station via a communication node. The communication node transmits information from the other nodes to another bed, one of several hospital networks, or the remote station via a cable, a wireless router, transceiver, or other wireless device, and receives information from the same for use by the other nodes. In some embodiments, both wired and wireless configurations are present on the hospital bed to easily accommodate user preferences. It should be appreciated that two or more nodes may be combined into a single node to carry out these functions. The particular configuration of the control system nodes is not intended to be limiting. In fact, these "functional" nodes can be separate or combined, using one or a plurality of sensors, transducers and processors to monitor the described conditions. In one embodiment the control system comprises a plurality of electronic nodes or modules that communicate on a peer-to-peer network. In another embodiment of the invention, the control system is a master/slave system utilizing a central processing unit (CPU) that is physically supported by the hospital bed and is in electronic communication with the network via a communication module. The CPU includes the necessary processors and memory for carrying out the functions of the hospital bed in response to user input as will be appreciated by those skilled in the art.

By providing the communication node/module on the hospital bed, the hospital bed acts as a communication center or link for transmitting data and/or information related to the hospital bed to the network.

Room Location Module/Location Detection System

In one embodiment, the hospital bed comprises a location detection system for locating beds in a facility, and specifically detects the bed bay or zone in a room that a bed is located. A room location module may be mounted at each bed bay location in each room of the hospital. The room location module could be mounted on the ceiling, wall, floor, or any location that permits the room location module to carry out its intended function. The room location module is programmed with a bed bay location ID to transmit to the bed once the bed has "docked" with the room location module. The location ID may simply be a serial number of the location module that is entered into a look-up table stored in accessible memory of the remote station and associated with the bed bay in which the location module is installed. In one embodiment, a motion detector is integrated into each room location module to detect when the bed is moved into the associated bay location.

Once the bed is detected, a synchronization cycle is initiated. In one embodiment, the room location module, via a room module transmitter, wirelessly transmits the bed bay location ID to a bed receiver located on the bus so that the bed "knows" its bay location. The bed bay location ID can then be broadcast over the bus to the communication node and to the remote station. As a result, the bed acts as a communication link between the location module and the remote station. A separate look-up table is utilized by the remote station to correlate the location ID to a patient for which the specific bed is associated. The remote station then correlates the location ID and patient to the particular bed bay or zone in which the specific bed is now located such that the software application installed on the remote station can accurately manage data corresponding to the specific bed and the patient.

The room location module can use a variety of systems for transmitting and receiving the bed bay location ID. In one embodiment, the location module includes at least one infrared (IR) transmitter for transmitting the bed bay location ID to the receiver and the receiver includes at least one IR sensor for receiving the bed bay ID from the IR transmitter. In another embodiment, the location module may include a radio frequency identification (RFID) tag for transmitting the location ID using radio frequency. A person skilled in the art will appreciate that a variety of known RFID systems, including active, semi-active, and passive RFID systems, can be utilized. Examples of such RFID systems include, without limitation, an RFID tag mat that includes an array of RFID tags, an RFID swipe card having at least one active or passive RFID tag, or a magnetic RFID tag. Other embodiments of the invention can include one of: an ultrasonic transmitter for transmitting the location ID using ultrasonic signals; an inductively coupled transmitter for transmitting the location ID using principles of magnetic inductive coupling; or a modulated light transmitter for transmitting the location ID using modulated light. It should be appreciated that in each of these embodiments, the receiver is particularly adapted for receiving the specific signal types mentioned, i.e., the receiver may be a RFID reader, or include an ultrasonic sensor, an inductively coupled sensor, or a modulated light sensor. In another embodiment, the location module uses WiFi technology, or a mesh network, to transmit and receive bed bay location IDs. In a further embodiment of the invention, the location module comprises an ID transmitter integrated into a power cord interface to communicate with the ID transmitter through a power cord. The receiver would then communicate the location information, e.g., bed bay location ID, to the remote station located on the network. In yet another embodiment of the invention, the location module comprises an Ethernet port and the receiver comprises an Ethernet transceiver for communicating the location information to the remote station. In a further embodiment, the location module uses a combination of these methods for transmitting and receiving the bed bay location ID.

In another embodiment of the invention, the location detection system allows locating a bed by separately determining first and second areas of the location. In one embodiment, the first area is the room, e.g., Room 1, in which the bed is located, and the second, subarea, is the zone in the room in which the bed is located, e.g., zones A, B. In this instance, a first location module would be enabled to only provide first area or room locations, and not specific zone locations, to a remote station. A second location module associated with the bed and in electronic communication with the remote station would be enabled to transmit a second location ID to the remote station. The second location ID corresponds to the subarea or zone in which the bed is located. Thus, the first location ID provides the general vicinity in which the bed is located, while the second location ID further refines the description of the location to pinpoint the location of the bed. The second location module would be adapted to generally measure distances from walls located in the first area, e.g., Room 1, to further determine the position of the bed in the room. Sonic distance sensors, laser distance finders, or a hall-effect sensor operable with a room magnet or plurality of room magnets located in the room, can be employed to determine the zone location of the bed, for example.

As mentioned above, the bed bay location ID can also be correlated to a patient ID provided by the ADT system. As a result, the display at the remote station can indicate both the bed bay location ID and the corresponding patient ID. The room location module may be a standalone or networked device. When acting as a standalone device, the room location module simply comprises a battery-powered transmitter preprogrammed with the bed bay identification such that the hospital bed is able to determine its location even when the hospital network is unavailable.

The room location module could also include additional features to provide an intelligent room module. For instance, the intelligent room module may include interface buttons for operator selection that correspond to the bed or room being clean, dirty, empty, occupied, ready for occupancy, etc. An alternative intelligent room module may also include a graphic display such as a touch-screen display with multiple nested user screens to access or transmit patient, bed, or room data. The intelligent room module may transmit this information, e.g., bed/room clean/dirty, etc., directly or indirectly to the hospital network, beds or remote station, using wired or wireless communication paths. Communication can occur from the intelligent room modules directly to the hospital network, from the intelligent room modules to the beds then to the hospital network or to more than one available hospital network, or directly from the intelligent room modules to the remote station or to more than one remote station. The intelligent room modules may also be configured as wireless access points between the beds and multiple non-bed devices such as patient monitoring devices, patient treatment devices, diagnostic devices, and the like, or the intelligent room modules may be configured as wireless access points between the hospital network and the non-bed devices.

Bed Configuration Status Indicator

In one embodiment of the invention, the hospital bed comprises a system for monitoring a plurality of bed conditions. A status indicator node, in communication with the bus and the other nodes, is configured, as part of a bed status indication system, to establish a "desired" bed configuration based on a user-defined set of conditions to be monitored, monitor the user-defined set of conditions, and trigger an associated audible or visual indicator responsive to the monitored conditions to indicate whether the hospital bed is in the "desired" or an "undesirable" configuration, i.e., when one or more of the monitored conditions are in an "undesirable" state.

If each of the user-defined monitored conditions are in the "desired" state, a green indicator light is illuminated to indicate that the bed is in the desired configuration. If any one of the monitored conditions is not in the "desired" state, an amber indicator light is illuminated to indicate that the bed is not in the desired configuration. Of course, the status indicator node can be configured with any number of monitored conditions, or as few as one monitored condition. The indicator lights are preferably duplicated on a footboard user interface of the bed along with controls for other conventional features of the bed. Any suitable indicating devices may be used in place of or in addition to the green and amber indicator lights, such as audible alarms and the like, whether local or remote. The indicator lights are merely exemplary. In addition, if the bed is not in the desired configuration, a light positioned on a component that is out of place may be used to indicate that it needs to be moved, e.g., a light on one of the side rails. A text display on the footboard user interface or other location may also provide information as to which conditions are not in the "desired" state. The "desired" state for each monitored condition, e.g., side rail position, bed height, fowler angle, etc., can be modified as the patient's condition changes or based on standard hospital criteria, or the "desired" states can be reset to a predefined 'pre-set' configuration in the event of a significant clinical event such as surgery, or when a new patient is admitted.

Examples of "desired" states for monitored conditions may include:
- side rails in an up position
- bed brakes set
- bed height is below a predetermined level
- fowler angle is thirty degrees
- bed exit detection is active, e.g., alert is given if patient exits bed
- other patient or hospital specific conditions
- bed is identified with a bay location
- housekeeping status: bed occupied
- the weight of a patient on the bed
- bed scale 'zero' status
- patient is positioned proximal to the bed
- nurse is positioned proximal to the bed
- infusion pump is positioned proximal to the bed
- patient movement is regular and moderate In a further embodiment, a single global "correction" button on the footboard user interface of the hospital bed could transmit a signal to the status indicator node upon actuation to automatically activate a plurality of actuators (not shown) to "correct" the conditions that are not currently desired, such as by automatically raising the side rails, setting the brakes, lowering the bed height, adjusting the fowler angle, activating the bed exit system, and the like. The actuators are in electronic communication with the control system via the bus and may comprise motors, pumps, valves, solenoids, or any other mechanical or electrical devices capable of correcting the monitored bed conditions. The global correction button could also be a user-selectable button on the display at the remote station, or at any other networked location.

Fowler Monitoring System

As discussed, certain bed configurations may be desired to accommodate patient events (e.g., surgery) or clinical conditions (e.g., ventilator induced pneumonia (VIP)). In many of these cases, it may be desired that a clinically preferred fowler angle of the bed be indicated or required per accepted clinical standards. For example, a particular fowler angle may clinically improve respiration and may reduce the risks of contracting ventilator induced respiratory diseases such as VIP. In one embodiment of the invention, therefore, the hospital bed comprises a fowler monitoring system for monitoring and controlling the fowler angle of the head-end of the bed.

A fowler monitoring system, of the present invention, can be activated by a nurse or other operator via a touch button or other interface (such as at a footboard user interface), which instructs the bed articulation/height node to monitor the fowler angle and sound an alarm (not shown) or give other notification when the fowler angle is too low. The fowler monitoring system can also be configured to modify the "desired" configuration of the hospital bed by providing a predefined "desired" configuration of the hospital bed, i.e., the fowler angle within a predetermined range, to be monitored by the status indicator node. Other medical or clinical conditions may have predefined "desired" configurations that can be programmed into the status indicator node such that, when appropriate, a user can select these predefined "desired" configurations either at the hospital bed or the remote station, or other networked station for monitoring.

The fowler monitoring system can also track the fowler angle over time and provide associated statistics. For instance, the fowler monitoring system can determine how long the fowler angle has been over thirty degrees in the last 24 hours with associated date/time stamps such that the operator can determine when the fowler angle fell below thirty degrees. The fowler monitoring system can also be configured to automatically log the date/time when the fowler angle was below thirty degrees for immediate viewing by hospital personnel either locally, or at any remote station, including personal pagers, phones, radios, tablets, viewing screens, data assistants or any other means to communicate and present data to the clinical staff. In addition, the Bed Status system could proactively message the clinical staff based upon a configurable 'clinical response network' that would provide the appropriate level of response to a number of anticipated clinical situations. All of this data can also be associated with the patient ID through an interface (not shown) with the ADT system, or any other information system as previously discussed.

For further examples of functions, controls, and other systems that may be incorporated into the bed of the present invention, reference is made to copending U.S. applications entitled PATENT HANDLING DEVICE INCLUDING LOCAL STATUS INDICATION, ONE-TOUCH FOWLER ANGLE ADJUSTMENT, AND POWER-ON ALARM CONFIGURATION, Ser. No. 11/557,349, filed Nov. 7, 2006; LOCATION DETECTION SYSTEM FOR PATIENT HANDLING DEVICE, Ser. No. 11/277,838, filed Mar. 29, 2006; and DIAGNOSTIC CONTROL SYSTEM FOR A PATIENT, Ser. No. 11/362,365, filed Feb. 23, 2006, which are herein incorporated by reference in their entireties.

The Use of Loads Cells and Tilt Sensors to Monitor Patients on a Hospital Bed

As described above and referring to FIGS. 5-7 and 17A-17D, load cells 602 can be positioned at one or more locations in the frame system of the bed such that measurements of various load signals can be achieved. Load cells generate load signals indicative of forces applied to the load cells.

Accurate load cell readings are important for various reasons such as determining the weight fluctuations of a patient over time and the patient's center of gravity at any given time.

FIGS. 5-7 and 17A-17D illustrate one embodiment of the present invention where the load cells 602 are respectively located proximate to the four corners of the intermediate frame, with the intermediate frame being operatively connected to the load frame via the system of load cells. More specifically, the load cells are coupled with the respective ends of the superior components of the intermediate frame and with complementary areas on the inferior components of the load frame. The superior components of the intermediate frame and the inferior components of the load frame are longitudinally adjacent but are not in contact, the sole physical connection between these components being through the load cells.

In a hospital bed according to one embodiment of the present invention, the load cell measurements can be used together with other measured or input information, such as the articulation angle of a section of the lying surface support or the entire load frame in order to determine, for example, a patient's weight. For example, when the patient support is angled to the Trendelenburg and reverse Trendelenburg positions, the actual load can be calculated by knowing the angle of the load frame and respective loads measured by each load cell, independent of the load frame's position. As depicted in FIG. 44, one or more tilt sensors 603a, 603b can determine the angular position of the load frame while the load's center of gravity shifts.

Medical personnel require accurate readings of the patient's weight independent of the bed's articulation. Such a measurement is possible by calculating the bed's angle relative to baseline and load cell measurements.

A tilt sensor, which incorporates an accelerometer, is attached to any part of the frame system that can be elevated, angled and/or articulated.

The tilt sensor provides a signal that is read and measurements are calculated after a given time period, such as 50 ms. It can run continuously, intermittently or upon command from the user, such as when components of the frame system are in an articulated position. The tilt sensor is connected to at least one motherboard, processor or any electronic board via a communications network, fiber optic, or wireless connection to allow for a reading of the tilt sensor signal.

In one embodiment, the tilt sensor is designed with a solid state accelerometer, such as the ADXL202E accelerometer from Analog Devices, Inc. of One Technology Way, Norwood, Mass., schematically represented in FIG. 62. Angular solid state sensors or electronic angular sensors, where a change in angle of the sensor changes the impedance of the sensor which can be measured, could also be used. Other accelerometers may also be used within the present invention, as would be understood by a worker skilled in the art to which this invention relates. The accelerometer of this embodiment is a 2-axis acceleration sensor with a direct interface to low-cost microcontrollers. This interface is possible through a duty cycle (ratio of the pulse width to the total period) output. The outputs of the accelerometer can be analog or digital signals whose duty cycles are proportional to acceleration. The outputs can be directly measured with an integrated microprocessor counter, without any external converter.

Figure 64:
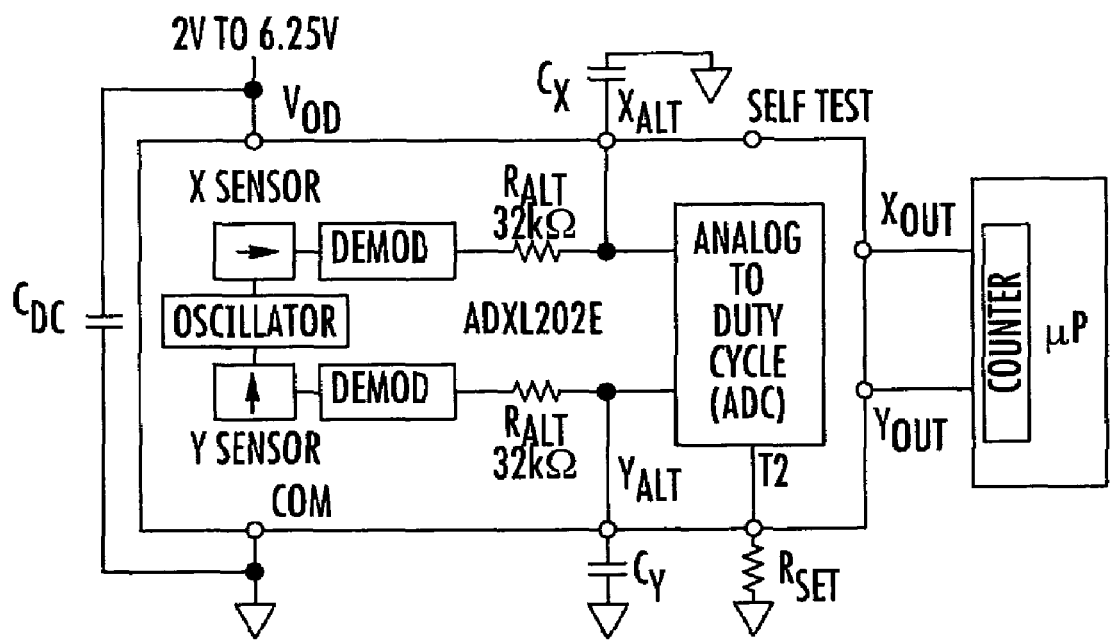
FIG. 64 depicts the functional block diagram of an accelerometer used in an embodiment of the present invention.

FIG. 64 depicts a functional block diagram of the accelerometer used in this embodiment. For each axis, a circuit output converts the signal into a modulated duty cycle that is decoded by the microprocessor. The accelerometer of this embodiment must be capable of measuring positive and negative accelerations to at least +−2 g, so as to measure static acceleration forces such as gravity and therefore be used in a tilt sensor.

Theoretically, a 0 g acceleration produces a 50% nominal duty cycle. Acceleration is calculated as follows:

$$A(g) = (T1/T2 - 0.5)/12.5\%$$

$$T2(s) = R_{SET}(\Omega)/125 \text{ M}\Omega$$

The 12.5% corresponds to the theoretical gain of the accelerometer. When used as a tilt sensor, the accelerometer uses the force of gravity as the input vector to determine the orientation of the object in space. The accelerometer is more sensitive to tilt when its reading axis is perpendicular to the force of gravity, that is to say, parallel to the earth's surface. When the accelerometer is orientated on axis to gravity, that is to say, near its +1 g or −1 g reading, the change in output acceleration per degree of tilt is negligible. When the accelerometer is perpendicular, the output varies nearly 17.5 mg per degree of tilt, but at 45 degrees the output only varies 12.2 mg by degree and the resolution declines. This is illustrated in the following table:

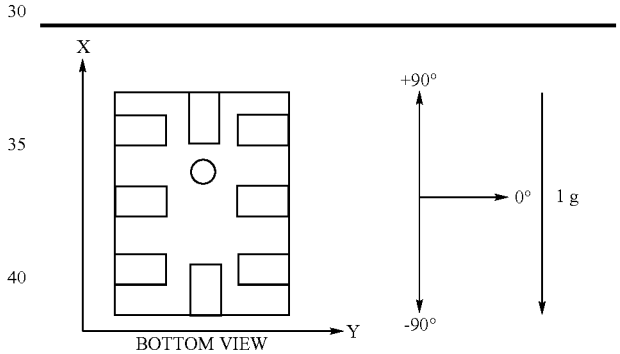

| X Axis Orientation to Horizon (°) | X Output (g) | X Output Δ per Degree of Tilt (mg) | Y Output (g) | Y Output (g) Δ per Degree of Tilt (mg) |
|---|---|---|---|---|
| −90 | −1.000 | −0.2 | 0.000 | 17.5 |
| −75 | −0.966 | 4.4 | 0.259 | 16.9 |
| −60 | −0.866 | 8.6 | 0.500 | 15.2 |
| −45 | −0.707 | 12.2 | 0.707 | 12.4 |
| −30 | −0.500 | 15.0 | 0.866 | 8.9 |
| −15 | −0.259 | 16.8 | 0.966 | 4.7 |
| 0 | 0.000 | 17.5 | 1.000 | 0.2 |
| 15 | 0.259 | 16.9 | 0.966 | −4.4 |
| 30 | 0.500 | 15.2 | 0.866 | −8.6 |
| 45 | 0.707 | 12.4 | 0.707 | −12.2 |
| 60 | 0.866 | 8.9 | 0.500 | −15.0 |
| 75 | 0.966 | 4.7 | 0.259 | −16.8 |
| 90 | 1.000 | 0.2 | 0.000 | −17.5 |

It is also to be noted that the gravity value varies according to the sine of the angle, which also influences the precision and consequently the orientation of the tilt sensor of this embodiment. The sensor precision can be improved by using both Xout and Yout signals in the angular determination. By doing so, the low sensitivity range (around 0 degrees) is reduced.

Figure 65:
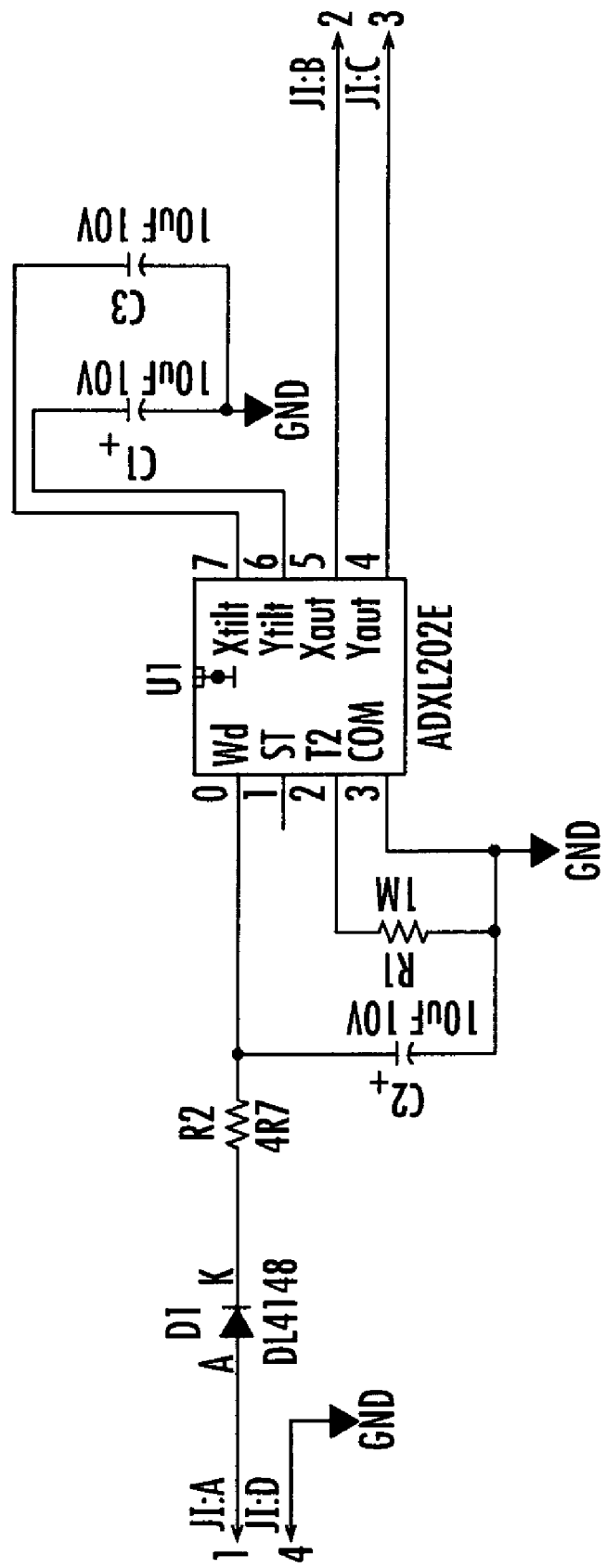
FIG. 65 displays a tilt sensor circuit according to an embodiment of the present invention.

The tilt sensor circuit used in one embodiment was therefore designed from the Analog Devices Inc. accelerometer following the recommended design parameters. The schematic of the circuit for this embodiment is shown at FIG. 65.

D1 is added to protect the circuitry against polarity inversion.

$R_{SET}$ value was set to 1 MΩ. Therefore, T2 value is:

T2=1 MΩ/125 MΩ9=0.008

T2 total period is thus 8 ms, therefore giving a 125 Hz frequency.

In order to determine the actual values of the zero and the gain, the tilt sensor circuit must be calibrated. Since the zero and the gain are known after calibration, only T1/T2 is unknown. It is this duty cycle that varies according to the angle. The microprocessor thus takes this reading and calculates the corresponding angle.

The tilt sensor circuit comprises an analog potentiometer which outputs a PWM (pulse width modulation) signal with a good signal-to-noise ratio. This PWM signal is sent to a microcontroller wherein the period of the signal is measured and the on-time of the signals. A ratio of these results is proportional to the sine of the angle. By using the cosine of this angle within a formula (discussed below) the precise angle can be determined. This analysis can be accomplished by a microprocessor.

To calibrate the tilt sensor circuit, two duty cycle readings must be taken at known angles. With these two PWM readings, the two unknowns (zero and gain) can be computed. It is preferable to take a PWM reading when the tilt sensor is at its zero position, as readings are usually precise at this position. This also provides a reading of the PWM value corresponding to the zero of the tilt sensor, since a sensor in zero position gives 0 g.

The tilt sensors of this embodiment are used to indicate the angle of the load frame, such as the Trendelenburg and reverse Trendelenburg angles. A compensation of the weight read by the load cells according to the Trendelenburg angle can then be computed. Consequently, the weight value displayed is thus in the required margin.

Figure 66:
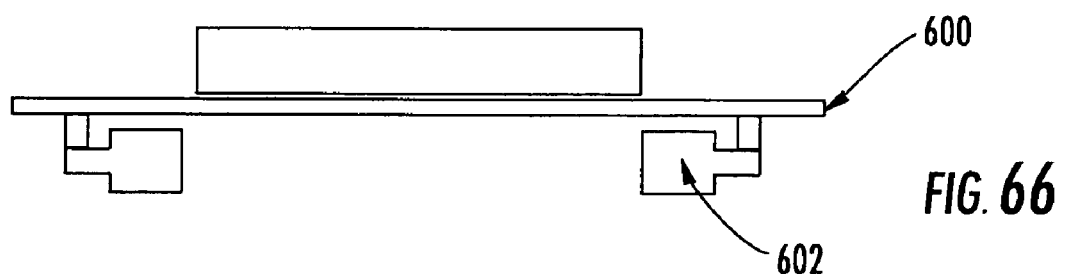
FIG. 66 depicts a horizontal patient support with a load according to an embodiment of the present invention.
Figure 67:
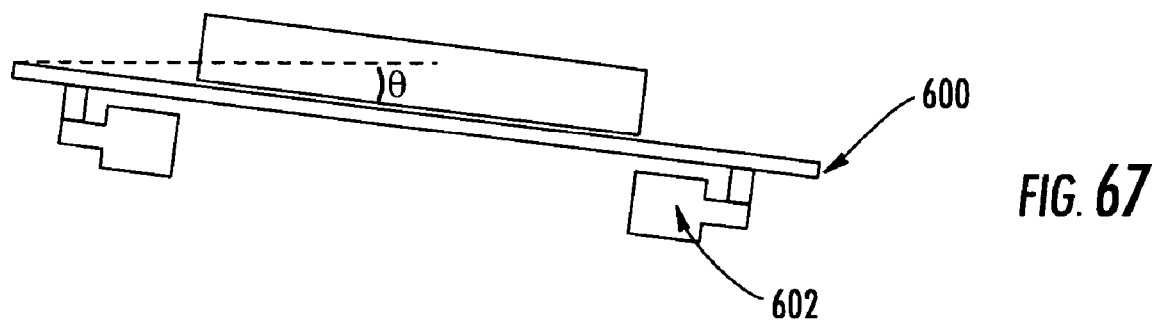
FIG. 67 depicts an incline patient support with a load at angle D according to an embodiment of the present invention.

As previously indicated, the axis in which the tilt sensor is positioned is important to obtain precise readings. For example, the position of a head section of the lying surface support may vary between 0 and 80 degrees. Given that the tilt sensor of the embodiment is more precise from −45 to 45 degrees than from 0 to 90 degrees, the tilt sensor would be positioned in the bed so that the zero of the sensor is at 45 degrees. In computation, one would account for this position by adding 45 degrees to each angle read. The calculation of load and calibration values is readily apparent in referring to FIGS. 66 and 67, where:

X patient load;

$Y_+$ weight of patient support frame which changes with the Trendelenburg angle;

$Z_+$ load cell factor which is not influenced by the Trendelenburg angle;

$Y_-$ weight of bed frame which changes with the reverse Trendelenburg angle;

$Z_-$ load cell factor which is not influenced by the reverse Trendelenburg angle;

θ bed frame angle; and

T load cell readings.

At θ=0°, $T_0° = X + Y_+ + Z_+$

At θ=12°, $T_{12}° = (X + Y_+)\cos θ + Z_+$

During calibration, the load frame without the patient is measured at 0° and at 12°, providing:

$$X = 0$$

$$T_0° = \text{first measurement at } 0°$$

$$T_{12}° = \text{second measurement at } 12°$$

$$Y_+ = T_0° - Z_+$$

$$Y_+ \cos θ = T_{12}° - Z_+$$

$$Y_+ = \frac{T_{12}° - Z_+}{\cos θ}$$

$$T_0° - Z_+ = \frac{T_{12}° - T_0° \cos θ}{\cos θ}$$

$$Z_+ = \frac{T_{12}° - T_0° \cos θ}{1 - \cos θ}$$

if θ = 12°

$$Z_+ = \frac{T_{12}° - T_0° \cos 12°}{1 - \cos 12°}$$

$$Z_+ = (T_{12}° - T_0° * 0.97815) * 45.761565$$

$$Y_+ = T_0° - Z_+$$

$Z_+$ and $Y_+$ for each load cell are determined during calibration. In a similar manner, $Z_-$ and $Y_-$ are determined using measurements at 0° and −12°, providing:

$$Z_- = (T_{-12}° - T_0° * 0.97815) * 45.761565$$

$$Y_- = T_0° - Z_-$$

When determining the patient's weight, X, the following calculations are made for each load cell:

$$T_θ = (X + Y)\cos θ + Z$$

$$T_θ = X \cos θ + Y \cos θ + Z$$

$$X \cos θ = T_θ - Y \cos θ - Z$$

$$X = \frac{T_θ - Y \cos θ - Z}{\cos θ}$$

$$X = \frac{T_θ - Z}{\cos θ - Y}$$

The processor determines the load frame's angular position (Trendelenburg or reverse Trendelenburg) prior to choosing $Y_+$ or $Y_-$ and $Z_+$ or $Z_-$. When the load frame's angle is 0°, the processor chooses $Y_+$ and $Z_+$ to calculate the load.

The center of gravity can be calculated as follows, using for example four load cells (schematically represented in FIG. 62) positioned in a rectangle relative to the patient:

X length (head to foot)

Y width (left to right)

LC(0) load cell value foot left

LC(1) load cell value head right

LC(2) load cell value foot right

LC(3) load cell value head left

W total weight of the patient

H(X) distance between the head load cells and foot load cells

H(Y) distance between the right load cells and left load cells $$CG[X] = \frac{LC(3) + LC(1)}{\frac{W}{100}} * H(X) * 0.01$$

$$CG[Y] = \frac{LC(3) + LC(0)}{\frac{W}{100}} * H(Y) * 0.01$$

This embodiment of a load cell system can be used for monitoring movement of a patient. The system can be integrated into the bed or can be part of a lying surface such as a mattress. In addition, the load cell system can comprise a number of load cells or load sensors, for example a load cell which can be embedded in the bed proximally positioned at each of a supported person's limbs and optionally at the center of the bed. The load cell system also can be comprised of a mesh of load cells for example. The signals from the load cells can be monitored and processed by a processing unit in the load cell system or a central processing unit capable of monitoring, processing, and controlling signals from the bed's various subsystems. Instead of forming part of a lying surface such as a mattress the load cell system can also integrated into the lying surface support. The load cell system can provide a measure for the pressure, weight, or mass load of a certain load cell, for example foot left or right load cell values and head left or right load cell values and additional information about the location of the center of gravity.

In one embodiment of the present invention, the tilt sensors can provide a means for determining possible interference between components of the bed. For example, if a particular component is in a certain relative position, a second component might not be able to perform certain functions associated with it. In this embodiment, there can furthermore be a movement termination based on the evaluation of tilt sensors readings.

In a further embodiment of the present invention, tilt sensors can be used to evaluate a patient's position over a period of time through the collection of angle variation data.

In one embodiment, a collection of angular data from the tilt sensors can also provide assistance for the maintenance of the bed. For example it can help to determine the angle of a particular bed component and the period of time that that position is held, especially when a particular position results in higher stress levels being applied to specific components of the bed.

In another embodiment of the present invention, tilt sensors can be positioned on the elevation system for determination of the height of the bed surface.

In another embodiment of the present invention, tilt sensors are wireless. In a further embodiment, tilt sensors do not have an on board power supply and are powered in the same way as for example an RFID tag, by the scanning frequencies sent by a scanner for example. In another embodiment, tilt sensors are integrated within load cells.

A worker skilled in the art would understand that tilt sensors could be positioned in a plurality of other components of the bed, for example, the side rails, a control panel, on an intravenous apparatus support attached to a bed, etc.

In one embodiment the control and diagnostic system can comprise an additional scale subsystem providing a calibration process for calibrating the scale subsystem to provide accurate reading of a patient's weight and subsequently to calibrate a motion detection system for monitoring movement of the patient. It may be necessary to calibrate the load cells' electronics in order to provide match the sensor signals with the scale subsystem electronics.

In one embodiment, the tilt sensors can be used with a control and diagnostic system as a means for fault detection. For example, where no change in an angle is detected when an actuator is being activated to modify the angle, the situation can be indicative of a blockage related to the actuator movement or an actuator malfunction.

Figure 68:
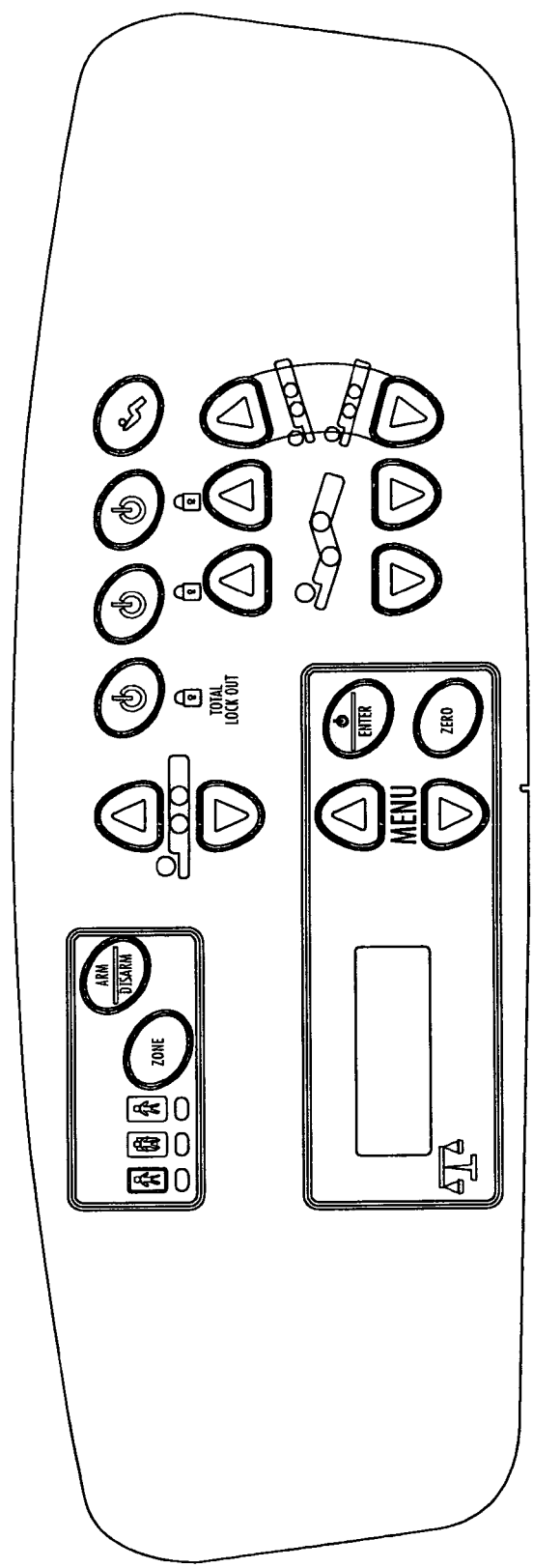
FIG. 68 illustrates part of a user interface according to one embodiment of the present invention intended for use by a patient.

FIG. 68 illustrates a schematic view of a console, which can be part of a user interface embedded into a bed. The console can be integrated into the footboard of the bed illustrated in FIG. 1 and provide access to the bed's functions. The console has backlit zone indicators, which can indicate a set zone mode of the bed for indicating a preset restriction level for movement of a supported person. Indicators can also be multi-color backlit to provide an indication of whether the system is in an armed or a disarmed state.

Buttons can be used to set and switch between the zone alarm as indicated by the zone alarm indicators. Buttons can arms or disarm the zone alarm functionality in a toggling fashion. Buttons can be sectional or full color or multi-color back-lit to indicate an armed or disarmed state of the zone alarm system. Interface elements can be used to raise or lower the bed surface. While pushing the arrow-up button the bed raises and while pushing the arrow-down button the bed lowers. Pushing and holding both buttons and may cause the movement to stop or continue the movement according to the button which was pressed first. Button can lock out some or all functionality accessible through this or other consoles until the button is pressed again. Buttons can be used to lock-out access to reorient the respective head and knee sections of the bed. Button, when pressed, causes the bed to assume a cardiac position or other predetermined shape of the bed surface. Each of buttons when pressed individually inclines or reclines the overall bed surface without affecting the shape of the bed surface. Interface elements provide button groups which when pressed can reorient the head or the knee sections of the bed and can be used in order to achieve respective desired angles between the upper body and the upper leg, as well as the upper leg and the lower leg of a supported person. Display can be used to display information about certain functions or the state of certain parts of the bed and its system components. Button groups can be used to scroll through information, which is available in form of a menu for display but exceeds the amount of information, which can be displayed simultaneously on display. Buttons can be used to select or enter information and to interact with the menu following a command and control concept.

Figure 69:
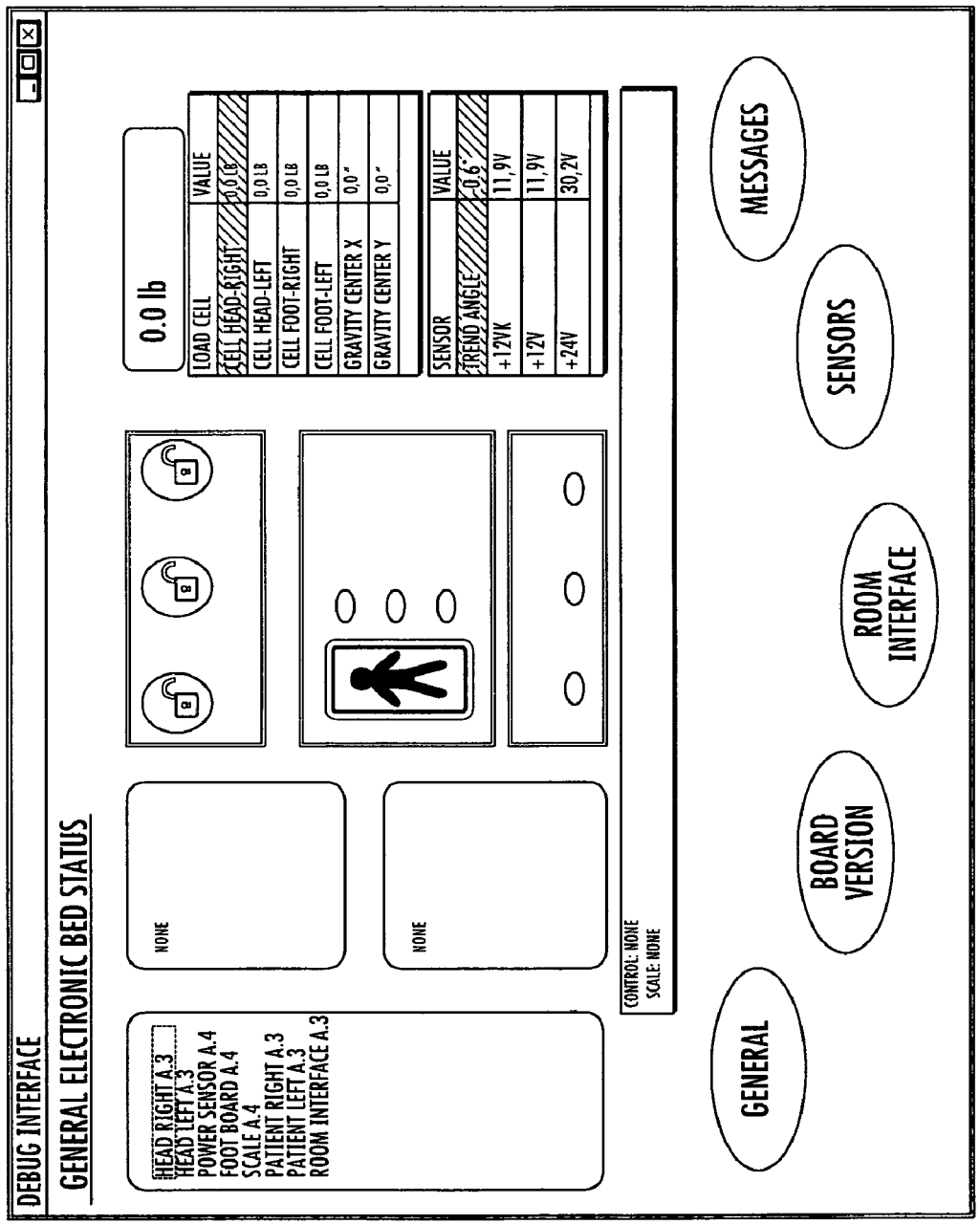
FIG. 69 illustrates the window content of a step in a series of user-patient support interaction processes displayed on a detached device such as a general purpose computer according to one embodiment of the present invention.

FIG. 69 illustrates the window content of a step in a series of user-bed interaction processes that can be displayed on a detached device such as a general purpose computer. This is part of an interface which for example can provide remote access to control, diagnose, or monitor functions of the bed system. The interface can provide functions to select certain components from a list of components or subsystems of the bed system for detailed investigation. The user interface may change its look and feel by changing some or all of its user interface components when selecting to investigate a specific component of the bed system. The user interface can provide and display information in a categorized graphical fashion and can utilize a button status field, a motor status field, fields for monitoring vital information about a supported person etc. The user interface can also provide a menu system to select from providing access to different aspects of interaction of the bed system such as for example a monitoring interface, a maintenance interface, an operator interface etc. Switching between these modes may require authorization and may be password or security code protected.

Figure 70:
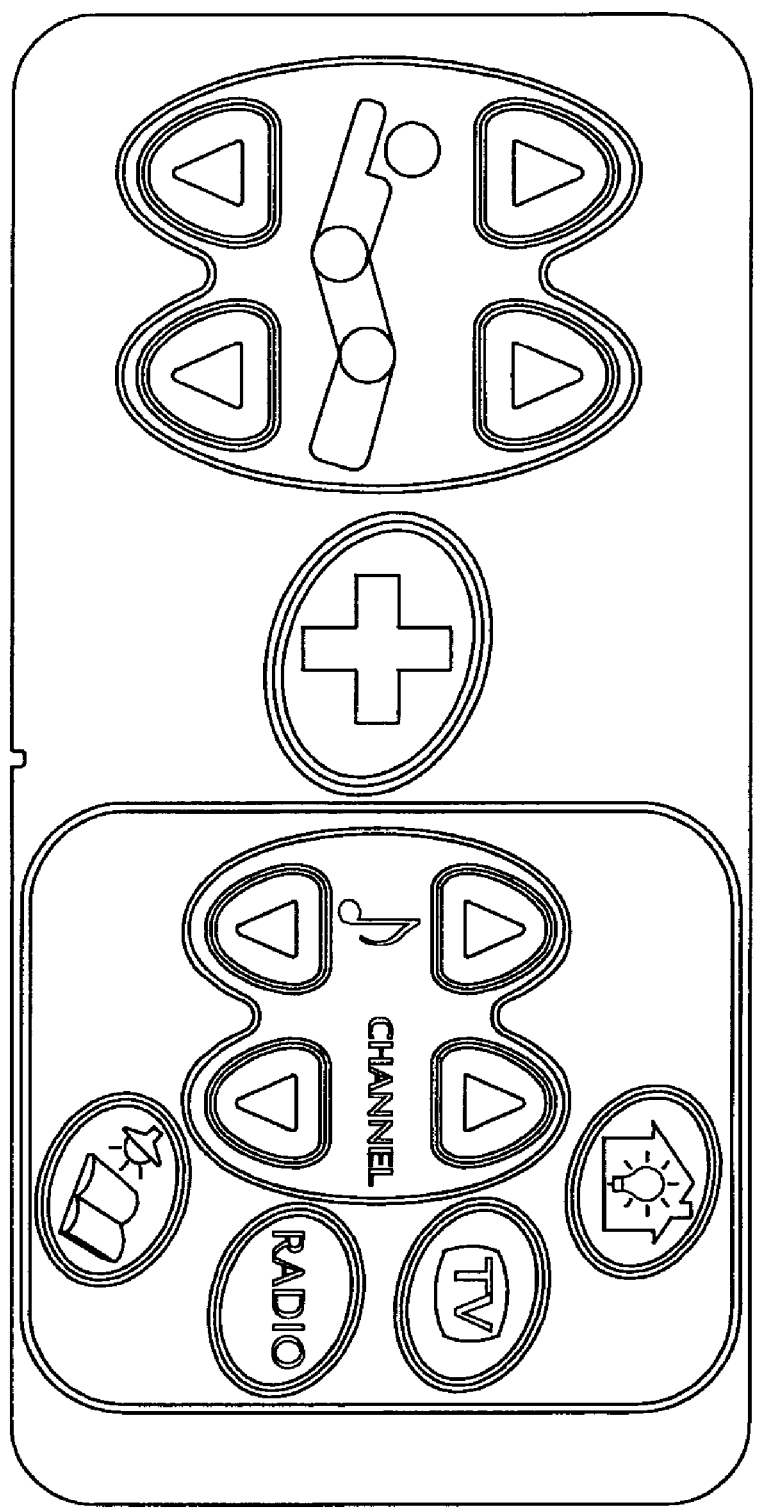
FIG. 70 illustrates part of a user interface according to one embodiment of the present invention intended for use by a patient.

FIG. 70 illustrates an embodiment of a part of the user interface intended for use by the supported person. As illustrated, the user interface for the supported person can provide access to reclining functions, emergency call functions or control of entertainment equipment.

As noted previously FIG. 8A, illustrates a schematic diagram of the system architecture of a bed control and diagnostic system. The architecture can be divided into a number of user interface and control subsystem components. The system architecture comprises a power or AC control system for supplying electrical power, an actuator subsystem providing ability for positioning and orienting parts of the bed, a number of sensor and detector subsystems for sensing and detecting the state of parts of the bed, and a diagnostic subsystem as indicated. The diagnostic subsystem can interact with the sensor and detector subsystem or it can have its own redundant sensor and detector system. The user interface subsystem can comprise a number of control consoles and comprising indication or display systems. The display systems can have a touch screen or a regular display with separate buttons. The sensor system can comprise a scale subsystem including a load cell system and tilt sensor. The system architecture can further comprise a room or other interface for communicating information from the bed to a remote user interface system or vice versa.

FIG. 62 illustrates the information made available by a load cell system, which is used for monitoring movement of a patient. The system can be integrated into the patient support or can be part of a person support element such as a lying surface. In addition, the load cell system can comprise a number of load cells or load sensors for example a load cell which can be embedded in the bed proximally positioned at each of a supported person's limbs and optionally at the center of the bed. The load cell system also can be comprised of a mesh of load cells for example. The signals from the load cells can be monitored and processed by a processing unit in the load cell system or a central processing unit capable of monitoring, processing, and controlling signals from the bed's subsystems. Instead of forming part of a support element, the load cell system can be integrated into the surface of the bed frame. The load cell system can provide a measure for the pressure, weight, or mass load of a certain load cell, for example foot left or right load cell values and head left or right load cell values and additional information about the location of the center of gravity.

Figure 71:
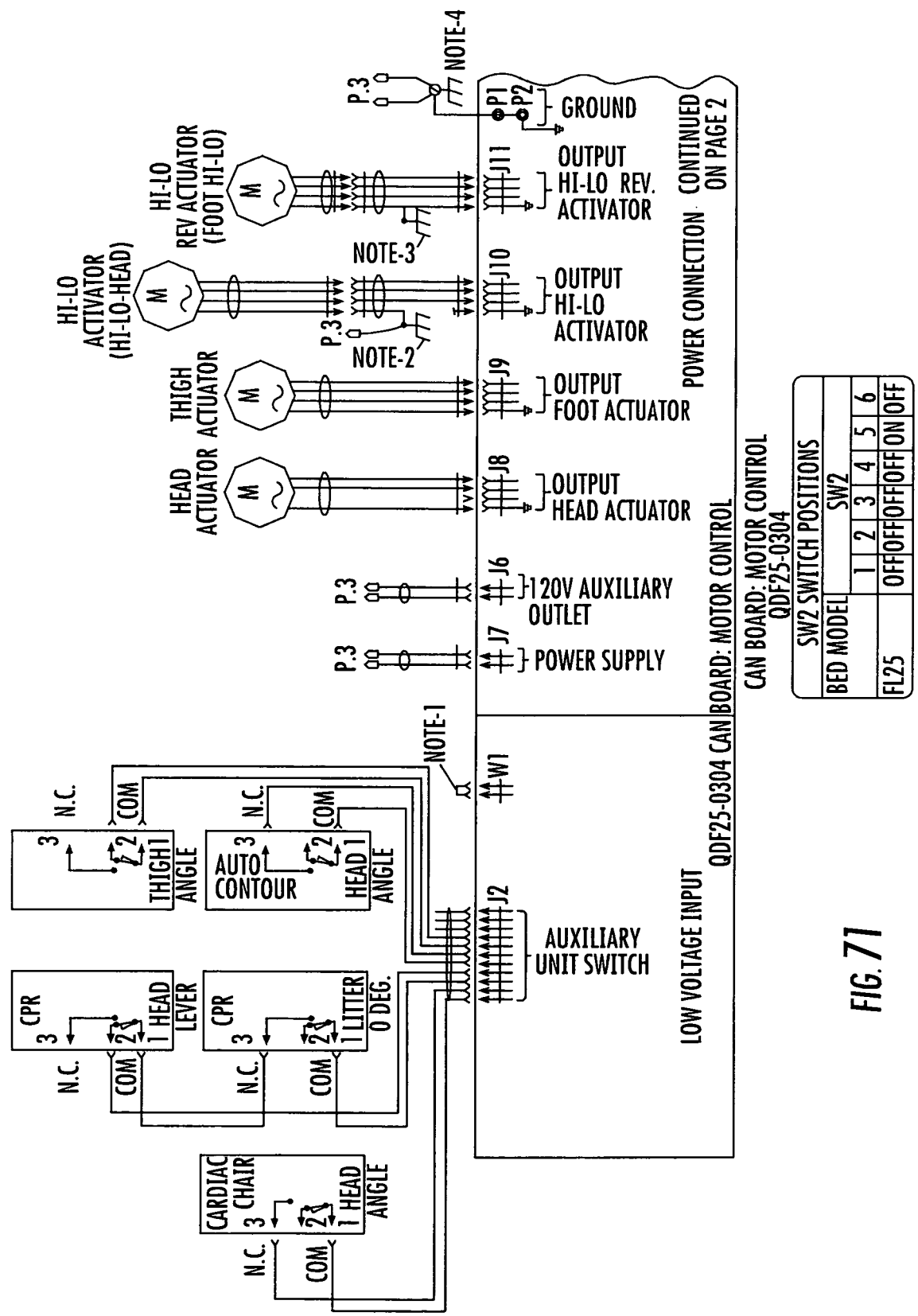
FIG. 71 illustrates a motor control and drive system according to one embodiment of the present invention.

FIG. 71 schematically illustrates an embodiment of the motor control subsystem with a number of attached actuators and limit switches. It is understood that, depending on the functionality of the bed, there can be a different number of actuators or limit switches than illustrated. In this embodiment the surface of the bed can be shaped by orienting a head, thigh, and a foot section where the bed surface for a supported person is intended to fold and provide an adjustable angle between the upper body and the thigh as well as under the knee between the thigh and the lower leg. The head actuator can position the end of the head section, and the thigh actuator can position the knee section of the bed surface relative to an even or flat support structure. The HI-LO head actuator can position the head-end of the even support structure relative to the frame of the bed which is in contact with the floor. The HI-LO foot actuator can position the foot-end of the even support structure relative to the frame of the bed, for example. The two HI-LO actuators can pivot the support surface horizontally whereas the head and the thigh actuator can shape the support surface by pivotally adjusting sections of the bed surface.

The motor control subsystem is connected to a number of limit switch or angle sensor systems which ensures that the actuators do not move or position parts beyond predetermined limit angles or distances. When a part or section of the bed reaches a predetermined limit position while moving, the motor control subsystem can receive a status change signal via one or more limit sensor signals and can interrupt the respective movement. The motor control subsystem can have a safety control feature that does not allow any further continued movement in that same direction or orientation unless the limit condition indicated by the limit sensor system is resolved. Provided that no movement of other degrees of freedom of the bed takes place, the limit condition typically can be resolved by reversing the original movement.

Figure 72:
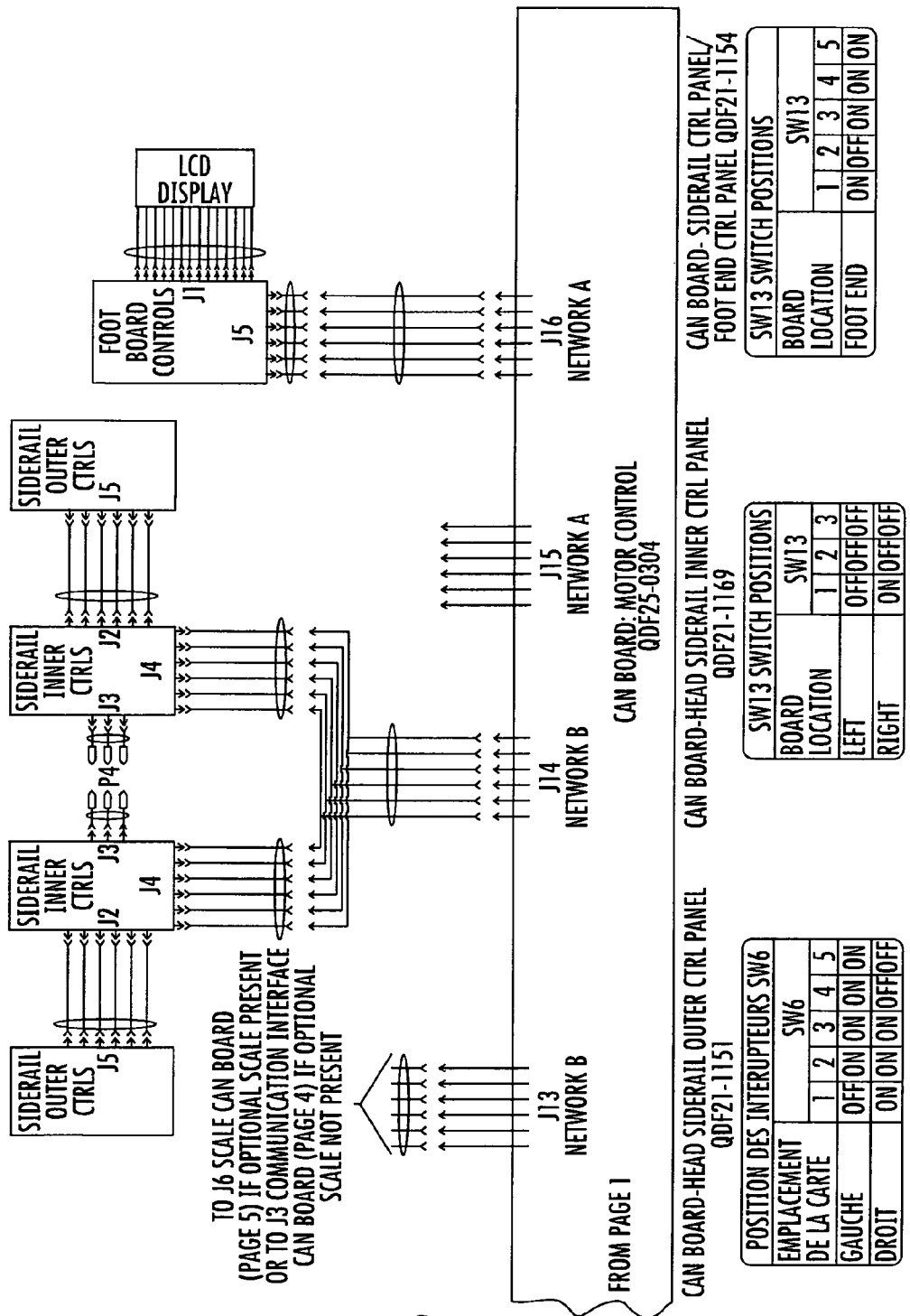
FIG. 72 illustrates an interface controller according to one embodiment of the present invention.

FIG. 72 schematically illustrates an embodiment of the user interface controller with a number of attached user interface consoles. The bed can have a number of user-interface consoles, each providing access to a certain set of bed system functions. For example the bed can have user interface consoles integrated into one or both of the side rails of the bed providing easy access to certain bed system functions for a supported person or for a person at the side of the bed. The bed can also have a user interface console located at the foot or the head section of the bed. Each such interface console may be integrated into a respective foot or head board of the bed for example. A foot or a head interface console may provide access to a set of bed system functions different from each other as well as different from the side rail consoles. There can be inner or outer side rail consoles intended for access from within or from outside of the bed. An embodiment of a side rail console is illustrated in FIG. 70 and an embodiment of a footboard interface console is illustrated in FIG. 68. The footboard console can have a display system included. The display system can be a touch screen display or a simple passive display system with a separate input system as illustrated in FIG. 68. In addition the interface controller can have a remote control interface to which a remote console can be connected. The remote control interface can provide wired or wireless connection of a special purpose or a general purpose computing device for example. A number of different bus systems and control protocols are available to communicate through the remote control interface as known to a person skilled in the art. The interface controller may also provide a number of additional control or remote control interfaces.

Figure 73:
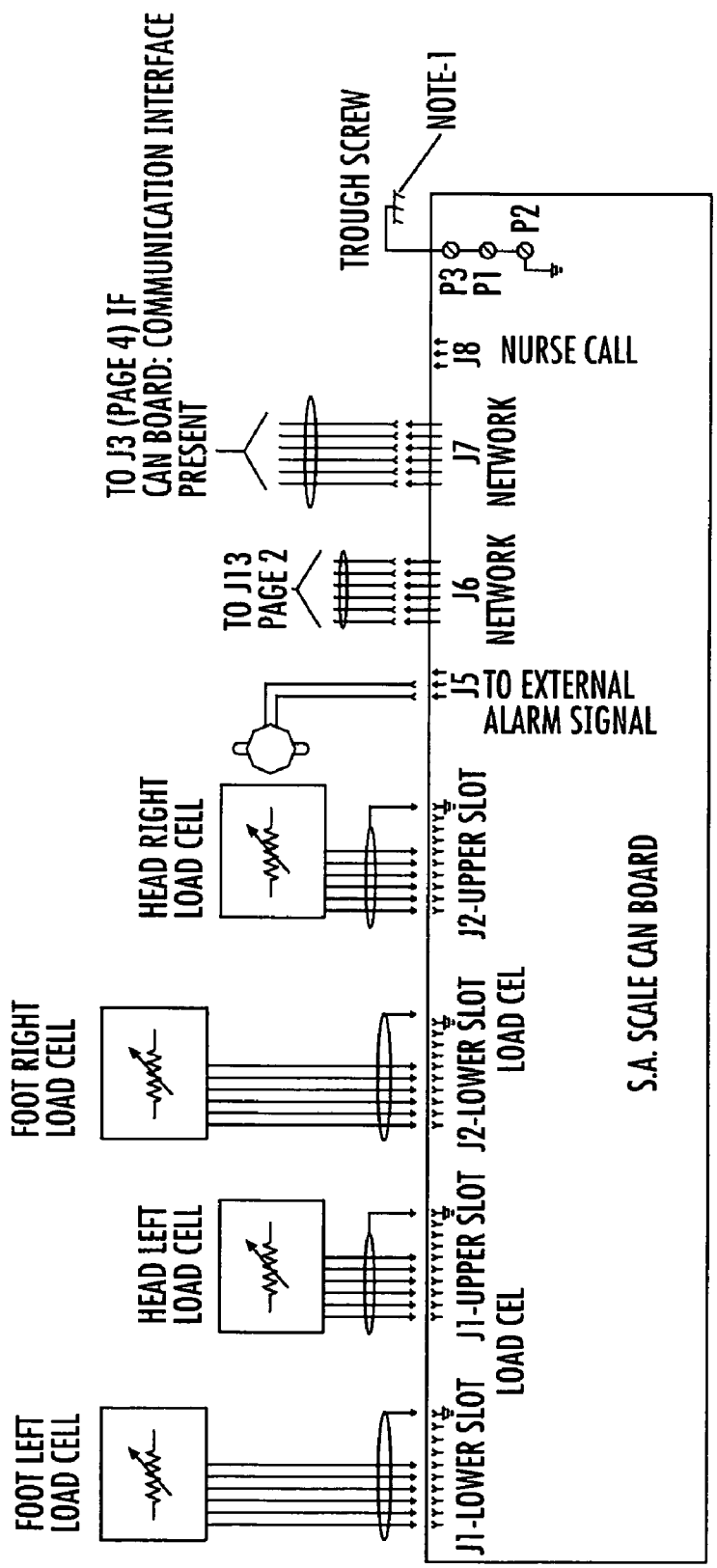
FIG. 73 illustrates a scale subsystem according to one embodiment of the present invention.

FIG. 73 illustrates a part of a scale subsystem. The scale subsystem can connect to a number of load sensors or load cells. The number of load sensors can be different from that illustrated. In this embodiment, four load sensors which are capable of sensing pressure and can be calibrated to provide a measure of force or mass applied to each sensor are attached to the scale subsystem control interface. The scale subsystem controller can process signals incoming from the load cells and can be used to detect the status of a supported person. The scale control subsystem can be configured to provide a messaging signal or to alert monitoring personnel through an external alarm system interface for example. When each load cell is properly calibrated, the scale control subsystem can also provide a measure of the weight of a supported person, which is then compensated by the angle of the bed to provide the actual weight. The weight information can be utilized and can also be recorded in another subsystem of the bed which may be desired for patient monitoring for example. As previously described, the angle of the bed and the load sensor measurements are used to calculate the patient's actual weight, independent of the bed's position.

Figure 74:
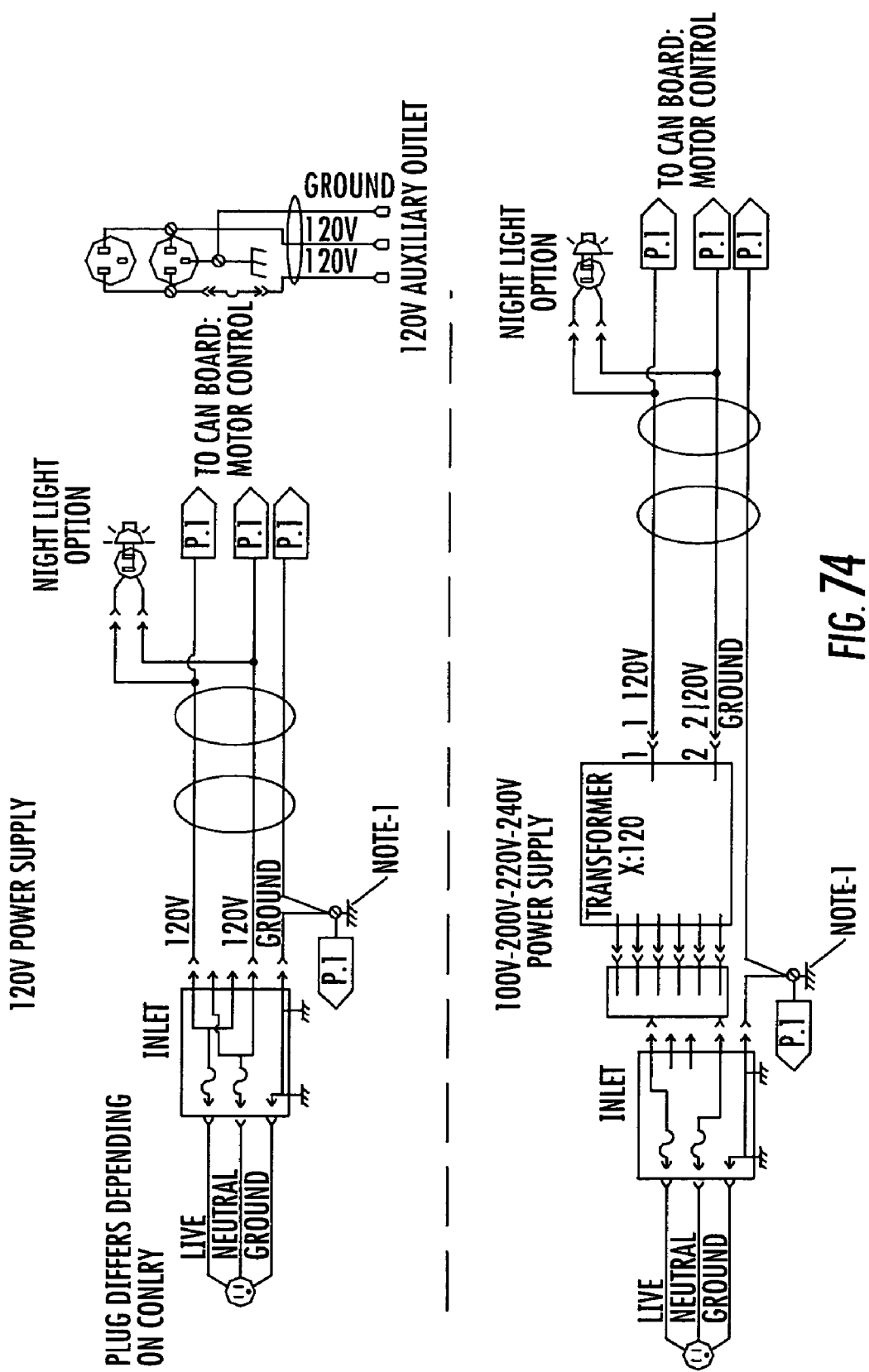
FIG. 74 illustrates a power supply system according to one embodiment of the present invention.

FIG. 74 illustrates an embodiment of a power supply system. The power supply system may include an adaptation subsystem including a transformer and an adaptive wiring and plugging subsystem to achieve compatibility with standard power outlets and the different voltage standards of other regions or countries.

Figure 75:
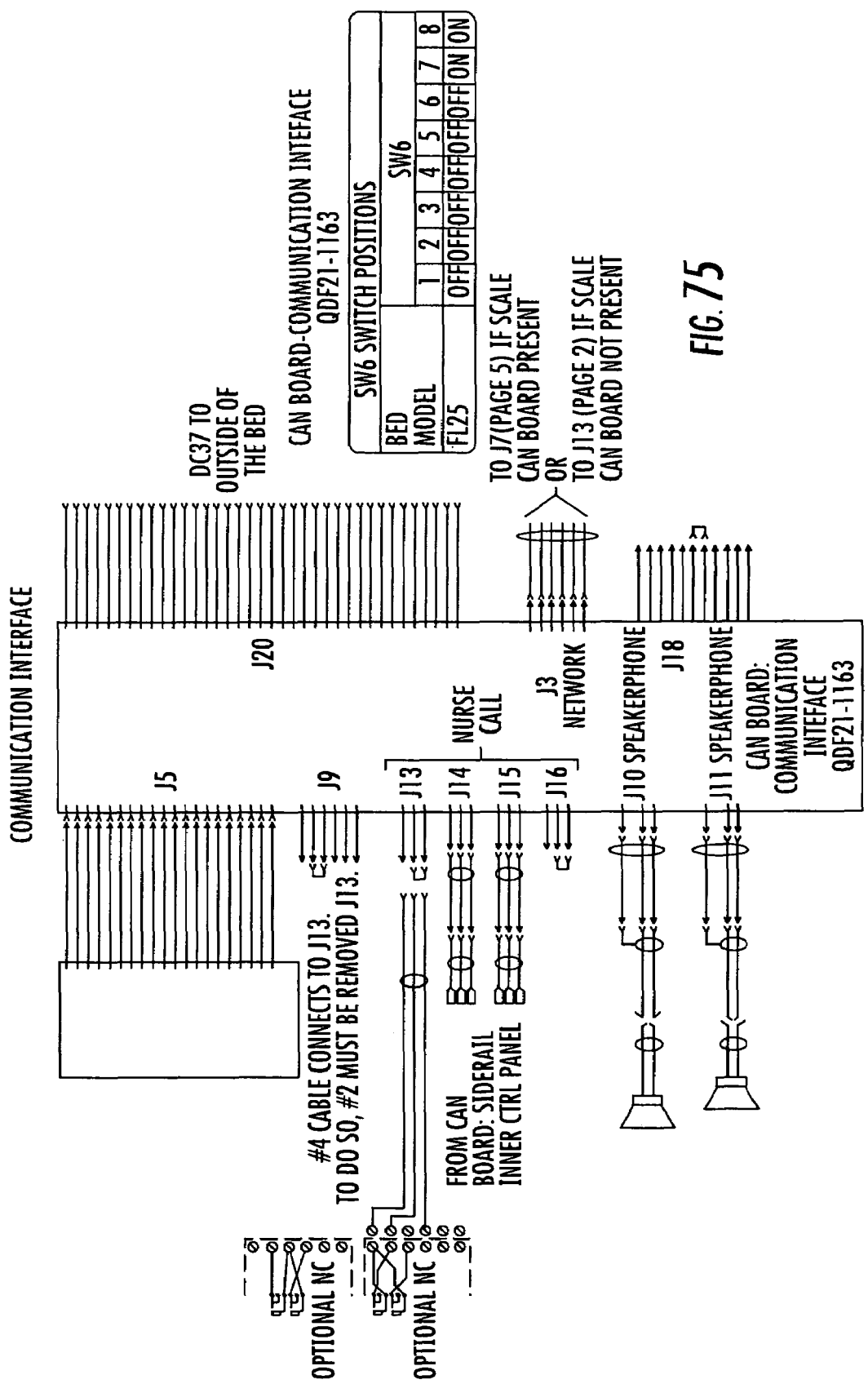
FIG. 75 illustrates a communication interface according to one embodiment of the present invention.

FIG. 75 schematically illustrates the communication interface of the CAN board controller for communication with other components of the bed. The communications interface includes sub-interfaces for side rail consoles, footboard consoles, remote monitoring consoles, external alarm system, speakers, an entertainment system etc.

Actuator Speed Compensation Circuit

Figure 76:
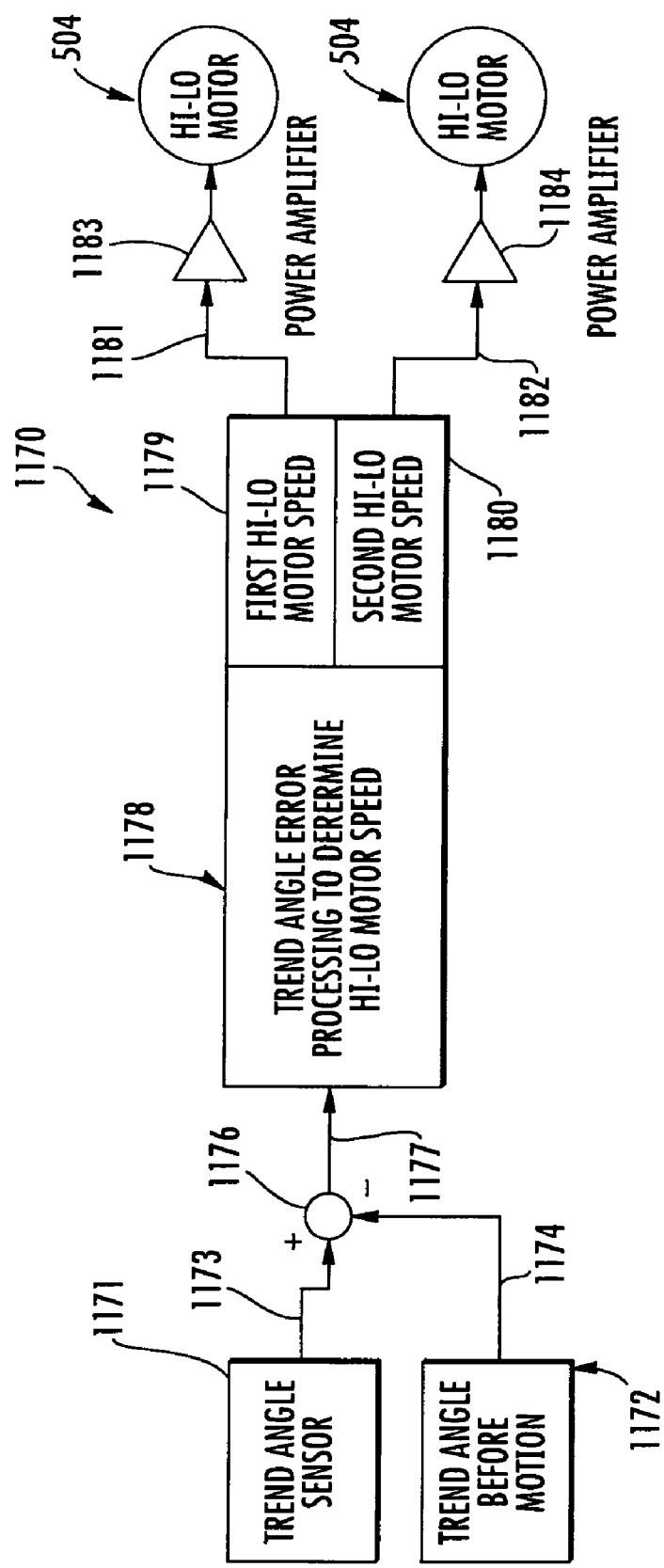
FIG. 76 illustrates a motor speed compensation circuit embodying the invention.

Referring to FIG. 76, the bed of the present invention optionally incorporates an actuator speed compensation circuit 1170. Circuit 1170 includes at least one angle sensor 1171 located at any convenient location on the upper frame of the bed, for example, to the deck frame, to provide an actual angle of inclination indication relative to horizontal. An angle store 1172 is provided to store the angle value before a change in elevation is initiated. The respective outputs 1173 and 1174 from the actual angle sensor 1171 and the angle store 1172 are connected to a common node 1176 which forms the input 1177 to an angle processor 1178.

The processor 1178 contains and processes an algorithm that monitors the angle of the upper frame and, when necessary, adjusts the relative speed of rotation of either one or both of the actuators 504, also known as Hi-Lo actuators or motors, so as to maintain the appropriate angle for the upper frame. For example, and in this particular embodiment, the angle sensor 1171 produces a linearly varying first signal which is compared to a stored second signal representative of the angle in existence prior to the initiation of a height change. The sum of the two signals at the node 1176 will produce an input signal at 1177 to the processor 1178 which will then process the input signal to produce, in accordance with the algorithm, at least a first actuator speed control signal at 1179 for one of the actuators 504 and, depending on the setup of the bed and algorithm used, a second motor speed control signal for the other motor actuator 504. The first and second motor speed control signals are fed through respective outputs 1181, 1182 from the processor 1178 through respective power amplifiers 1183, 1184 to the respective actuators 504 in order to effect a driving force of the actuators at the proper speed to maintain unchanged the angle, in existence prior to beginning the elevation change, throughout the change in elevation of the upper frame relative to the base frame.

According to one embodiment of the present invention, actuators 504 have the linear speed and are configured to initially operate at maximum capacity during initiation of a height adjustment (either raising or lowering) of the upper frame. Absent any load upon the upper frame, both actuators 504 will continue to operate at maximum capacity and will exhibit substantially equal speeds, resulting in both ends (head-end and foot-end) of the upper frame raising or lowering at the same speed, thereby maintaining the angle of the upper frame.

Typically, however, the upper frame will be supporting a load, such as, for example, a person sitting or lying upon the patient support deck. Furthermore, this load is frequently distributed unevenly across the frame such that a first end of the frame will be subject to a greater load than the opposite, second end of the frame. In this situation, initiation of a height change in the upper frame results in both actuators 504 initially operating at their maximum capacity. However, due to the unevenly distributed load, the actuator at the first end of the frame functions at a decreased speed. As a result of this decreased speed, the first end of the frame raises or lowers at a slower rate than the opposite, second end of the frame, resulting in a change in the angle of the upper frame.

Processor 1178 detects the change in the angle of the upper frame by means of the angle sensor 1171. The speed of the actuator at the second end of frame is subsequently adjusted so as to substantially match the lower speed of the actuator at the first end of the frame. In this manner, the speeds of the two actuators remain substantially matched during adjustments in the height of the upper frame, thereby allowing the angle of the frame to be maintained.

To illustrate the above process, consider the following example where a 200 lb person sits on the head-end of the patient support deck. The head-end actuator operates at its maximum capacity upon initiation of a height change in the frame, yet due to the 200 lb load at the head-end of the patient support deck, the speed of the head-end actuator decreases by 20% compared to when no load is present. Processor 1178 detects the initial changes in the angle of the upper frame and reduces the speed of the foot-end actuator by 20% so as to assure that both ends of the upper frame raise or lower at the same rate. The head-end actuator returns to its maximum, unloaded rate upon removal of the 200 lb load from the head-end of the patient support deck. This increase in speed in the head-end actuator is detected as initial deviations in the angle of the upper frame, upon which the speed of the foot-end actuator is increased to match the speed of the head-end actuator.

Figure 77:
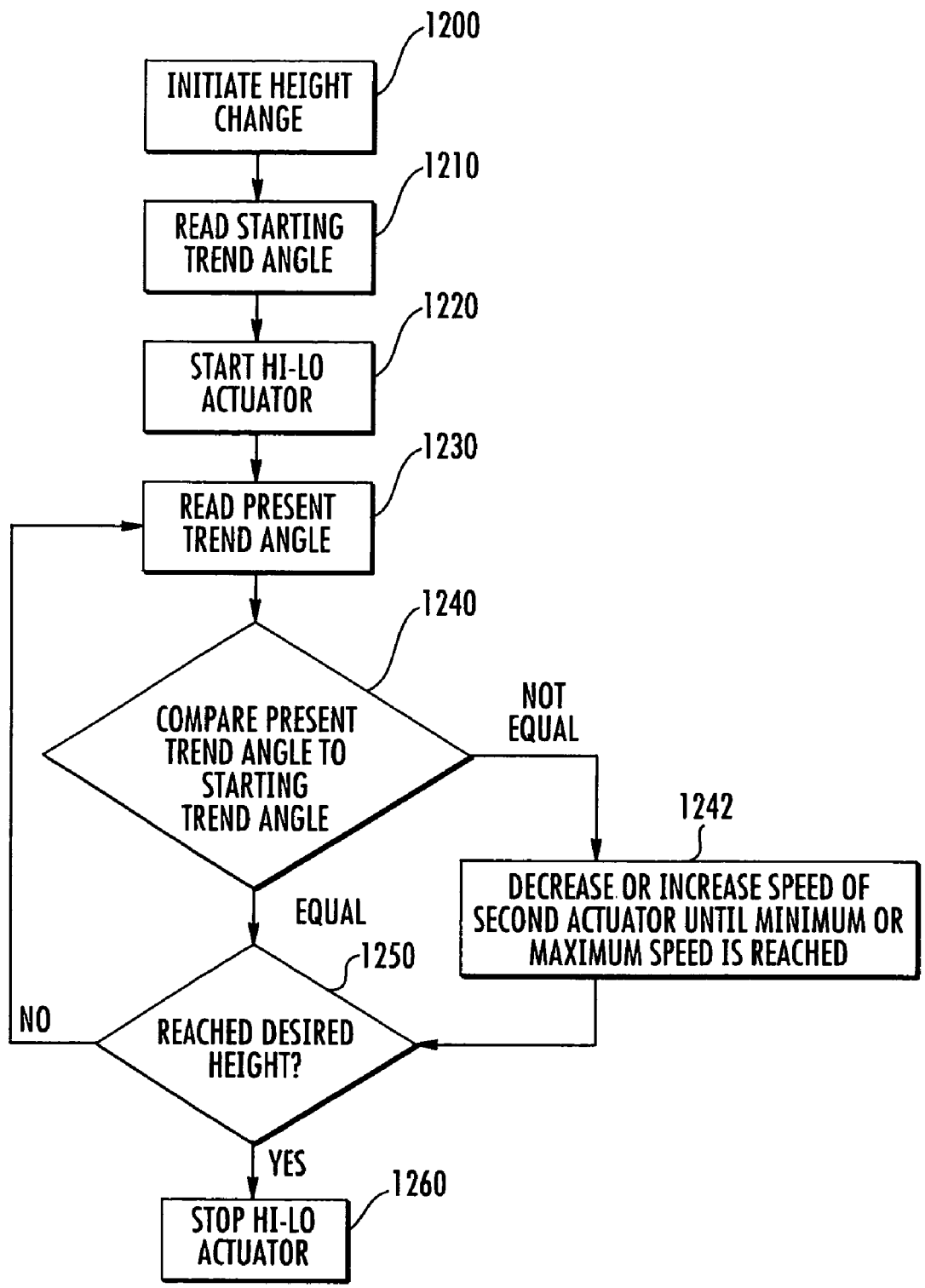
FIG. 77 is a flow chart of an algorithm utilized by the motor speed compensation circuit according to one embodiment of the invention.

To carry out the above example, processor 1178 is programmed with one or more specific algorithms for monitoring and adjusting the angle of the upper frame. One example of such an algorithm is illustrated in the flow chart of FIG. 77. According to this illustrated algorithm of FIG. 77, the first step 1200 involves the motor speed compensation circuit 1170 receiving and initiating the appropriate procedure for changing the height of the upper frame. At this step 1200, the current angle of the upper frame is determined by means of the angle sensor 1171 and stored in the angle store 1172. Both Hi-Lo actuators 504 are then activated in step 1200. At step 1230, the angle sensor 1171 is then checked again to determine the current angle of the upper frame. A comparison of the current angle to the starting angle retained in the angle store 1172 is then carried out at step 1240. If the two angles are found to be equal, the algorithm proceeds on to step 1250 to determine if the upper frame has reached the desired height. If it is determined that the desired height has been achieved, both actuators 504 are stopped, otherwise the algorithm loops back to step 1230 and repeats. If it is determined at step 1240 that the current angle is beginning to vary from the starting angle, the algorithm proceeds on to step 1242 and, for example, decreases the speed of the second motor actuator 504, thereby causing both ends of the upper frame to raise or lower at the same rate, thereby maintaining the angle of the frame.

According to an alternative embodiment of the present invention, corrections to the angle during the raising or lowering of the upper frame are achieved through adjustment of the speed of the actuator supporting the greatest load. Specifically, instead of decreasing the speed of the motor subject to less load, the current embodiment increases the speed of the motor supporting the greatest load. In this manner, the decreased speed caused by an increased load is directly addressed by increasing the power output of the actuator. However, unlike the previously described approach, the current embodiment requires that the actuators be configured to run at less than maximum capacity when in an unloaded state.

Figure 78:
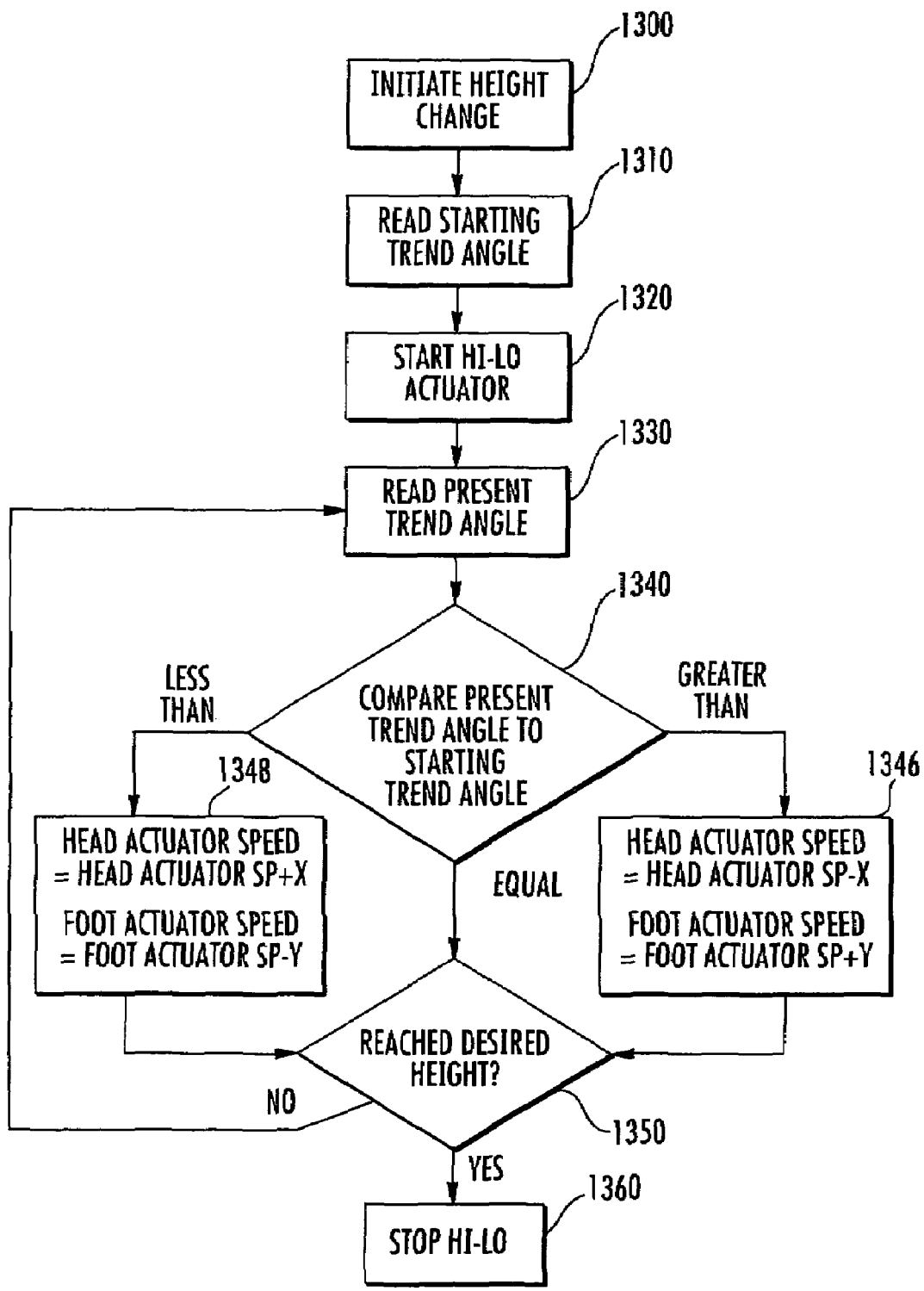
FIG. 78 is a flow chart of an algorithm utilized by the motor speed compensation circuit according to another embodiment of the invention.

According to yet another alternative embodiment of the present invention, corrections to the angle during the raising or lowering of the upper frame are achieved through adjustment of the speeds of both actuators 504. To accomplish such a task, an algorithm such as the one illustrated in the flow chart of FIG. 78 is carried out by the processor 1178. Steps 1300-1340 and 1350-1360 are similar to the primary steps 1200-1240 and 1250-1260 required in the algorithm of FIG. 77, and as such, will not be discussed. However, according to the illustrated algorithm of FIG. 78, upon determining that the starting angle is greater than the current angle, the speed of one of the actuators is decreased while the speed of the opposite actuators is increased. For example, as illustrated in the flow chart of FIG. 78, step 1346 may require that the actuator located at the head-end of the bed unit be decreased by amount X, while the actuator located at the foot-end of the bed unit is increased by an amount Y, where X and Y represent either a specific amount of speed, or, alternatively, a percentage of the current speed of the head-end and foot-end actuators, respectively. Similarly, if the current angle is found to be less than the starting angle, step 1348 can require that the speed of the actuator located at the head-end of the bed unit be increased by an amount X, while the speed of the actuator located at the foot-end of the bed unit be decreased by an amount Y. It should be understood that the above actions may need to be reversed depending on where the angle sensor 1171 is located and how it is interpreted. For example, step 1346 may instead require that the actuator located at the head-end of the unit be increased by an amount X, while the speed of the actuator located at the foot-end of the unit be decreased by an amount Y.

In addition to the algorithms discussed above with reference to FIGS. 77 and 78, other equivalent actuator control schemes can, if desired, be utilized. For example, instead of controlling actuator speed, one such scheme may call for the selective activation of actuator, thereby turning one actuator on or off, prior or subsequent to the other actuator, in order to correct for deviations in the angle of the upper frame.

It is understood that variations may be made to the above description without departing from the spirit of the invention. The foregoing description is therefore not intended to limit the scope of the invention in any way.

What is claimed is:

1. A method of actuating a brake on a caster wheel of a patient support apparatus to stop motion of the apparatus, the patient support apparatus including a support frame and a plurality of caster wheels supporting the frame, a patient support surface supported by the support frame, and at least one manually operable brake for manually braking the caster wheels, the patient support apparatus further including an actuator for selectively outputting a driving force and a control system, said method comprising:
    electrically coupling the control system to the actuator;
    generating actuating signals with said control system based on input from a user;
    transmitting the actuating signals to the actuator to thereby actuate the actuator to output a driving force; and
    mechanically coupling the driving force of the actuator with the manually operable brake to thereby actuate the manually operable brake and thereby brake the caster wheels.

2. The method according to claim 1, further comprising inputting a control signal into the control system using a user actuatable device.

3. The method according to claim 1, wherein said mechanically coupling comprises selectively mechanically coupling.

4. The method according to claim 1, further comprising selectively drivingly decoupling the driving force of the actuator from the brake.

5. The method according to claim 1, further comprising providing a user actuatable device responsive to pressure and selectively applying pressure to the user actuatable device wherein said applying pressure to the user actuatable device initiates said generating actuating signals.

6. The method according to claim 5, further comprising positioning the user actuatable device at or near the patient support surface.

7. The method according to claim 6, wherein the patient support apparatus includes a headboard, a footboard, and siderails, said positioning the user actuatable device includes positioning the user actuatable device at or near the headboard, a footboard, and siderails.

8. The method according to claim 1, further comprising supporting the support frame on a forward pair of bearings and a rearward pair of bearings, and providing a brake for each pair of bearings.

9. The method according to claim 8, further comprising providing an actuator for each brake.

10. The method according to claim 9, further comprising providing a plurality of user actuatable devices for selectively actuating the actuators, actuating one of said user actuatable devices for selectively powering one of the actuators, and actuating the other of said user actuatable devices for selectively powering the other of the actuators.

11. The method according to claim 1, further comprising selectively drivingly decoupling the actuator from the brake to provide an override.

12. A method of actuating a brake for a caster wheel on a patient support apparatus, the patient support apparatus including a patient support surface, a frame supporting the patient support surface, the frame including a plurality of caster wheels, the patient support apparatus further including a headboard, a footboard, siderails, and a manual brake operatively associated with the patient support apparatus for braking one or more of the caster wheels, and an actuator, said method comprising:
    providing a user actuatable device at or near the headboard, footboard, or siderails;
    generating an activation signal based on user input to the user actuatable device;
    powering the actuator to generate an actuation force in response to the activation signal; and
    transmitting the actuation force from the actuator to the manual brake to thereby brake the at least one or more caster wheels.

13. The method according to claim 12, wherein said transmitting comprises releasably linking the actuator with the brake.

14. The method according to claim 13, further comprising selectively releasing the linking to thereby provide an override.

15. The method according to claim 12, further comprising monitoring the status of the brake, and displaying the status of the brake.

16. The method according to claim 15, wherein said displaying includes displaying the status of the brake at of near the headboard, footboard, or siderails.

* * * * *

UNITED STATES PATENT AND TRADEMARK OFFICE
CERTIFICATE OF CORRECTION

PATENT NO. : 7,690,059 B2
APPLICATION NO. : 11/612428
DATED : April 6, 2010
INVENTOR(S) : Guy Lemire et al.

It is certified that error appears in the above-identified patent and that said Letters Patent is hereby corrected as shown below:

Column 3:
Line 56, "scaling" should be --sealing--.

Column 87:
Line 9, "T2=1 MΩ/125 MΩ9=0.008" should be --T2=1 MΩ/125 MΩ=0.008--.

Column 88:
Line 10, Insert --$T_0°=Y_+ + Z_+$
    $T_{12}°=Y_+ \cos\Theta + Z_+$-- after "$T_{12}°$=second measurement at 12°".

Line 17, "$T_0° - Z_+ = \dfrac{T_{12}° - T_0° \cos\Theta}{\cos\Theta}$" should be --$T_0° - Z_+ = \dfrac{T_{12}° - Z_+}{\cos\Theta}$--.

Signed and Sealed this

Third Day of August, 2010

David J. Kappos
*Director of the United States Patent and Trademark Office*